US012214211B2

(12) United States Patent
O'Connor et al.

(10) Patent No.: US 12,214,211 B2
(45) Date of Patent: Feb. 4, 2025

(54) MEDICAL TREATMENT SYSTEM WITH COMPANION DEVICE

(71) Applicant: ZOLL Medical Corporation, Chelmsford, MA (US)

(72) Inventors: James P. O'Connor, Billerica, MA (US); Kristen B. McCarthy, Southborough, MA (US); Mark Weary, Billerica, MA (US); Brett B. Bonner, Littleton, MA (US); Dan E. Goldman, Shrewsbury, MA (US); Martin F. Trew, Wharton, NJ (US); Shannon L. Peterson, Meredith, NH (US); Denise R. Eizadkhah, Bridgewater, NJ (US)

(73) Assignee: ZOLL Medical Corporation, Chelmsford, MA (US)

( * ) Notice: Subject to any disclaimer, the term of this patent is extended or adjusted under 35 U.S.C. 154(b) by 518 days.

(21) Appl. No.: 17/467,087

(22) Filed: Sep. 3, 2021

(65) Prior Publication Data

US 2022/0072321 A1     Mar. 10, 2022

Related U.S. Application Data

(60) Provisional application No. 63/167,312, filed on Mar. 29, 2021, provisional application No. 63/074,874, filed on Sep. 4, 2020.

(51) Int. Cl.
*A61N 1/39*      (2006.01)
*A61B 5/00*      (2006.01)
(Continued)

(52) U.S. Cl.
CPC ....... *A61N 1/3925* (2013.01); *A61N 1/39044* (2017.08); *A61N 1/3993* (2013.01);
(Continued)

(58) Field of Classification Search
CPC .............. A61N 1/3925; A61N 1/39044; A61N 1/3993; A61M 2205/18; A61M 2205/505;
(Continued)

(56) References Cited

U.S. PATENT DOCUMENTS 3,513,850 A     5/1970   Weber
3,865,101 A     2/1975   Saper et al.
(Continued)

FOREIGN PATENT DOCUMENTS

CN            1613097        5/2005
CN           101226452        7/2008
(Continued)

OTHER PUBLICATIONS

International Search Report and Written Opinion Corresponding to PCT/US2021/049153 mailed Feb. 10, 2022.
(Continued)

*Primary Examiner* — Brian T Gedeon
(74) *Attorney, Agent, or Firm* — Finch & Maloney PLLC

(57) ABSTRACT

A medical treatment system includes a medical treatment device for monitoring and providing treatment to a patient and a companion device communicatively coupled to the medical treatment device. The medical treatment device may display case information including physiological information visually rendered from physiological sensor inputs in a first display format and transmit the case information and medical data to the companion device. The companion device may include a device interface having a display screen to accept user input instructions for the medical treatment device during a medical event. The companion device may process the case information and medical data received from the medical treatment device and also cause display, at the device interface, of multiple data display views in which each of the display views is selectable via a (Continued)

respective display view selection portion of the device interface.

63 Claims, 46 Drawing Sheets

(51) Int. Cl.
  *G16H 10/60*  (2018.01)
  *G16H 20/40*  (2018.01)
  *G16H 40/63*  (2018.01)
(52) U.S. Cl.
  CPC ............. *G16H 10/60* (2018.01); *G16H 20/40* (2018.01); *G16H 40/63* (2018.01)
(58) Field of Classification Search
  CPC .. A61M 2205/6018; A61M 2205/6072; A61M 2230/005; A61M 2230/04; G16H 10/60
  See application file for complete search history.

(56) References Cited

U.S. PATENT DOCUMENTS

| | | |
|---|---|---|
| 3,991,304 A | 11/1976 | Hillsman |
| 4,019,501 A | 4/1977 | Harris |
| 4,077,400 A | 3/1978 | Harrigan |
| 4,088,138 A | 5/1978 | Diack et al. |
| 4,095,590 A | 6/1978 | Harrigan |
| 4,193,064 A | 3/1980 | Snyder |
| 4,198,963 A | 4/1980 | Barkalow et al. |
| 4,198,964 A | 4/1980 | Honneffer |
| RE30,372 E | 8/1980 | Mirowski et al. |
| 4,273,114 A | 6/1981 | Barkalow et al. |
| 4,326,507 A | 4/1982 | Barkalow |
| 4,481,944 A | 11/1984 | Bunnell |
| 4,491,423 A | 1/1985 | Cohen |
| 4,588,383 A | 5/1986 | Parker et al. |
| 4,610,254 A | 9/1986 | Morgan et al. |
| 4,619,265 A | 10/1986 | Morgan et al. |
| 4,757,821 A | 7/1988 | Snyder |
| 4,797,104 A | 1/1989 | Laerdal et al. |
| 4,863,385 A | 9/1989 | Pierce |
| 4,928,674 A | 5/1990 | Halperin et al. |
| 4,932,879 A | 6/1990 | Ingenito et al. |
| 5,081,993 A | 1/1992 | Kitney et al. |
| 5,086,391 A | 2/1992 | Chambers |
| 5,193,537 A | 3/1993 | Freeman |
| 5,218,969 A | 6/1993 | Bredesen et al. |
| 5,241,302 A | 8/1993 | Thong |
| 5,247,945 A | 9/1993 | Heinze et al. |
| 5,255,187 A | 10/1993 | Sorensen |
| 5,285,792 A | 2/1994 | Sjoquist et al. |
| 5,327,887 A | 7/1994 | Nowakowski |
| 5,330,526 A | 7/1994 | Fincke et al. |
| 5,342,404 A | 8/1994 | Alt et al. |
| 5,348,808 A | 9/1994 | Goto et al. |
| RE34,800 E | 11/1994 | Hutchins |
| 5,391,187 A | 2/1995 | Freeman |
| 5,409,010 A | 4/1995 | Beach et al. |
| 5,414,644 A | 5/1995 | Seaman et al. |
| 5,431,685 A | 7/1995 | Alt |
| 5,454,779 A | 10/1995 | Lurie et al. |
| 5,466,244 A | 11/1995 | Morgan |
| 5,472,453 A | 12/1995 | Alt |
| 5,474,574 A | 12/1995 | Payne et al. |
| 5,496,257 A | 3/1996 | Kelly |
| 5,507,778 A | 4/1996 | Freeman |
| 5,511,553 A | 4/1996 | Segalowitz |
| 5,514,079 A | 5/1996 | Dillon |
| 5,533,958 A | 7/1996 | Wilk |
| 5,534,851 A | 7/1996 | Russek |
| 5,562,710 A | 10/1996 | Olsen et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,626,151 A | 5/1997 | Linden |
| 5,645,522 A | 7/1997 | Lurie et al. |
| 5,645,571 A | 7/1997 | Olson et al. |
| 5,662,690 A | 9/1997 | Cole et al. |
| 5,700,281 A | 12/1997 | Brewer et al. |
| 5,735,879 A | 4/1998 | Gliner et al. |
| 5,782,878 A | 7/1998 | Morgan et al. |
| 5,787,880 A | 8/1998 | Swanson et al. |
| 5,792,190 A | 8/1998 | Olson et al. |
| 5,813,403 A | 9/1998 | Soller et al. |
| 5,853,005 A | 12/1998 | Scanlon |
| 5,853,292 A | 12/1998 | Eggert et al. |
| 5,913,685 A | 6/1999 | Hutchins |
| 5,993,398 A | 11/1999 | Alperin |
| 6,021,349 A | 2/2000 | Arand et al. |
| 6,024,699 A | 2/2000 | Surwit et al. |
| 6,055,447 A | 4/2000 | Weil et al. |
| 6,073,033 A | 6/2000 | Campo |
| 6,120,442 A | 9/2000 | Hickey |
| 6,125,299 A | 9/2000 | Groenke et al. |
| 6,155,257 A | 12/2000 | Lurie et al. |
| 6,178,357 B1 | 1/2001 | Gliner et al. |
| 6,185,458 B1 | 2/2001 | Ochs et al. |
| 6,193,519 B1 | 2/2001 | Eggert et al. |
| 6,220,866 B1 | 4/2001 | Amend et al. |
| 6,224,562 B1 | 5/2001 | Lurie et al. |
| 6,238,349 B1 | 5/2001 | Hickey |
| 6,261,238 B1 | 7/2001 | Gavriely |
| 6,269,267 B1 | 7/2001 | Bardy et al. |
| 6,270,456 B1 | 8/2001 | Iliff |
| 6,273,088 B1 | 8/2001 | Hillsman |
| 6,306,107 B1 | 10/2001 | Myklebust et al. |
| 6,321,113 B1 | 11/2001 | Parker et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,371,765 B1 | 4/2002 | Wall et al. |
| 6,390,996 B1 | 5/2002 | Halperin et al. |
| 6,428,323 B1 | 8/2002 | Pugh |
| 6,443,735 B1 | 9/2002 | Eggert et al. |
| 6,443,889 B1 | 9/2002 | Groth et al. |
| 6,503,087 B1 | 1/2003 | Eggert et al. |
| 6,551,243 B2 | 4/2003 | Bocionek et al. |
| 6,564,088 B1 | 5/2003 | Soller et al. |
| 6,572,547 B2 | 6/2003 | Miller et al. |
| 6,572,560 B1 | 6/2003 | Watrous et al. |
| 6,575,914 B2 | 6/2003 | Rock et al. |
| 6,671,545 B2 | 12/2003 | Fincke |
| 6,676,613 B2 | 1/2004 | Cantrell et al. |
| 6,725,447 B1 | 4/2004 | Gilman et al. |
| 6,752,771 B2 | 6/2004 | Rothman et al. |
| 6,766,188 B2 | 7/2004 | Soller |
| 6,827,695 B2 | 12/2004 | Palazzolo et al. |
| 6,849,045 B2 | 2/2005 | Iliff |
| 6,865,413 B2 | 3/2005 | Halperin et al. |
| 6,936,049 B2 | 8/2005 | Svadovskiy |
| 6,961,612 B2 | 11/2005 | Elghazzawi et al. |
| 6,970,743 B2 | 11/2005 | Weinberg et al. |
| 6,980,112 B2 | 12/2005 | Nee |
| 7,010,344 B2 | 3/2006 | Burnes et al. |
| 7,011,637 B2 | 3/2006 | Sherman et al. |
| 7,056,295 B2 | 6/2006 | Halperin |
| 7,072,712 B2 | 7/2006 | Kroll et al. |
| 7,072,840 B1 | 7/2006 | Mayaud |
| 7,074,199 B2 | 7/2006 | Halperin et al. |
| 7,079,887 B2 | 7/2006 | Burnes et al. |
| 7,108,665 B2 | 9/2006 | Halperin et al. |
| 7,118,542 B2 | 10/2006 | Palazzolo et al. |
| 7,122,007 B2 | 10/2006 | Querfurth |
| 7,122,014 B2 | 10/2006 | Palazzolo et al. |
| 7,164,945 B2 | 1/2007 | Hamilton et al. |
| 7,174,891 B2 | 2/2007 | Lurie et al. |
| 7,184,963 B1 | 2/2007 | Shannon |
| 7,213,009 B2 | 5/2007 | Pestotnik et al. |
| 7,242,979 B1 | 7/2007 | Kelly et al. |
| 7,306,560 B2 | 12/2007 | Iliff |
| 7,447,643 B1 | 11/2008 | Olson et al. |
| 7,549,961 B1 | 6/2009 | Hwang |

(56) References Cited

U.S. PATENT DOCUMENTS

| | | |
|---|---|---|
| 7,853,327 B2 | 12/2010 | Patangay et al. |
| 8,315,688 B2 | 11/2012 | Jeda |
| 8,337,404 B2 | 12/2012 | Osorio |
| 8,392,217 B2 | 3/2013 | Iliff |
| 8,510,126 B2 | 8/2013 | Martin et al. |
| 8,738,129 B2 | 5/2014 | Packer |
| 9,153,112 B1 | 10/2015 | Kiani et al. |
| 9,161,696 B2 | 10/2015 | Ai-Ali |
| 9,241,666 B2 | 1/2016 | Packer et al. |
| 9,286,440 B1 | 3/2016 | Carter et al. |
| 9,658,756 B2 | 5/2017 | Freeman et al. |
| 9,980,674 B2 | 5/2018 | Packer et al. |
| 10,099,063 B2 | 10/2018 | Peterson et al. |
| 10,137,265 B2 | 11/2018 | Freeman et al. |
| 10,159,846 B2 | 12/2018 | Aoyama et al. |
| 10,303,852 B2 | 5/2019 | Peterson et al. |
| 10,322,060 B2 | 6/2019 | Fleischacker et al. |
| 10,959,683 B2 | 3/2021 | Freeman et al. |
| 10,976,908 B2 | 4/2021 | Freeman et al. |
| 10,980,706 B2 | 4/2021 | Fleischacker et al. |
| 2001/0018562 A1 | 8/2001 | Sherman et al. |
| 2001/0047140 A1 | 11/2001 | Freeman |
| 2002/0024888 A1 | 2/2002 | Schreiber |
| 2002/0044059 A1 | 4/2002 | Reeder |
| 2002/0133197 A1 | 9/2002 | Snyder et al. |
| 2002/0139369 A1 | 10/2002 | Maguire |
| 2002/0156654 A1 | 10/2002 | Roe et al. |
| 2002/0184055 A1 | 12/2002 | Naghavi et al. |
| 2003/0036683 A1 | 2/2003 | Kehr et al. |
| 2003/0036924 A1 | 2/2003 | Rosen et al. |
| 2003/0036925 A1 | 2/2003 | Miller |
| 2003/0055458 A1 | 3/2003 | Hamilton et al. |
| 2003/0055460 A1 | 3/2003 | Owen et al. |
| 2003/0083699 A1 | 5/2003 | Hamilton et al. |
| 2003/0089371 A1 | 5/2003 | Robertson et al. |
| 2003/0095150 A1 | 5/2003 | Trevino et al. |
| 2003/0120164 A1 | 6/2003 | Nielsen et al. |
| 2004/0006290 A1 | 1/2004 | Sherman et al. |
| 2004/0016434 A1 | 1/2004 | Jamison et al. |
| 2004/0064342 A1 | 1/2004 | Browne et al. |
| 2004/0039419 A1 | 2/2004 | Stickney et al. |
| 2004/0049118 A1 | 3/2004 | Ideker et al. |
| 2004/0049233 A1 | 3/2004 | Edwards |
| 2004/0054261 A1 | 3/2004 | Kamataki et al. |
| 2004/0058305 A1 | 3/2004 | Lurie et al. |
| 2004/0064169 A1 | 4/2004 | Briscoe et al. |
| 2004/0082888 A1 | 4/2004 | Palazzolo et al. |
| 2004/0099267 A1 | 5/2004 | Ahlmen et al. |
| 2004/0122476 A1 | 6/2004 | Wung |
| 2004/0143298 A1 | 7/2004 | Nova et al. |
| 2004/0147818 A1 | 7/2004 | Levy et al. |
| 2004/0152954 A1 | 8/2004 | Pearce et al. |
| 2004/0162510 A1 | 8/2004 | Jayne et al. |
| 2004/0162586 A1 | 8/2004 | Covey et al. |
| 2004/0162587 A1 | 8/2004 | Hampton et al. |
| 2004/0186357 A1 | 9/2004 | Soderberg et al. |
| 2004/0212344 A1 | 10/2004 | Tamura et al. |
| 2004/0214148 A1 | 10/2004 | Salvino et al. |
| 2004/0254773 A1 | 12/2004 | Zhang et al. |
| 2005/0061315 A1 | 3/2005 | Lee et al. |
| 2005/0085799 A1 | 4/2005 | Luria et al. |
| 2005/0101889 A1 | 5/2005 | Freeman et al. |
| 2005/0119586 A1 | 6/2005 | Coyle et al. |
| 2005/0187484 A1 | 8/2005 | Sano et al. |
| 2005/0225448 A1 | 10/2005 | Schenker |
| 2005/0240087 A1 | 10/2005 | Keenan et al. |
| 2005/0277872 A1 | 12/2005 | Colby, Jr. et al. |
| 2006/0007188 A1 | 1/2006 | Reiner |
| 2006/0022833 A1 | 2/2006 | Ferguson et al. |
| 2006/0041278 A1 | 2/2006 | Cohen et al. |
| 2006/0047188 A1 | 3/2006 | Bohan |
| 2006/0111933 A1 | 5/2006 | Wheeler |
| 2006/0116908 A1 | 6/2006 | Dew et al. |
| 2006/0122864 A1 | 6/2006 | Gottesman et al. |
| 2006/0129191 A1 | 6/2006 | Sullivan et al. |
| 2006/0142648 A1 | 6/2006 | Banet et al. |
| 2006/0173501 A1 | 8/2006 | Stickney et al. |
| 2006/0224053 A1 | 10/2006 | Black et al. |
| 2006/0229557 A1 | 10/2006 | Fathallah et al. |
| 2006/0270952 A1 | 11/2006 | Freeman et al. |
| 2007/0017521 A1 | 1/2007 | Ben et al. |
| 2007/0032830 A1 | 2/2007 | Bowers |
| 2007/0060785 A1 | 3/2007 | Freeman et al. |
| 2007/0068528 A1 | 3/2007 | Bohm et al. |
| 2007/0162076 A1 | 7/2007 | Tan et al. |
| 2007/0167845 A1 | 7/2007 | Sasagawa et al. |
| 2007/0169779 A1 | 7/2007 | Freeman |
| 2007/0175980 A1 | 8/2007 | Alsafadi |
| 2007/0191687 A1 | 8/2007 | Justus |
| 2007/0197882 A1 | 8/2007 | Smith et al. |
| 2007/0219588 A1 | 9/2007 | Freeman |
| 2007/0276270 A1 | 11/2007 | Tran |
| 2008/0027338 A1 | 1/2008 | Lu et al. |
| 2008/0053445 A1 | 3/2008 | Kroupa et al. |
| 2008/0108884 A1 | 5/2008 | Kiani |
| 2008/0114221 A1 | 5/2008 | Tso |
| 2008/0139948 A1 | 6/2008 | Stahmann et al. |
| 2008/0171311 A1 | 7/2008 | Centen et al. |
| 2008/0174563 A1 | 7/2008 | Kim |
| 2008/0176199 A1 | 7/2008 | Stickney et al. |
| 2008/0214948 A1 | 9/2008 | Myklebust et al. |
| 2008/0236585 A1 | 10/2008 | Parker et al. |
| 2008/0261192 A1 | 10/2008 | Huang et al. |
| 2008/0295839 A1 | 12/2008 | Habashi |
| 2008/0306766 A1 | 12/2008 | Ozeki et al. |
| 2008/0312565 A1 | 12/2008 | Celik-Butler et al. |
| 2009/0005651 A1 | 1/2009 | Ward |
| 2009/0012395 A1 | 1/2009 | Reynolds et al. |
| 2009/0024175 A1 | 1/2009 | Freeman |
| 2009/0035740 A1 | 2/2009 | Reed et al. |
| 2009/0046096 A1 | 2/2009 | Rampersad |
| 2009/0054735 A1 | 2/2009 | Higgins et al. |
| 2009/0054743 A1 | 2/2009 | Stewart |
| 2009/0069642 A1 | 3/2009 | Gao et al. |
| 2009/0073114 A1 | 3/2009 | Bay et al. |
| 2009/0076344 A1 | 3/2009 | Libbus et al. |
| 2009/0076345 A1 | 3/2009 | Manicka et al. |
| 2009/0089095 A1 | 4/2009 | Esham et al. |
| 2009/0102800 A1 | 4/2009 | Keenan |
| 2009/0119128 A1 | 5/2009 | Fitzgerald et al. |
| 2009/0150184 A1 | 6/2009 | Spahn |
| 2009/0151724 A1 | 6/2009 | Wondka et al. |
| 2009/0163838 A1 | 6/2009 | Hecox et al. |
| 2009/0192823 A1 | 7/2009 | Hawkins et al. |
| 2009/0216556 A1 | 8/2009 | Martin et al. |
| 2009/0270931 A1 | 10/2009 | Liden |
| 2009/0320836 A1 | 12/2009 | Baker, Jr. |
| 2010/0010319 A1 | 1/2010 | Tivig et al. |
| 2010/0018530 A1 | 1/2010 | Schindhelm et al. |
| 2010/0069723 A1 | 3/2010 | Islam |
| 2010/0087883 A1 | 4/2010 | Sullivan et al. |
| 2010/0113960 A1 | 5/2010 | Scheib |
| 2010/0131293 A1 | 5/2010 | Linthicum et al. |
| 2010/0152801 A1 | 6/2010 | Koh et al. |
| 2010/0161353 A1 | 6/2010 | Mayaud |
| 2010/0179395 A1 | 7/2010 | Bloem |
| 2010/0211127 A1 | 8/2010 | Eerden |
| 2010/0234695 A1 | 9/2010 | Morris |
| 2010/0234696 A1 | 9/2010 | Li et al. |
| 2010/0249540 A1 | 9/2010 | Lisogurski |
| 2010/0249617 A1 | 9/2010 | Leung et al. |
| 2010/0256539 A1 | 10/2010 | Strand et al. |
| 2010/0274100 A1 | 10/2010 | Behar et al. |
| 2010/0298899 A1 | 11/2010 | Donnelly et al. |
| 2010/0302281 A1 | 12/2010 | Kim |
| 2010/0305412 A1 | 12/2010 | Darrah et al. |
| 2011/0046688 A1 | 2/2011 | Schwibner et al. |
| 2011/0055720 A1 | 3/2011 | Potter et al. |
| 2011/0074831 A1 | 3/2011 | Lynch et al. |
| 2011/0082510 A1 | 4/2011 | Sullivan |
| 2011/0118561 A1 | 5/2011 | Tari et al. |
| 2011/0130636 A1 | 6/2011 | Daniel et al. |
| 2011/0172550 A1 | 7/2011 | Martin et al. |
| 2011/0197885 A1 | 8/2011 | Wondka et al. |

(56) References Cited

U.S. PATENT DOCUMENTS

| | | |
|---|---|---|
| 2011/0202100 A1 | 8/2011 | Tan et al. |
| 2011/0208540 A1 | 8/2011 | Lord et al. |
| 2011/0224565 A1 | 9/2011 | Ong et al. |
| 2011/0284004 A1 | 11/2011 | Silver |
| 2011/0295078 A1 | 12/2011 | Reid et al. |
| 2012/0000464 A1 | 1/2012 | Gajic et al. |
| 2012/0075103 A1 | 3/2012 | Powell et al. |
| 2012/0108911 A1 | 5/2012 | Drysdale et al. |
| 2012/0123218 A1 | 5/2012 | Renes |
| 2012/0123223 A1 | 5/2012 | Freeman et al. |
| 2012/0156933 A1 | 6/2012 | Kreger et al. |
| 2012/0184882 A1 | 7/2012 | Totman et al. |
| 2012/0278099 A1 | 11/2012 | Kelly et al. |
| 2013/0009783 A1 | 1/2013 | Tran |
| 2013/0030173 A1 | 1/2013 | Wang et al. |
| 2013/0096649 A1 | 4/2013 | Martin et al. |
| 2013/0111342 A1 | 5/2013 | Alameh et al. |
| 2013/0124090 A1 | 5/2013 | Gotschall et al. |
| 2014/0043149 A1 | 2/2014 | Cowan et al. |
| 2014/0068489 A1 | 3/2014 | Wyland et al. |
| 2014/0201627 A1 | 7/2014 | Freeman et al. |
| 2014/0272860 A1 | 9/2014 | Peterson et al. |
| 2015/0227694 A1 | 8/2015 | Grimley et al. |
| 2015/0359489 A1 | 12/2015 | Baudenbacher et al. |
| 2016/0133160 A1 | 5/2016 | Packer et al. |
| 2016/0171167 A9 | 6/2016 | Merry et al. |

FOREIGN PATENT DOCUMENTS

| | | |
|---|---|---|
| CN | 101296730 | 10/2008 |
| CN | 101626797 | 1/2010 |
| CN | 101835447 | 9/2010 |
| CN | 101849241 | 9/2010 |
| EP | 1834622 | 9/2007 |
| EP | 1933114 | 6/2008 |
| GB | 2314618 | 1/1998 |
| GB | 2314648 | 1/1998 |
| GB | 2344529 | 6/2000 |
| GB | 2446124 | 8/2008 |
| JP | 09-262213 | 10/1997 |
| JP | 2003-521972 | 7/2003 |
| JP | 2004280807 | 10/2004 |
| JP | 2005-524436 | 8/2005 |
| JP | 2005-524498 | 8/2005 |
| JP | 2006503659 | 2/2006 |
| JP | 2007-125151 | 5/2007 |
| JP | 2007195977 | 8/2007 |
| JP | 2007-233850 | 9/2007 |
| JP | 2007244879 | 9/2007 |
| JP | 2008529714 | 8/2008 |
| JP | 2008534083 | 8/2008 |
| JP | 2008-200111 | 9/2008 |
| JP | 2008250291 | 10/2008 |
| JP | 2008301984 | 12/2008 |
| JP | 2009-233042 | 10/2009 |
| JP | 2010502285 | 1/2010 |
| JP | 2010-217153 | 9/2010 |
| JP | 2011036371 | 2/2011 |
| JP | 2000176025 | 6/2020 |
| WO | 1996/010984 | 4/1996 |
| WO | 1998/030282 | 7/1998 |
| WO | 1999/024114 | 5/1999 |
| WO | 1999/025306 | 5/1999 |
| WO | 1999/063926 | 12/1999 |
| WO | 1999/065560 | 12/1999 |
| WO | 2001/056652 | 8/2001 |
| WO | 2001/066182 | 9/2001 |
| WO | 2002/015836 | 2/2002 |
| WO | 2002/072197 | 9/2002 |
| WO | 2002/078775 | 10/2002 |
| WO | 2003/009895 | 2/2003 |
| WO | 2004/037154 | 5/2004 |
| WO | 2004/054656 | 7/2004 |
| WO | 2004/073493 | 9/2004 |
| WO | 2004/078259 | 9/2004 |
| WO | 2005/021089 | 3/2005 |
| WO | 2008/027418 | 3/2008 |
| WO | 2008/086496 | 7/2008 |
| WO | 2009/037621 | 3/2009 |
| WO | 2010/059049 | 5/2010 |
| WO | 2011/116340 | 9/2011 |
| WO | 2012/017342 | 2/2012 |
| WO | 2012/065131 | 5/2012 |
| WO | 2012/148934 | 11/2012 |
| WO | 2011/122402 | 7/2013 |
| WO | 2020/006391 A1 | 1/2020 |

OTHER PUBLICATIONS

European Office Action Corresponding to 21786666.4 mailed Mar. 1, 2024.

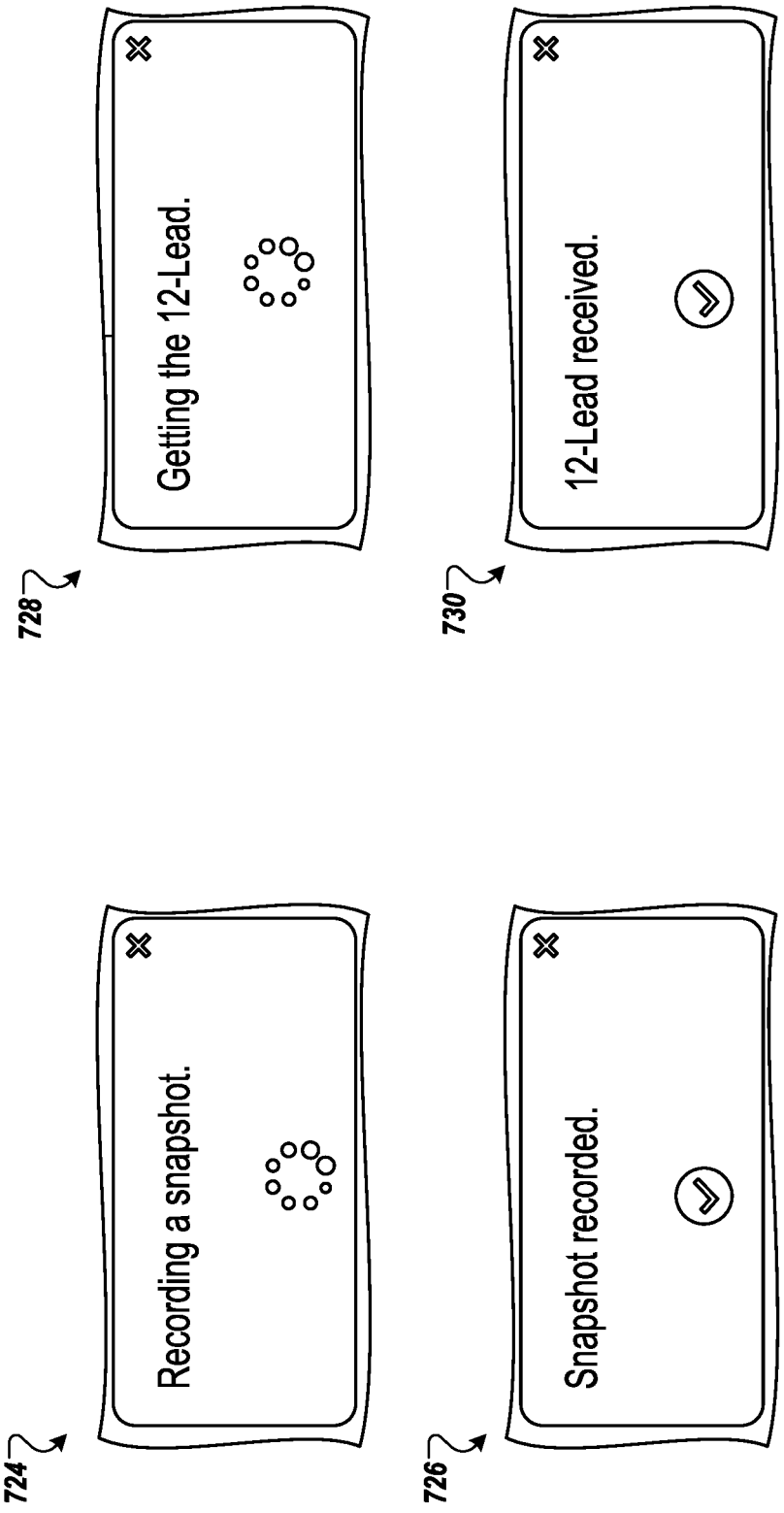

| Time (12h) | HR (bpm) | NIBP (mmHg) | SpO2 (%) | EtCo2 (%) | RR (br/min) |
|---|---|---|---|---|---|
| 09:35:00 | 130 | 120/80 | 97 | 97 | 97 |
| 09:34:30 | 135 | 122/78 | 98 | 98 | 98 |
| 09:34:00 | 131 | 118/80 | 95 | 95 | 95 |
| 09:33:00 | 134 | 120/80 | 97 | 97 | 97 |

FIG. 8C-2

| TIME ▽ | ALARMS ▽ | TYPE ▽ | PRIORITY ▽ |
|---|---|---|---|
| 01:03:14 AM | BPM out of range #2109 | Patient Safety | High |
| 00:59:02 AM | Check airway tube #1900 | Self Check | Medium |
| 24:00:00 AM | No breaths detected #2108 | Patient Safety | High |
| 23:01:59 PM | FiO2 threshold reached #2107 | Patient Safety | High |
| 23:00:09 PM | SpO2 out of range #2100 | Patient Safety | High |
| 22:20:15 PM | Room air in use #1800 | Use Environment | Low |
| 21:06:04 PM | O2 flow hampered #2200 | Use Environment | Medium |
| 21:00:09 PM | SpO2 out of range #2100 | Patient Safety | High |

FIG. 13A

FIG. 13B

MEDICAL TREATMENT SYSTEM WITH COMPANION DEVICE

RELATED APPLICATIONS

This application claims priority to U.S. Provisional Patent Application Ser. No. 63/167,312 filed Mar. 29, 2021 and to U.S. Provisional Patent Application Ser. No. 63/074,874 filed Sep. 4, 2020. The above identified applications are each hereby incorporated by reference in its entirety.

BACKGROUND

Multiple medical devices may be used in medical situations (for example, emergency situations). These devices can be used by different personnel. For example, automated external defibrillators (AEDs) may be used by non-trained medical device personnel such as first responders. Additionally, emergency medical technicians (EMT) may use different or additional devices in responding to an emergent situation, which may differ from devices used at a hospital. In addition, there may be one or more information display devices such as liquid-crystal display (LCD) panels, portable computing devices such as tablets, mobile communication devices (e.g., iPhone), smart watches (e.g., iPad, Apple Watch provided by Apple, Inc.), or other types wearable computing and display devices, upon which information from the one or more medical devices can be presented.

In one example, the medical situation is sudden cardiac arrest which is a frequent cause of death. One treatment for cardiac arrest is quick and competent chest compressions to keep blood flowing from a patient's heart to vital parts of the body. Along with chest compressions, a rescuer can ventilate the patient by either providing positive pressure breaths into the patient's mouth or nose or utilizing a device that pushes air into the patient's lungs. Rescuers, such as lay responders, emergency medical technicians (EMTs), rescue team supervisors, paramedics, doctors, or other rescuers, can benefit from feedback about performance of cardiopulmonary resuscitation (CPR) and from information about the patient's medical status during treatment of the patient. Information about the patient's health status, physiologic data and information about treatment delivered to the patient can be collected by sensors.

SUMMARY OF ILLUSTRATIVE EMBODIMENTS

The foregoing general description of the illustrative implementations and the following detailed description thereof are merely exemplary aspects of the teachings of this disclosure and are not restrictive.

This document describes various systems and methods for systems and methods for monitoring treatment delivered by one or more medical treatment devices during an emergency medical treatment event via a companion device communicatively coupled to a medical treatment device (e.g., a defibrillator or electric shock delivery device, patient monitor, ventilator). In one aspect, the present disclosure relates to a medical treatment system, including a medical treatment device configured to monitor and provide treatment to the patient, the medical treatment device including at least one physiological sensor input configured to generate physiological signals corresponding to the patient during the medical event, a medical treatment device screen for presenting medical information based on the generated physiological signals, and at least one first processor operably coupled with the at least one physiological sensor input, and the medical treatment device screen. The at least one first processor is configured to receive and process the physiological signals corresponding to the patient, generate medical data based on the processed physiological signals, display, on the medical treatment device screen in a first display format, case information including physiological information visually rendered from the generated medical data, and transmit the case information and generated medical data to a companion device. In some embodiments the companion device is communicatively coupled to the medical treatment device via a communication link and includes a device interface having a display screen configured to allow a user to input one or more instructions for the medical treatment device during the medical event. The companion device can include at least one second processor operably coupled with the device interface and configured to process the case information and generated medical data received from the medical treatment device. The at least one second processor can also cause display, at the device interface in a second display format, of a real time device view of the case information including the physiological information displayed on the medical treatment device screen. The second display format can provide a visual reproduction of the first display format and transmit, responsive to detecting at least one user input at the device interface, one or more instruction signals to the medical treatment device.

In some implementations, the visual reproduction of the first display format at the second display format includes providing a replication of the first display format.

In some implementations, providing the visual reproduction of the first display format at the second display format includes adjusting one or more visual aspects of the case information presented in the second display format from the case information displayed in the first display format. In some implementations, the one or more visual aspects include one or more of a layout, color, font, magnification, resolution, size, or screen position of the case information.

In some implementations, providing the visual reproduction of the first display format at the second display format includes adding or subtracting one or more items of the case information displayed in the second display format from the case information displayed in the first display format.

In some implementations, the communication link is a wireless communication link. In some embodiments, the wireless communication link is at least one of: a Wi-Fi link, or a Bluetooth link. In some embodiments, the wireless communication link is a preconfigured pairing between the medical treatment device and the companion device. In some implementations, the at least one first processor is further configured to detect, via the wireless communication link, a wireless communication signal associated with the preconfigured pairing for the companion device, and connect, responsive to the detection of the wireless communication signal, to the companion device via the wireless communication link. In some implementations, transmitting the generated medical data to the companion device includes automatically initiating transmission of the generated medical data upon connecting to the companion device. In some implementations, the at least one first processor is further configured to detect, based on a loss of the wireless communication signal, a disconnection of the companion device from the medical treatment device, and halt, responsive to detecting the disconnection, transmitting the generated medical data to the companion device. In some implementations, the at least one second processor is configured to detect, via the wireless communication link, a proximal presence of the medical treatment device, and connect, via the preconfigured pairing, to the medical treatment device with a proximity-based connection.

In some implementations, the at least one second processor is further configured to cause display, at the device interface, of a verification input that, when actuated, causes the connected medical treatment device to generate an indication of pairing between the companion device and the medical treatment device. In some implementations, the at least one second processor is further configured to, responsive to detecting actuation of the verification input at the device interface, transmit an instruction signal to the medical treatment device for generating the indication of pairing between the companion device and the medical treatment device. In some implementations, the indication of pairing at the medical treatment device is at least one of a visual indication or an audio indication. In some implementations, the visual indication is a flashing light. In some implementations, the audio indication is a tonal sound pulse.

In some implementations, the companion device is one of multiple companion devices connectable to the medical treatment device. In some implementations, the at least one first processor is further configured to simultaneously transmit at least a portion of the generated medical data to each of the companion devices for display at a respective device interface for each of the companion devices.

In some implementations, the display screen of the device interface is a touchscreen for receiving user inputs corresponding to the generated input signals.

In some implementations, the at least one user input includes an input for providing an instruction signal of the one or more instruction signals to the medical treatment device.

In some implementations, transmitting the one or more instruction signals to the medical treatment device includes responsive to detecting selection of one of the at least one user input, transmitting an instruction signal of the one or more instruction signals to update at least one of patient information, treatment information, or diagnostic information for the medical event.

In some implementations, the at least one user input includes a patient information input. In some implementations, the at least one second processor is further configured to, responsive to detecting a user input signal associated with the patient information input, cause display of a patient information input interface at the device interface. In some implementations, the patient information input interface includes patient information input fields for entering patient background information. In some implementations, the patient information input fields include at least one of a patient age input field, a patient gender input field, a patient name input field, patient weight input field, patient height input field, or a patient identification input field. In some implementations, the patient information input fields include a case identification input field. In some implementations, transmitting the one or more instruction signals from the at least one second processor to the medical treatment device includes transmitting, upon submission of patient information at a portion of the patient information input fields, the submitted patient information to the medical treatment device.

In some implementations, the at least one first processor is further configured to, responsive to receiving the portion of the submitted patient information, link the submitted patient information with the case information for the patient. In some implementations, the at least one first processor is further configured to, responsive to linking the submitted patient information with the case information for the patient, transmit a linking confirmation signal to the companion device. In some implementations, the at least one second processor is further configured, responsive to receiving the linking confirmation signal from the medical treatment device, cause display at the device interface of a patient information transfer confirmation message.

In some implementations, the at least one first processor is further configured to, responsive to receiving the portion of the submitted patient information, store the submitted patient information with the case information in a data storage region of the medical treatment device. In some implementations, the at least one first processor is further configured to, responsive to storing the submitted patient information with the case information for the patient, transmit a storage confirmation signal to the companion device. In some implementations, the at least one second processor is further configured, responsive to receiving the storage confirmation signal from the medical treatment device, cause display at the device interface of a patient information transfer confirmation message.

In some implementations, the device interface includes at least one sensor configured to scan patient information from a document, and the at least one second processor is further configured to automatically populate respective input fields of the patient information input fields with the scanned patient information. In some implementations, the at least one sensor is a camera. In some implementations, the document is a government-issued identification card.

In some implementations, the at least one user input includes a treatment marker input. In some implementations, the at least one second processor is further configured to, responsive to detecting a user input signal associated with the treatment marker input, cause display of a treatment marker input interface at the device interface.

In some implementations, the treatment marker input interface includes treatment marker selectors for marking patient treatment events at the medical treatment device. In some implementations, the treatment marker selections include at least one of drugs, oxygen, anticoagulants, or return of spontaneous circulation (ROSC). In some implementations, the treatment marker selections include a customizable treatment marker selection for manually entering a treatment name. In some implementations, transmitting the one or more instruction signals from the at least one second processor to the medical treatment device includes transmitting, upon submission of one or more treatment marker selections, a treatment marker instruction signal for recording the one or more treatment marker selections to the medical treatment device.

In some implementations, the at least one first processor is further configured to, responsive to receiving the treatment marker instruction signal, record the one or more treatment marker selections at a data storage region of the medical treatment device. In some implementations, the at least one first processor is further configured to, responsive to commencing recording the one or more treatment marker selections, transmit an in-progress treatment marker recording confirmation signal to the companion device. In some implementations, the at least one second processor is further configured to, responsive to receiving the in-progress treatment marker recording confirmation signal from the medical treatment device, cause display at the device interface of an in-progress treatment marker recording confirmation message. In some implementations, the at least one first processor is further configured to, responsive to completion of recording of the one or more treatment marker selections, transmit a treatment marker recording completion confirmation signal to the companion device.

In some implementations, the at least one second processor is further configured to, responsive to receiving the treatment marker recording completion confirmation signal from the medical treatment device, cause display at the device interface of a treatment marker recording completion confirmation message. In some implementations, the device interface includes at least one audio sensor configured to receive an audio input of one or more of the treatment marker selections, and transmitting the one or more instruction signals from the at least one second processor to the medical treatment device includes transmitting, upon receiving the audio input, a treatment marker instruction signal for recording the one or more treatment marker selections to the medical treatment device. In some implementations, the at least one audio sensor includes a microphone.

In some implementations, the at least one user input includes a 12-lead ECG analysis input. In some implementations, transmitting the one or more instruction signals from the at least one second processor to the medical treatment device includes transmitting, responsive to detecting selection of the 12-lead ECG analysis input, a 12-lead analysis instruction signal for initiating a 12-lead ECG analysis at the medical treatment device. In some implementations, the at least one first processor is further configured to, responsive to receiving the 12-lead analysis instruction signal, perform a 12-lead ECG analysis at the medical treatment device. In some implementations, the at least one first processor is further configured to, responsive to commencing the 12-lead ECG analysis, transmit an in-progress 12-lead analysis confirmation signal to the companion device.

In some implementations, the at least one second processor is further configured to, responsive to receiving the in-progress 12-lead analysis confirmation signal from the medical treatment device, cause display at the device interface of an in-progress 12-lead analysis confirmation message. In some implementations, the at least one first processor is further configured to, responsive to completion of the 12-lead ECG analysis, transmit a 12-lead analysis completion confirmation signal to the companion device. In some implementations, the at least one second processor is further configured to, responsive to receiving the 12-lead analysis completion confirmation signal from the medical treatment device, cause display at the device interface of a 12-lead analysis completion confirmation message.

In some implementations, the 12-lead ECG analysis input provides for user selection of a previously-performed 12-lead ECG analysis for viewing at the device interface of the companion device. In some implementations, the at least one second processor is further configured to, responsive to detecting selection of the previously-performed 12-lead ECG analysis for viewing, issue an instruction signal to the medical treatment device to obtain 12-lead ECG analysis data associated with the previously-performed 12-lead ECG analysis. In some implementations, the at least one second processor is further configured to, responsive to receiving the 12-lead ECG analysis data from the medical treatment device, cause display of the 12-lead ECG analysis data for the previously-performed ECG at the device interface of the customized companion device.

In some implementations, the at least one user input includes a defibrillator snapshot input. In some implementations, transmitting the one or more instruction signals from the at least one second processor to medical treatment device includes transmitting, responsive to detecting selection of the medical treatment device snapshot input, a snapshot instruction signal for initiating capture of a snapshot of the medical treatment device screen.

In some implementations, the at least one first processor is further configured to, responsive to receiving the snapshot instruction signal, cause capture of a snapshot of the medical treatment device screen. In some implementations, the at least one first processor is further configured to, responsive to causing capture of the snapshot of the medical treatment device screen, transmit an in-progress snapshot confirmation signal to the companion device. In some implementations, the at least one second processor is further configured to, responsive to receiving the in-progress snapshot confirmation signal from the medical treatment device, cause display at the device interface of an in-progress snapshot confirmation message. In some implementations, the at least one first processor is further configured to, responsive to a completed capture of the snapshot of the medical treatment device screen, transmit a snapshot completion confirmation signal to the companion device. In some implementations, the at least one second processor is further configured to, responsive to receiving the snapshot completion confirmation signal from the medical treatment device, cause display at the device interface of a snapshot completion confirmation message.

In some implementations, the at least one user input includes a case event summary input. In some implementations, the at least one second processor is further configured to, responsive to detecting selection of the case event summary input, cause display of an event summary interface at the device interface. In some implementations, the event summary interface includes a chronological listing of events associated with care of the patient recorded at the medical treatment device. In some implementations, the at least one second processor is further configured to responsive to detecting selection of the case event summary input, obtaining the chronological listing of the events from the medical treatment device. In some implementations, the at least one second processor is further configured to, responsive to selection of an event in the chronological listing of events at the event summary interface, cause display of details associated with the selected event. In some implementations, the displayed details for the selected event include a snapshot of the medical treatment device screen at a time associated with the selected event.

In some implementations, the at last one user input includes an alarm summary input. In some implementations, the at least one second processor is further configured to, responsive to detecting selection of the alarm summary input, cause display of an alarm interface at the device interface. In some implementations, the alarm interface includes a listing of one or more alarm-causing events at the medical treatment device. In some implementations, the alarm-causing events include physiological alarm events and technological alarm events. In some implementations, the at least one sensor input includes at least one physiological senor input, and the physiological alarm events include threshold limits associated with the at least one physiological sensor. In some implementations, the technological alarm events include technical issues associated with the medical treatment device.

In some implementations, the at least one user input includes a non-invasive blood pressure (NIBP) initiation input. In some implementations, transmitting the one or more instruction signals from the at least one second processor to the medical treatment device includes transmitting, responsive to detecting selection of the NIBP initiation input, a NIBP instruction signal for initiating a NIBP measurement at the medical treatment device.

In some implementations, one or more additional physiological sensor inputs communicatively coupled to the companion device, and the one or more additional physiological sensor inputs are configured to generate one or more additional physiological signals corresponding to the patient during the medical event. In some implementations, the at least one second processor is further configured to receive and process the one or more additional physiological signals corresponding to the patient, generate additional medical data based on the processed one or more additional physiological signals, and display, at the device interface, additional case information including additional physiological information visually rendered from the generated additional medical data. In some implementations, the at least one second processor is further configured to transmit the additional case information to the medical treatment device for display at the medical treatment device screen. In some implementations, the one or more additional physiological sensor inputs include at least one of a continuous NIBP sensor, an ultrasound imaging sensor, or a laryngoscopic sensor.

In some implementations, the at least one second processor is further configured to receive, from the medical treatment device, an amount of shock energy available at the medical treatment device, and cause display, at the device interface, of the amount of shock energy stored at a high-voltage capacitor.

In some implementations, the at least one second processor is further configured to receive, from the medical treatment device, a number of shocks applied by the medical treatment device to the patient, and cause display, at the device interface, of the number of shocks applied by the medical treatment device to the patient. In some implementations, the device view displayed at the display interface is one of multiple views for displaying at the display interface of the companion device, and the at least one second processor is further configured to cause display of a portion of the views at the display interface.

In some implementations, the views for displaying at the display interface includes a trend view for presenting trend data from the generated medical data associated with the patient care during the medical event.

In some implementations, the at least one sensor input includes at least one physiological senor input, and the trend data includes physiological values from the at least one physiological sensor input over time. In some implementations, the trend data includes at least one of $SpO_2$, $ETCO_2$, systolic blood pressure, diastolic blood pressure, mean arterial pressure, or heart rate values over time. In some implementations, the trend view includes display of a portion of the trend data in a graphical format. In some implementations, the trend view includes display of a portion of the trend data in a tabular format.

In some implementations, the at least one second processor is configured to cause display, at the device interface, of multiple data display views in which each of the display views is selectable via a respective display view selection portion of the device interface. The display views can include the real time device view of the case information including the physiological information displayed on the medical treatment device screen and a working view including one or more customized display sections. The display sections, for example, may be customized for various caregiver roles.

In some implementations, the medical treatment device further includes at least one caregiver performance sensor input configured to generate caregiver performance signals associated with the respective caregiver role during the medical event, and the at least one first processor is further configured to receive and process the caregiver performance signals and generate caregiver performance data from the processed caregiver performance signals. The case information can further include caregiver performance information visually rendered from the generated caregiver performance data.

In some implementations, the at least one caregiver performance sensor input includes a chest compression sensor input, and the caregiver performance information includes chest compression information. In some implementations, the chest compression sensor input is a motion sensor input. In some implementations, the chest compression information includes chest compression feedback during the medical event, and the chest compression feedback includes at least one of compression depth feedback, compression rate feedback, or release velocity feedback. In some implementations, the compression depth feedback includes a visual indication of a respective depth of each chest compression applied to the patient. In some implementations, the visual indication of the respective depth of each chest compression applied to the patient is displayed relative to a target range of chest compression depth.

In some implementations, the respective caregiver role is administering chest compressions to the patient during the medical event.

In some implementations, the at least one caregiver performance sensor input includes at least one ventilation sensor input, and the caregiver performance information includes ventilation case information derived from the at least one ventilation sensor input.

In some implementations, the at least one ventilation sensor input includes an airflow sensor input.

In some implementations, the ventilation case information includes ventilation feedback during the medical event, and the ventilation feedback includes at least one of tidal volume, ventilation rate, or minute volume.

In some implementations, the respective caregiver role is administering ventilation to the patient during the medical event.

In some implementations, the one or more customized data sections of the working view includes a ventilation performance data section displaying the ventilation case information.

In some implementations, the ventilation case information includes a summary of ventilation performance during the medical event. In some implementations, the summary of ventilation performance includes display of at least one of average tidal volume, average ventilation rate, average minute volume, or percentage of ventilations within a target volume range or a target rate range.

In some implementations, the at least one second processor is configured to cause display of the summary of the ventilation performance in the working view in real-time during the medical event. In some implementations, the at least one second processor is configured to cause display of the summary of the ventilation performance in the working view upon completion of the medical event.

In some implementations, the chest compression information includes a summary of chest compression performance during the medical event. In some implementations, the summary of chest compression performance includes at least one of average compression depth, average compression rate, average release velocity, pre-shock pause, post-shock pause, or percentage of compressions within a target compression depth range. In some implementations, the at least one second processor is configured to cause display the summary of the chest compression performance in the working view in real-time during the medical event. In some implementations, the at least one second processor is configured to cause display of the summary of the chest compression performance in the working view upon completion of the medical event.

In some implementations, the medical treatment device is a ventilator. The companion device may be communicatively coupled to the ventilator via a network and may include a device interface having a display screen configured to allow a user to input one or more instructions for the ventilator during the medical event, and at least one second processor operably coupled with the device interface, the at least one second processor configured to process the case information and medical data received from the ventilator, cause display, at the device interface, of a real time view of the processed case information and medical data received from the ventilator, and transmit, responsive to detecting at least one user input at the device interface, one or more instruction signals to the medical treatment device.

In some embodiments, the ventilator is a portable ventilator for providing pre-hospital ventilation treatment to the patient. The portable ventilator may weigh no more than 10 pounds, no more than 5 pounds, between 5 to 10 pounds, or between 7 to 12 pounds. The ventilator display interface for the portable ventilator may include a plurality of indicator lights configured to indicate that the case information falls within a range of a plurality of ranges bounded by one or more thresholds. The plurality of indicator lights may be configured to display a plurality of colors, where each color of the plurality of colors is associated with one range of the plurality of ranges of the case information. The ventilator display interface may include a screen having a display area no greater than 4 square inches, between 3 to 6 square inches, or between 2 to 5 square inches. In some embodiments, a surface area of any face of the portable ventilator is no more than 25 square inches, no more than 20 square inches, or between 15 to 25 square inches. In one or more examples, a display area of the display screen of the companion device is larger than the display area of the screen of the ventilator display interface.

In some embodiments, the ventilator includes an oxygen inlet configured to supply oxygen for providing positive pressure ventilation to the patient; and a ventilation outlet configured to be pneumatically coupled with the oxygen inlet and to deliver the positive pressure ventilation having the supplied oxygen to the patient. The one or more instruction signals may include one or more control signals for the ventilator to administer the positive pressure ventilation to the patient.

In some embodiments, the one or more instruction signals may include one or more control signals for adjusting one or more ventilator control settings. The one or more ventilator control settings may include at least one of a fraction of inspired oxygen ($FIO_2$) setting, a positive end-expiratory pressure (PEEP) setting, a tidal volume ($V_t$) setting, an inspiratory:expiratory ratio (I:E) setting, a ventilator mode setting, or a peak inspiratory pressure (PIP) threshold setting.

In some embodiments, the physiological information may include at least one of an airway pressure ($P_{AW}$) waveform, a tidal volume ($V_t$) waveform, a peripheral capillary oxygen saturation ($SpO_2$) waveform, or an invasive blood pressure (IBP) waveform. In some embodiments, the physiological information may include graphs of at least one of end-tidal carbon dioxide ($ETCO_2$), non-invasive blood pressure (NIBP), fraction of inspired oxygen ($FIO_2$), pulse rate (PR), breaths per minute (BPM), minimum volume ($V_{min}$), plateau pressure ($P_{Plat}$), or peak inspiratory pressure (PIP) over time. In some embodiments, the physiological information may include current values of at least one of fraction of inspired oxygen ($FIO_2$), peak inspiratory pressure (PIP), tidal volume ($V_t$), breaths per minute (BPM), end-tidal carbon dioxide ($ETCO_2$), non-invasive blood pressure (NIBP), invasive blood pressure (IBP), heart rate (HR), or ventilator mode.

In some embodiments, the at least one user input may include an input for providing an instruction signal of the one or more instruction signals to the ventilator. Transmitting the one or more instruction signals to the ventilator may include, responsive to detecting selection of one of the at least one user input, transmitting an instruction signal of the one or more instruction signals to update at least one of patient information, treatment information, or diagnostic information for the medical event.

In some embodiments, the at least one user input may include a patient information input. The at least one second processor may be further configured to, responsive to detecting a user input signal associated with the patient information input, cause display of a patient information input interface at the device interface. The patient information input interface may include a plurality of patient information input fields for entering patient background information. The plurality of patient information input fields may include a patient gender input field and a patient height input field. Transmitting the one or more instruction signals from the at least one second processor to the ventilator may include transmitting, upon submission of a respective patient gender at the patient gender input field and a respective patient height at the patient height input field, the respective patient gender and the respective patient height to the ventilator. The at least one first processor may be further configured to, responsive to receiving the respective patient gender and the respective patient height, automatically adjust a tidal volume ($V_t$) setting at the ventilator based on the respective patient gender and the respective patient height.

In some embodiments, the at least one user input may include a ventilation settings input. The at least one second processor may be further configured to, responsive to detecting a user input signal associated with the ventilation settings input, cause display of a ventilation settings interface at the device interface. The ventilation settings interface may include a plurality of ventilation setting inputs for adjusting a plurality of ventilation settings on the ventilator. The plurality of ventilation settings may include at least one of a positive end-expiratory pressure (PEEP) setting, a tidal volume ($V_t$) setting, a breaths per minute (BPM) setting, an inspiratory:expiratory ratio (I:E) setting, a peak inspiratory pressure (PIP) threshold setting, a peripheral capillary oxygen saturation ($SpO_2$) setting, a fraction of inspired oxygen ($FIO_2$) setting, or a ventilation mode adjustment setting at the device interface. Responsive to detecting selection of one of the ventilation setting inputs at the ventilation settings interface, the at least one second processor may be configured to cause display of a setting adjusting interface for the respective ventilation setting. The setting adjustment interface may include an interface for inputting a numeric value for the respective ventilation setting. Transmitting the one or more instruction signals from the at least one second processor to the ventilator may include transmitting, upon submission of a ventilation setting adjustment at a respective ventilation setting adjustment interface, the ventilation setting adjustment for the respective setting to the ventilator. The at least one first processor may be further configured to, responsive to receiving the ventilation setting adjustment for the respective setting, automatically adjust the respective setting on the ventilator based on the ventilation setting adjustment. Responsive to receiving a confirmation signal from the ventilator confirming adjustment of the respective setting, the at least one second processor may be configured to cause display, at one or more of a plurality of selectable display views at the companion device, of an event marker associated with the adjustment of the respective setting at the ventilator. The confirmation signal may include a time that the adjustment of the respective setting occurred at the ventilator. The event marker may be displayed in the one or more selectable display views at a position relative to the time that the adjustment of the respective setting occurred. Responsive to detecting selection of the ventilation mode adjustment setting at the ventilation settings interface, the at least one second processor may be configured to cause display of a mode selection interface at the device interface. The mode selection interface may include a plurality of ventilation mode inputs, each ventilation mode input associated with a respective operating mode of the ventilator. The plurality of ventilation mode inputs may include at least one of an assist/control (AC) mode, a synchronized intermittent mandatory ventilation (SIMV) mode, a continuous positive airway pressure (CPAP) mode, or a bilevel (BL) mode. Transmitting the one or more instruction signals from the at least one second processor to the ventilator may include transmitting, upon detecting selection of a respective ventilation mode input at the mode selection interface, the respective ventilation mode input to the ventilator. The at least one first processor may be further configured to, responsive to receiving the respective ventilation mode input, automatically adjust the respective operating mode at the ventilator. Responsive to receiving a confirmation signal from the ventilator confirming adjustment the respective operating mode, the at least one second processor may be configured to cause display, at the one or more of a plurality of selectable display views at the companion device view, of an event marker associated with the adjustment of the respective operating mode at the ventilator. The confirmation signal may include a time that the adjustment of the respective operating mode occurred at the ventilator. The event marker may be displayed in the one or more of selectable display views at a position relative to the time that the adjustment of the respective operating mode occurred.

In some embodiments, the at least one user input includes an alarm summary input. The at least one second processor may be further configured to, responsive to detecting selection of the alarm summary input, cause display of an alarm interface at the device interface. The alarm interface may include a listing of one or more alarm-causing events at the defibrillator. The listing of the one or more alarm-causing events may include, for each listed alarm-causing event, at least one of a respective alarm triggering time, a respective alarm description, a respective alarm type, or a respective alarm priority. The respective alarm type may be one of a patient safety alarm, a self-check alarm, or a use and environment alarm.

In some embodiments, the at least one second processor may be configured to cause display, within the one or more of a plurality of selectable display views at the companion device view, of an alarm marker associated with each detected alarming condition at the ventilator. At least one of a color or a shape of the displayed alarm marker is based on a priority level associated with the respective detected alarming condition. The alarm marker may be displayed in the one or more selectable display views at a position relative to the time that the adjustment of the respective operating mode occurred.

In some embodiments, the ventilator display interface may include a screen configured to display the case information in a first display format. The at least one second processor may be configured to cause display, at the device interface in a second display format, of a real time device view of the case information including the physiological information displayed on the ventilator screen, where the second display format provides a visual reproduction of the first display format. Providing the visual reproduction of the first display format in the second display format may include adjusting one or more visual aspects of the case information presented in the second display format from the case information displayed in the first display format. The one or more visual aspects may include one or more of a layout, color, font, magnification, resolution, size, or screen position of the case information. Providing the visual reproduction of the first display format in the second display format may include rotating a display orientation of the case information presented within the display screen.

In some implementations, the at least one second processor may be configured to cause display, at the device interface, of a plurality of data display views where each of the plurality of display views is selectable via a respective display view selection portion of the device interface; and the plurality of display views includes the real time view of the case information including the physiological information stored in the memory of the ventilator, and a working view including one or more customized display sections for a respective caregiver role. The ventilator may further include at least one caregiver performance sensor input configured to generate caregiver performance signals associated with the respective caregiver role during the medical event, where the at least one first processor is further configured to receive and process the caregiver performance signals, and generate caregiver performance data from the processed caregiver performance signals, and where the case information further includes caregiver performance information visually rendered from the generated caregiver performance data. The at least one caregiver performance sensor input may include at least one CPR sensor input where the caregiver case information includes CPR case information derived from the at least one CPR sensor input. The at least one CPR sensor input includes a chest compression sensor input where the CPR case information including chest compression information. The chest compression sensor input may be a motion sensor input. The chest compression case information may include chest compression feedback during the medical event where the chest compression feedback includes at least one of compression depth feedback, compression rate feedback, or release velocity feedback. The at least one first processor may be configured to detect, from the processed chest compression sensor input, a compression rate of compressions delivered to the patient; and synchronize delivery of positive pressure ventilation delivered to the patient with delivered compressions based on the detected compression rate. The at least one second processor may be configured to cause display of a visual depiction of the synchronization of the delivered positive pressure ventilation and the delivered compressions. The working view may be displayed at an interface screen of the device interface separate from the device view. The one or more customized display sections may be unavailable for viewing at the one or more device view display sections. The working view may be a scrollable interface to provide more information than is displayed at the device view. A portion of the one or more customized display sections may be manually selectable by the caregiver. In one or more general examples, the at least one second processor is configured to cause display, at the device interface, of a working view including one or more customized display sections, wherein the one or more customized display sections are user selected to include selected medical data or physiological information. In one or more examples, the one or more customized display sections of the working view are customizable during a medical event based on user input.

In one aspect, the present disclosure relates to a method for providing resuscitative care to a patient during a medical event, the method including receiving and processing, by at least one first processor of a medical treatment device, physiological signals corresponding to the patient generated by at least one physiological sensor input communicatively coupled to the medical treatment device; generating, by the at least one first processor, medical data based on the processed physiological signals; displaying, by the at least one first processor on a medical treatment device screen in a first display format, case information comprising physiological information visually rendered from the generated medical data; and transmitting, by the at least one first processor, the case information and generated medical data to a companion device communicatively coupled to the medical treatment device, the companion device including a device interface having a display screen configured to allow a user to input one or more instructions for the medical treatment device during the medical event, and at least one second processor operably coupled with the device interface. The method can include processing, by the at least one second processor, the case information and generated medical data received from the medical treatment device; causing display, by the at least one second processor at the device interface in a second display format, of multiple data display views where each of the display views is selectable via a respective display view selection portion of the device interface, and one of the display views is case type view including one or more case type display sections customized to a type of case associated with the medical event.

In some implementations, the case type view is one of multiple case type views that are each selectable for viewing via a respective user input at the device interface.

In some implementations, the case type views include two or more of basic monitoring case type view, advanced monitoring case type view, cardiac arrest case type view, traumatic brain injury (TBI) case type view, respiratory distress case type view, or critical care monitoring case type view.

In some implementations, a method for providing resuscitative care to a patient during a medical event includes receiving and processing, by at least one first processor of a ventilator, signals corresponding to the patient generated by at least one physiological sensor input communicatively coupled to the ventilator; generating, by the at least one first processor, medical data based on the processed signals; displaying, by the at least one first processor on a ventilator display interface, case information including physiological information visually rendered from the generated medical data; transmitting, by the at least one first processor via a network, the case information and at least a portion of the generated medical data to a companion device communicatively coupled to the ventilator, the companion device including a device interface having a display screen configured to allow a user to input one or more instructions for the ventilator during the medical event, and at least one second processor operably coupled with the device interface; processing, by the at least one second processor, the case information and generated medical data received from the ventilator; causing display, by the at least one second processor at the device interface, of a real time view of the processed case information and medical data received from the ventilator; and transmitting, by the at least one second processor responsive to detecting at least one user input at the device interface, one or more instruction signals to the ventilator.

In some implementations, the at least one user input includes an input for providing an instruction signal of the one or more instruction signals to the ventilator. The at least one user input may include a patient information input. The at least one second processor may be further configured to, responsive to detecting a user input signal associated with the patient information input, cause display of a patient information input interface at the device interface. The patient information input interface may include a plurality of patient information input fields including, in some examples, a patient gender input field and/or a patient height input field. Transmitting the one or more instruction signals from the at least one second processor to the ventilator may include transmitting, upon submission of a respective patient gender at the patient gender input field and a respective patient height at the patient height input field, the respective patient gender and the respective patient height to the ventilator. The at least one first processor may be further configured to, responsive to receiving the respective patient gender and the respective patient height, automatically adjust a tidal volume ($V_t$) setting at the ventilator based on the respective patient gender and the respective patient height.

In some embodiments, a medical treatment system for providing resuscitative care to a patient during a medical event may include a plurality of medical treatment devices configured to monitor and provide treatment to the patient, each of the plurality of medical treatment devices including at least one sensor input configured to generate signals corresponding to the patient during the medical event, a medical treatment device screen for presenting medical information based on the generated signals, and at least one first processor operably coupled with the at least one sensor input, and the medical treatment device screen. The at least one first processor may be configured to receive and process the signals corresponding to the patient, generate medical data based on the processed signals, display, on a device screen of the respective medical treatment device, case information including physiological information visually rendered from the medical data, and transmit the case information and at least a portion of the generated medical data to a companion device. The companion device may be communicatively coupled to each of the plurality of medical treatment devices via a network, the companion device including a device interface having a display screen configured to allow a user to input one or more instructions for the plurality of medical treatment devices during the medical event, and at least one second processor operably coupled with the device interface. The at least one second processor may be configured to process the case information and medical data received from each of the plurality of medical treatment devices, cause display, at the device interface, of one or more real time combined device views of the case information from each of the plurality of medical treatment devices, the case information including a portion of the physiological information displayed on the respective medical treatment device screen of each of the plurality of medical treatment devices, and transmit, responsive to detecting at least one user input at the device interface associated with a respective medical treatment device of the plurality of medical treatment devices, one or more instruction signals to the respective medical treatment device. In other examples, the system may comprise one or more medical treatment devices.

In some embodiments, a first medical treatment device of the plurality of medical treatment devices may include a ventilator, and a second medical treatment device of the plurality of medical treatment devices includes a defibrillator. The defibrillator may include a high-voltage capacitor configured to store and release electrical charge for providing electrotherapy to the patient, and an electrode output configured to be electrically coupled with the high-voltage capacitor and to transmit at least a portion of the electrical charge from the high-voltage capacitor to the patient. The one or more instruction signals may include one or more control signals for the defibrillator to administer the electrotherapy to the patient. The physiological information may include an ECG waveform, a pulse oximetry ($SpO_2$) waveform, and a $CO_2$ waveform. The physiological information may include a current pulse oximetry ($SpO_2$) value, a current end-tidal carbon dioxide ($ETCO_2$) value, a current blood pressure value, and a current heart rate (HR) value.

In some embodiments, the ventilator includes an oxygen inlet configured to supply oxygen for providing positive pressure ventilation to the patient, and a ventilation output configured to be pneumatically coupled with the oxygen inlet and to deliver the positive pressure ventilation to the patient. The physiological information may include graphs of at least one of end-tidal carbon dioxide ($ETCO_2$), non-invasive blood pressure (NIBP), fraction of inspired oxygen ($FIO_2$), pulse rate (PR), breaths per minute (BPM), minimum volume ($V_{min}$), plateau pressure ($P_{Plat}$), or peak inspiratory pressure (PIP) over time. The physiological information maya include current values of at least one of fraction of inspired oxygen ($FIO_2$), peak inspiratory pressure (PIP), tidal volume ($V_t$), breaths per minute (BPM), end-tidal carbon dioxide ($ETCO_2$), non-invasive blood pressure (NIBP), invasive blood pressure (IBP), heart rate (HR), or ventilator mode.

In embodiments, one of the one or more real time combined device views includes a working view including one or more customized display sections for a respective caregiver role. The respective caregiver role may be a supervisor role.

In some embodiments, at least one of the medical treatment devices further may include at least one caregiver performance sensor input configured to generate caregiver performance signals associated with the respective caregiver role during the medical event. The at least one first processor may be further configured to receive and process the caregiver performance signals and generate caregiver performance data from the processed caregiver performance signals where the case information further includes caregiver performance information visually rendered from the generated caregiver performance data. The at least one caregiver performance sensor input includes at least one CPR sensor input where the caregiver case information includes CPR case information derived from the at least one CPR sensor input. The at least one CPR sensor input may include a chest compression sensor input, and where the CPR case information includes chest compression information. The chest compression sensor input may be a motion sensor input. The chest compression case information may include chest compression feedback during the medical event where the chest compression feedback includes at least one of compression depth feedback, compression rate feedback, or release velocity feedback. The at least one first processor may be configured to detect, from the processed chest compression sensor input, a compression rate of compressions delivered to the patient; and synchronize delivery of positive pressure ventilation delivered to the patient with delivered compressions based on the detected compression rate. The at least one second processor may be configured to cause display of a visual depiction of the synchronization of the delivered positive pressure ventilation and the delivered compressions.

In some embodiments, one of the one or more real time combined device views may include a trend view for presenting trend data from the generated medical data from one or more of the medical treatment devices associated with the patient care during the medical event. The at least one sensor input may include at least one physiological senor input where the trend data includes physiological values from the at least one physiological sensor input over time. The trend data may include at least one of pulse oximetry ($SpO_2$), end-tidal carbon dioxide ($ETCO_2$), systolic blood pressure, diastolic blood pressure, mean arterial pressure, or heart rate values over time. The trend data may include at least one of pulse rate (PR), respiratory rate/breathing rate (RR/BR), pleth variability index (PVI), respiratory rate (BPM), inspiratory:expiratory (I:E) ratio, tidal volume ($V_t$), fraction of inspired oxygen ($FIO_2$) setting, peak inspiratory pressure (PIP), or a positive end-expiratory pressure (PEEP). The trend view may include display of a portion of the trend data in a tabular format and/or in a graphical format. The at least one second processor may be configured to cause display, at the trend view, of an event marker associated with at least one of adjustment of a respective setting or an alarming condition at one of the medical treatment devices. The event marker may be displayed at one or more trend graphs in the trend view at a position relative to the time that the adjustment of the respective setting or alarming condition occurred.

In some embodiments, the at least one user input includes an input for providing an instruction signal of the one or more instruction signals to the plurality of medical treatment devices. The input for providing the instruction signal to the plurality of medical treatment devices may include a patient information input. The at least one second processor may be further configured to, responsive to detecting a user input signal associated with the patient information input, cause display of a patient information input interface at the device interface. the patient information input interface may include a plurality of patient information input fields for entering patient background information. Transmitting the one or more instruction signals from the at least one second processor to the plurality of medical treatment devices may include transmitting, upon submission of respective patient background information, the respective patient background information to the plurality of medical treatment devices.

In some embodiments, a method for providing resuscitative care to a patient during a medical event includes receiving and processing, by at least one first processor of each of a plurality of medical treatment devices, signals corresponding to the patient generated by at least one physiological sensor input communicatively coupled to the plurality of medical treatment devices; for each of the plurality of medical treatment devices, generating, by the respective at least one first processor, medical data based on the processed signals; displaying, by the respective at least one first processor on a medical treatment device screen in a first display format, case information including physiological information visually rendered from the generated medical data; transmitting, by the respective at least one first processor via a network, the case information and at least a portion of the generated medical data to a companion device communicatively coupled to the respective medical treatment device, the companion device including a device interface having a display screen configured to allow a user to input one or more instructions for the respective medical treatment device during the medical event, and at least one second processor operably coupled with the device interface; processing, by the at least one second processor, the case information and generated medical data received from a respective medical treatment device of the plurality of medical treatment devices; causing display, by the at least one second processor at the device interface, of one or more real time device views of the case information from each of the plurality of medical treatment devices including a portion of the physiological information displayed on the respective medical treatment device screen of each of the plurality of medical treatment devices; and transmitting, by the at least one second processor responsive to detecting at least one user input at the device interface associated with a respective medical treatment device of the plurality of medical treatment devices, one or more instruction signals to the respective medical treatment device.

In some embodiments, a first medical treatment device of the plurality of medical treatment devices includes a ventilator, and a second medical treatment device of the plurality of medical treatment devices includes a defibrillator. One of the one or more real time combined device views may include a working view including one or more customized display sections for a respective caregiver role. The respective caregiver role may be a supervisor role.

In some embodiments, one of the one or more real time combined device views includes a trend view for presenting trend data from the generated medical data from one or more of the plurality of medical treatment devices associated with the patient care during the medical event. The at least one user input includes an input for providing an instruction signal of the one or more instruction signals to the plurality of medical treatment devices. The input for providing the instruction signal to the plurality of medical treatment devices includes a patient information input. In a further aspect, the present disclosure related to a medical treatment system, including a medical treatment device configured to monitor the patient. The medical treatment device can include at least one sensor input configured to generate signals corresponding to at least one physiological condition of the patient during the medical event, a medical treatment device display interface for presenting medical information based on the generated signals, and at least one first processor operably coupled with the at least one sensor input, and the medical treatment device display interface, the at least one first processor configured to receive and process the signals corresponding to at least one physiological condition the patient, generate medical data based on the processed signals, display, at the medical treatment device display interface, case information including physiological information visually rendered from the medical data, and transmit at least a portion of the generated medical data to a companion device. The companion device may be communicatively coupled to the medical treatment device via a network and may include a device interface having a display screen and at least one second processor operably coupled with the device interface, the at least one second processor configured to provide for at least one of display of information based on the received medical data or provide an interface for user input to enable control of the medical treatment device. The medical treatment system of this further aspect may be provided in combination with any one or more of the functions described herein, such as relating to display of the device view, the working view, control of settings of the medical treatment or monitoring device with which the companion device is coupled, provision of trend information, provision of alarms and/or the setting thereof, the recordal of events, the display of events or other functionality.

In a further aspect, the present disclosure relates to a computer program which may be embodied as a computer program product for execution by a companion device, where the companion device, on execution of the computer program, is configured to form a medical treatment system with a medical treatment device that is configured to monitor a patient. The companion device may be configured to form a communicative coupling to the medical treatment device via a network. The medical treatment device can include at least one sensor input configured to generate signals corresponding to at least one physiological condition of the patient during the medical event, a medical treatment device display interface for presenting medical information based on the generated signals, and at least one first processor operably coupled with the at least one sensor input, and the medical treatment device display interface, the at least one first processor configured to receive and process the signals corresponding to at least one physiological condition the patient, generate medical data based on the processed signals, display, at the medical treatment device display interface, case information including physiological information visually rendered from the medical data. The companion device may be further configured to receive at least a portion of the generated medical data. The computer program may cause the companion device to provide for at least one of display of information on a display screen of the companion device based on the received medical data or provide an interface for user input to enable control of the medical treatment device. For example, a user of the companion device may submit user input used by the medical treatment device to adjust one or more treatment protocols.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 7C-1 illustrates exemplary confirmation messages for recording a snapshot at a medical treatment device;

FIG. 7C-2 illustrates exemplary confirmation messages for performing a 12-lead ECG analysis;

FIGS. 8C-1 and 8C-2 illustrate an exemplary advanced monitoring case type view user interface screen;

FIG. 13A illustrates an exemplary alarm summary user interface screen;

FIG. 13B illustrates an exemplary patient information input user interface screen;

FIGS. 13D-1 and 13D-2 illustrate exemplary setting adjustment user interface screens.

DETAILED DESCRIPTION OF ILLUSTRATIVE EMBODIMENTS

Figure 1A:
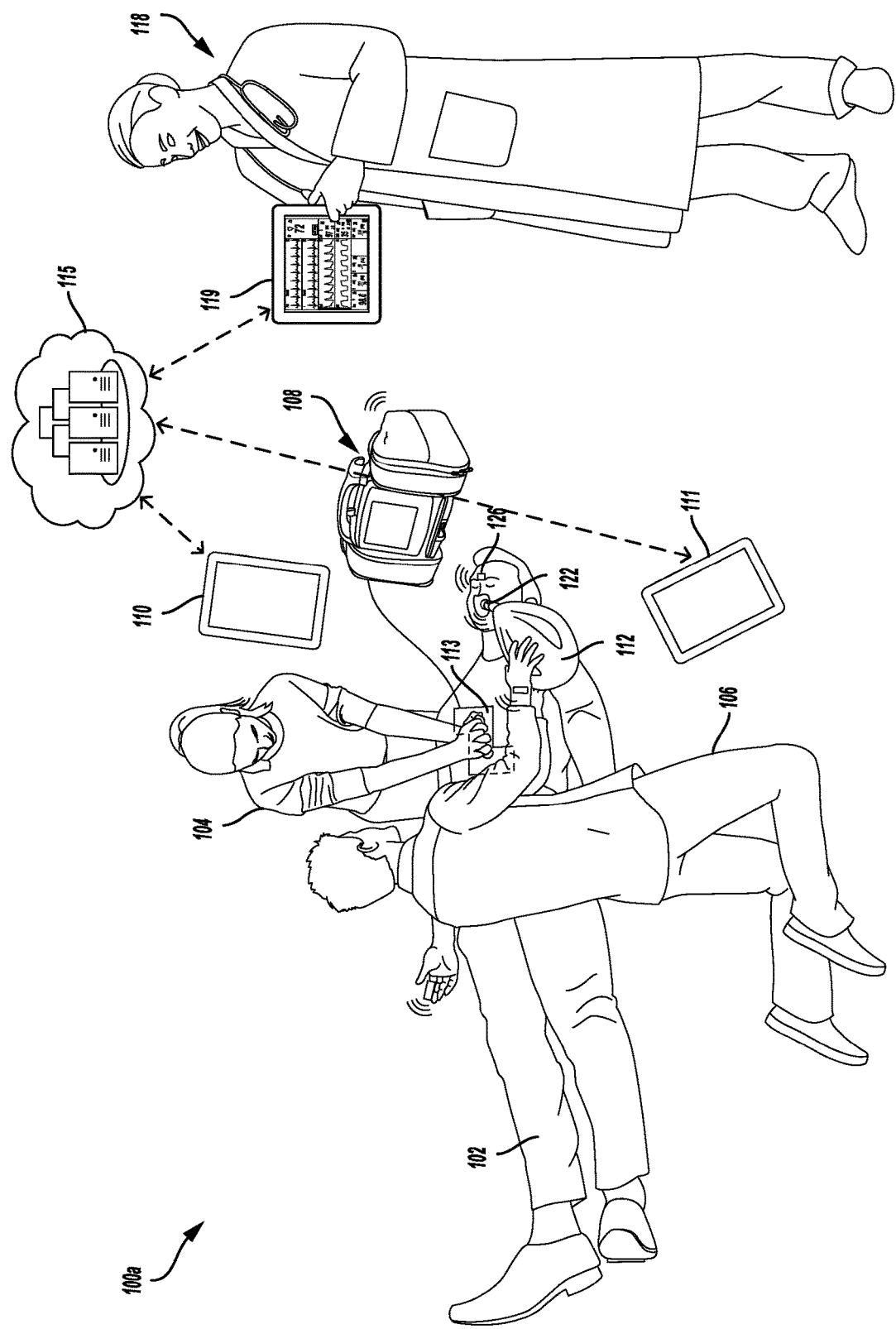
FIGS. 1A-1D illustrate schematic diagrams of emergency care scenes in accordance with some embodiments.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

Aspects of the present disclosure are directed to systems and methods for monitoring treatment delivered by one or more medical treatment devices during an emergency medical treatment event via a companion device communicatively coupled to a medical treatment device (e.g., a defibrillator or electric shock delivery device, patient monitor, ventilator) via a wireless communication link. The companion device may be fully customizable based upon the type of medical event and roles/preferences of the device user (e.g., a medical team member, CPR provider of chest compressions and/or ventilations, supervisor, documenter, or drug infuser). In some embodiments, enabling connection of the companion device to the medical treatment device provides the technical advantage of enabling a user to view real-time sensor data associated with patient treatment, providing medical professionals enhanced treatment flexibility and oversight. For example, the size and/or position of the display region of the medical treatment device is no longer limiting to care providers' ability to monitor treatment. In another example, users having different roles or responsibilities at a treatment scene, in some embodiments, are enabled to view customized information. The customized information presented at the companion device, for example, may at least partially differ from the information being presented at the medical treatment device, providing the technical advantage of presenting, to a team of caregivers, more information than could reasonably be displayed in a screen region of the medical treatment device. Additionally, in some embodiments, each companion device is pairable with a single defibrillator, ventilator, or other medical treatment device and receives real-time data via a secure link, such that historic patient data can remain securely stored at the medical treatment device without the need to retain any patient-related medical data locally at the companion device 110, 111, 119, 204. This provides the technical advantage of security and patient information privacy during data review by multiple medical personnel. In various embodiments, the companion device(s) are pre-configured to be associated with a particular medical treatment device (e.g., defibrillator, patient monitor, ventilator) so as to streamline wireless communication pairing without having to undergo a time-consuming inquiry and response negotiation for a secure connection to be established.

In some embodiments, the companion device configured to operate with a medical treatment device can be used in an emergency medical services (EMS) environment by trained emergency responders at the scene of an emergency or during prehospital transport. It can also be used in EMS during the ground and air transport of patients between medical facilities. The companion device, in some examples, can also be used in a hospital emergency room, general medical-surgical and intermediate care floors, cardiac care unit, electrophysiology (EP) lab, operating rooms, and other similar areas of the hospital and/or for intra-hospital transport of patients.

In an example scenario, during the course of treating a cardiac arrest victim (a "code"), an emergency department (ED) medical caregiver personnel such as a nurse or physician brings in a medical treatment device such as a defibrillator/monitor and applies electrocardiographic (ECG) diagnostic electrodes and/or therapeutic defibrillation electrodes to the patient along with other physiologic sensors such as pulse oximetry, capnography, blood pressure, near infrared spectroscopy, etc. In addition, there are also sensor inputs for measuring caregiver performance such as motion and flow sensors that measure caregiver performance of both diagnostic and treatment activities. For example, a motion sensor (e.g., accelerometer) may be placed on the patient's sternum during chest compressions and may be used to measure parameters indicative of chest compression performance, such as compression depth, rate, release velocity, amongst others; and/or a flow sensor may be placed along the patient's airway during ventilation and may be used to measure parameters indicative of ventilation performance, such as tidal volume, ventilation rate, etc. In an effort to reduce the size and weight of the medical treatment device to enhance portability and usability, the size of the information display screen, such as a Liquid Crystal Display (LCD) or Light Emitting Diode (LED) display, on the defibrillator/monitor is often reduced to the point where the display area is too small to concurrently display all medical device data, including the sensor information gathered from the patient as well as all the information gathered about diagnostics, treatment, device performance, caregiver performance, etc. In fact, in many cases while a defibrillator/monitor may only be a volume of less than 0.5 ft.$^3$ and a display size of just 8.5" diagonal, the amount of information gathered and generated by the defibrillator/monitor at any one time would easily fill an entire display screen of 36" diagonal or more. This presents a dilemma for the clinician using the medical device: the choice of what information to display is oftentimes difficult and displaying one particular parameter comes at the expense of losing visibility of another parameter. In addition, front line caregivers such as nurses in hospitals or Emergency Medical Technicians (EMT) in the pre-hospital environment often received highly protocolized training, leaving them ill-equipped to determine what information should be viewed on the display (and therefore also what is NOT visible and missing on the display as a consequence); as a result, sometimes potential clues are missed in the diagnosis and treatment of the patient, resulting in misdiagnosis and at times potentially either ineffective or harmful medical treatment of the patient.

Referring back to the embodiment of a nurse treating a patient undergoing cardiac arrest in the hospital, it would be desirable for the ED medical supervisor to be able to view in some fashion various medical device data independent of what is being viewed by the caregiver on the medical treatment device. Ideally this independent viewing of the medical device data does not result in the act of viewing by the supervisor interfering in any way with the caregiver's operation of the medical treatment device. This is accomplished by having at least one companion device 110, 111, 119, 204 by which the supervisor or other medical personnel can access the medical device data. The companion device 110, 111, 119, 204 may be a portable computing device such as a tablet, personal display/digital assistant device, or phone. The companion device 110, 111, 119, 204 may also be a larger wall-mounted touch screen display mounted on the wall of the patient's room. The companion device 110, 111, 119, 204 allows for the supervisor to display the larger set of medical device data available on the medical treatment device compared to what can be viewed on the limited display screen area of the medical treatment device. By viewing the larger set of medical device data on the companion device 110, 111, 119, 204, the supervisor will be better able to assess the appropriateness of the caregiver's diagnosis and treatment of the patient. It is, however, easy to "get lost" in all the data, even for the supervisor and for the supervisor to lose sight of the treatment plan and strategy of the caregiver. This difficulty may be solved by providing a display mode on the companion device 110, 111, 119, 204 that provides a visual reproduction of the medical treatment device (e.g. defibrillator/monitor) display, termed the device view. In some examples, a visual reproduction can encompass an exact replication of the data displayed at the medical treatment device. In other examples, a visual reproduction of case information at the companion device 110, 111, 119, 204 can include data and formatting variations that can enhance viewing and comprehension of the case information by a companion device user. In some examples, display layout, magnification of each data section, physiologic waveform selection, physiologic numeric readout selection, resolution, waveform duration, waveform size, text size, font, and/or display colors can vary from what is displayed at the medical treatment device. In one example, font and size of one or more items of displayed case information may be enlarged and/or highlighted to draw the eyes of the user of the companion device 110, 111, 119, 204 to the respective case information. In this important way, the supervisor can understand the scope of the medical device data upon which the caregiver is making their sometimes-flawed decisions. At least one other display mode is available on the companion device 110, 111, 119, 204 which allows for a customizable display format, termed the working view. The ability to provide a working view at the companion device may, in one or more examples, form an aspect of the disclosure. Thus, in a further aspect, the present disclosure relates to a medical treatment system, including a medical treatment device configured to monitor the patient. The medical treatment device can include at least one sensor input configured to generate signals corresponding to at least one physiological condition of the patient during the medical event, a medical treatment device display interface for presenting medical information based on the generated signals, and at least one first processor operably coupled with the at least one sensor input, and the medical treatment device display interface, the at least one first processor configured to receive and process the signals corresponding to at least one physiological condition the patient, generate medical data based on the processed signals, display, at the medical treatment device display interface, case information including physiological information visually rendered from the medical data, and transmit at least a portion of the generated medical data to a companion device. The companion device may be communicatively coupled to the medical treatment device via a network and may include a device interface having a display screen and at least one second processor operably coupled with the device interface, the at least one second processor configured to process the medical data received from the medical treatment device, cause display, at the device interface, of a working view. In one or more examples, the working view provides a customizable view of physiological information based on the received portion of the medical data from the medical treatment device. The working view may be customizable in real-time during a medical event based on user input.

If, after viewing the working view and device view, the supervisor deems a particular piece of medical device data to be relevant to the caregiver's decision process and the device view is missing that relevant medical device data, then an instruction can be sent to the medical treatment device to effectuate a change to its operation. In some embodiments, the change in operation may comprise a command to initiate taking of one or more measurements, or collection of data, relating to a condition of the patient. In some embodiments, the change in operation may be in the form of a command to initiate a blood pressure reading via an oscillometric blood pressure cuff, if the supervisor notices that the time duration since the last blood pressure reading has been exceeded. In another embodiment, a 12-lead may be initiated from the companion device 110, 111, 119, 204 in the case of heart attack victims. Alternatively, the change in operation may be a change of the display format of the medical treatment device. For instance, when treating a patient who is having difficulty breathing (dyspnea), the caregiver may have made the choice to not include either the capnograph waveform or EtCO2 values on the display screen of the medical treatment device. The supervisor sees in the working view that the capnographic waveform is indicative of obstructive lung disease and toggles over to the device view and sees that the capnographic information is not being displayed (upon which the caregiver is basing their potentially flawed medical decisions). Based on this, the supervisor can initiate an instruction from the companion device 110, 111, 119, 204 to the medical treatment device to alter its display format and display the capnographic information. Alternatively, the instruction may take the form of a request to alter the display format. The request may be in the form of a text request to the caregiver operating the medical treatment device (e.g., "Important patient info: please display capnograph.").

The companion display device allows convenient access by the supervisor to various medical device data as the medical event progresses. For example, after first arriving to the patient's room during the emergency situation, the supervisor may retrieve the companion device 110, 111, 119, 204 from a pocket on a garment worn by the supervisor (in the case of an iPhone), or from a storage compartment, such as a bag or storage rack of the companion device 110, 111, 119, 204, for example, by the head of the patient's bed (in the case of a tablet computer). The supervisor then may choose to immediately be able to see a visual reproduction of the medical treatment device screen through a device view capability at the companion device 110, 111, 119, 204. In some examples, a visual reproduction can encompass an exact replication of the data displayed at the medical treatment device. In other examples, a visual reproduction of case information at the companion device 110, 111, 119, 204 can include data and formatting variations that can enhance viewing and comprehension of the case information by a companion device user. In some examples, display layout, magnification of each data section, physiologic waveform selection, physiologic numeric readout selection, resolution, waveform duration, waveform size, text size, font, and/or display colors can vary from what is displayed at the medical treatment device. The supervisor may also set up a working view to customize the presentation. Since the working view provides a page with no limitation on what can be shown, the supervisor may add more display cards or data sections that are not shown on the device view, such as particular trend information, 12-lead ECG data, CPR performance summaries, etc., to have more information readily available. As a result, the supervisor may then toggle between the device view and the working view. As the code progresses, the caregiver, e.g., nurse, emergency technician, begins chest compressions and is peering at the screen of the medical treatment device to view the chest compression dashboard. To evaluate the performance of the caregiver, the supervisor may view, in real-time, a summary of chest compression performance as displayed on a working view of the companion device 110, 111, 119, 204, and may also periodically navigate to the device view to see what the caregiver is seeing, to determine how best to coach the caregiver.

In some embodiments, users at a companion device 110, 111, 119, 204 can control one or more functional operations and/or provide one or more inputs to the medical treatment device, providing the technical advantage of ease of access to a user entry screen and avoidance of disrupting treatment being provided to the patient by other caregivers. In one example, the companion device 110, 111, 119, 204 includes a user-friendly, convenient touchscreen, keypad, or other control interface for submitting information and/or commands. The information and/or commands may be used by the medical treatment device to adjust one or more treatment protocols, providing the technical advantage of quickly and easily customizing treatment for a patient, such as providing an age or size of the patient for use in treatment algorithms of the medical treatment device.

The supervisor or other medical personnel (e.g., a documenter), in some embodiments, can log treatment markers from the companion device 110, 111, 119, 204, rather than having to initiate recording of the treatment marker on the medical treatment device. In such a case, an instruction may be sent back to the medical treatment device from the companion device 110, 111, 119, 204 to log the event marker in its treatment record, and potentially to send back to a cloud server storing the medical device data. Accordingly, the treatment record may be stored on the medical treatment device itself, without requiring storage thereof on the companion device 110, 111, 119, 204. Or, in some cases, the instruction to log the event marker may be sent from the companion device 110, 111, 119, 204 not only to the medical treatment device, but also a cloud server that stores the treatment record. Alternatively, the cloud server may poll the medical treatment device for the most current treatment record without requiring direct communication between the cloud server and the companion device 110, 111, 119, 204. It may be preferable for the medical treatment device to be operated only by the person immediately using it without interference, instead of having others move or otherwise engage with it. Further, as the code progresses, the supervisor may want to actively look back within the existing case to see events of interest, such as the presenting ECG rhythm when a previous determination of shockability had been made, or what the effect of certain vital signs were once medications were delivered. If more than one companion device 110, 111, 119, 204 is paired with the medical treatment device and is available, then it may be possible to set up the working view of the companion device 110, 111, 119, 204 with only the chest compression dashboard to provide chest compression feedback on the performance of manual compressions. Also, a ventilation dashboard can be displayed at the companion device 110, 111, 119, 204 to provide ventilation feedback, so as to use one or more of the companion devices 110, 111, 119, 204 as a dedicated feedback device. Accordingly, it may be possible to set up the working view of the companion device 110, 111, 119, 204 with only the ventilation dashboard to provide ventilation feedback on the performance of manual ventilations.

In some implementations, the companion device 110, 111, 119, 204 can display sensor data in real-time from one or more physiological sensors connected to the medical treatment device. In some examples, the companion device 110, 111, 119, 204 can display a visual reproduction of the information displayed at the medical treatment device in a first display. This first display view, referred to as a device view, allows additional medical team members to participate in patient treatment without having to be immediately proximate to the medical treatment device. For example, a rescue team supervisor who oversees and coordinates patient treatment during a critical patient care event (e.g., chest pain, cardiac arrest, traumatic brain injury (TBI), respiratory distress, or critical care monitoring) can view, in real-time, the same waveforms and patient data displayed at the medical treatment device. This allows supervisors or other medical team members to observe both rescuer treatment actions and patient data simultaneously so that the supervisors can provide recommendations to further enhance patient treatment and coordinate treatment by multiple rescuers. In some examples, the device view displays a visual reproduction of case information displayed at the medical treatment device. The medical device data displayed in the device view of the companion device 110, 111, 119, 204 is a visual reproduction of that information displayed at a display interface of the medical treatment device 202 when one or more of the following visual elements of the display interface of the medical treatment device 202 is reproduced in the device view: the display layout, magnification of each data section, physiologic waveform selection, physiologic numeric readout selection, resolution, waveform duration, waveform size, text size, font, and display colors. In some examples, the visual reproduction of the display screen of the medical treatment device 202 at the companion device 110, 111, 119, 204 can exactly replicate at is displayed at the medical treatment device 202 or one or more of the visual elements may be altered from what is displayed at the medical treatment device 202. In one example, font and size of one or more items of displayed case information may be enlarged and/or highlighted to draw the eyes of users of the companion device 110, 111, 119, 204 to the respective case information. Waveforms or other data of a certain type may be magnified or color coded in a particular fashion. For example, ECG waveforms, such as in a 12-lead analysis, may be magnified similarly, or certain waveforms may be emphasized in resolution, color, or other manner of reproduction. Or, in some embodiments, numerical values representing non-continuous physiological measurements (e.g., NIBP, $SpO_2$, HR, $EtCO_2$) may be shown in a similar sized font or layout. In some cases, for example, a visual reproduction may be a replication of the information as presented on the display interface of the medical treatment device, or alternatively with slight variations thereof.

Rescuers and other medical team members may also wish to view additional information than what is provided in the device view. In some implementations, the companion device 110, 111, 119, 204 can also display, in a second display view, referred to as a "working view," that is separate from the device view and accessible to the user on the same companion device 110, 111, 119, 204 (e.g., via a selection tab or other user input selection), one or more patient data dashboards customized to preferences or treatment roles of a user of the companion device 110, 111, 119, 204. In some examples, the data dashboards display physiological sensor data such as ECG waveforms, pulse oximetry waveforms, and $CO_2$ waveforms. In some examples, the pulse oximetry waveforms can include waveforms for one or more of peripheral capillary oxygen saturation ($SpO_2$), carbon monoxide saturation (SpCO), methemoglobin (SpMet), total hemoglobin (SpHB), blood oxygen content (SpOC), pleth variability index (PVI), or perfusion index (PI). The working view, in some examples, can be a scrollable display screen that includes data dashboards displaying treatment-based sensor data associated with treatment devices or methods instead of or in addition to the information displayed within the device view. For example, a CPR data dashboard can display real-time CPR information, for example, including chest compression depth and chest compression rate. The displayed CPR information may provide real-time feedback to a rescuer delivering CPR chest compressions to a patient regarding whether the depth of each chest compression is within a target range and a target compression rate. In some cases, a rescue team member providing CPR chest compressions to a patient may select to have the chest compression dashboard displayed more prominently than other dashboards within the working view to more easily view feedback associated with administration of CPR chest compressions. Similarly, in some embodiments, a ventilation dashboard can display real-time ventilation information including, in some examples, ventilation rate, tidal volume, and minute volume. In some situations, a rescuer providing ventilation to a patient may select to have the ventilation dashboard displayed within the working view to more easily view feedback associated with providing patient ventilation. Companion device 110, 111, 119, 204 users may be enabled to add or remove any dashboards to suit their viewing preferences. In some cases, the working view may be created and customized ad hoc during medical treatment by controls that allow the viewer of the companion device 110, 111, 119, 204 to format the medical device data as they wish.

Additionally, companion device users, in some embodiments, can view case information for a medical event that is tailored to a particular type of medical event in another implementation of the working view, referred to as a "case type view." In one or more examples, the provision of a "case type view" at the companion device may comprise an aspect of the disclosure. For example, certain types of medical events may have certain waveforms, data dashboards, and information that are more pertinent to the type of care being delivered to the patient, and each case type view may be preconfigured with those most pertinent data dashboards. The "case type" views can include a "basic monitoring" view that displays ECG and $SPO_2$ waveforms and heart rate, blood pressure, and $SPO_2$ trends. A TBI view can display ECG, $ETCO_2$, and $SPO_2$ waveforms, heart rate and respiratory rate trends, and a TBI dashboard. A "advanced monitoring" view can display ECG, $ETCO_2$, and $SPO_2$ waveforms and heart rate, 12-lead results, ST trending, blood pressure, $SPO_2$, $ETCO_2$, and respiratory rate trends. A "respiratory distress" view can display ECG, $ETCO_2$, and $SPO_2$ waveforms, heart rate, blood pressure, $SPO_2$, $ETCO_2$, and respiratory rate trends, and a ventilation (BVM) dashboard. A "cardiac arrest" view can display ECG and $SPO_2$ waveforms, $SPO_2$ and $ETCO_2$ trends, and CPR and ventilation dashboards. A "critical care monitoring" view can display ECG, $ETCO_2$, $SPO_2$, and invasive blood pressure (IBP) 1/2/3 waveforms and heart rate (HR), respiratory rate (RR), NIBP, $ETCO_2$, $SPO_2$, and IBP1/2/3 trends. By providing pre-configured display views tailored to different types of medical treatment events, the companion device 110, 111, 119, 204 provides caregivers the technical flexibility to quickly view a user-friendly display of case information that is pertinent to the given event. The case information, in some implementations, can include physiological information derived from physiological sensors, medical treatment data derived from therapy delivery sensors and/or manual inputs, and caregiver performance data derived from caregiver performance sensors. In some examples, the companion device 110, 111, 119, 204 can also display working views that are customized to a role of each caregiver in a rescue team. For example, a CPR working view may automatically cause the chest compression dashboard to be prominently displayed at the companion device 110, 111, 119, 204 for viewing by a rescuer administering CPR.

In some implementations, companion device 110, 111, 119, 204 users can also view data trends during a medical event in a third display view of the companion device 110, 111, 119, 204, referred to as a "trends view." The trends view, which can be a separately selectable view from the device view and working view, can display physiological sensor value trends (e.g., ST trending, $SPO_2$, $ETCO_2$, blood pressure, heart rate) over time during the medical event. In some cases, the trend data can be displayed in a graphical or tabular format.

In some examples, physicians and other medical personnel who may not be directly involved with rescue efforts can use a customized companion device 110, 111, 119, 204 to monitor patient status and provide treatment recommendations based on case information displayed at the companion device 110, 111, 119, 204. In some situations, a physician with a companion device 110, 111, 119, 204 may be at a workstation or office in communication (such as via Wi-Fi) via the internet with the medical treatment device in order to receive real-time case information but not in the immediate vicinity of the patient and rescue team administering treatment.

Aspects of the present disclosure are also directed to allowing a user, via inputs at a user interface screen of the companion device 110, 111, 119, 204, to supply inputs to the medical treatment device. During treatment of a critically ill patient, rescuers in the immediate vicinity of a patient are often consumed with tending to the medical needs of the patient, whether that includes administering electric shock or ventilation via the medical treatment device, administering chest compressions, administering ventilation, or treating wounds. Additionally, user input interfaces (e.g., keypads and other buttons for inputting information) that are local to the medical treatment device can be cumbersome to operate in time-critical situations. Instead, in some examples, users at a companion device 110, 111, 119, 204 who may not be providing direct patient care can control one or more functional operations and/or provide one or more inputs at a user-friendly, convenient touchscreen at the companion device 110, 111, 119, 204 without interfering with patient treatment. In some examples, companion device 110, 111, 119, 204 users can input patient information, record treatment markers, initiate 12-lead ECG analyses, or record a device snapshot. Therefore, allowing a user to provide instructions to activate one or more operations of the medical treatment device via the companion device 110, 111, 119, 204 provides enhanced technical flexibility that is not available when operating locally at the medical treatment device by allowing supervisors or other personnel at the scene of a medical event to observe, in real-time, how the medical event is progressing without having to hover over the treatment area, which may impede patient care.

In response to receiving user inputs at the companion device 110, 111, 119, 204 associated one of the control operations at the medical treatment device, the companion device 110, 111, 119, 204, in some implementations, transmits an instruction signal to cause the respective operation to occur at the medical treatment device. In some examples, instruction signals sent from the companion device 110, 111, 119, 204 to the medical treatment device can instruct the medical treatment device to update patient information, treatment information, or diagnostic information for the medical event. In response to receiving the respective signal, the medical treatment device performs the respective operation associated with the instruction signal, which may include storing provided information (e.g., transmitting patient information for updating at the medical treatment device) or recording a treatment marker (e.g., transmitting a treatment/event marker for the medical treatment device to record in the patient care record) or initiating a snapshot (e.g., transmitting an instruction signal for the medical treatment device to initiate a snapshot of ECG associated with the time of the instruction input) or activating an analysis feature (e.g., instruction signal for the medical treatment device to perform a 12-lead analysis) at the medical treatment device. In some embodiments, the instruction signals can also include control signals for causing the medical treatment device (a defibrillator) to initiate electrotherapy or apply another therapeutic treatment. When the medical treatment device is a ventilator, the instruction signals can include control signals to administer the positive pressure ventilation to the patient. In some examples, upon initiation and/or completion of the respective operation, the medical treatment device transmits a notification signal to the companion device 110, 111, 119, 204. In response to receiving the notification signal from the medical treatment device, the companion device 110, 111, 119, 204 can cause display of a notification message at the companion device 110, 111, 119, 204 that the respective action is being performed; and then a subsequent notification signal from the medical treatment device for the companion device 110, 111, 119, 204 to display a notification message that the respective action has been performed. Thus, the systems and methods described herein provide a technical solution to the technical problem of enabling control of a medical treatment device by more than one user providing inputs at one or more companion devices 110, 111, 119, 204 that are remote from the medical treatment device. For example, before the improvements described in the present disclosure were developed, personnel were limited to providing inputs or controlling operations directly at the medical treatment device interface. Because of this technical inconvenience, treatment markers, 12-lead analyses, and snapshots failed to be recorded at significant treatment points, reducing the effectiveness of event debriefs, personnel evaluations, and patient condition analyses. Therefore, the systems and methods described herein provide a solution to the clinical and technical problem of providing patient care during critical medical events based on all available information in real-time (e.g., how treatment has been provided and how a patient is responding to all types of administered treatment). Further, the systems and methods described herein also solve the clinical and technical problem of allowing supervising personnel to provide real-time treatment feedback to rescuers and others providing direct medical care, which creates a more beneficial training environment for both new and seasoned rescue teams and individuals.

Referring to FIG. 1A, at an emergency care scene 100a, a rescuer 104 performs cardiopulmonary resuscitation (CPR) on a victim or patient 102 (the terms are used interchangeably here to indicate a person who is the subject of intended or actual CPR and related treatment, or other medical treatment), such as an individual who has apparently undergone sudden cardiac arrest. The emergency care scene 100a can be, for instance, at the scene of an accident or health emergency, in an ambulance, in an emergency room or hospital, or another type of emergency situation. The rescuer 104 can be, for instance, a civilian responder with limited or no training in lifesaving techniques; a first responder, such as an emergency medical technician (EMT), police officer, or firefighter; or a medical professional, such as a physician or nurse. The rescuer 104 may be acting alone or may be acting with assistance from one or more other rescuers, such as a partner EMT 106. In the example of FIG. 1A, the rescuer 104 can deliver chest compressions to the patient 102 and the rescuer 106 can deliver ventilations to the patient using a ventilation device 112 (e.g., bag-valve mask).

In this illustration, the rescuers 104,106 can deploy a defibrillator 108, such as an automated external defibrillator (AED), a professional defibrillator, or another type of defibrillating apparatus, to treat the patient 102. The defibrillator 108 is connected to electrode pads 113 intended to be placed on the patient's chest via one or more cables. The electrode pads 113 may acquire signals indicative of the patient's ECG and the defibrillator 108 may analyze those signals and, if the signals determine that the patient is in need of defibrillation, provide defibrillation treatment to the patient 102 as appropriate through the electrode pads 113. In some examples, the defibrillator 108 can instruct one or more of the rescuers 104, 106 in providing CPR or other treatment to the patient 102.

The rescuers 104, 106 can use companion devices 110, 111 such as smartphones, tablets, or wearable devices (e.g., watches or glasses) to assist in treating the patient 102. For instance, the companion devices 110, 111, 119, 204 can provide prompting to assist a rescuer in delivering chest compressions, ventilations, mouth-to-mouth resuscitation, defibrillation, or other treatments to the patient 102. A supervisor 118 can use a companion device 119 to coordinate treatment provided by the multiple rescuers 104, 106. Additional computing devices, such as laptop computers or computing devices integrated into an ambulance, can be used to analyze health data about the patient or data indicative of treatment delivered to the patient or to communicate such data to a remote location (e.g., a dispatch center, an emergency room, or a remote server).

One or more sensors (e.g., sensors 122, 126 in the example of FIG. 1A through FIG. 1C) can be used to monitor the patient 102. For instance, the sensors 122, 126 monitor parameters indicative of the patient's health status, e.g., physical parameters such as the patient's heart rate, electrocardiogram (ECG), blood pressure, temperature, respiration rate, blood oxygen level, end-tidal carbon dioxide level ($ETCO_2$), pulmonary function, blood glucose level, or other parameters indicative of the patient's health status. Some sensors, such as heart rate or ECG sensors, can be included in pads 110 of the defibrillator 108. One or more sensors monitor the treatment delivered to the patient 102. For instance, a compression puck can be positioned beneath the hands of rescuer 104 as the rescuer 104 administers CPR by detecting a rate, depth, or duration of compressions delivered to the patient 102. Additionally, airflow sensor 122 on ventilation device 112 can monitor volume and rate of ventilations administered to the patient 102 by rescuer 106. Some sensors can monitor both parameters indicative of the patient's health status and parameters indicative of the treatment delivered to the patient. For example, ventilation sensors 122 can provide information about the patient's health status or information about the treatment delivered to the patient to the defibrillator 108, one or more of the companion devices 110, 111, 119 or other computing devices at the emergency care scene 100a or to remote computing devices 115 such as cloud servers that host data storage or web portals for the medical treatment system.

Figure 1B:
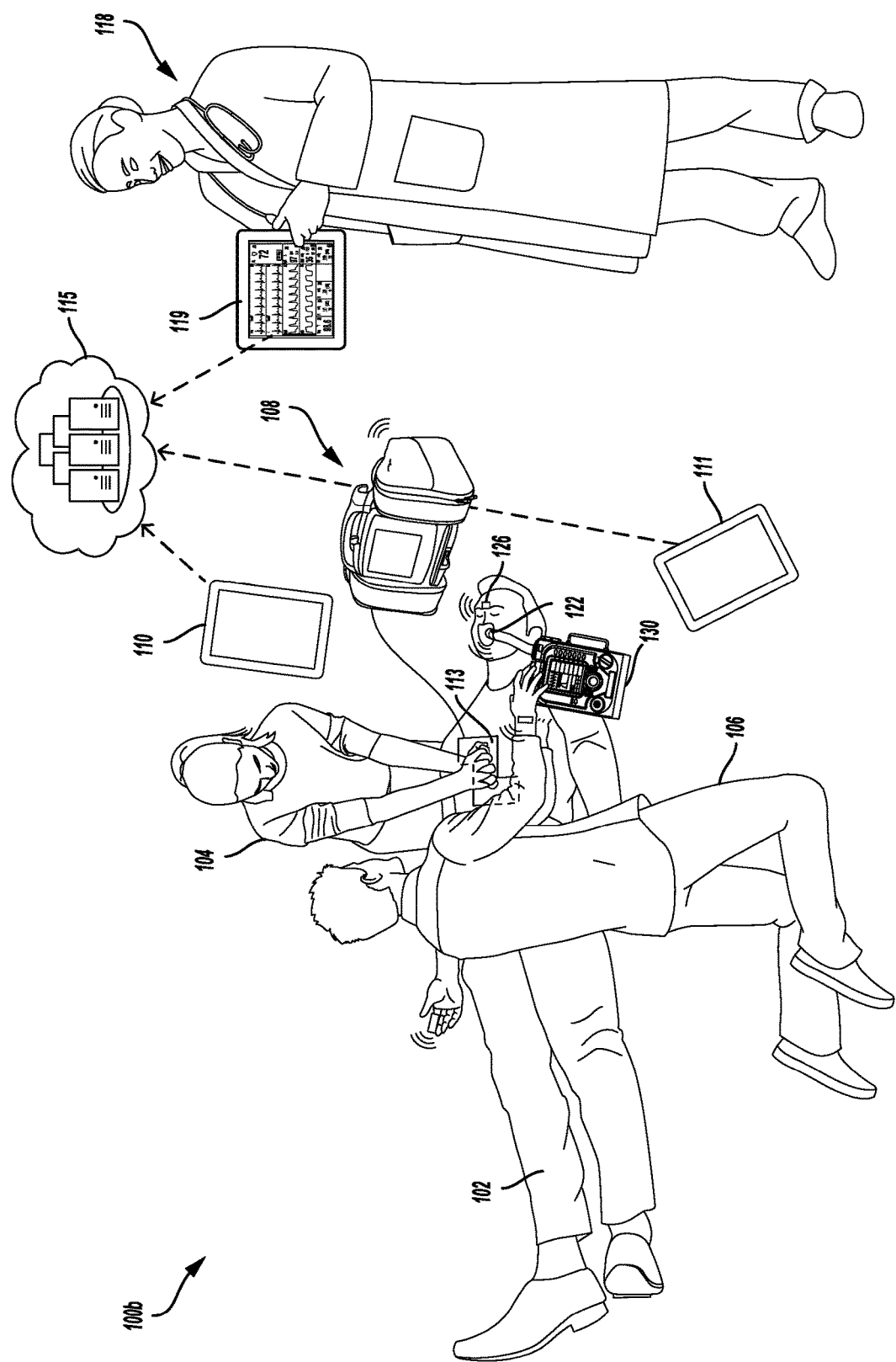
Figure 1C:
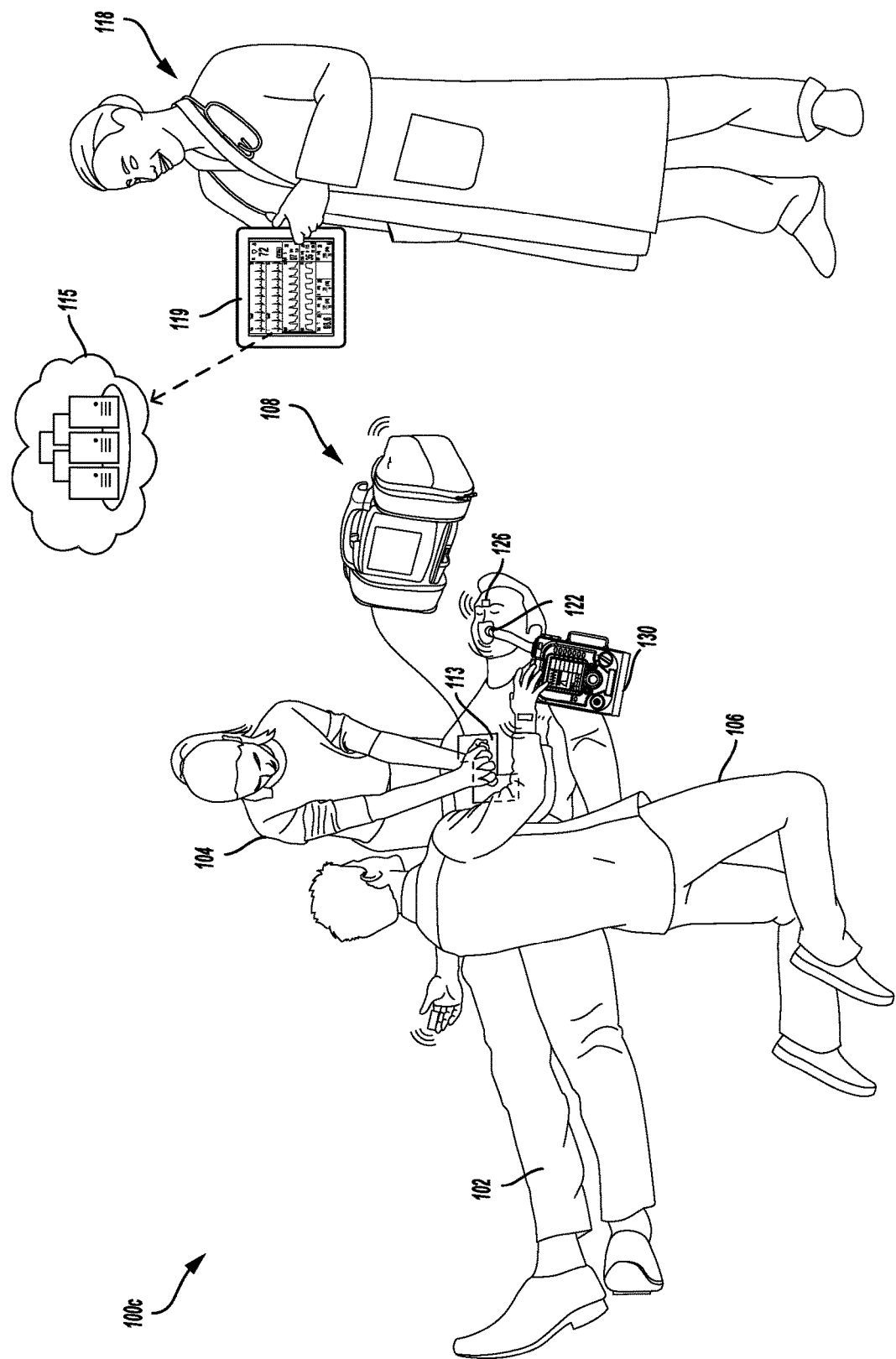

FIG. 1B and FIG. 1C illustrate alternative examples of emergency scenes 100b, 100c that include multiple medical treatment devices 108, 130 in communication with one or more companion devices 110, 111, 119. For example, emergency scene 100b shown in FIG. 1B shows a defibrillator 108 in communication with companion device 110 that rescuer 104 uses to assist in providing defibrillation treatments to the patient 102. Ventilator 130 (in one example, ventilator 1000 shown in FIG. 10) communicates with companion device 111 that rescuer 106 uses to assist in providing ventilation treatment to the patient 102. In some implementations, the ventilator 130 is a portable ventilator that can be used in the hospital and/or pre-hospital environments such as aeromedical and ground transport, mass casualty situations, and extreme environments. In one example, the ventilator 130 weighs less than 10 pounds to provide for easy transport at emergency scenes so that pre-hospital ventilation can be delivered to a patient. In some implementations, sensor data obtained by the one or more sensors 122, 126 associated with each of the medical treatment devices 108, 130 can be transmitted to the respective connected companion device 110, 111 for display within one or more user interface views. While the user interface screens at the companion devices 110, 111 may display some of the same sensor data (e.g., $SpO_2$, HR, blood pressure values), in some implementations, the data displayed may be associated with the respective connected companion device 110, 111. For example, the companion device 110 can display ECG and defibrillator shock information received from the defibrillator 108, and companion device 111 can display processed ventilator sensors data such as airway pressure ($P_{AW}$), plateau pressure ($P_{Plat}$), peak inspiratory pressure (PIP), or fraction of inspired oxygen ($FIO_2$).

In addition, each of the companion tablets 110, 111 can transmit instruction signals to the respective medical treatment device 108, 130 responsive to received user inputs at the companion tablet 110, 111. The transmitted instruction signals can provide information and/or initiate one or more functional operations of the respective medical treatment device 108, 130. For example, in response to a user input, the companion device 110 can transmit an instruction signal to the defibrillator 108 to perform a 12-lead ECG analysis. Additionally, the companion device 111, in response to receiving a user input changing an operation mode of the ventilator 130, can transmit an instruction signal to the ventilator 130 to change the operation mode (e.g., assist/control (AC) mode, a synchronized intermittent mandatory ventilation (SIMV) mode, a continuous positive airway pressure (CPAP) mode, or a bilevel (BL) mode).

In some implementations, patient treatment information associated with both medical treatment devices 108, 130 and caregiver performance data can be displayed at a single companion device 110, 111, 119 within the same user interface. For example, FIG. 1C illustrates another example of an emergency scene where medical treatment devices 108, 130 both communicate with companion tablet 119 via a wireless communication link. In some examples, supervisor 118 can monitor patient treatment information received from the defibrillator 108 and the ventilator 130 at the companion device 119. In some examples, the patient treatment information can be displayed within one or more selectable views at the companion device 119 or within a single user interface view. In addition, the user interface views at the companion device 119 can include user inputs that allow the supervisor to transmit instruction signals to provide data or issue commands to control one or more functional operations of the medical treatment devices 108, 130. Providing the ability for a single caregiver to view case information from multiple medical treatment devices 108, 130 provides a technical solution to a clinical problem and technical problem in that a caregiver and/or supervisor using the companion device 119 can provide enhanced coaching and support to other rescuers 104, 106 no matter the environment in which emergency care is being provided and may enable control of one or more of the multiple treatment devices in terms of their operation or what they display. Further, in certain emergency care situations where patient access or rescue personnel are limited, providing a single caregiver with the ability to monitor case information simultaneously from multiple medical treatment devices 108, 130 and transmit instruction signals to control operation of the medical treatment devices 108, 130 enables patients to receive advanced medical care in remote or non-traditional care environments.

Figure 1D:
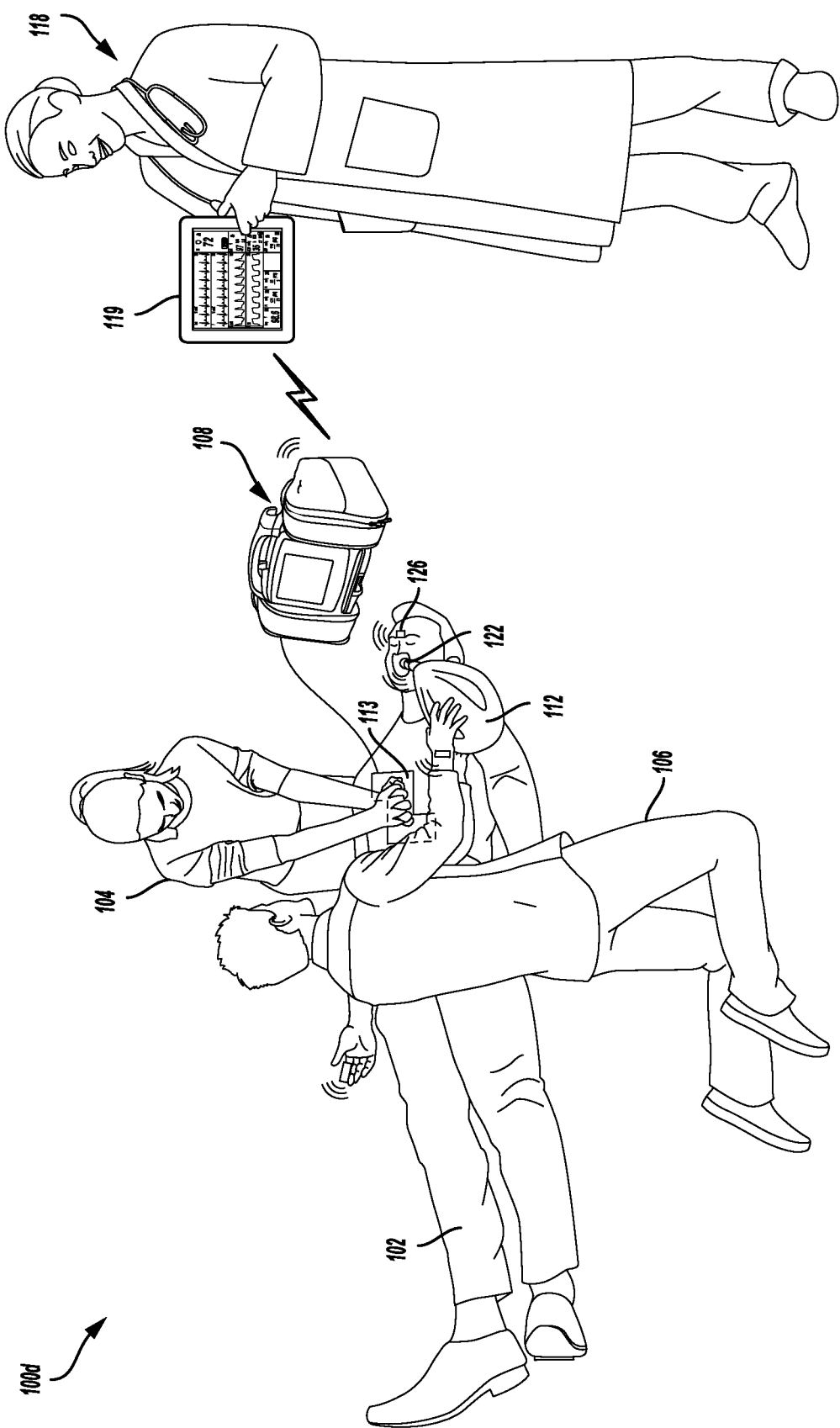

FIG. 1D illustrates another embodiment of an emergency scene 100d, including medical treatment device 108 in direct wireless communication with companion device 119 (e.g., without communication via a local area network (LAN), wide area network (WAN), the Internet, a cloud service, or other intervening network communication). For example, the wireless communication may include Wi-Fi, Bluetooth, near field communication (NFC), Zigbee, or other wireless communication. The wireless communication channel, in some implementations, is a secure channel. For example, the wireless communication channel may be password protected, encoded, or otherwise protected from connection from unauthorized devices. While illustrated as a communication with just the single companion device 119, in other embodiments, two or more companion devices may be in direct wireless communication with one or more medical treatment devices.

A local wireless communication channel can be established among two or more of the devices at the emergency care scene to enable data to be securely and accurately shared among the devices. For instance, referring to FIG. 2, health data about the patient, data indicative of treatment delivered to the patient, or other types of data can be exchanged over the wireless communication channel 200. The exchange of data over the wireless communication channel 200 enables treatment by multiple rescuers to be coordinated in an efficient and accurate manner. In some examples, a wireless communication channel is established among only some of the devices involved in treatment of the patient (e.g., between two of the devices). In some examples, a wireless communication channel is established among all of the devices involved in treatment of the patient.

Figure 2:
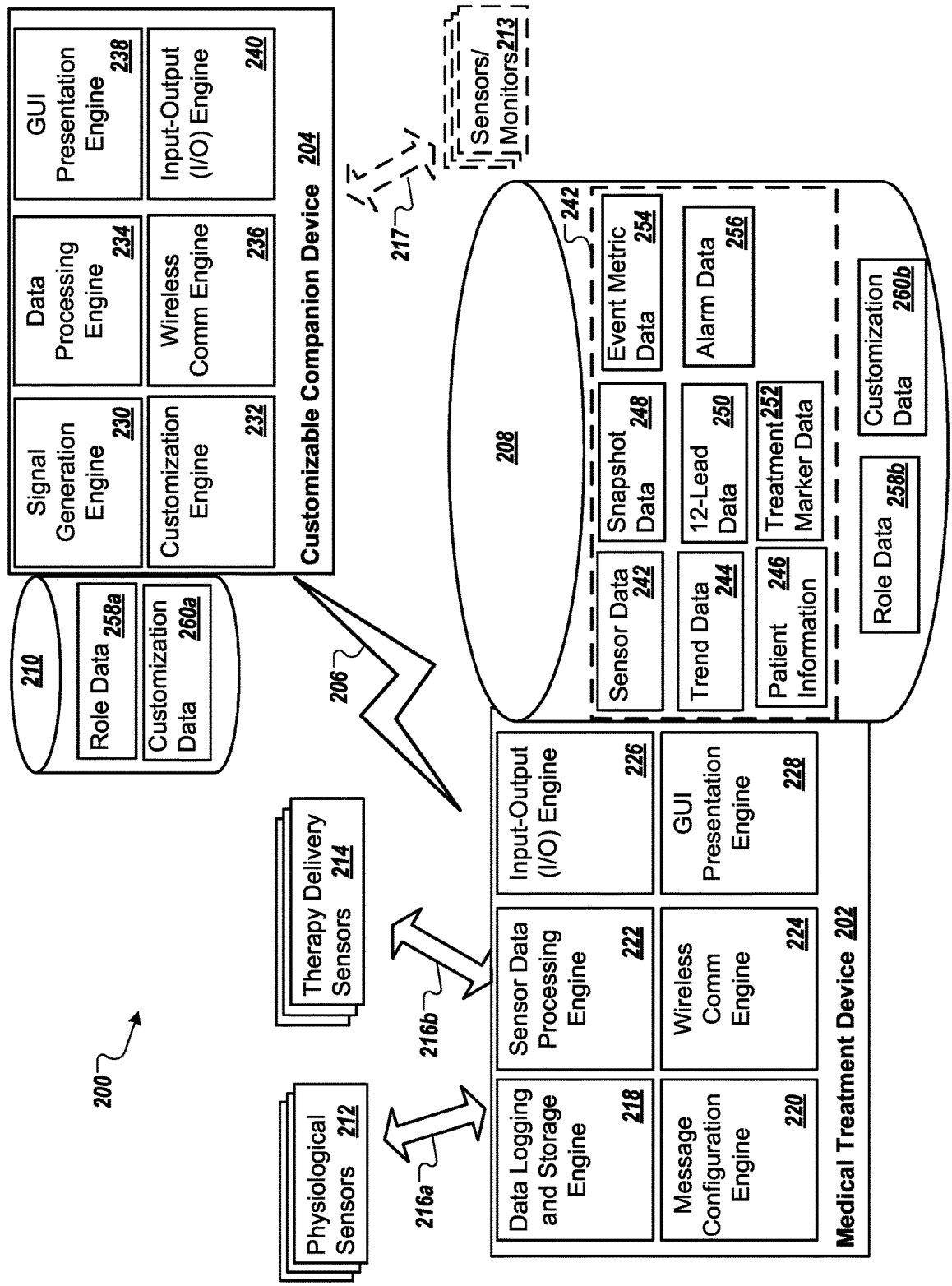
FIG. 2 illustrates an example environment for providing and monitoring patient treatment with a set of devices within a medical treatment system.

Turning to FIG. 2, in some implementations, an example environment 200 for customizing display of case information at a companion device includes a medical treatment system with a set of devices for providing treatment to a patient during a medical event. The system may include a medical treatment device 202 (e.g., medical treatment devices 108, 130) and one or more companion devices 204 (e.g., companion devices 110, 111, 119) communicatively coupled to the medical treatment device 202 via communication link 206. The devices 202, 204, in the illustrated example, of the medical treatment system may be co-located at a treatment delivery site, such as a hospital, medical clinic, or ambulance. In other implementations, one or more of companion devices 204 may be added to the system at some point during delivery of a medical therapy or subsequent to delivery of therapy. Conversely, at least one companion device 110, 111, 119, 204 may be removed from co-location during or subsequent to delivery of therapy. The devices may be configured for data communication in a wired or wireless manner for transferring information between certain devices 202, 204 of the system during and/or subsequent to delivery of therapy.

In some implementations, the wireless communication link 206 for connecting the medical treatment device 202 and the companion device 110, 111, 119, 204, in some examples, may be a Wi-Fi network, other short-range wireless communication network or near field communication (NFC) network, local area network (LAN), wide area network (WAN), or the Internet. In other examples, the devices 202, 204 can be configured to communicate over longer communications ranges such as over a cellular communication network. In some implementations, the medical treatment device 202 may function as a wireless access point to provide a direct wireless connection with the companion device 110, 111, 119, 204. In other examples, the wireless communication link 206 can be provided via Bluetooth personal area network.

In some embodiments, different devices 202, 204 may be configured to communicate with one another over different types of communication links 206. In some implementations, the devices 202, 204 can be configured to transmit data via a short-range wireless communication transmitter, e.g., a Bluetooth beacon, to a receiver. In one example, a first companion device 110, 111, 119, 204 may communicate with the medical treatment device 202 via a Wi-Fi communication link while a second companion device 110, 111, 119, 204 may communicate with the medical treatment device via a Bluetooth communication link. In some implementations, a companion device 110, 111, 119, 204 can connect to the medical treatment device 202 via the wireless communication link without having to physically access or interact with the medical treatment device 202. In some examples, transport layer security (TLS) is used at an application level to provide a secure (encrypted) connection between the devices 202, 204. As a second layer of protection, encrypted Wi-Fi or encrypted Bluetooth can be used at a physical layer.

In some implementations, when the wireless communication link 206 is a cellular communication link, the functionality of the medical treatment device 202 can be extended to clinicians who are off-scene and/or performing remote telemedicine. For example, when EMS are transporting a patient to the hospital in an ambulance, a medical team awaiting the arrival of the patient to the hospital can stream real-time case information at a companion device 110, 111, 119, 204 at the hospital via cellular link. In some examples, the wireless communication link 206 can include combinations of multiple wireless communication networks based on proximity of the medical treatment device 202 to the companion device 110, 111, 119, 204.

In some implementations, each of the medical treatment device 202 and the companion device 110, 111, 119, 204 includes a respective wireless communication engine 224, 236 for enabling wireless communication between the devices 202, 204 via the wireless communication link 206. For example, the wireless communication engine 224 of the medical treatment device 202 can be configured to transmit messages generated by message configuration engine 220 to the companion device 110, 111, 119, 204. Wireless communication engine 236 of the companion device 110, 111, 119, 204 can be configured to transmit instruction signals generated by signal generation engine 230, for some examples, such instruction signals may be for controlling one or more functional operations of the medical treatment device 202. In some examples, the wireless communication engines 224, 236 are configured to apply encryption protocols to outgoing signals being transmitted to the other device 204, 202. Similarly, the wireless communication engines 224, 236 can decrypt incoming signals from the other device 204, 202.

In certain embodiments, the wireless communication engine 224 of the medical treatment device 202 can be configured to detect that a respective companion device 110, 111, 119, 204 is within communication range and in response, initiates one or more actions to connect to the companion device 110, 111, 119, 204 via the wireless communication link 206. In some implementations, a companion device 110, 111, 119, 204 that is pairable with the medical treatment device 202 can be preconfigured to automatically connect to the medical treatment device 202 via the wireless communication link 206 when within communication range, without having to discriminate between other devices that happen to be within range and/or negotiate a wireless communication connection. Further, rather than requiring a user to potentially spend significant amounts of time in manually configuring the system of each companion device 110, 111, 119, 204 to connect to the medical treatment device 202, or accessing a screen to view and then select from possible device connections, companion devices 110, 111, 119, 204 located at the emergency scene may be pre-configured to dynamically join and/or leave the secure network or pairing with the medical treatment device 202, for example, automatically and/or with one or more simple actions (e.g., switch actuation, pressing a button, near field communication connection, radio frequency, location/proximity recognition, gestural code, tap/bump recognition, motion-activated, sound/vibration, voice command/recognition, amongst others) and/or merely by being in close physical proximity to one another such as by a Bluetooth proximity connection. For example, upon selecting icon 601 in a device view 600 of the companion device (FIG. 6A), a device user can view all available pre-configured wireless communication links that are available for the companion device 110, 111, 119, 204 to connect to the medical treatment device 202. The user can also view other available networks that have not been pre-configured for connection. In some examples, the companion device 110, 111, 119, 204 may be pre-configured for pairing to other medical treatment devices, and those preconfigured networks can also be displayed upon selecting icon 601.

Once such connection via the wireless communication link 206 is made, despite the presence of numerous other devices located nearby, patient information (e.g., physiological data, patient history, rescue info) can be sent back and forth between the connected devices 202, 204 in a reliable and secure manner (e.g., according to HIPAA standards, 802.11i protocols) using any suitable type of communication. Companion devices 110, 111, 119, 204 that are correctly paired with their respective medical treatment devices 202 can help avoid risk of erroneous patient information to be transmitted between medical devices, which could be detrimental to patient outcomes. In some embodiments, to maintain accurate and secure communications, the proximity-based interaction may invoke an authentication protocol, such as the use of encrypted keys, vector initialization, hash encryption, digital certificates, etc., ensuring no drops and/or leakage of data transfer between devices. Additionally, the wireless communication engine 224 of the medical treatment device 202 can be configured to simultaneously cause transmission of real-time streaming data to multiple companion devices 204 via separate wireless communication links 206 for each companion device 110, 111, 119, 204.

In some implementations, a number of additional security-oriented design elements can also be implemented for the medical treatment system to ensure that data exchanged between the medical treatment device 202 and companion device 110, 111, 119, 204 remains secure. For example, the medical treatment device 202 and/or the companion device 110, 111, 119, 204 can use certificate-based authentication to ensure the authenticity of the respective paired device. In some examples, upon initial connection and setup, the devices 202, 204 can execute an association process to tie a particular companion device 110, 111, 119, 204 to a single medical treatment device 202 so that only the companion device 110, 111, 119, 204 (and any other similarly paired companion devices) can interoperate with the medical treatment device 202. In some embodiments, any Representational State Transfer (REST) or WebSocket communications may require an authenticated connection to enable data exchange between the device 202, 204. The medical treatment device 202, in some examples, prohibits connection to open Wi-Fi communication links and may only connect to manually defined (e.g., supervisor-defined) Wi-Fi networks. As an additional security measure, when the wireless communication link 206 is a Bluetooth connection, the devices are paired during initial setup when initial connection settings are configured. Further, the data and computer architecture of the medical treatment device 202 can be designed for additional security, which can include separating communications and clinical control onto separate microprocessors.

In some examples, when there are more than one companion devices 110, 111, 119, 204 paired with the medical treatment device 202, one of the companion devices 110, 111, 119, 204 may be designated in advance as the primary companion device. The primary companion device may be so designated by the medical treatment device 202 during device setup, pairing and provisioning by receiving and storing an encrypted token from the medical treatment device 202. The encrypted token may be sent with every instruction from the primary companion device 110, 111, 119, 204 to the medical treatment device 202.

Figure 6A:
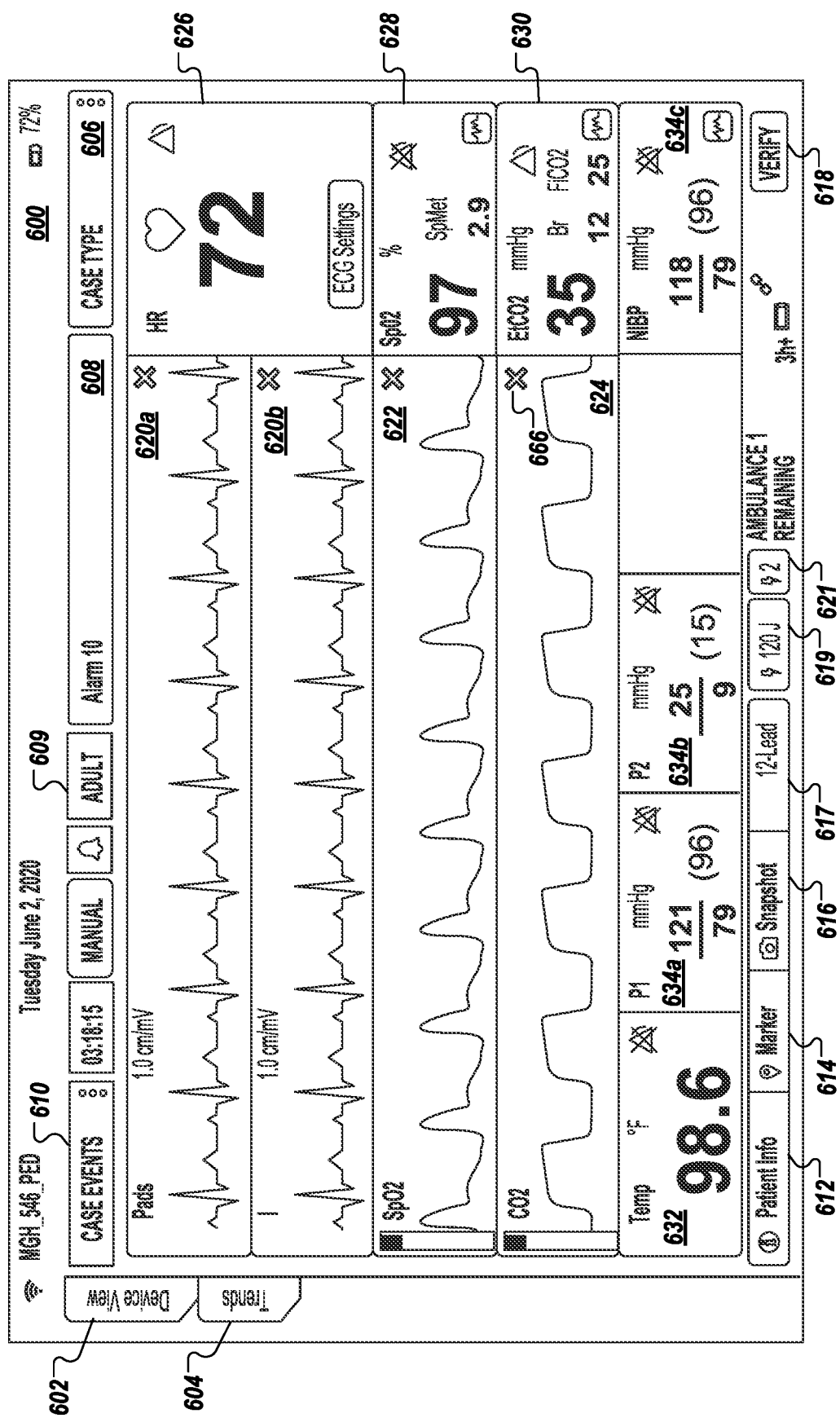
FIGS. 6A-6C illustrate example graphical user interface screens for display at a companion device.

In some implementations, the companion device 110, 111, 119, 204 can display status information for the medical treatment device 202 at one or more of the display views (FIG. 6A through FIG. 6C and FIG. 8B through FIG. 8G) of the companion device 110, 111, 119, 204. For example, as shown in FIG. 6A, device view 600 can include status bar 603 that displays an amount of battery life, connection status, and a unique name for the medical treatment device 202.

Additionally, in some implementations, the companion device 110, 111, 119, 204 includes a control for confirming connection between the companion device and a particular medical treatment device. This provides the technical advantage of confirming wireless pairing between a companion device and one of multiple medical treatment devices deployed to a same site. The provision of a user input at the companion device, such as by way of actuation of a user interface option, may be configured to provide for transmission of one or more signals to the medical treatment device to which the companion device is already paired, wherein the one or more signals comprise a request for the medical treatment device to identify itself. The medical treatment device, in response to receipt of the one or more signals, may be configured to provide an output to identify itself to the user of the companion device. The medical treatment device may be configured to provide a predetermined indication on its display to indicate it has received the request to identify itself. In other examples, the output may comprise an audible output to identify itself. In one or more examples, this confirming connection feature may comprise a key aspect of the functionality of the companion device. In the illustrated example, the status bar 603 can include a verification input (e.g., input selector 618 in device view user interface of FIG. 6A) that allows the companion device 110, 111, 119, 204 to cause an indicator to flash at the medical treatment device 202 to confirm that the companion device 110, 111, 119, 204 is connected to the correct medical treatment device 202 at time of use. For example, one or more display views of the companion device 110, 111, 119, 204 (e.g., device view UI screen 600 in FIG. 6A) can include a paired device verification input 618 that allows a companion device user to verify which medical treatment device 202 the companion device 110, 111, 119, 204 is connected to. In some examples where multiple medical events are occurring at the same time, such as in a trauma unit of a hospital or on a scene of a mass casualty, there may be multiple rescue teams operating multiple medical treatment devices within close proximity of one another. In such situations, it may be easy to mix up companion devices that are paired to respective medical treatment devices. Therefore, in some implementations, when the verification input 618 is selected, the companion device 110, 111, 119, 204 may generate an instruction signal that causes the connected medical treatment device 202 to generate an indication of being paired with the companion device 110, 111, 119, 204. In some implementations, upon receiving a verification signal from the companion device 110, 111, 119, 204, the medical treatment device 202 may output a visual and/or audible indication of being connected to the companion device 110, 111, 119, 204. In some examples, the indication can be a flashing light and/or a tonal sound pulse.

Figure 3:
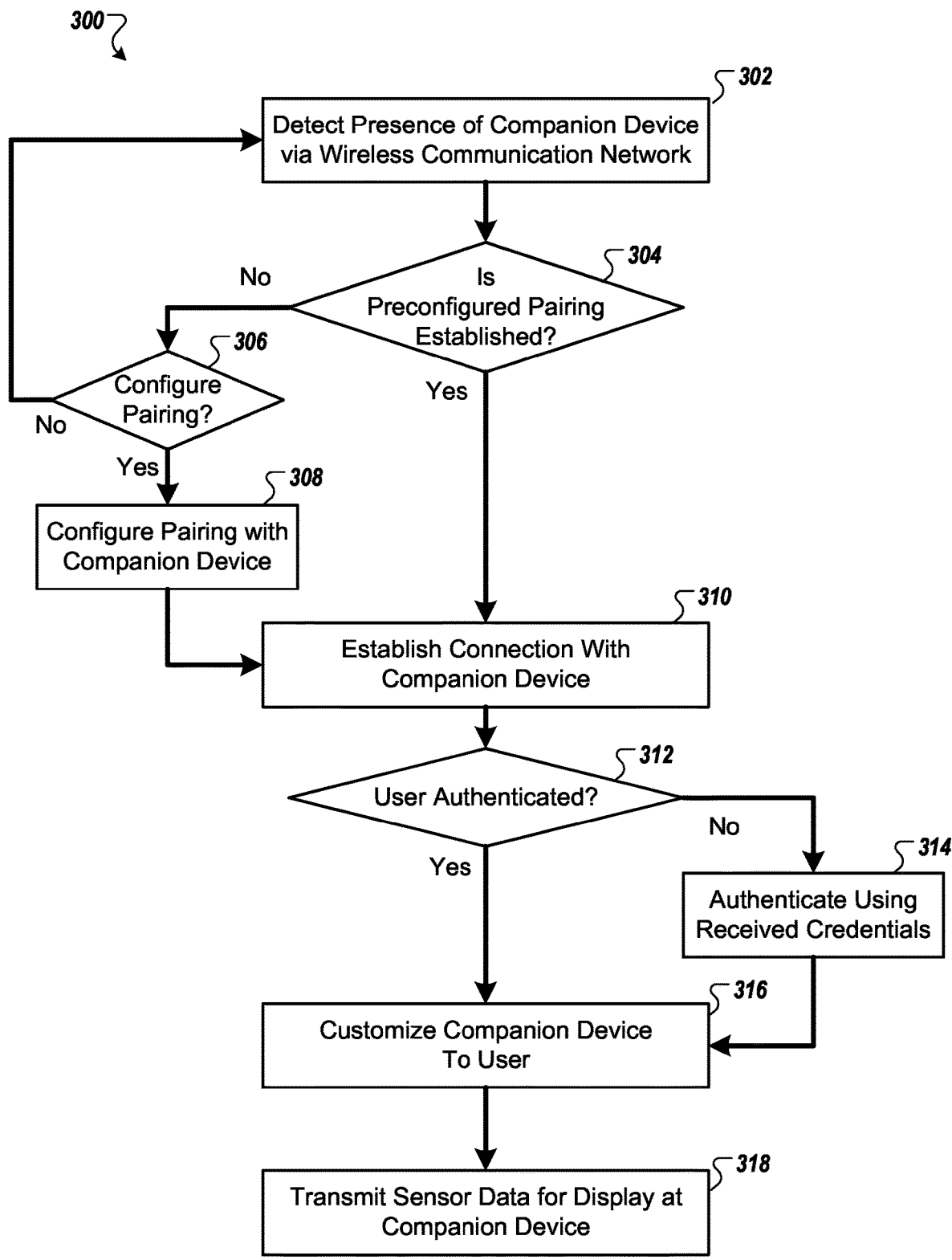
FIG. 3 is a flow chart of an example method for configuring connection between a medical treatment device and a companion device.

Turning to FIG. 3, in some implementations, an example method 300 for configuring connection between a medical treatment device 202 and a companion device 110, 111, 119, 204 is illustrated. In some examples, the method 300 begins with medical treatment device 202, such as a defibrillator, detecting the presence of a companion device 110, 111, 119, 204 based on the companion device 110, 111, 119, 204 via wireless communication network 206 due to the companion device 110, 111, 119, 204 being within communication range of the medical treatment device 202 (302). If the medical treatment device 202 and the detected companion device 110, 111, 119, 204 already have a preconfigured pairing with each other established (304), then in some examples, the medical treatment device 202 and the companion device 110, 111, 119, 204 establish a wireless connection (306). In some embodiments, the previously paired medical treatment device 202 and the companion device 110, 111, 119, 204 may automatically connect to one another. In other examples, upon detection of the respective device, the medical treatment device 202 and/or the companion device 110, 111, 119, 204 may present a notification to a user at a display interface requesting user authorization for connection to the other device 202, 204. In response to presenting the notification, if one or both of the devices 202, 204 receives an input confirming the connection to the other device 202, 204, then the wireless communication link between the devices 202, 204 is established.

If a preconfigured pairing between the two devices 202, 204 has not been established, then in some aspects, a determination may be made whether to establish a wireless connection between the devices 202, 204 (306). In some examples, only devices 202, 204 that have been through an initial setup and pairing process can wirelessly connect to one another. In another example, a supervisor or system administrator may be authorized to configure a pairing between the medical treatment device 202 and the companion device (308) prior to initial connection between the devices 202, 204 (310). In one example, this initial pairing can include one or more types of wireless communication links such as Wi-Fi, Bluetooth, or Zigbee connections.

In certain embodiments, if a credentialed user has been authenticated at the companion device (312), then in some examples, the companion device 110, 111, 119, 204 may customize one or more companion device display views to user preferences or a treatment role of the user (316) based on stored role data 258a customization data 260a as discussed further below. In some examples, if less than a threshold amount of time has passed between uses of the companion device 110, 111, 119, 204, the companion device 110, 111, 119, 204 may automatically authenticate a previous user to use the companion device 110, 111, 119, 204. Otherwise, if more than the threshold period of time has passed and/or a new user is logging in to use the companion device, then in some implementations, the companion device 110, 111, 119, 204 may authenticate the user with received credentials, such as username/password inputs, at least one biometric input provided at a biometric input interface (e.g., fingerprint, iris recognition, facial recognition), and/or a badge scan via a scanning sensor on the companion device (e.g., RFID scan or a computer-readable code such as a QR code) (314). In some examples, upon authentication, the user may provide one or more inputs confirming or modifying a treatment role of the user in the associated medical event. Based on the indicated treatment role, the companion device 110, 111, 119, 204 may further customize the display views at the companion device 110, 111, 119, 204 to the indicated role of the user. In some embodiments, based on the customized display interface screens being presented at the companion device as well as user inputs received at the display interface, the medical treatment device 202 may transmit requested sensor data for display at the companion device in the customized format (318). In some implementations, in response to establishment of the connection between the companion device 110, 111, 119, 204 and medical treatment device 202 and/or authentication of the device user, the medical treatment device 202 may automatically begin streaming case information via the wireless communication link 206 for display at the companion device 110, 111, 119, 204 without any user intervention.

Although described as a particular series of steps, in other embodiments, more or fewer steps may be included. For example, the medical treatment device 202 may only connect to a companion device 110, 111, 119, 204 that has had a preconfigured pairing established. On the other hand, if it is determined that a predetermined pairing exists between the medical treatment device 202 and a detected companion device 110, 111, 119, 204, one or more additional steps related to ensuring data security of the wireless connection may be performed. In further embodiments, certain steps may be performed in a different order, or two or more steps may be performed in parallel. For example, a user may be authenticated at the companion device 110, 111, 119, 204 prior to a connection being established between the medical treatment device 202 and the companion device 110, 111, 119, 204. Other modifications of the method 300 are possible while remaining in the scope and purpose of the method 300.

Returning to FIG. 2, in some implementations, the companion device 110, 111, 119, 204 includes a signal generation engine 230 that generates instruction signals, data requests, and other data signals for transmitting to the medical treatment device 202. In some examples, in response to receiving user inputs (e.g., selections at a touchscreen of the companion device 110, 111, 119, 204) to view one or more items of case information at customized user interface screens on the companion device 110, 111, 119, 204, the signal generation engine 230 can generate a data request message from transmitting to the medical treatment device 202. In some examples, the data requests can be of one or more data requests type based on a type and amount of data being requested. For example, one type of data request includes a request for a single type of data from the medical treatment device (e.g., trends data) or for a relatively small number of pieces of data (e.g., ventilation data for generating a ventilation dashboard). Another type of data request can include requests for complex data groupings, such as all case information necessary to recreate a device view or requested case type view. Generating specific data requests of the medical treatment device 202 allows the companion device to flexibly modify the set of data it has subscribed to at any moment. In some examples, data subscriptions for the companion device 110, 111, 119, 204 correspond to all of the data requested by the companion device 110, 111, 119, 204 for display at any given time. Requesting data from the medical treatment device as a set of data subscriptions provides companion devices 110, 111, 119, 204 the ability to show different types of data on demand and minimizes bandwidth used by avoiding transmission of unnecessary data that the companion device user does not wish to have displayed.

In certain embodiments, the signal generation engine 230 can also generate instruction signals for causing one or more functional operations to occur at the medical treatment device 202. In some examples, the one or more functional operations can include linking and storing certain submitted data associated with the medical event (e.g., patient information or treatment marker data) and/or capturing or analyzing certain medical event data (e.g., generating 12-lead ECG analysis or recording a defibrillator snapshot). For example, the signal generation engine 230 can generate a patient information signal in response to receiving submission of patient identification information at a patient information input interface of the companion device 110, 111, 119, 204 (see interface 700 in FIG. 7A). The patient information signal can include the submitted patient information, and in response to receiving the signal, the medical treatment device 202 can link and store received patient information 246 with case information 242 for the patient within data repository 208. In addition, in response to receiving one or more treatment marker inputs at a treatment marker input interface of the companion device 110, 111, 119, 204 (see interface 712 in FIG. 7B), the signal generation engine 230 can generate a treatment marker signal, which can include submitted treatment marker data. In response to receiving the signal, the medical treatment device 202 stores the submitted treatment data 252 in data repository 208. In some implementations, in response to detecting selection of a snapshot input selector at the companion device 110, 111, 119, 204 (e.g., snapshot input selector 616 in FIG. 6A), the signal generation engine 230 can generate a snapshot instruction signal that, in response to being transmitted to the medical treatment device 202, causes the medical treatment device 202 to capture and store a snapshot (e.g., ECG record of the patient for a period of time, such as 9-12 seconds, before and after the instruction to capture the snapshot, physiological signal captured by another physiological sensor for a period of time before and/or after the instruction to capture the snapshot, a single captured frame of the medical treatment device interface or a recording of the medical treatment device screen for a predetermined number of seconds) as snapshot data 248 for the respective patient within the data repository 208. In response to detecting selection of a 12-lead ECG analysis input selector at the companion device 110, 111, 119, 204 (e.g., 12-lead analysis input selector 617 in FIG. 6A), in some examples, the signal generation engine 230 can generate a 12-lead analysis instruction signal that causes the medical treatment device 202 to perform a 12-lead analysis, which can be stored as 12-lead data 250 for the respective patient in data repository 208.

The medical treatment device 202, in some implementations, can include a message configuration engine 220 for generating messages for sending to the companion device 110, 111, 119, 204. In one example, in response to receiving a data request from the companion device 110, 111, 119, 204, the message configuration engine 220 can package the requested data in one or more predetermined message configurations or formats for transmission. In some implementations, real-time or near real-time data (e.g., case information derived from physiological sensors 212 and caregiver performance sensors 215) can be transmitted as streaming data in a JavaScript Object Notation (JSON) format sent over a WebSocket. Historical and bulk data transfers, in some examples, can be transmitted as Representational State Transfer (REST) data in JSON-formatted messages. Both types of message communications (streaming data and REST data) can occur over a transport layer security (TLS) connection, which can use a TCP/IP protocol. The TCP/IP protocol can be provided over Wi-Fi or Bluetooth physical media. When data transfer occurs in real-time or near real-time, case information is simultaneously displayed at the companion device 110, 111, 119, 204 and the medical treatment device 202 or an amount of latency for displaying the case information at the companion device 110, 111, 119, 204 is less than a predetermined threshold.

In addition to configuring messages for sending real-time case information for display at the companion device 110, 111, 119, 204, in some implementations, the message configuration engine 220 can generate one or more confirmation messages when an action is taken at the medical treatment device 202 in response to receiving an instruction signal from the companion device 110, 111, 119, 204. For example, in response to associating and storing submitted patient information provided by the companion device 110, 111, 119, 204, the message configuration engine 220 can generate a message confirming that the submitted patient information has been linked to the respective case information within data repository 208. The message configuration engine 220 can also generate treatment marker recording confirmation messages confirming that recording of the submitted treatment marker at the medical treatment device 220 has commenced and/or completed (see FIG. 7B for notifications 714, 718 displayed at the companion device 110, 111, 119, 204 in response to receiving the treatment marker recording messages). Snapshot recording confirmation messages confirming that recording and storing of a snapshot at the medical treatment device 220 has commenced and/or completed can also be generated (see FIG. 7C-1 for notification messages 724, 726 displayed at the companion device 110, 111, 119, 204 in response to receiving the snapshot recording confirmation messages). 12-lead ECG analysis confirmation messages confirming that a 12-lead ECG analysis has commenced and/or completed can also be generated (see FIG. 7C-2 for notification messages 728, 730 displayed at the companion device 110, 111, 119, 204 in response to receiving the snapshot recording confirmation messages).

In some implementations, the companion device 110, 111, 119, 204 can also provide caregivers the ability to view and scroll through past case information 242 at the companion device 110, 111, 119, 204. In some examples, while viewing past case information 242, the companion device 110, 111, 119, 204, 204 can provide users the ability to jump to a current (live) view at any time during the medical event. In one example, the companion device 110, 111, 119, 204 may indicate on the display screen whether a live view is being displayed. In some embodiments, companion device users can jump forward and backward in time in discrete time segments (e.g., 5, 10, 15, 20, 30 seconds) to view a patient's physiological condition and caregiver performance data at different points during the medical event. In one example, the companion device display interface can provide a touch spot for each waveform that provides for playback of the respective waveform. Additionally, the companion device 110, 111, 119, 204 can play back past medical event data at different speeds (e.g., 0.5×, 1×, 2×) to gain a better perspective of how treatment has progressed. In some examples, the companion device 110, 111, 119, 204 can display past medical data for a number of different monitored physiological sensor inputs (e.g., ECG, SpO2, CO2), vital sign data, and caregiver performance data. Additionally, even when non-real-time data is being displayed at the companion device 110, 111, 119, 204, the medical treatment device 202 continues to transmit real-time streaming case information to the companion device 110, 111, 119, 204. In one example, the companion device 110, 111, 119, 204 can also provide a lookback feature for limited time increments (e.g., 10, 20, 30 seconds) that allows the user to quickly view waveform data at the lookback increment. In example, the lookback feature can be activated via a touch spot on the respective waveform.

In some implementations, the medical treatment device 202 can include an input/output (I/O) engine 226 that may gather information from a number of sensors (e.g., physiological sensors 212, caregiver performance sensors 215) built into the medical treatment device 202 and/or in communication with the medical treatment device 202. The I/O engine 226 can also receive user inputs at a user input interface (e.g., keypad or touchscreen) on the medical treatment device 202. In some examples, raw sensor data from sensors 212, 214, 215 can be processed and analyzed by sensor data processing engine 222, which generates a number of clinical metrics and trends regarding aspects of the treatment session (e.g., for use by clinical personnel) that can be output by the medical treatment device 202 (e.g., displayed at a screen of the medical treatment device 202 or printed as a report). Data logging and storage engine 218 can store generated metrics and trends in data repository 208 for the respective patient and/or medical event as metric data 254, and trend data 244, respectively. GUI presentation engine 228, in some embodiments, causes data processed and analyzed by the sensor data processing engine 222 to be presented at a display interface screen on the medical treatment device 202.

In some examples, sensor processing engine 222 also processes raw ECG sensor data into first ECG information that is provided to GUI presentation engine 228 for display at medical treatment device 202 and second ECG information that is provided to GUI presentation engine 238 for display at companion device 110, 111, 119, 204. In some examples, because the display interfaces at the medical treatment device 202 and companion device 110, 111, 119, 204 can be differently sized, the sensor processing engine 222 can time-slice the first and second ECG information differently based on the display device. In one example, the local display for the medical treatment device 202 receives small intervals of first ECG information more frequently (e.g., 8 ms at a time) while the companion device 110, 111, 119, 204 receives larger intervals of second ECG information less frequently (e.g., 120 ms at a time). This configuration of first and second ECG information can allow the companion device 110, 111, 119, 204 to display ECG information in real-time yet also improves data transmission efficiency because sending larger data messages is more efficient than sending smaller data messages. Additionally, even though the content of the first and second ECG information is the same, the first and second ECG data may be represented differently. For example, the first ECG information displayed at the medical treatment device may include binary data records while the second ECG information the companion device 110, 111, 119, 204 receives may be a JSON representation as a Websocket stream. Additionally, both the first and second ECG information signals can carry additional information per-sample bit-flags that represent specific detected conditions associated with a processed ECG data sample (e.g., QRS detection, lead fault, implanted pace detection, internal pace blanking, defibrillator shock information such as energy and number of times shock has been administered). Other additional information, such as cable type and filter settings may be provided to both of the GUI presentation engines 228, 238 as additional messages separate from ECG waveform sample data.

In some aspects, a data processing engine 234 of the companion device 110, 111, 119, 204 can be configured to process case information 242 received from the medical treatment device 202 in one or more received data messages. GUI presentation engine 238 can cause the processed medical event data to be displayed in one or more display sections of a device interface at the companion device 110, 111, 119, 204. An I/O engine 240 can receive and process user inputs at a device interface, such as a touchscreen interface, where a user makes selections to customize the display of data at the companion device 110, 111, 119, 204 as well as to cause one or more functional operations to occur at the medical treatment device 202. GUI presentation engine 238, in some implementations, causes data processed and analyzed by the data processing engine 234 and configured by customization engine 232 to be presented at a display interface screen on the companion device 110, 111, 119, 204.

Customization engine 232, in some embodiments, can be configured to control and manage the configuration of display screens presented at the display interface of the companion device 110, 111, 119, 204 by the GUI presentation engine 238 based on a user role and/or data presentation preferences. In some examples, data storage region 210 of the companion device 110, 111, 119, 204 can store role data 258a and customization data 260a instead of or in addition to data repository 208 of the medical treatment device 208. In some examples, role data 258a define which data or data dashboards to display in one or more device display views at the companion device 110, 111, 119, 204 as well as the format for displaying the data and data dashboards. In some examples, the roles can include on-scene clinicians (chest compression team member, ventilation team member, drug infuser, supervisor, documenter), off-scene clinicians (attending physician), or non-clinicians (scribe/non-clinician). For example, the role data 258a can define how to display caregiver performance data for a chest compression team member, a ventilation team member, and a team supervisor. For a scribe or non-clinician, the user may only be given access to data input features of the companion device 110, 111, 119, 204 (e.g., patient information inputs and treatment marker recording). When the companion device user is an off-scene (remote) clinician, the user may only be given access to data viewing features, and features related to triggering events or entering patient data may be disabled at the companion device 110, 111, 119, 204.

In some embodiments, customization data 260a can include data display format preferences for different companion device users. For example, the data display preferences can indicate a user-defined working view layout for one or more data dashboards for viewing caregiver performance data. In some implementations, customization engine 232 can be configured to manage user authentication at the companion device 110, 111, 119, 204 (e.g., via user-provided credentials and/or biometric inputs) and access the respective customization data 260a for an authenticated user. In some implementations, once a device user has configured a working view layout, that layout can be stored as customization data 260a for the user and can be automatically loaded at the companion device 110, 111, 119, 204 during a future use by the respective user. The respective customization data 260a can be passed to signal generation engine 230 and/or GUI presentation engine 238 for requesting case information from the medical treatment device 202 and/or causing display of the requested data in a user-preferred format based on the customization data 260a. As discussed further below, the customization data 260a can also define which data or data dashboards to display in working views associated with specific types of medical events (see, for example, case type working views 814, 820, 824, 834, 840, and 844 displayed in FIG. 8B through FIG. 8G).

Figure 4A:
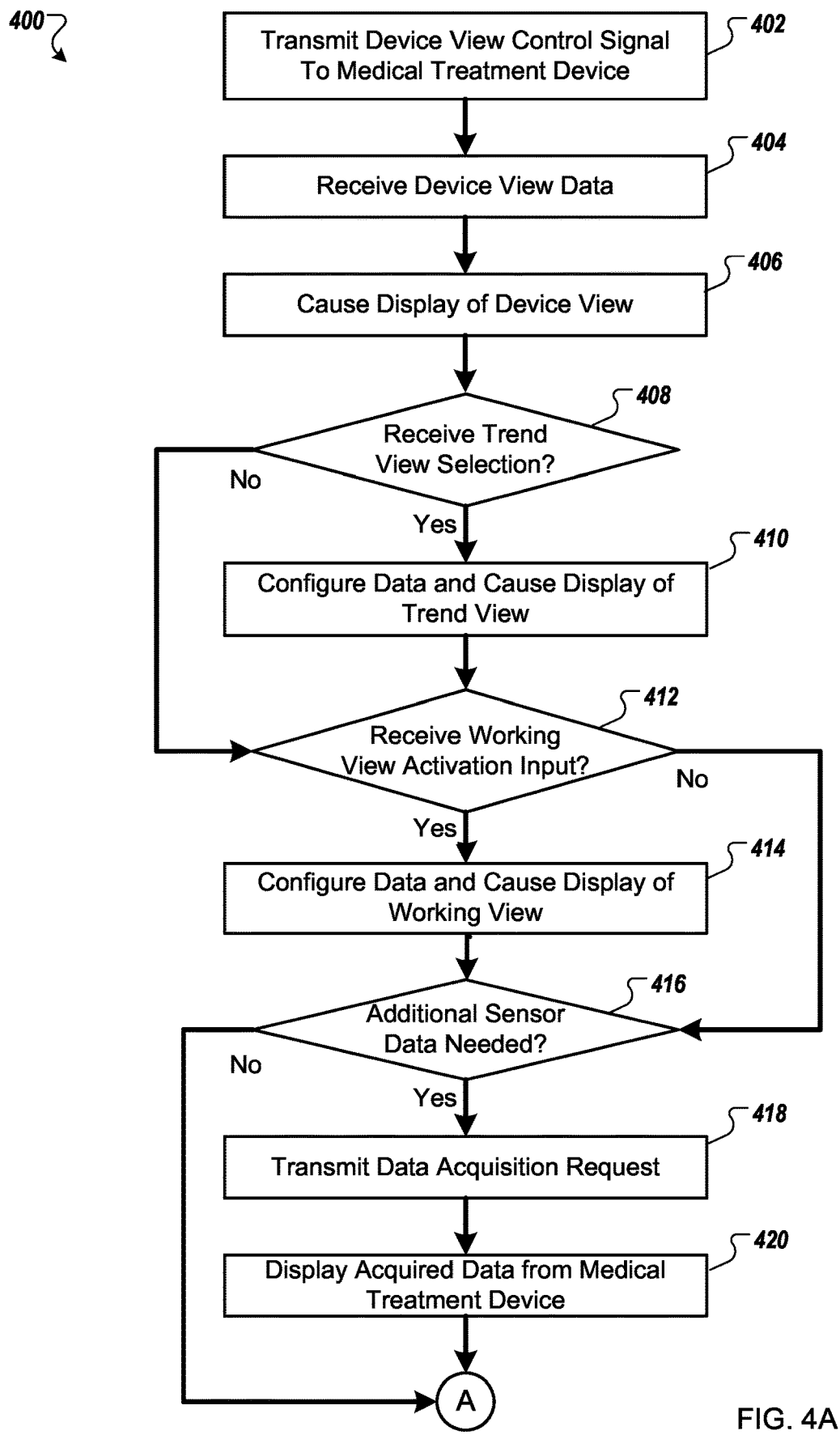
FIGS. 4A and 4B illustrate a flow chart of an example method for causing display of case information for a medical event at a companion device.
Figure 4B:
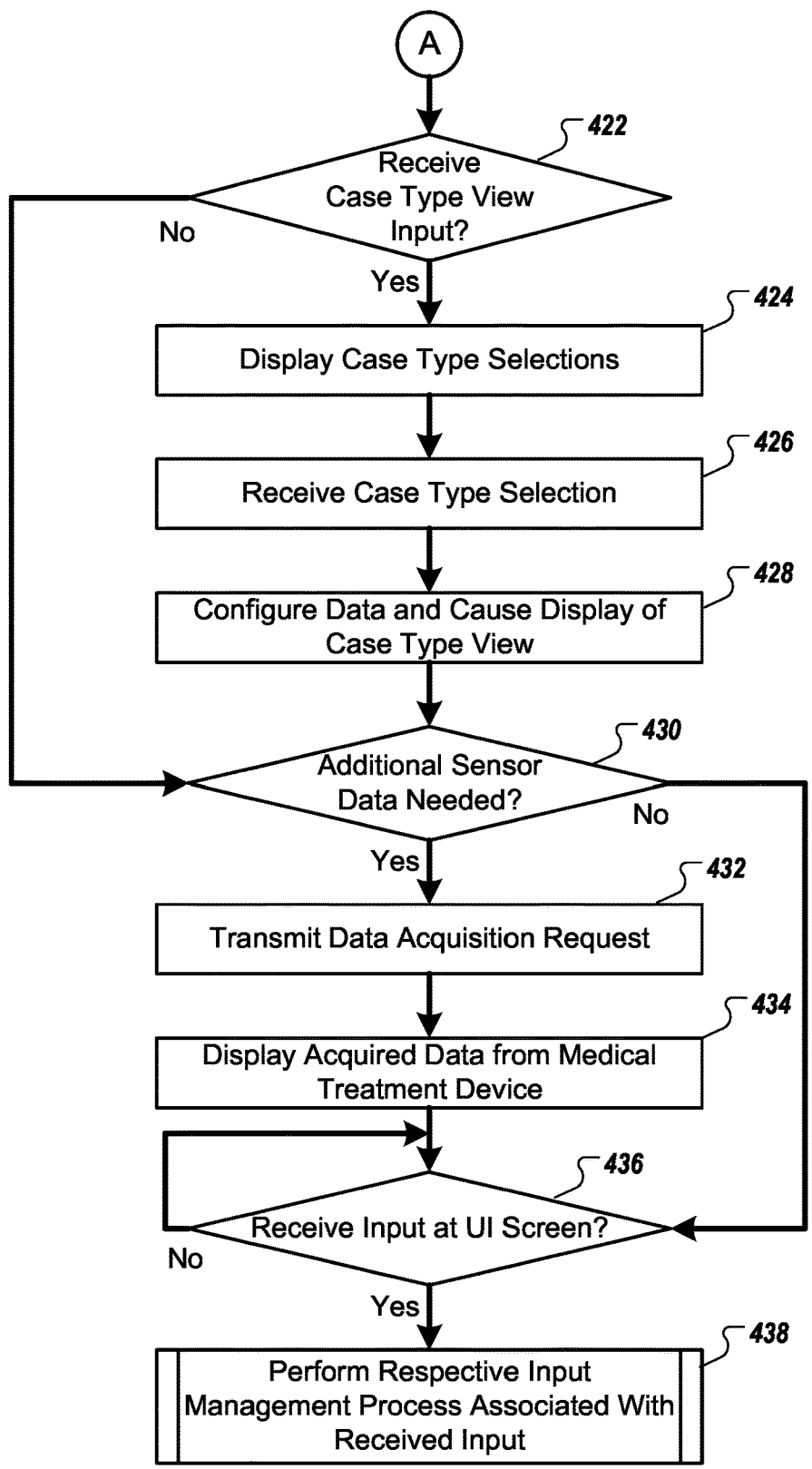

Turning to FIG. 4A and FIG. 4B, an example method 400 for causing display of case information 242 for a medical event at a companion device 110, 111, 119, 204 is illustrated. In some examples, the method 400 begins with companion device 110, 111, 119, 204 transmitting a device view instruction signal to a connected medical treatment device 202 such as a defibrillator (402). In some implementations, the instruction signal corresponds to a request for case information that is presented within a device display view at the companion device 110, 111, 119, 204. In some examples, the device view is one of multiple display views that can be presented at the companion device 110, 111, 119, 204 and corresponds to a display view that, in real-time, presents a visual reproduction of the data that is presented at a display interface of the medical treatment device 202. In some embodiments, in response to transmitting the request signal for device view case information, the medical treatment device 202 sends the requested data over the wireless communication link, which is received the companion device 110, 111, 119, 204 (404). In some examples, the companion device 110, 111, 119, 204 causes display of the received information within the device view at the display interface (406).

FIG. 6A illustrates a device view user interface (UI) screen 600 for a companion device 110, 111, 119, 204. In some examples, the device view UI screen 600 includes one or more selectable inputs at the display interface that cause more, different, or additional information to be displayed, cause one or more actions to be taken at the medical treatment device 202, or provide additional user input interface screens that allow users to submit information that can be transmitted to the medical treatment device 202. For example, the device view 600 can include one or more view selection tabs 602, 604 that allow the user to toggle between different display views for the display interface. In one example, user selection of selection tab 602 causes the device view UI screen 600 to be displayed at the companion device 110, 111, 119, 204. In some implementations, the device view UI screen 600 can display a replication or visual reproduction of the case information 242 displayed the medical treatment device 202. Additionally, the case information 242 may be displayed in the same or substantially the same format at the device view UI screen 600 as on the display screen of the medical treatment device 202. For example, the device view UI screen 600 can display a number of waveforms and metrics indicative of a condition of a patient and/or a status of medical treatment being administered to the patient. In one example, the device view UI screen 600 can include ECG waveforms 620a,b, a pulse oximetry ($SpO_2$) waveform 622, and carbon dioxide ($CO_2$) waveform 624. In other examples, the device view UI screen 600 can also display invasive blood pressure (IBP) waveforms. In some implementations, users can modify which ECG waveforms 620a,b are displayed within the device view via ECG settings user input 629. The UI screen 600 can also display current numeric values for heart rate (HR) 626, $SPO_2$ 628, $CO_2$ 630, temperature 632, and blood pressures

634a,b,c. In some implementations, each of the current numeric values 626, 628, 630 may be positioned directly adjacent to its respective waveform 620a,b, 622, 666 within the device view 600. The device view 600, along with the other companion device display views (trends view 636 (FIG. 6B), working view 668 (FIG. 6C), and case type views 814, 820, 824, 834, 840, and 844 (FIGS. 8B-8G)) can also include status bars and navigation ribbons with one or more selection buttons and treatment information (discussed further below) including a case event selector 610, patient type selector 609, alarm selector 608, case type selector 606, patient information input selector 612, treatment marker input selector 614, snapshot recording selector 616, 12-lead ECG analysis selector 617, shock energy value 619, and number of shocks applied 621.

In some implementations, the information displayed at the device view UI screen 600 may vary from the information displayed at a display interface of the medical treatment device 202. In some examples, the differences between the interfaces can include differences in a type of information displayed, a display layout, or a display format. For example, an amount of magnification of each data section, resolution, size, and screen position may vary between the device view UI screen 600 and the display interface of the medical treatment device 202. Additionally, relative waveform sizes and colors, fonts, and text size may vary between the device view 600 at the companion device 110, 111, 119, 204. In one example, the device view UI screen 600 may display numeric values of all physiological case information in a maximized, large-number format without waveforms. In some examples, one or more items of case information displayed at the device view UI screen 600 may vary from the case information displayed at the display of the medical treatment device 202. FIG. 6E illustrates a display interface 625 at a defibrillator 627. Like the device view 600 at the companion device 110, 111, 119, 204, the display interface 625 at the defibrillator can include ECG waveforms 620a,b, a $SPO_2$ waveform 622, and $CO_2$ waveform 624. The UI screen 600 can also display current numeric values for heart rate (HR) 626, $SPO_2$ 628, $CO_2$ 630, temperature 632, and blood pressures 634a,b,c. However, the display interface at the defibrillator 627 may not include the status bars and navigation ribbons with the case event selector 610, patient type selector 609, alarm selector 608, case type selector 606, patient information input selector 612, treatment marker input selector 614, snapshot recording selector 616, 12-lead ECG analysis selector 617, shock energy value 619, and number of shocks applied 621 that are displayed at the device view UI screen 600. In some implementations, when a shock is administered to a patient, the medical treatment device 202 automatically transmits shock information to the companion device 110, 111, 119, 204, which cause the shock energy value 619 and number of shocks applied value 621 to be updated. As the values are updated, the companion device 110, 111, 119, 204 can apply a burst of color or other indication to the respective display windows to draw a user's attention to the change in value.

In some implementations, view selection tabs 602, 604, 664 (shown in FIG. 6B and FIG. 6C) in the device view UI screen 600 and case type tabs (shown in FIG. 8B through FIG. 8G) allow caregivers to easily toggle between display views of the companion device 110, 111, 119, 204. Being able to switch back and forth between the display views and view real-time case information and caregiver performance data provides a technical solution to clinical problems of not being able to easily grasp a full situational picture when providing care or supervising the care being provided by other caregivers in a rescue team and the technical problem of limitations in display area and display visibility.

Returning to FIG. 4A, in some implementations, upon detection selection of a trends view input at the companion device 110, 111, 119, 204 (e.g., selection of trends view selector 604) (408), the companion device 110, 111, 119, 204 may configure the case information to cause display of a trends view display interface at the companion device 110, 111, 119, 204 (410). In some implementations, configuring trend data for display at the trends view display interface may include transmitting a signal to the medical treatment device 202 to request transmission of medical trend data for real-time display.

Figure 6B:
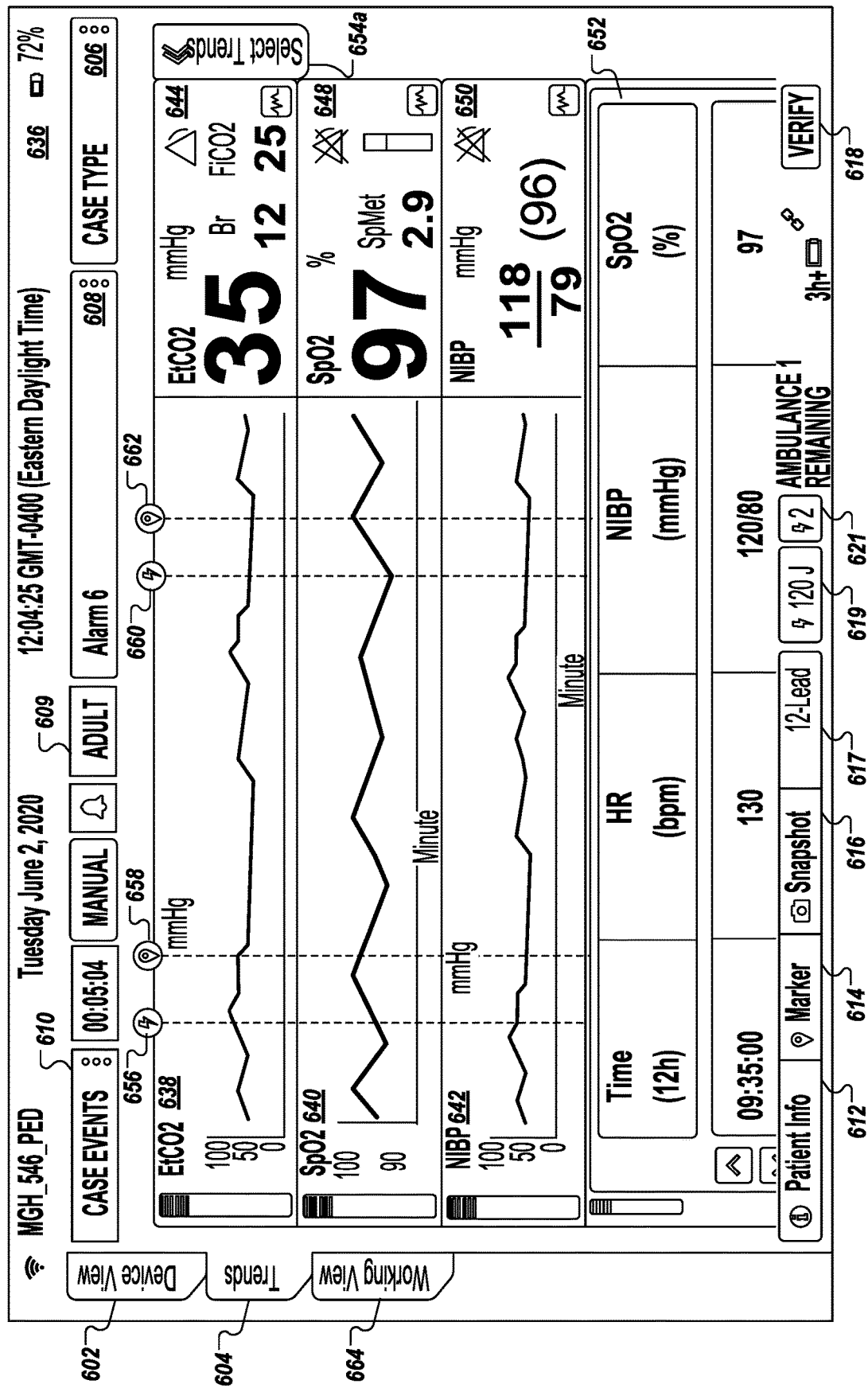

For example, FIG. 6B illustrates a trends view user interface (UI) screen 636 for a companion device 110, 111, 119, 204. In some implementations, the trends view UI screen 636 may display medical trend data in one or more formats for viewing by a device user. Upon selection of the trends view selector 604, in some examples, the companion device 110, 111, 119, 204 may initially present a default set of case information trends (e.g., measured physiological sensor data from the medical treatment device 202) within the trends view 636 in a graphical and/or tabular format. For example, the default set of case information trends presented in the trends view can include graphs of $ETCO_2$ 638, $SPO_2$ 640, and NIBP 642 values over time. The displayed trends at the trend view UI screen 636 can also include mean values of $ETCO_2$ 644, $SPO_2$ 648, and NIBP 650 over the course of the medical treatment event. Additionally, the trend data can also be displayed in a tabular format such as in data table 652 (a full view of data table 652 is shown in FIG. 8C-2). In some examples, the data table 652 can display one or more physiological information data trends (e.g., HR, $SPO_2$, NIBP) at predetermined time intervals (e.g., every 10 seconds, 20 seconds, 30 seconds, 1 minute, 3 minutes, 5 minutes). For example, each row of the data table 652 can correspond to values of one or more types of physiological information recorded at the predetermined time interval.

In some implementations, the companion device 110, 111, 119, 204 may annotate the trend graphs 638, 640, 642 with treatment marker annotations 656, 658, 660, 662 so that a companion device user can readily discern an impact of a respective treatment on a patient's condition over the course of time. As discussed further below (see FIG. 7B), the medical treatment device 202 may automatically record treatment marker events (e.g., detection of a shockable rhythm, application of electric shock to the patient, initiation of chest compressions, initiation of ventilations, etc.) or caregivers may manually input treatment marker data at the medical treatment device 202 for other activities (e.g., administration of a particular drug, placement of an IV, oxygen administration, etc.). Caregivers not actively using the medical treatment device 202 but rather using the companion device 110, 111, 119, 204 may manually input treatment marker data at the companion device 110, 111, 119, 204 that correspond to certain types of medical treatment (e.g., administration of oxygen or medication). In the trends view 636, treatment marker annotations 656, 660 may correspond to shocks applied to the patient by electrodes connected to a defibrillator (e.g., medical treatment device 202), treatment markers 658, 662 may correspond administrations of morphine to the patient, treatment markers may correspond to the initiation of interventions applied to the patient (e.g., when chest compressions and/or ventilations are applied or are paused). In some examples, upon selection of the trends view selector 604, the companion device 110, 111, 119, 204 may transmit a data request, alone or as part of a bulk data transfer request, for treatment marker data 252 to display overlaid on trend graphs 638, 640, 642. Upon selection of one of the treatment marker annotations 656, 658, 660, 662, the companion device 110, 111, 119, 204 may cause display of details about the selected treatment marker, such as amount of energy in an applied shock, amount of medication administered, display screen of defibrillator waveforms (e.g., waveforms 620*a*, 620*b*, 622, 624) at the time of treatment marker input, and/or a snapshot view of the ECG or other data from the display interface at the medical treatment device 202 and/or the device view 600 at the time associated with the selected treatment marker.

In some implementations, the trends view UI screen 636 can also include a trend selection tab 654*a* that allows a companion device user to customize the trends that are displayed within the display interface. For example, upon selecting the trend selection tab 654*a*, the companion device 110, 111, 119, 204 can display one or more trends for the user to select and/or de-select based upon trend viewing preferences. In one example, a user can select display waveforms and/or mean values for one or more of HR, pulse rate (PR), SPO$_2$, NIBP, invasive blood pressure (systolic BP, diastolic BP, mean arterial pressure), ETCO$_2$, respiratory rate/breathing rate (RR/BR), pleth variability index (PVI). Additionally, the user can select whether to display data table 652. In some embodiments, the user can also select a time interval for recording trend data that is displayed within the trend view 636, such as within data table 652. In some implementations, inputs provided at the trend selection tab 654*a* can also allow users to select the predetermined time interval e.g., every 10 seconds, 20 seconds, 30 seconds, 1 minute, 3 minutes, 5 minutes) for recording and/or displaying trend data in the trends view UI screen 636.

Returning to FIG. 4A, upon detection of a working view activation input at a display interface (e.g., working view selection tab 664 in FIG. 6B) (412), the companion device 110, 111, 119, 204 may configure the case information to cause display of a working view display interface at the companion device 110, 111, 119, 204 (414). In some examples, the working view display interface may be activated when the user configures the companion device 110, 111, 119, 204 to remove or add any displayed data section (e.g., waveform, data value, or dashboard). For example, selecting waveform delete input 666 at the device view UI screen 600 to the remove CO$_2$ waveform 624 may cause activation of a working view display interface at the companion device 110, 111, 119, 204. In other examples, a saved working view associated with a user account may be automatically presented upon logging in to use the companion device 110, 111, 119, 204. In some embodiments, the working view 668 can also be activated upon addition of any waveform, metric value, or dashboard for viewing. In some embodiments, the working view display interface may correspond to any type of customization of the case information displayed at the companion device 110, 111, 119, 204. Stated another way, the working view display interface corresponds to any set of displayed data in any format at the companion device 110, 111, 119, 204 that differs from the displayed data and format of the device view 600 (FIG. 6A).

Figure 6C:
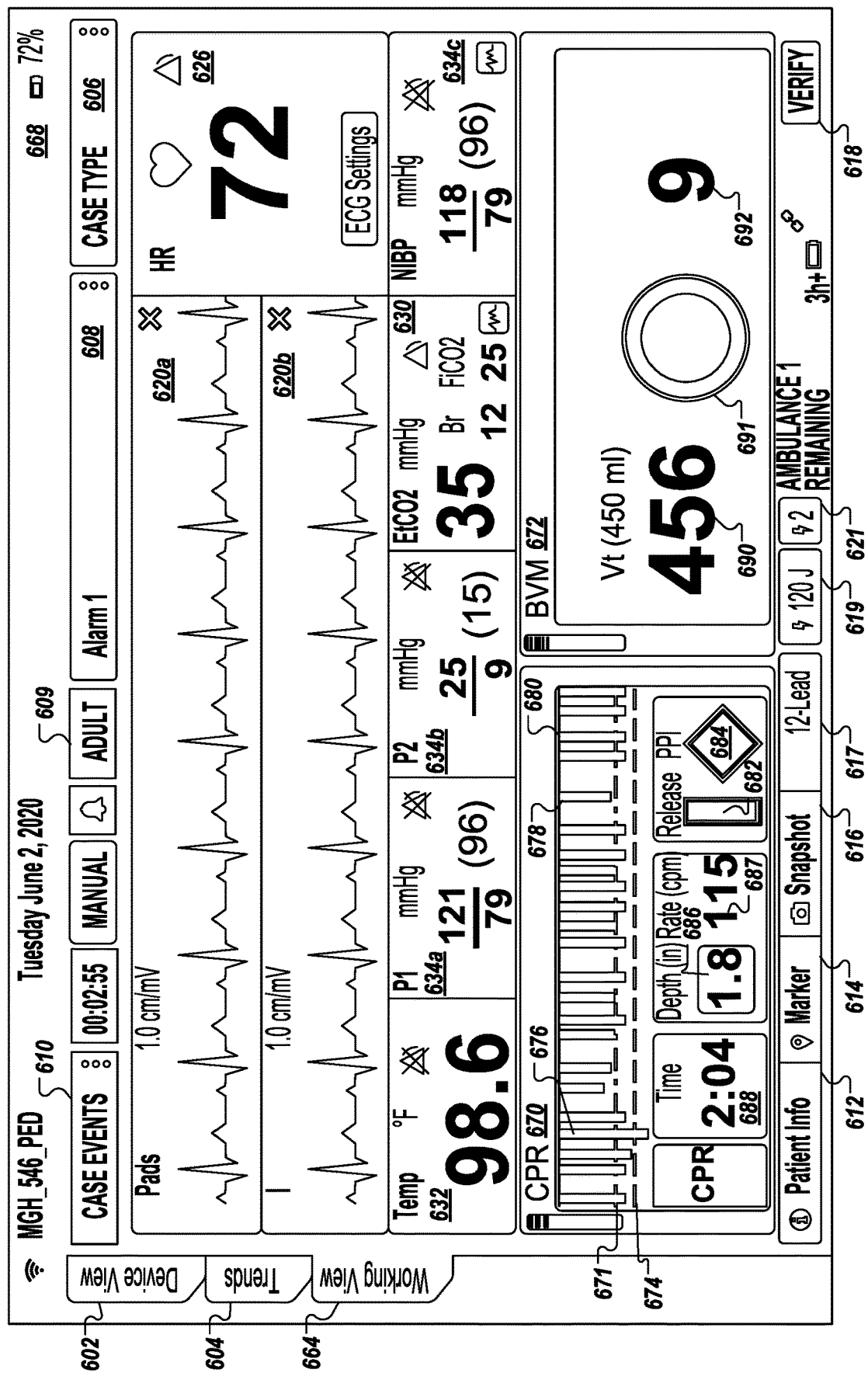

For example, FIG. 6C illustrates a working view user interface (UI) screen 668 for a companion device 110, 111, 119, 204 that includes one or more data sections customized to preferences and/or treatment role of the device user. In some implementations, the working view screen 668 can be a scrollable interface such that users can add as many data sections as desired to the working view 668 for ready viewing by scrolling up or down on the working view screen 668. In one example, the working view screen 668 includes the ECG waveforms 620*a,b* like in the device view but does display the SPO$_2$ waveform 622 or CO$_2$ waveform 624. The working view UI screen 668 can also include IBP waveforms. Additionally, the working view screen 668 also displays current numeric values for heart rate (HR) 626, SPO$_2$ 628, CO$_2$ 630, temperature 632, and blood pressures 634*a,b,c*. In some implementations, the device user can manually add/remove data sections or drag/reposition data sections in the working view 668 as desired. For example, each of the displayed data sections can function as a grab bar that can be moved to another position within the working view 668, which automatically causes other data sections to shift to support the selected adjustment. In some examples, the user can store a manually configured working view layout as customization data 260*a* so that the companion device 110, 111, 119, 204 can preconfigure the customized working view for the user for future medical events. In some examples, such as in a situation when a caregiver is supervising administration of chest compressions and bagged ventilation by other team members, the working view can include a chest compression dashboard 670 and a ventilation dashboard 672 that provide feedback to the user regarding how care is being administered to the patient.

In some implementations, the chest compression dashboard 670 displays chest compression case information from at least one chest compression sensor input. In one example, the chest compression sensor can be a motion sensor puck that is positioned beneath a caregiver's hands as the caregiver is administering chest compressions and detects chest compression depth and rate. Once compressions commence, the chest compression dashboard 670 can include a timer 688 indicating how long chest compressions have been going on during the medical event. As chest compressions are administered, the chest compression dashboard 670 can include a compression graph 680 that displays a depth of each compression in real-time as compared to a target range of minimum 671 and maximum 674 compression depths. For example, in the compression graph 680, each compression is displayed graphically as a bar where a length of each bar corresponds to a depth of compression (e.g., longer bar length corresponds to a deeper compression while a shorter bar length corresponds to a shallower compression). As shown in chest compression dashboard 670, compression 676 is deeper than a maximum threshold depth target 674 while compression 678 is shallower than a minimum threshold depth target 671. The chest compression dashboard 670 can also represent, graphically and/or numerically, a compression rate. For example, in compression graph 680, each compression may be plotted on a rolling basis with respect to time so that compressions that occur at a slower rate are spaced further apart than compressions that are spaced closer together. Compression depth may also be illustrated graphically in other ways such as by a circle with changing diameter that corresponds to relative depth of compression and/or color coded to reflect whether a respective compression is inside or outside a target range. For example, the chest compression dashboard 670 can include numerical indicators of compression depth 686 and compression rate 687. In some aspects, each the numerical indicators 686, 687 can be highlighted in a particular color when the respective depth or compression rate value is outside of a predetermined acceptable range of values. Additionally, the chest compression dashboard 670 can display real-time feedback on compression release velocity. For example, release velocity indicator 682 can graphically indicate whether a rescuer has fully released pressure on a patient's sternum when completing a compression. For example, a portion of the release velocity indicator may illuminate relative to the detected compression release velocity to provide real-time feedback on the quality of compression release. The chest compression dashboard 670, in some embodiments, can also include a perfusion performance indicator (PPI) 684 that indicates whether a depth and rate of compressions are within predetermined chest compression guidelines. In one example, the PPI 684 can be an outline of a shape (e.g., a diamond) that illuminates or becomes filled with a color when compressions are within the predetermined rate and depth (e.g., compressions are within predetermined guidelines when the PPI 684 is fully illuminated). When the PPI 684 is not fully illuminated, this provides the caregiver (supervisor or caregiver administering chest compressions) that chest compression performance is outside prescribed guidelines and that the caregiver should adjust the rate and/or depth of compressions to keep the PPI 684 fully illuminated. This feedback allows caregivers to adjust their compression depth immediately upon seeing that a compression is outside of the target range. Therefore, providing real-time caregiver performance feedback via the chest compression dashboard 670 provides a technical solution to a clinical problem of ensuring that a predetermined standard of chest compression performance is maintained through real-time feedback provided at the companion device 110, 111, 119, 204.

In some examples, the chest compression dashboard 670 can also include CPR performance summary metrics for the medical event (for example, see dashboards 651, 653 in FIG. 6F), which can include at least one of average compression depth, average compression rate, average release velocity, pre-shock pause, post-shock pause, or percentage of compressions within a target compression depth range. In some examples, the CPR summary metrics can be displayed within the dashboard 670 in real-time while CPR is in progress or after a CPR event has finished. In some implementations, the CPR summary metrics can be presented numerically or graphically within the chest compression dashboard 670. The CPR summary can provide a CPR rescuer with an unedited CPR report card to help a rescue team perform debriefs post-case.

In some implementations, ventilation dashboard 672 can provide real-time feedback to caregivers and supervisors regarding performance of bag valve mask (BVM) ventilation. In some examples, ventilation feedback displayed at the ventilation dashboard 672 can include information obtained from an airflow sensor input connected to the medical treatment device 202. In some examples, the displayed real-time ventilation feedback can include one or more of tidal volume 690, ventilation rate 692, or minute volume. In addition, the ventilation dashboard 672 can include a ventilation quality indicator (VQI) 691 that provides a graphical countdown timer until the next ventilation as well as a graphical representation of ventilation volume delivered. The graphical information provided by the VQI 691 provides visual feedback to the caregiver regarding how well the caregiver is administering ventilations. In one example, as a breath is delivered to a patient via ventilation, the VQI 691 fills up toward a target volume. In some implementations, if predetermined time limits are exceeded that indicate that too much time has elapsed since the last breath, the VQI 691 may flash and/or change colors (e.g., yellow and/or red) to indicate that another breath should be administered. In some embodiments, the VQI 691 can also display a numerical countdown of the amount of time until the next ventilation. In other examples, the VQI 691 can include an outline countdown indicator that draws an outline around the VQI 691 at a rate corresponding to the ventilation rate such that the caregiver is prompted to administer the next ventilation when the outline is complete.

In some examples, the ventilation dashboard can also include one or more ventilation summary metrics including at least one of average tidal volume, average ventilation rate, average minute volume, or percentage of ventilations within a target volume range or a target rate range. In some examples, the ventilation summary metrics can be displayed within the dashboard 672 in real-time while ventilation is in progress or after a ventilation event has finished. In some implementations, the ventilation summary metrics can be presented numerically or graphically within the ventilation dashboard 672. The ventilation summary can provide a ventilation rescuer with an unedited ventilation report card to help a rescue team perform debriefs post-case. In some examples, the ventilation summary metrics can be displayed within the dashboard 672 in real-time while ventilation is in progress or after ventilation has finished being administered to the patient. Like with the chest compression dashboard 670, the feedback provided at the ventilation dashboard 672 allows caregivers to adjust their ventilation rate and/or technique immediately upon seeing that the ventilation being administered is outside of target ranges. Therefore, providing real-time caregiver performance feedback via the ventilation dashboard 672 provides a technical solution to a clinical problem of ensuring that a predetermined standard of ventilation performance is maintained through real-time feedback provided at the companion device 110, 111, 119, 204.

Figure 6D:
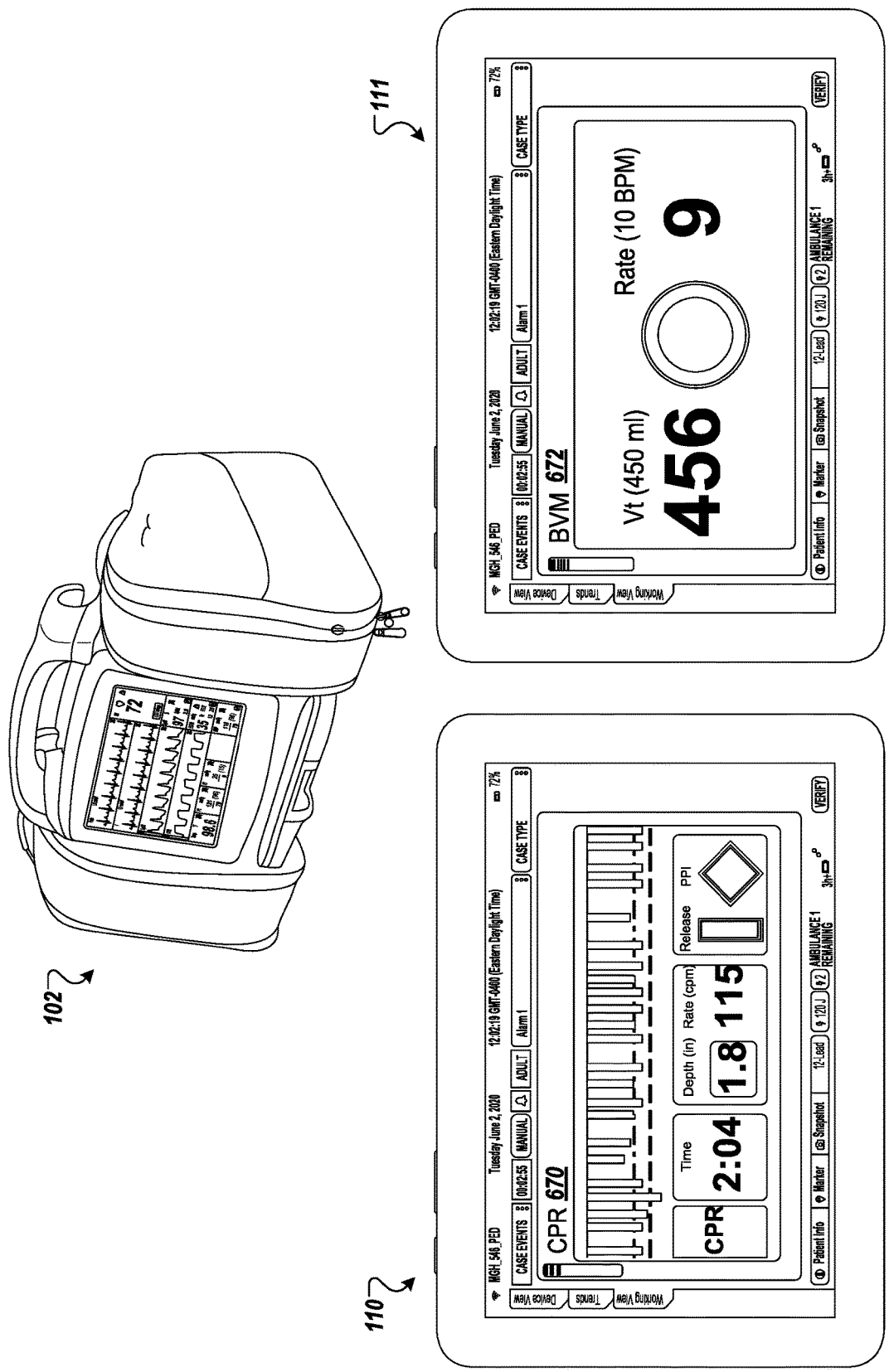
FIG. 6D illustrates exemplary working view user interface screens for companion devices associated with a respective medical treatment device.
Figure 6E:
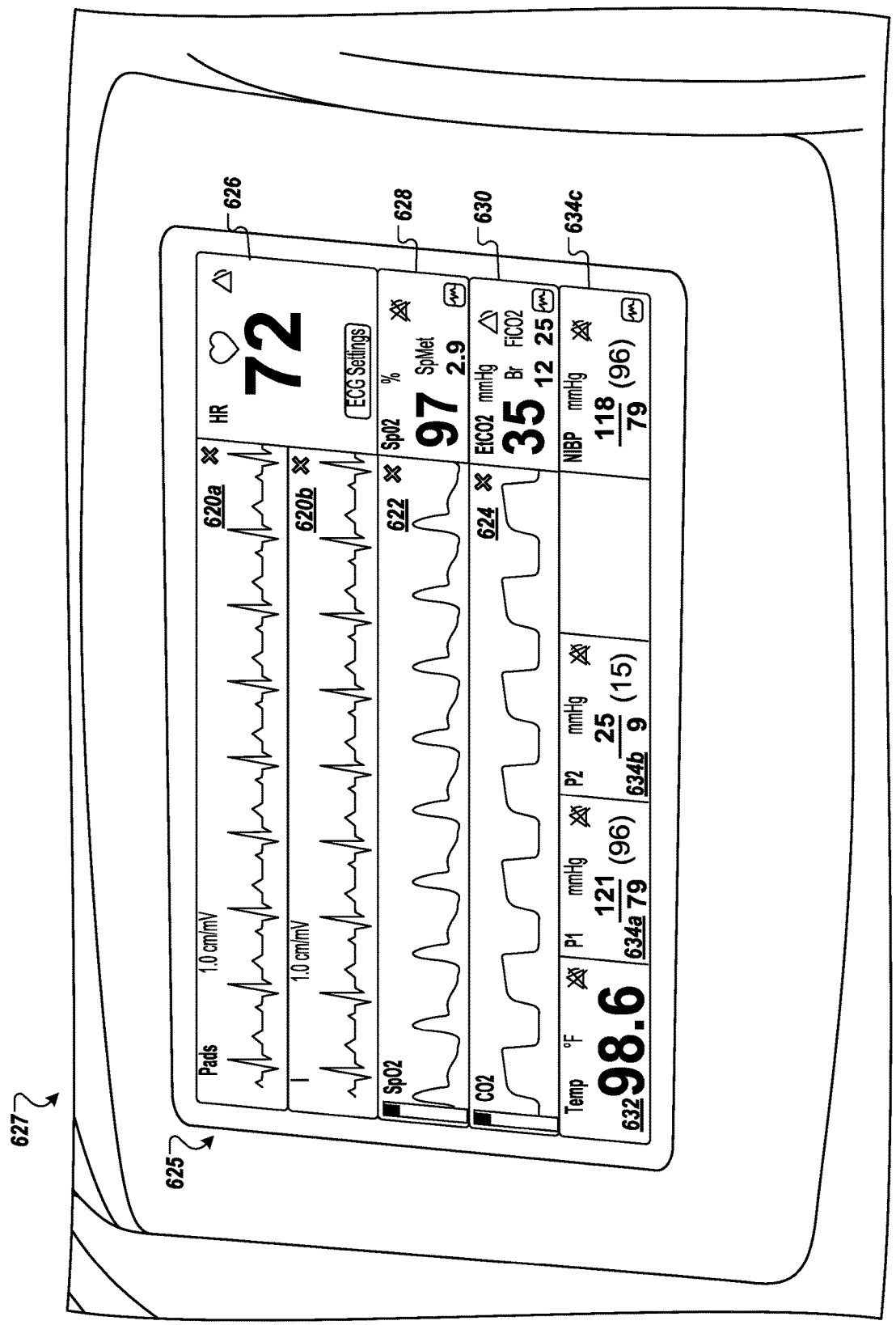
FIG. 6E illustrates a display interface at a medical treatment device in accordance with various embodiments.

FIG. 6D illustrates another implementation of working views of a companion device 110, 111, 119, 204 where the information displayed at a respective companion device is customized to a role of a given caregiver. The example shown in FIG. 6D may correspond to a patient treatment event similar to the treatment event illustrated in FIGS. 1A-1C where at least two companion devices 110, 111, 119 are wirelessly connected to a defibrillator 102 for use by a chest compression caregiver 104 and a ventilation caregiver 106, respectively. For example, as a patient is treated by a rescue team, the defibrillator 102 can display physiological information obtained from one or more connected physiological sensors at a defibrillator display interface 696 (e.g., defibrillator display interface 625 shown in FIG. 6E). In some embodiments, each of the companion devices 110, 111, 119, 204 can display a working view UI screen (e.g., working view 668 in FIG. 6C) that is configured for a treatment role of the respective caregiver. For example, at the companion device 110 used by the chest compression caregiver 104, the chest compression dashboard 670 may be displayed in the working view UI screen 697 more prominently than other data, waveforms, and dashboards. In one example, the UI screen 697 may be a "compression view" UI screen where only the chest compression dashboard is displayed. In a similar way, at the companion device 111 used by the ventilation caregiver 106, the ventilation dashboard 672 may be displayed in the working view UI screen 699 more prominently than other data, waveforms, and dashboards. In one example, the UI screen 699 may be a "ventilation view" UI screen where only the chest compression dashboard is displayed. In another example, the chest compression dashboard 670 and ventilation dashboard 670 can be displayed alone within a "full CPR" working view so that a supervisor can monitor both the CPR and ventilation caregivers at the same time or so that the CPR and ventilation caregivers can share the same companion device 110, 111, 119, 204 during the medical event.

Real-time display of customized working views within companion devices 110, 111, 119, 204 provides a technical solution to the clinical and technical problem of providing real-time, user-friendly treatment related feedback and data to multiple caregivers during an acute patient care event. Without the ability to transmit and display customized case information at companion devices based on caregiver roles during a medical event, caregivers are forced to crowd around a relatively small defibrillator interface that may be limited in its ability to simultaneously display all of the data sections that any of the caregivers may wish to be displayed at a given time. Therefore, having the ability to transmit medical treatment and caregiver performance data for display at one or more caregiver companion devices allows caregivers to focus on their respective roles and the information displayed in the working views, which can assist in coordination among caregivers in a rescue team in order to enhance patient care during medical events.

While not shown in FIG. 6D, the working view UI screens displayed at companion devices 110, 111 may include other data sections accessible by scrolling to another position within the working view. In some examples, the working view UI screens displayed at the companion devices 110, 111 can be configured immediately upon user login and correlation of the respective user 104, 106 with a customized working view configuration that includes a prominently displayed chest compression dashboard 670 or ventilation dashboard 672. In other examples, the caregivers 104, 106 may manually configure the working view UI screens at their respective companion devices 110, 111 by selecting each of the dashboards, waveforms, trends, or data metrics the respective caregiver 104, 106 wishes to display at the companion device 110, 111. In some examples, the display interface at the companion device 110, 111 may include one or more dropdown/selection menus that allow the caregiver to select the data sections for displaying within the working view. The caregivers 104, 106 can also manually position each of the data sections within the working view by selecting and dragging each of the data sections to a preferred location within the working view. In other implementations, upon logging in at the companion device, a caregiver 110, 111 can select a caregiver role (e.g., chest compression caregiver, ventilation caregiver, team supervisor) for a medical event, and the companion device can automatically configure the respective working view for the selected role.

Figure 6F:
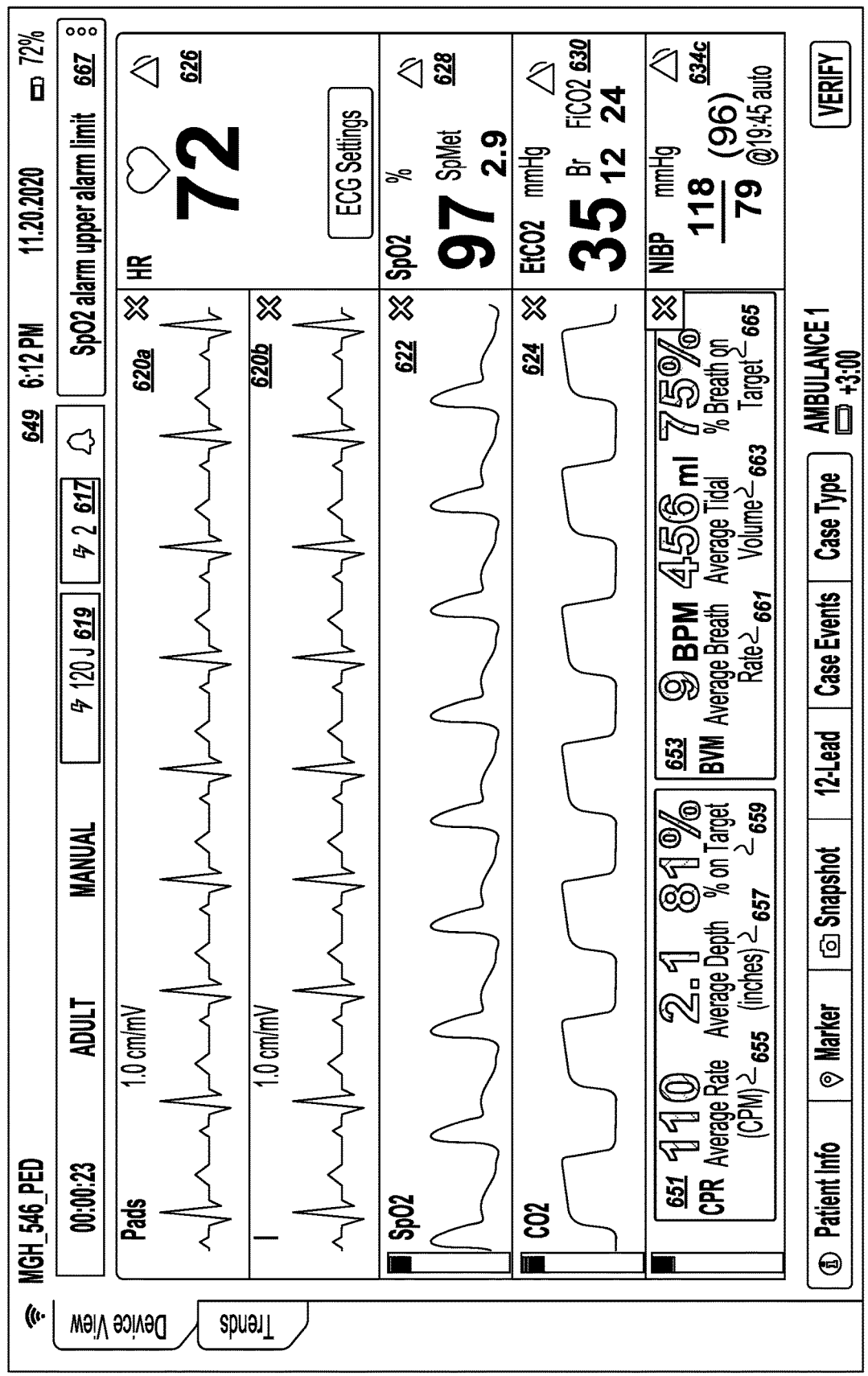
FIG. 6F illustrates a display interface at a medical treatment device in accordance with various embodiments.

FIG. 6F illustrates yet another example of a device view 649 of a companion device 110, 111, 119, 204. In addition to waveforms for ECG 620a,b, SPO$_2$622, and CO$_2$ 624 and discrete numeric values for HR 626, SPO$_2$628, ETCO$_2$630, and NIBP 634c, the UI screen 649 can also include chest compression dashboard 651 and ventilation dashboard 653 that provide summary metrics for caregiver performance (compression caregiver and ventilation caregiver). In one example, the device view 649 can be a visual reproduction of other a display interface of the medical treatment device or another device view of the companion device 110, 111, 119, 204 (e.g., device view 600 in FIG. 6A). As discussed above, in some examples, display layout, magnification of each data section, physiologic waveform selection, physiologic numeric readout selection, resolution, waveform duration, waveform size, text size, font, and/or display colors can vary from what is displayed at the medical treatment device. In addition, navigation and display bars may be displayed on opposite sides of the UI screen 649 as other display views of the companion device 110, 111, 119, 204 and/or medical treatment device 202 while still being a visual reproduction of another display view (e.g., device view 600 in FIG. 6A) or a display screen of a medical treatment device 202. For example, indicators for shock energy value 619, and number of shocks applied 621 may be displayed at a top edge of the UI screen 649 rather than at a bottom edge as in device view 600. Additionally, an alarm user input 667 may display a name of the most recent alarm or may cycle through all alarm conditions triggered within a predetermined period of time.

In some implementations, CPR summary dashboards 651, 653 may each present numeric summary metrics associated with compressions and/or ventilation (average compression rate 655, average compression depth 657, percentage of compressions within a target range 659, average breath rate 661, average tidal volume 663, percentage breaths on target 665) with one or more metrics highlighted in a different color based on its relative importance (e.g., percentage of compressions on target 659 and/or percentage of breaths on target 655 may be displayed in a larger font size and/or in a color that draws the attention of the viewer (e.g., yellow, orange, or red)). In some embodiments, each of the summary metrics 651-665 displayed within a respective dashboard 651, 653 may be displayed in a different colored font than other metrics displayed within the same dashboard 651, 653 to further assist the viewer in distinguishing between the displayed case information. In some implementations, summary dashboards 651, 653 may be available for selection and viewing at any of the display interfaces of the companion device 110, 111, 119, 204 (e.g., device view 600 (FIG. 6A) trends view 636 (FIG. 6B), working view 668 (FIG. 6C), and case type views 814, 820, 824, 834, 840, and 844 (FIG. 8B through FIG. 8G)). For example, upon selection of a corresponding user input at the display interface, the summary dashboards 651, 653 may be presented at the display interface.

In another embodiment, the device view 649 may be a visual reproduction of one or more working views such as working view 668 (FIG. 6C) in that it includes caregiver performance dashboards 651, 653 that are analogous to caregiver performance dashboard 670, 672 but provide caregiver performance case information in a different format (e.g., color, font, magnification, numeric versus graphical representation, etc.) and with different information highlighted in the dashboards 651, 653. In some examples, the dashboards 651, 653 may be configured particularly for a supervisor companion device 119, 204 such that the case information displayed within the dashboards 651, 653 draws the eye of the supervisor to one or more respective items of data to be able to quickly view how well the compression and ventilation caregivers are performing during a medical event. For example, the dashboards 651, 653.

Returning to FIG. 4A, in some implementations, upon configuration of a working view UI screen at the companion device 110, 111, 119, 204, if one or more items of physiological sensor data, treatment data, or caregiver performance data are needed to display within the working view (416), then in some examples, the companion device 110, 111, 119, 204 transmits a data acquisition request to the medical treatment device 202 requesting the one or more requested items of data (418). For example, if a companion device user selects a chest compression dashboard 670 for display within a working view at the companion device 110, 111, 119, 204 and it has not been displayed up to that point, then the companion device 110, 111, 119, 204 may transmit a data acquisition request to the medical treatment device 202 to obtain CPR case information (e.g., chest compression depth and rate data) for display within the chest compression dashboard 670. In some examples, upon receiving the requested data, the companion device 110, 111, 119, 204 configures the requested data for real-time display within a respective data section in the working view interface (420). In some embodiments, based on the type of data requested, the medical treatment device 202 may transmit the requested data as a streaming data message and/or a REST data message (bulk data transfer).

Continuing to FIG. 4B, upon detecting selection of case type selector 606 at one of the display views of the companion device 110, 111, 119, 204 (e.g., selector 606 in FIG. 6A through FIG. 6C) (422), in some implementations, the companion device 110, 111, 119, 204 causes display of a case type selection UI screen (424). Upon detecting selection of a case type at the case type selection UI screen (426), in some implementations, the companion device 110, 111, 119, 204 configures data for presentation at the selected case type UI screen (428). In some examples, each of the case type views is a working view that is specifically customized to a particular type of medical event in the displayed data sections are particularly relevant to the medical event.

Figure 8A:
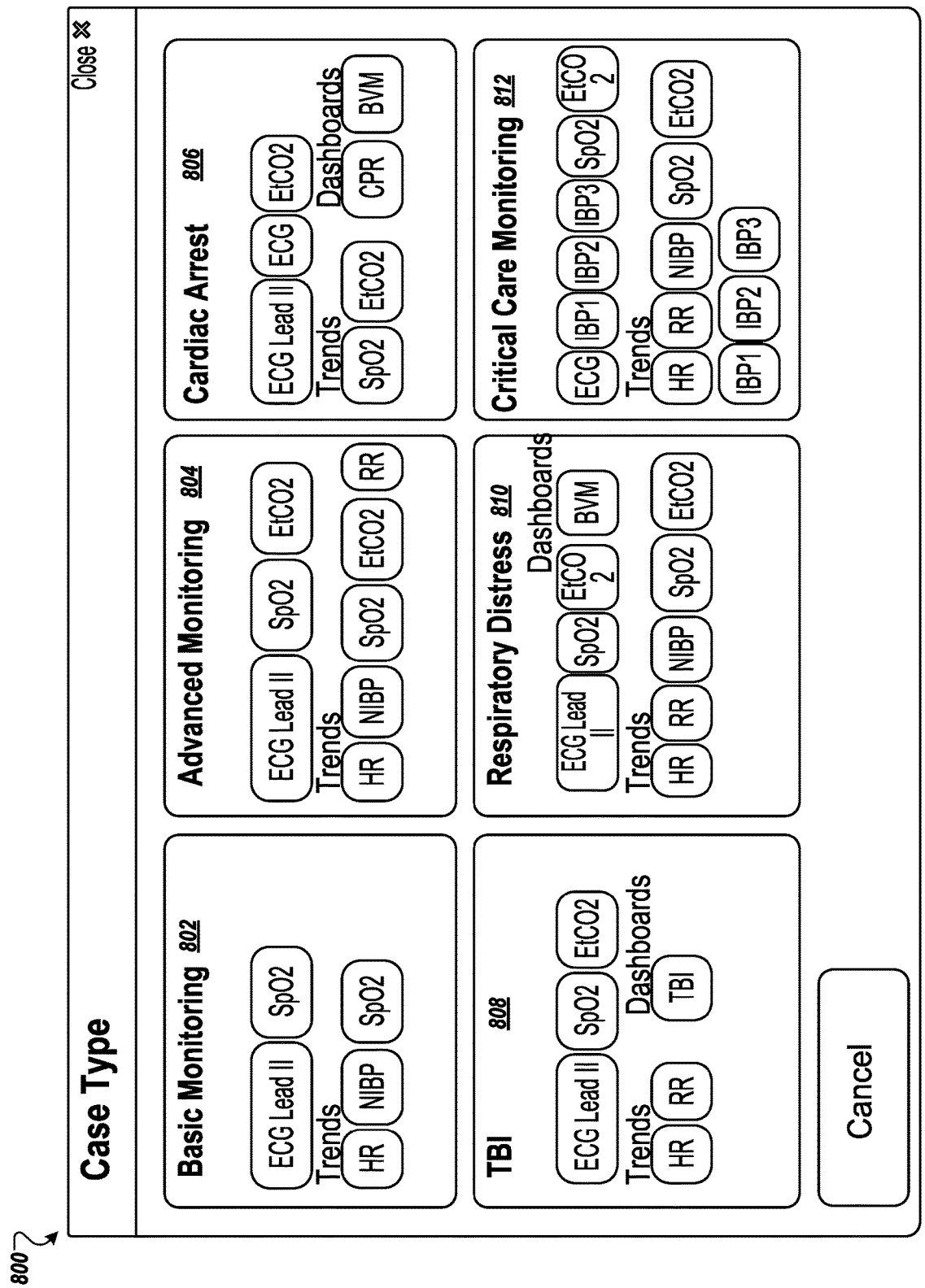
FIG. 8A illustrates an exemplary case type selection user interface screen.

For example, FIG. 8A illustrates a case type selection UI screen 800 for a companion device 110, 111, 119, 204, which is displayed in response to selection of case type selector 606. The case type selection UI screen 800, in some implementations, displays a display summary for one or more types of medical events that allows companion device users to see which metrics, trends, waveforms, and dashboards are associated with each of the selectable case types 802-812, which each correspond to one of the case type UI screens illustrated in FIG. 8B through FIG. 8G. In some implementations, the selectable case types can include basic monitoring 802, advanced monitoring 804, cardiac arrest 806, TBI 808 respiratory distress 810, and critical care monitoring 812. In some examples, the metrics, trends, waveforms, and dashboards are associated with each of the selectable case types 802-812 present the data that is most relevant to situations associated with a respective case type. Including pre-configured case type UI screens for display at the companion device 110, 111, 119, 204 provides a technical solution to a clinical problem due to the improved efficiency with which the companion device 110, 111, 119, 204 can be configured to display relevant case information in a user-friendly format without the caregiver having to think about which data sections (metrics, waveforms, trends, dashboards) are most relevant to a particular patient case. In some embodiments, once a respective case type view is displayed at the companion device 110, 111, 119, 204, the device user can modify a data section layout, add one or more data sections, or remove one or more data sections as desired. Additionally, companion device users can switch between case type views 802-812 as desired.

Figure 8B:
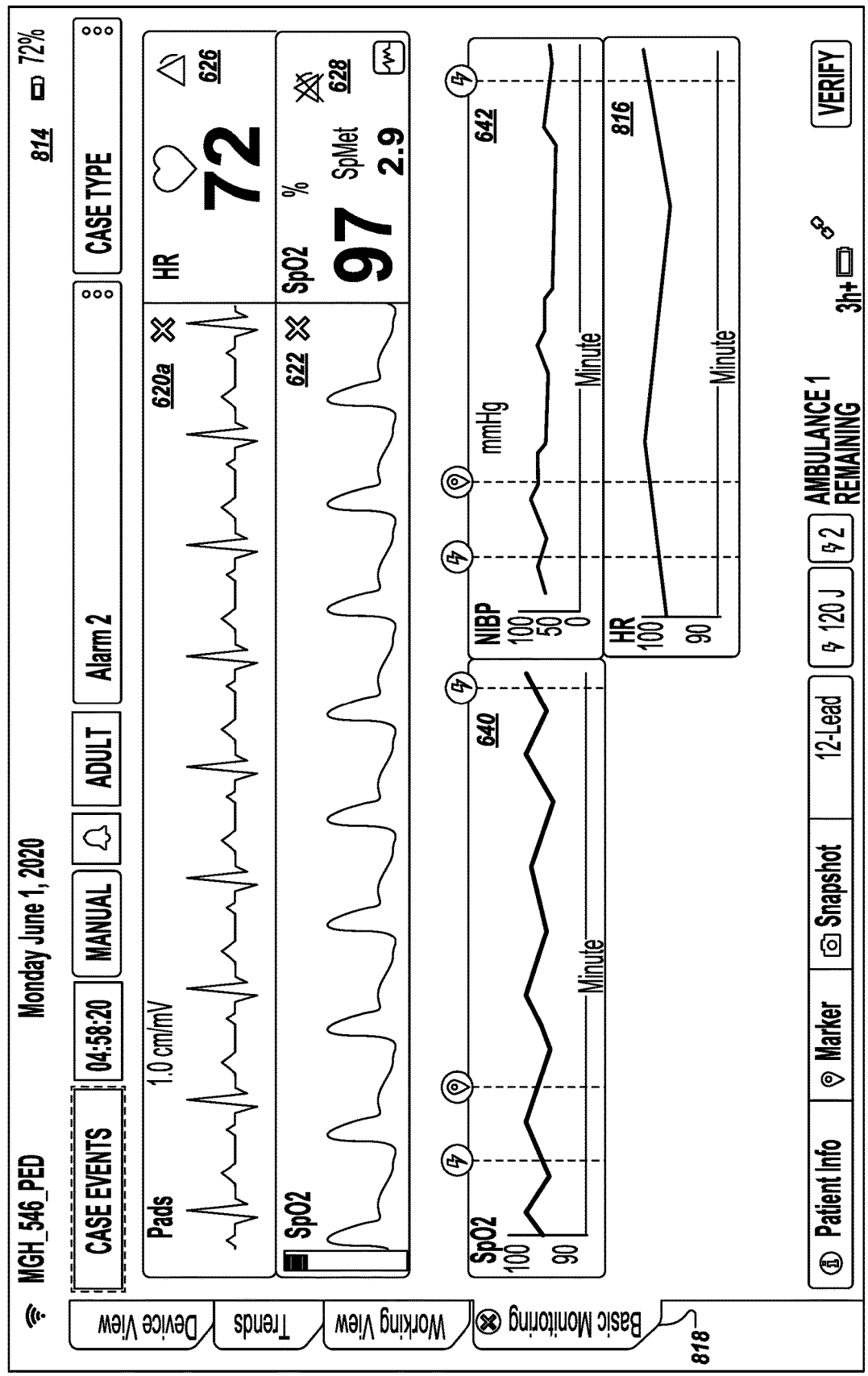
FIG. 8B illustrates an exemplary basic monitoring case type view user interface screen.
Figures 1, 8C:
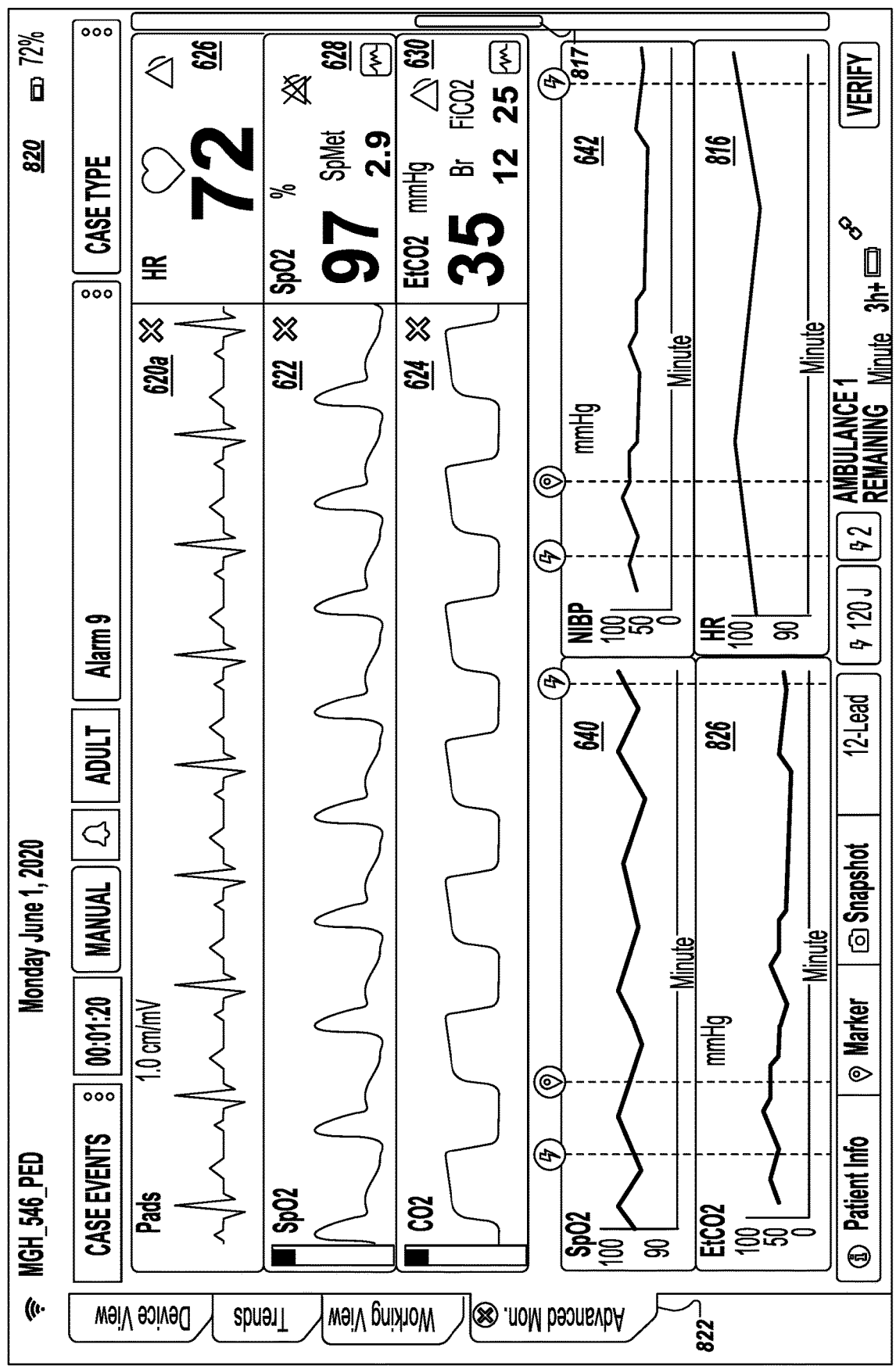

FIG. 8B illustrates a basic monitoring UI screen 814 that is configured for display at the companion device 110, 111, 119, 204 in response to selection of the basic monitoring selector 802 at the case type selection UI screen 800. In some implementations, caregivers may display the basic monitoring UI screen 814 when a patient is being transported from an incident site to a hospital when a reduced number of physiological sensors may be available for use with the medical treatment device 202 or a patient diagnosis has not yet been made. In one example, the basic monitoring UI screen 814 may include ECG waveform 620a, $SPO_2$ waveform 622, discrete numeric values for HR 626, $SPO_2$ 628, and NIBP 650, trend graphs for $SPO_2$ 640, NIBP 642, and HR 816, and data table 652 for displaying physiological trends (not shown in FIG. 8B). Additionally, once the basic monitoring case type selector 802 has been selected, a caregiver can toggle between the basic monitoring UI screen 814 and other companion device display views via basic monitoring tab 818. In some examples, the basic monitoring tab can include a user input 818 that allows the basic monitoring UI screen 814 to be closed or deactivated at the companion device 110, 111, 119, 204. Each of the case type views 814, 820, 824, 834, 840, and 844 in FIG. 8B through FIG. 8G can be deactivated by a user by a corresponding user input while in some implementations, the device view UI screen 600 (FIG. 6A), trends view UI screen 636 (FIG. 6B), and working view UI screen 668 (FIG. 6C), once activated, cannot be deactivated by a device user.

FIG. 8C-1 and FIG. 8C-2 illustrate an advanced monitoring UI screen 820 that is configured for display at the companion device 110, 111, 119, 204 in response to selection of the advanced monitoring selector 804 at the case type selection UI screen 800. In some implementations, UI screen 820 is a scrollable interface that includes a user input 817 that allows a device user to scroll up and down to view different portions of the UI screen 820 when all case information is not visible within a single viewing pane. For example, FIG. 8C-1 illustrates a first portion of UI screen 820. In some implementations, caregivers may display the advanced monitoring UI screen 820 when a patient is experiencing chest pain or another serious medical condition that does not fall into one of the other case type categories. In some examples, the advanced monitoring UI screen 820 may include Lead II ECG waveform 620a, $SPO_2$ waveform 622, $CO_2$ waveform 624, discrete numeric values for HR 626, $SPO_2$ 628, ETCO2 630, NIBP value, trend graphs for $SPO_2$ 640, NIBP 642, ETCO2 826, HR 816, and respiratory rate, and data table 652 (shown in FIG. 8C-2) for displaying physiological trends. In some examples, the advanced monitoring UI screen 820 can be a scrollable interface that allows users to view more content than what is visible in a single viewing pane. For example, upon scrolling, users can view the entirety of the trend graphs for $ETCO_2$ 826 and HR 816 as well as a tabular depiction of trends for HR, NIBP, $SPO_2$, and $ETCO_2$ recorded at predetermined time intervals. Additionally, once the advanced monitoring case type selector 802 has been selected, a caregiver can toggle between the advanced monitoring UI screen 814 and other companion device display views via advanced monitoring tab 822.

Figure 8D:
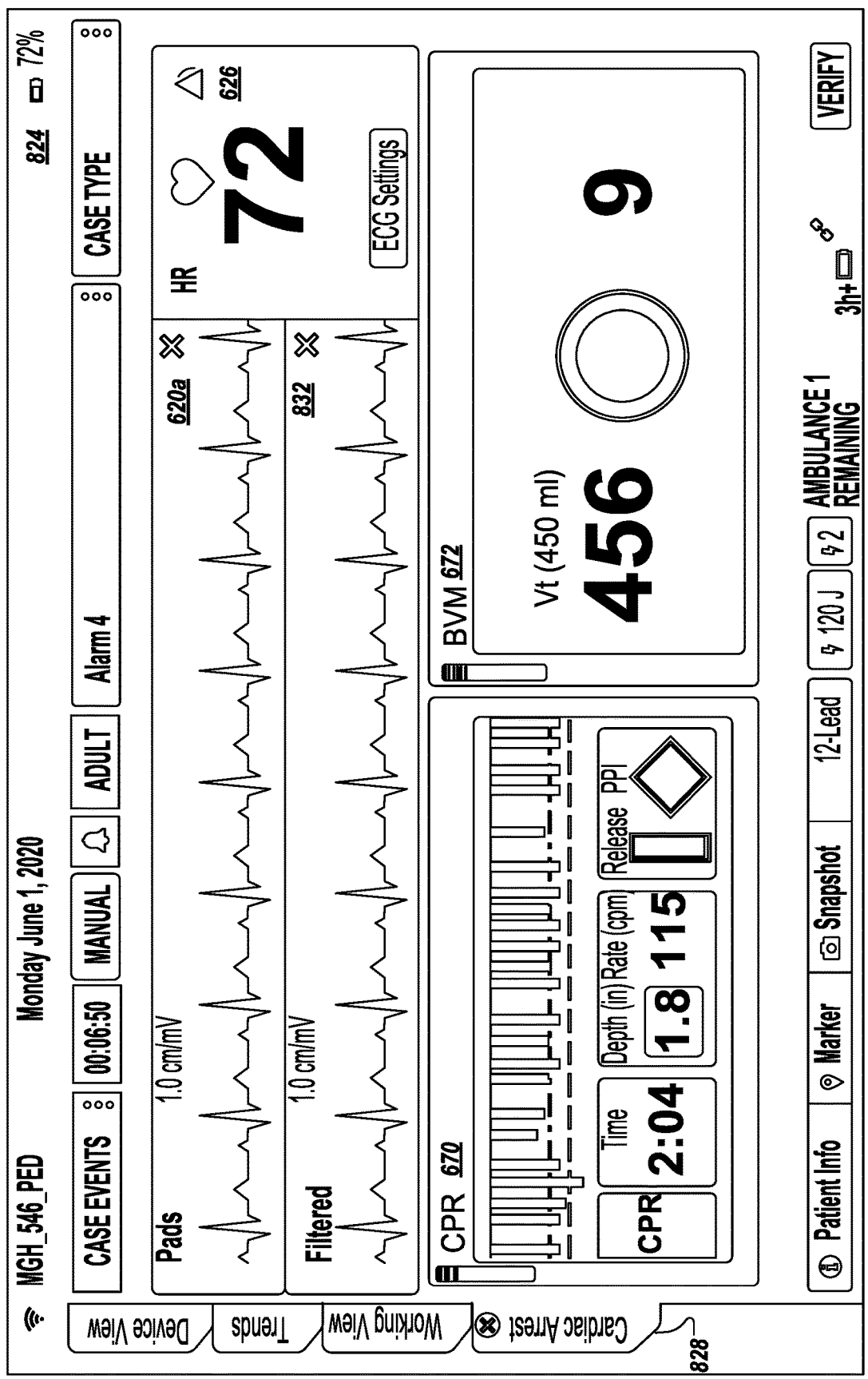
FIG. 8D illustrates an exemplary cardiac arrest case type view user interface screen.

FIG. 8D illustrates cardiac arrest UI screen 824 that is configured for display at the companion device 110, 111, 119, 204 in response to selection of the cardiac arrest selector 806 at the case type selection UI screen 800. In some implementations, when a patient goes into cardiac arrest, a caregiver can quickly and efficiently transition to the cardiac arrest UI screen 824, which displays a number of waveforms, dashboards, metrics, and trends that enhance a caregiver's ability to care for the patient during cardiac arrest. In some implementations, a layout of the cardiac arrest UI screen 824 and all other case type UI screens can be preconfigured to provide information so that information that is most relevant to providing patient care is immediately visible within the UI screen 824 without having to scroll to another position. For example, a Pads ECG waveform 620a and a filtered ECG waveform 832 may be positioned at the top of the cardiac arrest UI screen 824 along with a current numeric HR value 626. In one example, an $ETCO_2$ waveform can also be displayed. Also immediately visible upon transitioning to the cardiac arrest UI screen 824 may be chest compression dashboard 670 and ventilation dashboard 672, which allow the caregiver to monitor chest compression and ventilation performance during the cardiac arrest event. In some implementations, the cardiac arrest UI screen 824 may also include a $CO_2$ waveform, $ETCO_2$ value, trend graphs for $SPO_2$ and $ETCO_2$, and a trends data table 652 displaying time-incremented values for each of the displayed trend graphs. Additionally, once the cardiac arrest case type selector 806 has been selected, a caregiver can toggle between the cardiac arrest UI screen 824 and other companion device display views via cardiac arrest tab 828.

Figure 8E:
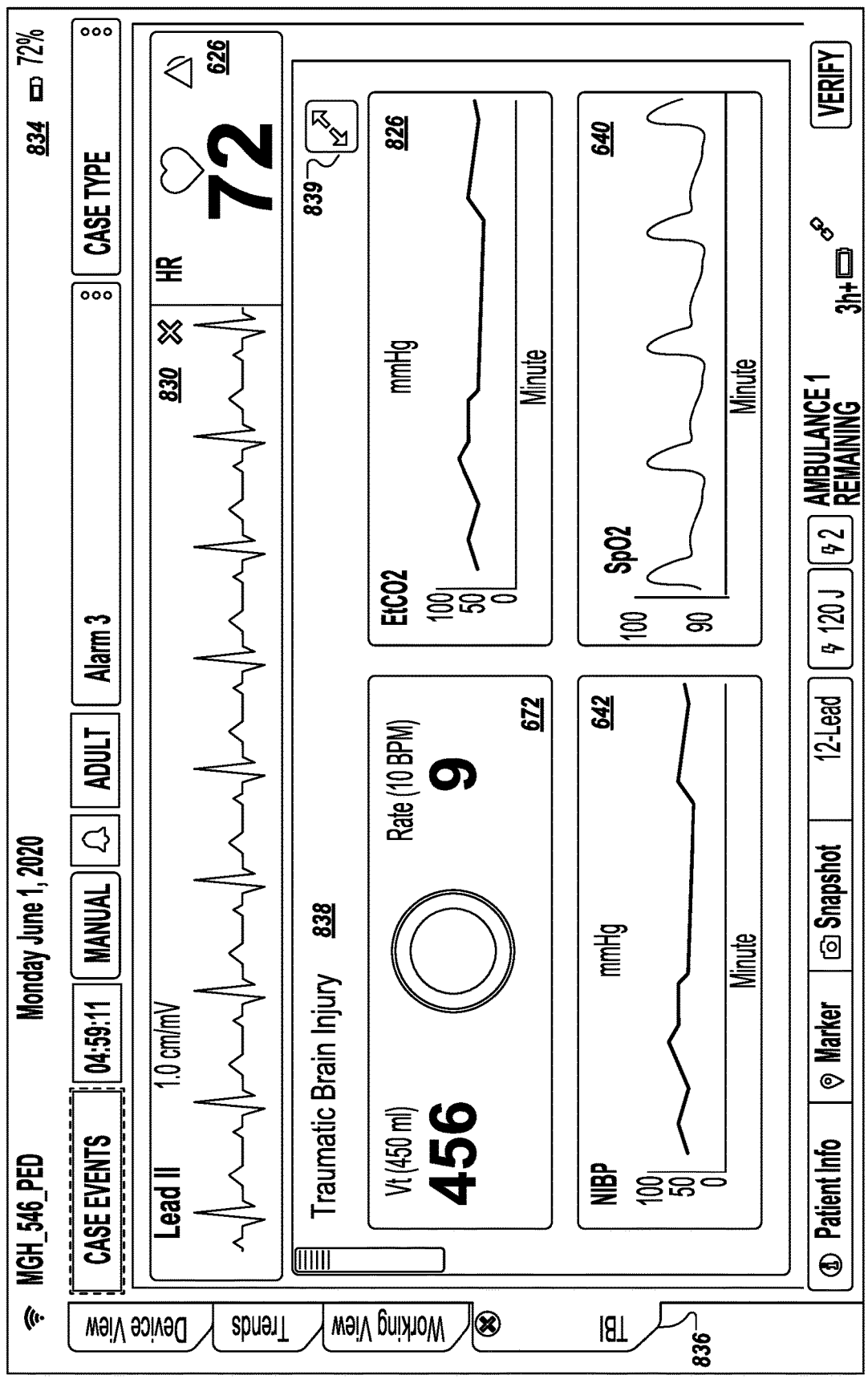
FIG. 8E illustrates an exemplary traumatic brain injury case type view user interface screen.

FIG. 8E illustrates a TBI UI screen 834 that is configured for display at the companion device 110, 111, 119, 204 in response to selection of the TBI selector 808 at the case type selection UI screen 800. In some implementations, caregivers may display the TBI UI screen 834 when a patient has experienced a TBI through a traumatic event such as impact due to car accident, gunshot wound, etc. In some implementations, the TBI UI screen 834 may display a Lead II ECG waveform 830, $ETCO_2$ waveform, numeric heart rate value 626, numeric NIBP value, and TBI dashboard 838. In some examples, TBI dashboard 838 may include a subset of dashboards and waveforms related to monitoring a status of a TBI including ventilation dashboard 672, and trend graphs for $ETCO_2$ 826, NIBP 642, $SPO_2$ 640, and systolic blood pressure (SBP). In addition, the UI screen 834 can also include data table 652 that displays time-incremented numeric values associated with each of the displayed trend graphs (not shown in FIG. 8E). In some implementations, the TBI dashboard 838 may include a dashboard expansion input 839 that causes the TBI dashboard 838 to expand to cover other case information displayed at the TBI dashboard 838 such that the case information displayed in the TBI dashboard 838 is enlarged. In some situations, enlarging the TBI dashboard 838 allows a device user to more easily view the case information displayed within the TBI dashboard 838. Additionally, when the expansion input 839 is selected when the TBI dashboard 838 is expanded, the dashboard 838 contracts to the original size. In some examples, the TBI UI screen 834 can be a scrollable interface that also displays graphs for $SPO_2$ and $CO_2$, current numeric values for $SPO_2$ and $ETCO_2$, and trend graphs for HR and RR. Additionally, once the TBI case type selector 808 has been selected, a caregiver can toggle between the TBI UI screen 834 and other companion device display views via TBI tab 836.

Figure 8F:
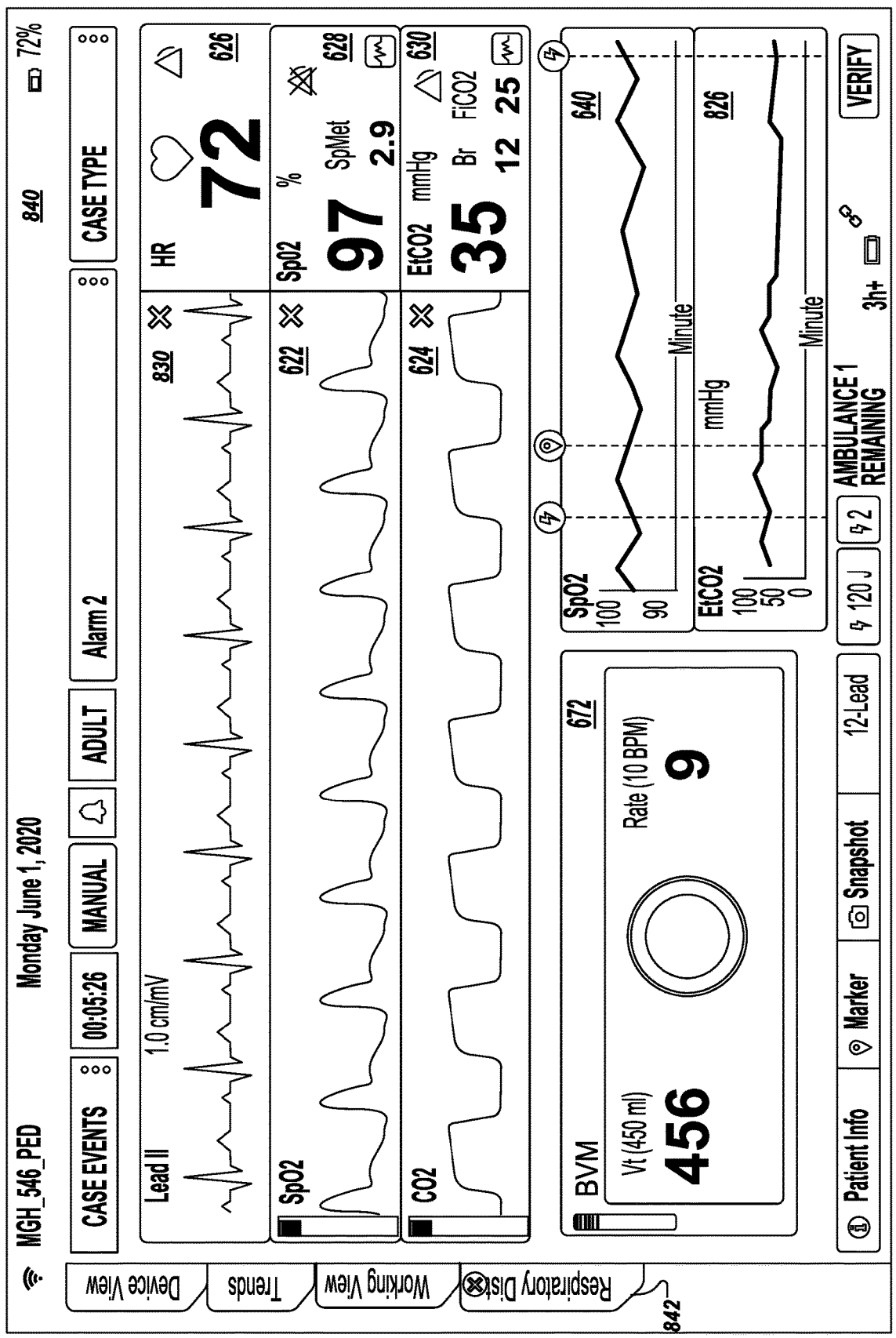
FIG. 8F illustrates an exemplary respiratory distress case type view user interface screen.

FIG. 8F illustrates a respiratory distress UI screen 840 that is configured for display at the companion device 110, 111, 119, 204 in response to selection of the respiratory distress selector 810 at the case type selection UI screen 800. In some implementations, caregivers may display the respiratory distress UI screen 840 when a patient is ill and exhibiting symptoms of a respiratory condition that causes respiratory distress such as chronic obstructive pulmonary disease (COPD), asthma, congestive heart failure, cystic fibrosis, pneumonia, etc. The respiratory distress UI screen 840 displays waveforms for ECG 630 (for example, ECG Lead II), $SPO_2$ 622, and $CO_2$ data, current numeric values for HR 626, $SPO_2$ 628, and $ETCO_2$ 630, a BVM dashboard 672, and trend graphs for $SPO_2$ 640 and $ETCO_2$ 826. In addition, the respiratory distress UI screen 840 can be a scrollable interface that allows users to view the entirety of the $ETCO_2$ trend graph 826 and also displays trend graphs for NIBP and HR as well as a tabular depiction of trends for HR, NIBP, $SPO_2$, and $ETCO_2$ recorded at predetermined time intervals in a non-continuous manner. Additionally, once the respiratory distress case type selector 810 has been selected, a caregiver can toggle between the respiratory distress UI screen 840 and other companion device display views via TBI tab 842.

Figure 8G:
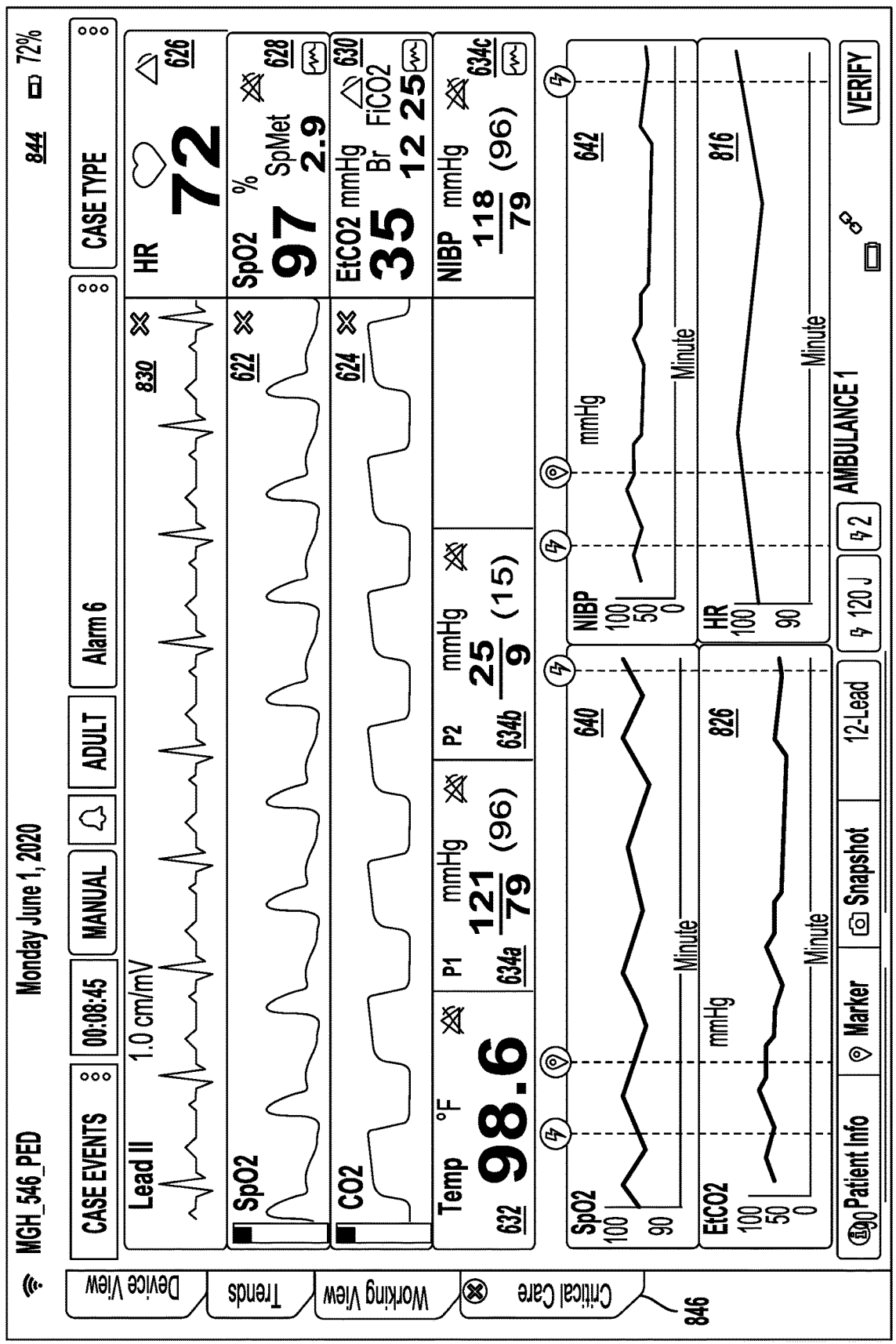
FIG. 8G illustrates an exemplary critical care monitoring case type view user interface screen.

FIG. 8G illustrates a critical care monitoring UI screen 844 that is configured for display at the companion device 110, 111, 119, 204 in response to selection of the critical care monitoring selector 812 at the case type selection UI screen 800. In some embodiments, caregivers may display the critical care monitoring UI screen 644 when transporting acutely ill patients between medical facilities or from an accident scene to a medical facility, such as when a patient is transferred via transport helicopter. The critical care monitoring UI screen 844 can display waveforms for ECG 630 (for example, ECG Lead II), $SPO_2$ 622, and $CO_2$ data, current numeric values for HR 626, $SPO_2$ 628, $ETCO_2$ 630, temperature 632, and blood pressures 634*a,b,c* (e.g., NIBP and IBP1/2/3, and graphical trend panel with trend graphs for $SPO_2$ 640, NIBP 642, $ETCO_2$ 826, HR 816, and respiratory rate. In some implementations, the UI screen 844 can also include data table 652 for monitoring parameters displayed in graphical trends. In addition, the respiratory distress UI screen 840 can be a scrollable interface that allows users to view the entirety of the $SPO_2$ 640 and NIBP 642 trend graphs and also displays trend graphs for $ETCO_2$ and HR, a tabular depiction of trends for HR, NIBP, $SPO_2$, and $ETCO_2$ recorded at predetermined time intervals, and a ventilation dashboard. The critical care monitoring UI screen 844 can also display case information for IBP readings. Additionally, once the critical care monitoring case type selector 812 has been selected, a caregiver can toggle between the critical care monitoring UI screen 844 and other companion device display views via critical care monitoring tab 846.

Returning to FIG. 4B, in some implementations, upon configuration of a case type view UI screen at the companion device 110, 111, 119, 204, if one or more items of physiological sensor data, treatment data, or caregiver performance data are needed to display within the case type view (430), then in some examples, the companion device 110, 111, 119, 204 transmits a data acquisition request 418 to the medical treatment device 202 requesting the one or more requested items of data (432). For example, if a companion device user selects to view the respiratory distress UI screen 840 (FIG. 8F) and ventilation dashboard 672 has not been displayed up to that point, then the companion device 110, 111, 119, 204 may transmit a data acquisition request to the medical treatment device 202 to obtain ventilation case information (e.g., ventilation tidal volume and ventilation rate) for display within the respiratory distress UI screen 840. In some examples, upon receiving the requested data, the companion device 110, 111, 119, 204 configures the requested data for real-time display within a respective data section in the case type interface (434).

In some embodiments, if the companion device detects an input selection of a data input, recording, or viewing selector (436), then in some examples, an input management process is performed that is associated with the respective detected input (FIG. 5A through FIG. 5F) (438). In some implementations, the data input, recording, or viewing selectors can include selectors displayed at any of the display views for the companion device (e.g., FIG. 6A through FIG. 6E, FIG. 8B through FIG. 8G) including case event selector 610, patient type selector 609, alarm selector 608, case type selector 606, patient information input selector 612, treatment marker input selector 614, and snapshot recording selector 616.

Although described as a particular series of steps, in other embodiments, more or fewer steps may be included. For example, if a working view is not selected for display, then the steps directed to configuring and displaying the working view (410-414) may not be performed. On the other hand, if multiple case type views are selected for display, one or more additional steps related to configure and display the selected case type views. In further embodiments, certain steps may be performed in a different order, or two or more steps may be performed in parallel. For example, a user may be authenticated at the companion device if the case type selector 606 is selected before a working view is activated, then the steps directed to configuring and displaying a case type view (422-434) may be performed prior to the steps for configuring and displaying the working view (410-414). In some examples, the portions of the method 400 that are performed are dependent upon the selections made by a user of the companion device 110, 111, 119, 204. Other modifications of the method 400 are possible while remaining in the scope and purpose of the method 400.

Turning to FIG. 5A through FIG. 5F, example methods for managing inputs provided at the companion device and instructing that corresponding actions be taken at an associated medical treatment device are illustrated. In some examples, each of the methods described in FIG. 5A through FIG. 5F is associated with a respective user input at one of the display screens at the companion device such as case event selector 610, alarm selector 608, case type selector 606, patient information input selector 612, treatment marker input selector 614, and snapshot recording selector 616. In addition to the input selections described in FIG. 5A through FIG. 5H, other user inputs can also be provided at the display views of the companion device 110, 111, 119, 204. For example, at patient type selector 609, a user can select whether the patient is an adult, pediatric, or neonatal patient, which can be transmitted to the medical treatment device 202. In some examples, the patient type 609 can impact alarm setpoints, waveform scale, defibrillation energy, and/or type of monitored case information. In one or more examples, the input of data at the companion device that influences the operation of the medical treatment device may be advantageous during a medical event and/or to allow for an alternative user interface to that provided at the medical treatment device and/or to prevent interference with case information displayed at the medical treatment device.

Figure 5A:
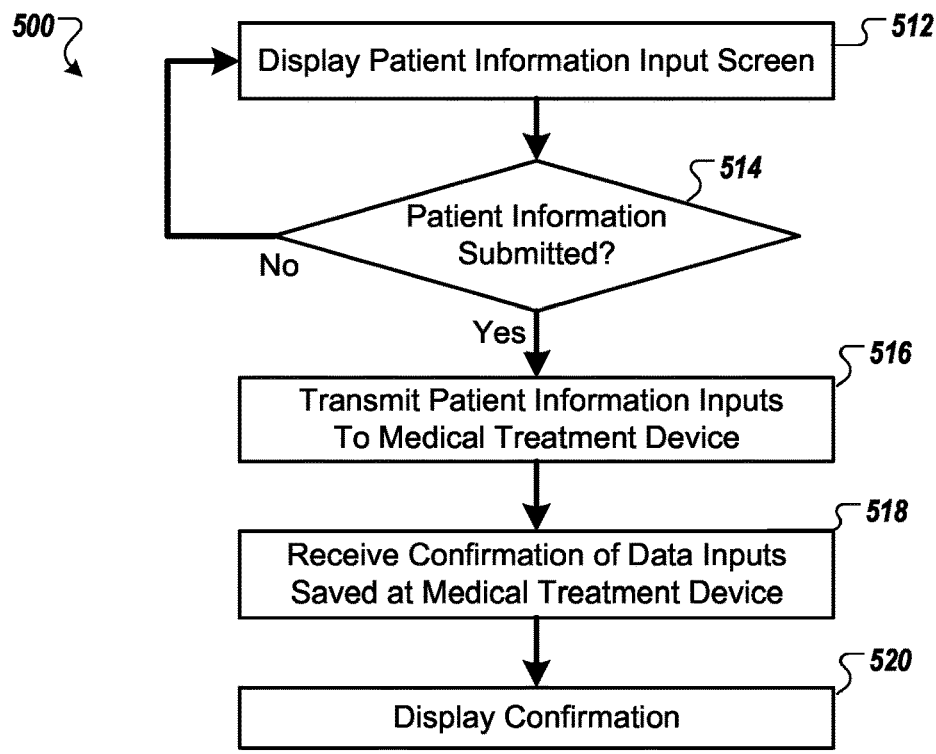
FIGS. 5A-5H illustrate flow charts of example methods for managing user inputs at a companion device.
Figure 7A:
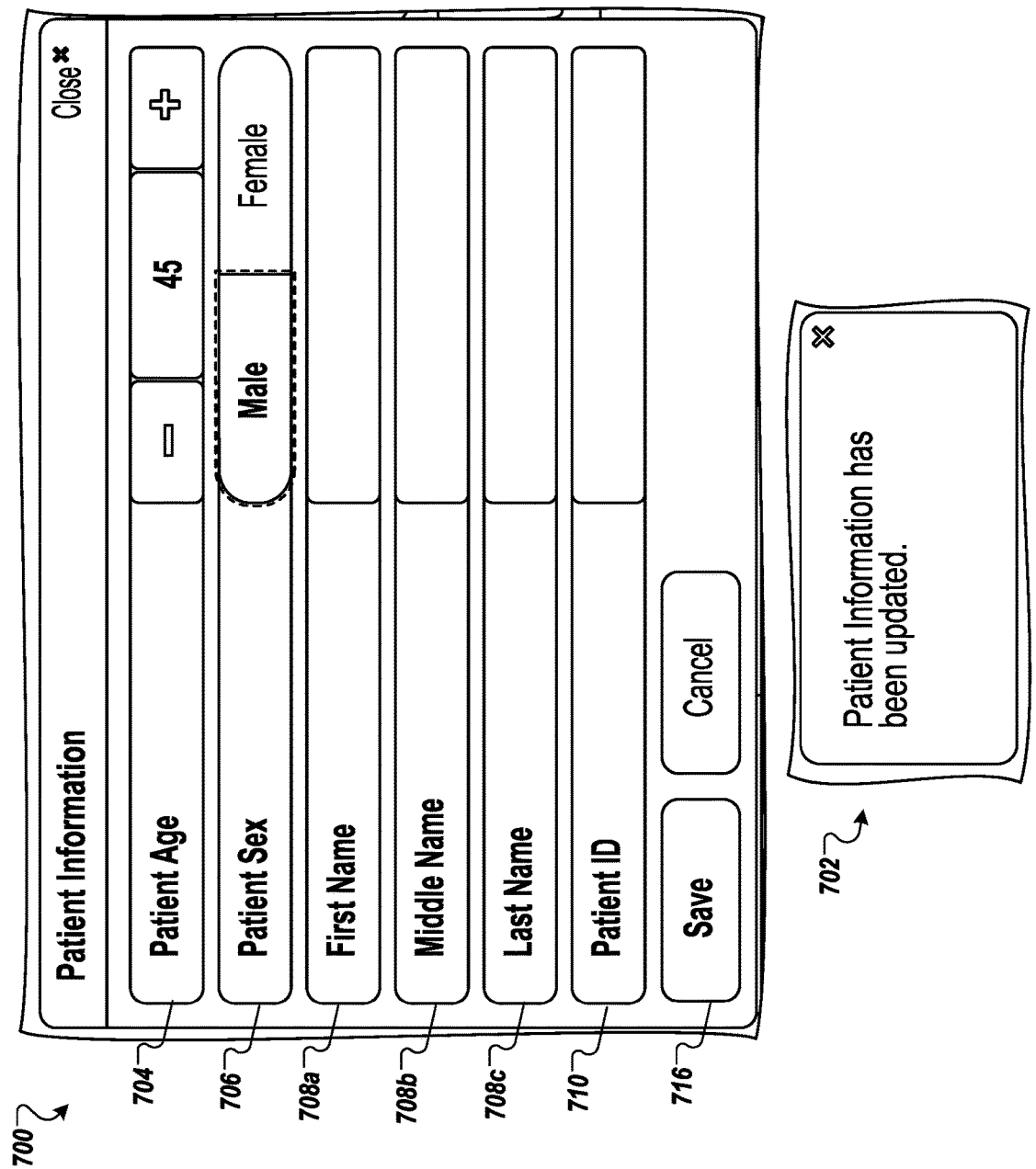
FIG. 7A illustrates an exemplary patient information input user interface screen and associated confirmation message.

For example, FIG. 5A illustrates a method 500 for providing patient input information at a companion device. In some implementations, in response to selection of patient input selector 612, the companion device 110, 111, 119, 204 displays a patient information input UI screen that allows a companion device user to input patient background and demographic information at one or more input fields (512). For example, FIG. 7A illustrates a patient information input UI screen 700 where a companion device user can input patient information associated with a respective medical event. In one example, the input fields can include one or more patient name input fields 708*a,b,c*, a patient gender input field 706, a patient age input field 704, and a patient identification code input field 710. Other patient information input fields can include a patient height input field or a patient weight input field. In some embodiments, the patient information input fields can also include a case identification input field. In some examples, a companion device user may manually type in the patient information in each of the input fields at the patient information UI screen 700. In other examples, the companion device can be configured to scan an image of a government-issued document or identification card via an installed camera or image capture device at the companion device, extract the relevant patient information from the scanned document, and automatically populate the input fields of the patient information UI screen 700 with the extracted information. Additionally, in some implementations, when the companion device 110, 111, 119, 204 displays the patient information input UI screen 700, a request can be transmitted to the medical treatment device 202 for any patient information 246 already stored in data repository, which can be automatically populated at the UI screen 700. In some implementations, device users can edit any of the information provided in automatically populated input fields.

In some examples, upon detecting that one or more input fields of patient information have been submitted at the patient information input UI screen (e.g., detecting that "save" button 716 has been selected (514), then the companion device transmits an instruction signal to the medical treatment device 202 with the submitted patient information and instructs the medical treatment device 202 to link and store the submitted patient information 246 with the respective case information 242 in data repository 208 (516). In some aspects, once the patient information has been saved, the medical treatment device 202 sends a confirmation signal to the companion device indicating that the information has been saved. In response to receiving the confirmation signal (518), in some implementations the companion device 110, 111, 119, 204 causes display of a confirmation message at a display interface confirming that the submitted patient information has been linked to the respective case information 242 and updated at the medical treatment device 202 (520). For example, confirmation message 702 illustrated in FIG. 7A is an example of a patient information update confirmation message. In other examples, separate confirmation messages may be displayed when the patient information has been transferred to the medical treatment device 202 and when the patient information has been stored at the medical treatment device 202.

Figure 13B:
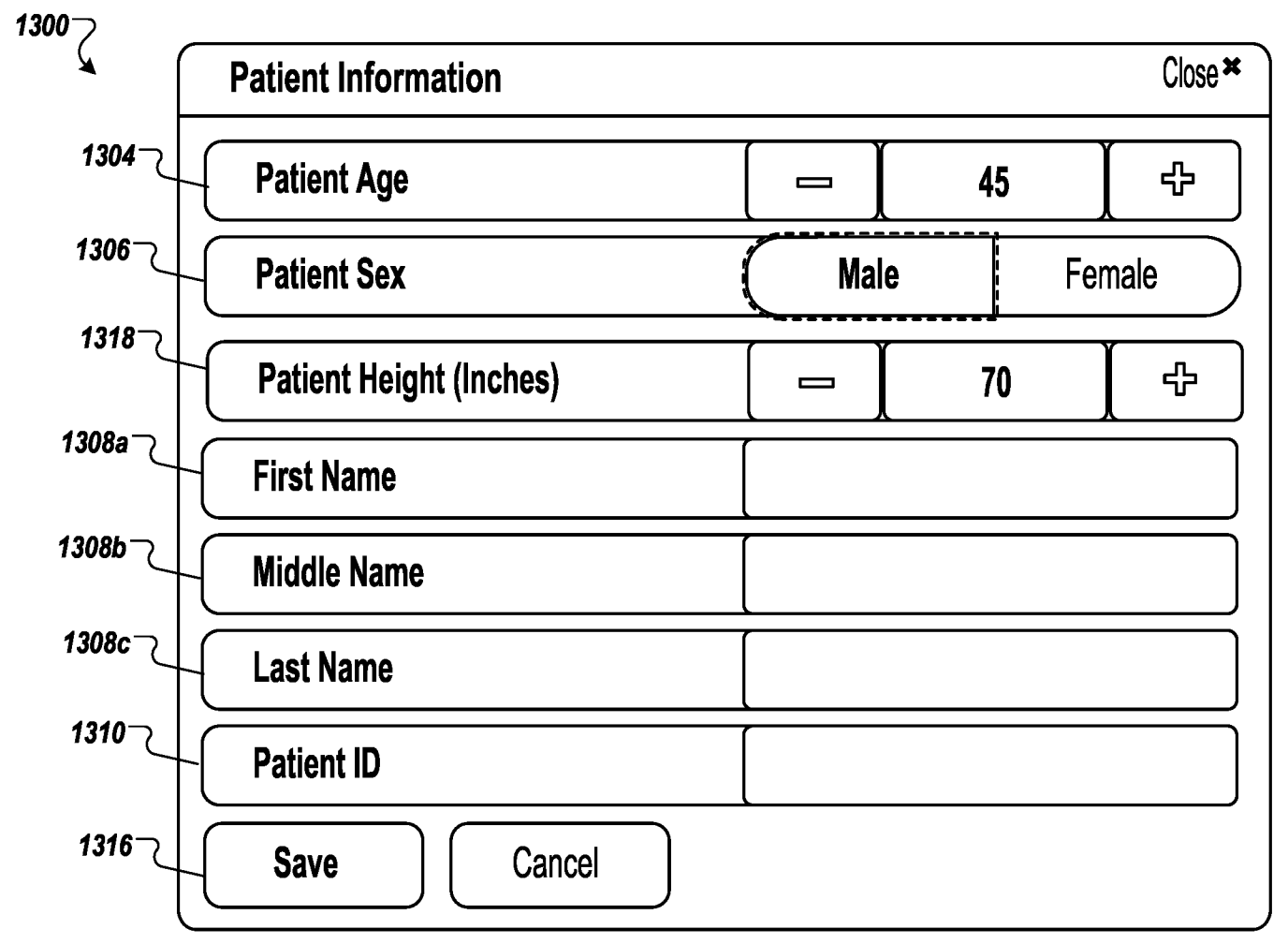

In another example, when the medical treatment device is a ventilator (e.g., ventilator 130 in FIGS. 1B-1C and ventilator 1000 in FIG. 10), in some examples, patient height, gender, and/or weight can be used to determine ventilation volume and rate for administering to the patient. For example, FIG. 13B illustrates another example of a patient information input UI screen 1300 where a companion device user can input patient information associated with a medical event at which a ventilator 130, 1000 is being used to provide treatment to a patient. Like the patient information input UI screen 700, the UI screen 1300 can include input fields for patient name 1308*a,b,c*, gender 1306, age 1304, and identification code 1310. In addition, the UI screen 1300 can also include a patient height input field 1318. In some examples, upon detecting that one or more input fields of patient information have been submitted at the patient information input UI screen (e.g., detecting that "save" button 1316 has been selected), the companion device 110, 111, 119, 204 in communication with ventilator 130, 1000 transmits the submitted patient information including the patient gender and height information. In response to receiving the patient gender and height information, the ventilator 130, 1000 automatically adjusts ventilator settings for tidal volume and/or ventilation rate that correspond to the ideal body weight for the respective submitted patient gender and height information.

In some examples, a supervisor or other caregiver that is not actively hands on providing direct patient care may have more flexibility to attend to administrative items like inputting patient information, viewing information streaming in real time from the medical treatment device (e.g., defibrillator, patient monitor, ventilator) that may or may not be immediately provided on the screen of the medical treatment device, and/or documenting other aspects of the medical event. Additionally, inputting patient information at an input interface at the medical treatment device 202 may be cumbersome and tedious. Therefore, providing the patient information input interface at the companion device frees up caregivers to better pay attention to their assigned tasks without getting tied up trying to tediously input patient information at the input interface of the medical treatment device.

Figure 5B:
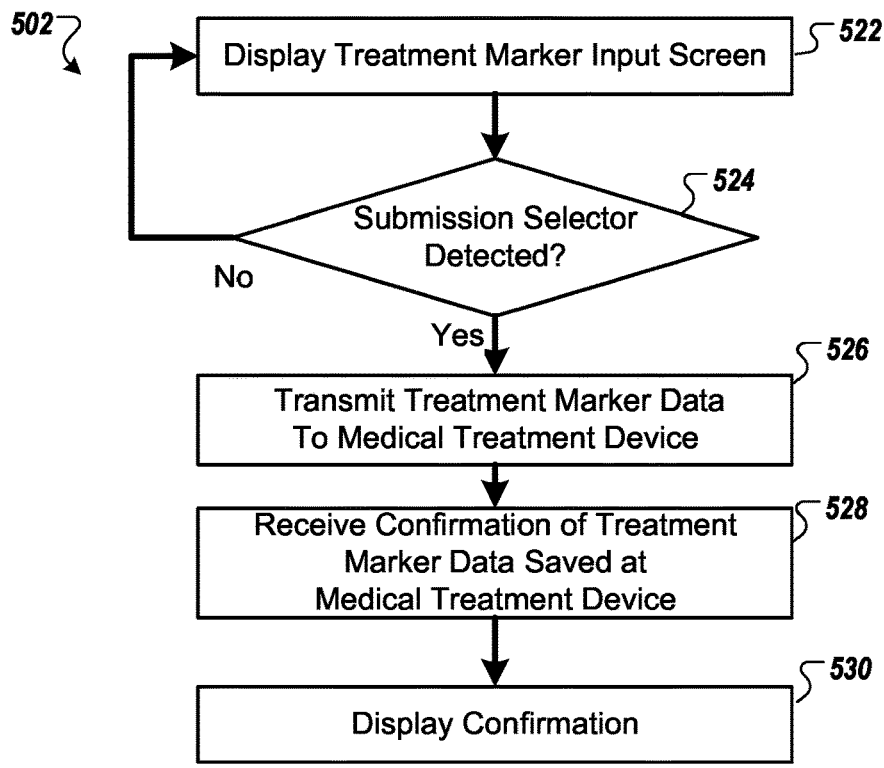
Figure 7B:
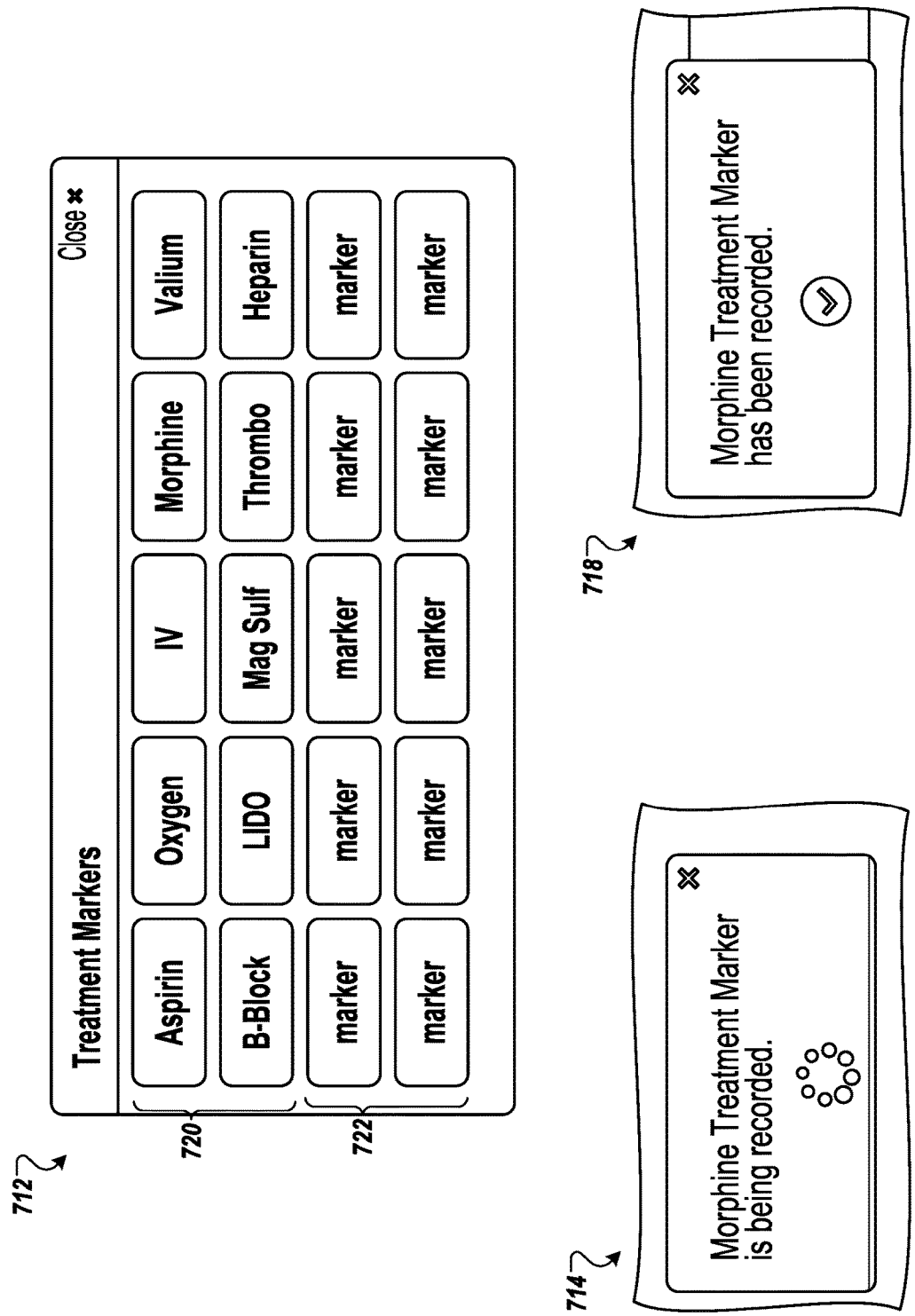
FIG. 7B illustrates an exemplary treatment marker input user interface screen and associated confirmation messages.

Turning to FIG. 5B, a method 502 for inputting treatment marker information at a companion device is illustrated. In some implementations, in response to selection of treatment marker selector 614, the companion device 110, 111, 119, 204 displays a treatment marker input UI screen that allows a companion device user to input treatment marker information at the companion device (522). For example, FIG. 7B illustrates a treatment marker input UI screen 712 where a companion device user can input treatment marker information associated with a respective medical event. In some examples, the medical treatment device 202 can automatically record treatment markers that the device 202 can automatically detect such as detection of a shockable ECG rhythm, administration of a defibrillation shock to the patient, starting chest compressions and/or ventilations. However, other treatment measures that are not detectable by the medical treatment device 202 can have an impact on patient response indicated in the waveforms, metric values, and trends displayed at the medical treatment device 202 and in the display views at the companion device 110, 111, 119, 204. For example, as shown in trends view UI screen 636 (FIG. 6B), visual indications of treatment markers 656, 658, 660, 662 are overlaid on trend graphs 638, 640, 642 to provide additional context regarding patient response to a treatment associated with the respective marker. Therefore, providing treatment markers indicating when certain medications or therapeutic measures have been taken can provide context to caregivers monitoring patient response during a medical event and can also enhance post-event debriefing and analysis. In one example, when a treatment is administered to a patient, a caregiver can open up the treatment marker input UI screen 712 to indicate what type of treatment (drugs, oxygen, anticoagulant) was administered. In some examples, the caregiver can also provide amplifying information such as time of administration, dosage, type of intravenous (IV) fluid, etc. As shown at the treatment marker input UI screen 712, treatment markers can include a number of preset treatment markers 720 for administration of aspirin, oxygen, IV fluid, morphine, valium, b-block, lidocaine (LIDO), magnesium sulfate, anticoagulant (thrombo), heparin, or return of spontaneous circulation (ROSC).

In some examples, the treatment marker input UI screen 712 can also include one or more customizable treatment markers 722 that allow companion device users to add additional treatment markers to further enhance a caregiver's ability to add meaningful annotations to the case information displayed at the medical treatment device 202 and companion device 110, 111, 119, 204. Further, allowing caregivers to input treatment marker information at the companion device 110, 111, 119, 204 frees up other caregivers who are providing direct patient care (e.g., CPR, ventilation, or shocks) to focus on their respective tasks without having to stop to input treatment marker information. In some examples, the treatment marker UI screen 712 can also include a selector for enabling audio input of treatment marker selection information that is detected by an audio sensor (e.g., a microphone), translated, and converted into one or more of the selections at the UI screen 712. In some examples, the device user can also add amplifying information to annotate the treatment marker data by providing audio voice notes that are detected by the audio sensor and converted into text notes by the companion device 110, 111, 119, 204. In still other examples, the treatment marker UI screen 712 may include a selector to enable scanning of an identification code (e.g., barcode) associated with the treatment marker that is converted into a treatment marker selection. In one example, the device user may scan a barcode of a medication being administered to the patient, and the companion device 110, 111, 119, 204 may convert the scanned identification code into medication type and/or dosage.

In some examples, upon detecting that treatment marker information has been submitted at the treatment marker input UI screen (e.g., that one or more of the treatment markers 720, 722 have been selected) (524), then the companion device 110, 111, 119, 204 transmits an instruction signal to the medical treatment device 202 with the submitted treatment marker information and instructs the medical treatment device 202 to link and store the submitted treatment marker data 252 with the respective case information 242 in data repository 208 (526). In some aspects, once the treatment marker data 252 has been saved, the medical treatment device 202 sends a confirmation signal to the companion device 110, 111, 119, 204 indicating that the data has been saved. In response to receiving the confirmation signal (528), in some implementations the companion device 110, 111, 119, 204 causes display of a confirmation message at a display interface confirming that the submitted treatment marker data 252 has been linked to the respective case information 242 and updated at the medical treatment device 202 (530). In some examples, the medical treatment device may send confirmation signals to the companion device both when linking and saving of the treatment marker data 252 has commenced and concluded. In such an example, separate confirmation messages may be displayed to confirm that a submitted treatment marker is being recorded (linked and saved) and that recording/saving of the submitted treatment marker has been completed. For example, FIG. 7B illustrates an in-progress treatment marker recording confirmation message 714 that the companion device 110, 111, 119, 204 displays in response to receiving a confirmation signal from the medical treatment device 202 that linking/storing of a submitted morphine treatment marker has commenced. This recording confirmation message 714 may be beneficial to put the caregiver at ease (during a stressful situation) that the treatment marker is indeed being recorded. Similarly, treatment marker recording completion message 718 may be displayed upon receiving confirmation from the medical treatment device 202 that linking and saving of the morphine treatment marker has completed.

Figure 5C:
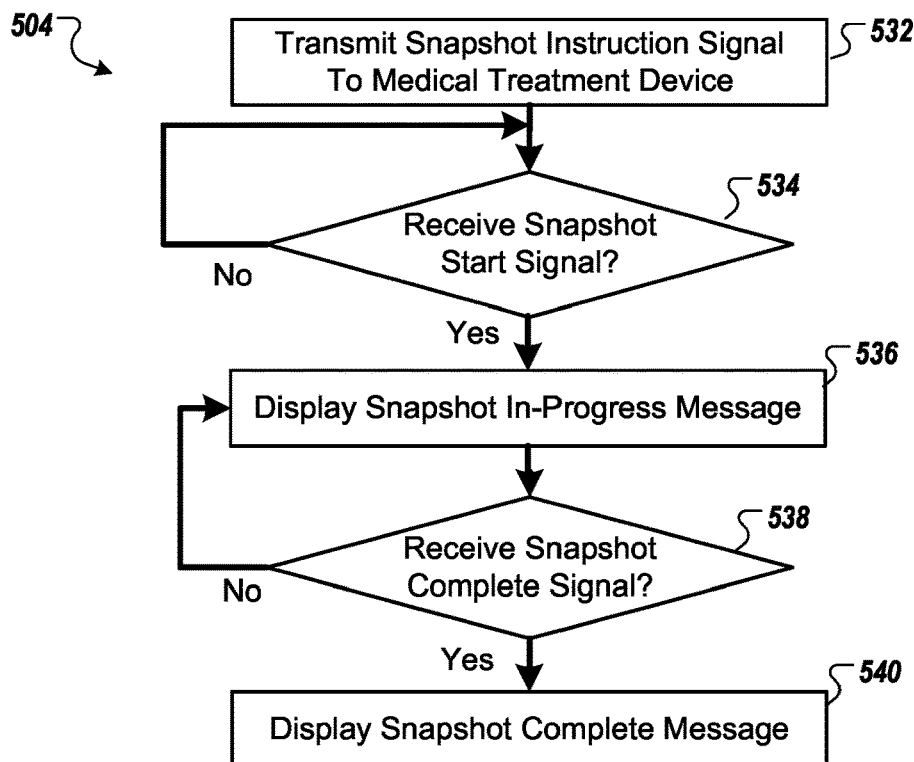

Turning to FIG. 5C, a method 504 for initiating a snapshot at a medical treatment device via a companion device is illustrated. In some implementations, upon receiving selection of snapshot recording selector 616 at one of the display views of the companion device, the companion device 110, 111, 119, 204 can generate and transmit a snapshot instruction signal to the medical treatment device (defibrillator) (532). In some embodiments, in response to receiving the snapshot instruction signal and commencing capturing the snapshot of the display, the medical treatment device 202 transmits a confirmation message to the companion device that capture of the snapshot has commenced. In some implementations, a snapshot can include a data for one or more waveforms of medical data being monitored by the medical treatment device over a predetermined period of time such as ECG waveforms. In some implementations, snapshot data can include medical waveform data for predetermined periods of time before and after a snapshot is initiated. In one example, the waveform data is captured between 5 and 15 seconds. In one example, snapshot data may be captured for multiple waveforms of physiological data in addition to ECG data (e.g., $SPO_2$, $CO_2$, NIBP, IBP1/2/3, etc.) In response to receiving the confirmation message (534), in some implementations, the companion device displays a snapshot in-progress notification message (snapshot recording message 724 in FIG. 7C-1) indicating that recording (capture and storage) of the snapshot at the medical treatment device has commenced (536). This snapshot recording message 724 may be beneficial for the caregiver to know that the snapshot is indeed being recorded. In some implementations, once the snapshot has been captured, the medical treatment device may transmit a snapshot completion confirmation signal to the companion device 110, 111, 119, 204 indicating that recording of the snapshot has completed. In response to receiving the snapshot completion confirmation signal (538), in some examples, the companion device displays a snapshot completion notification message (snapshot completion message 726 in FIG. 7C-1) to indicate to the companion device user that recording of the snapshot has completed (540).

Figure 5D:
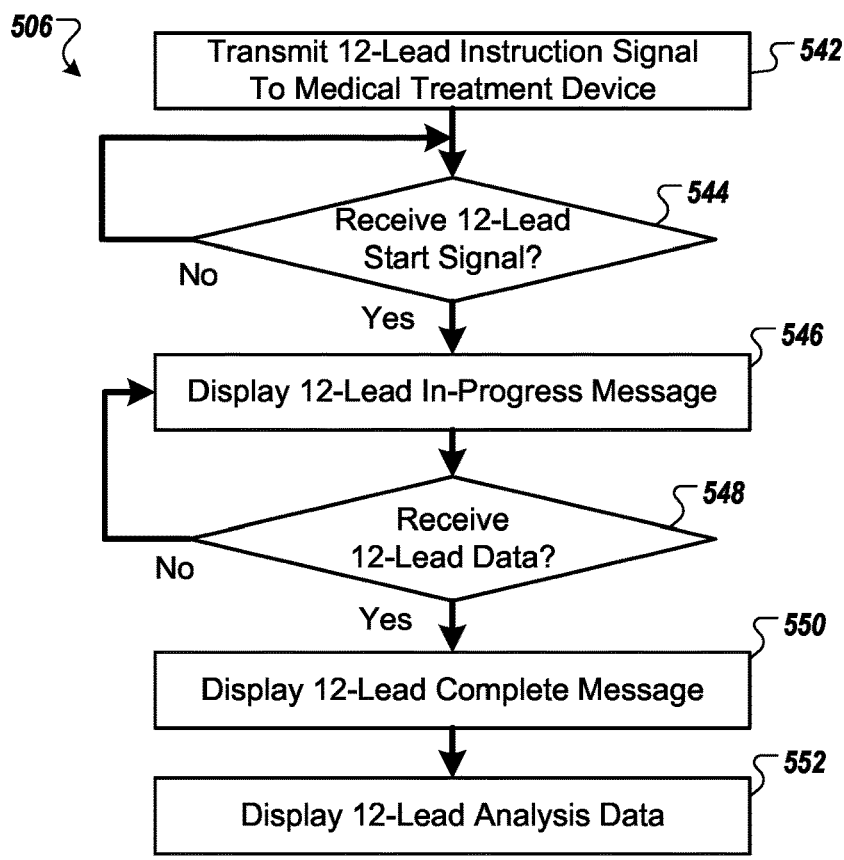

Turning to FIG. 5D, a method 506 for initiating a 12-lead ECG analysis at a medical treatment device via a companion device is illustrated. In some implementations, upon receiving selection of 12-lead ECG analysis selector 617 at one of the display views of the companion device, the companion device 110, 111, 119, 204 can generate and transmit a 12-lead analysis signal to the medical treatment device (defibrillator) (542). In some embodiments, in response to receiving the 12-lead analysis instruction signal and commencing 12-lead ECG analysis, the medical treatment device 202 transmits a confirmation message to the companion device that the 12-lead analysis has commenced. In response to receiving the confirmation message (544), in some implementations, the companion device displays a 12-lead analysis in-progress notification message (12-lead analysis message 728 in FIG. 7C-2) indicating that performance of the 12-lead ECG analysis at the medical treatment device 202 has commenced (546). This 12-lead analysis message 728 recording message 724 may be beneficial for the caregiver to know that the 12-lead is in progress. In some implementations, once the 12-lead analysis has completed, the medical treatment device 202 may transmit a 12-lead analysis completion confirmation signal to the companion device 110, 111, 119, 204 along with 12-lead data 250 for the completed 12-lead analysis. In response to receiving the snapshot completion confirmation signal (548), in some examples, the companion device 110, 111, 119, 204 displays a 12-lead analysis completion notification message (12-lead analysis completion message 730 in FIG. 7C-2) to indicate to the companion device user that the 12-lead ECG analysis has completed (550). In some examples, the companion device 110, 111, 119, 204 also displays the received 12-lead data for the analysis at a display view of the companion device 110, 111, 119, 204 (552).

Figure 7D:
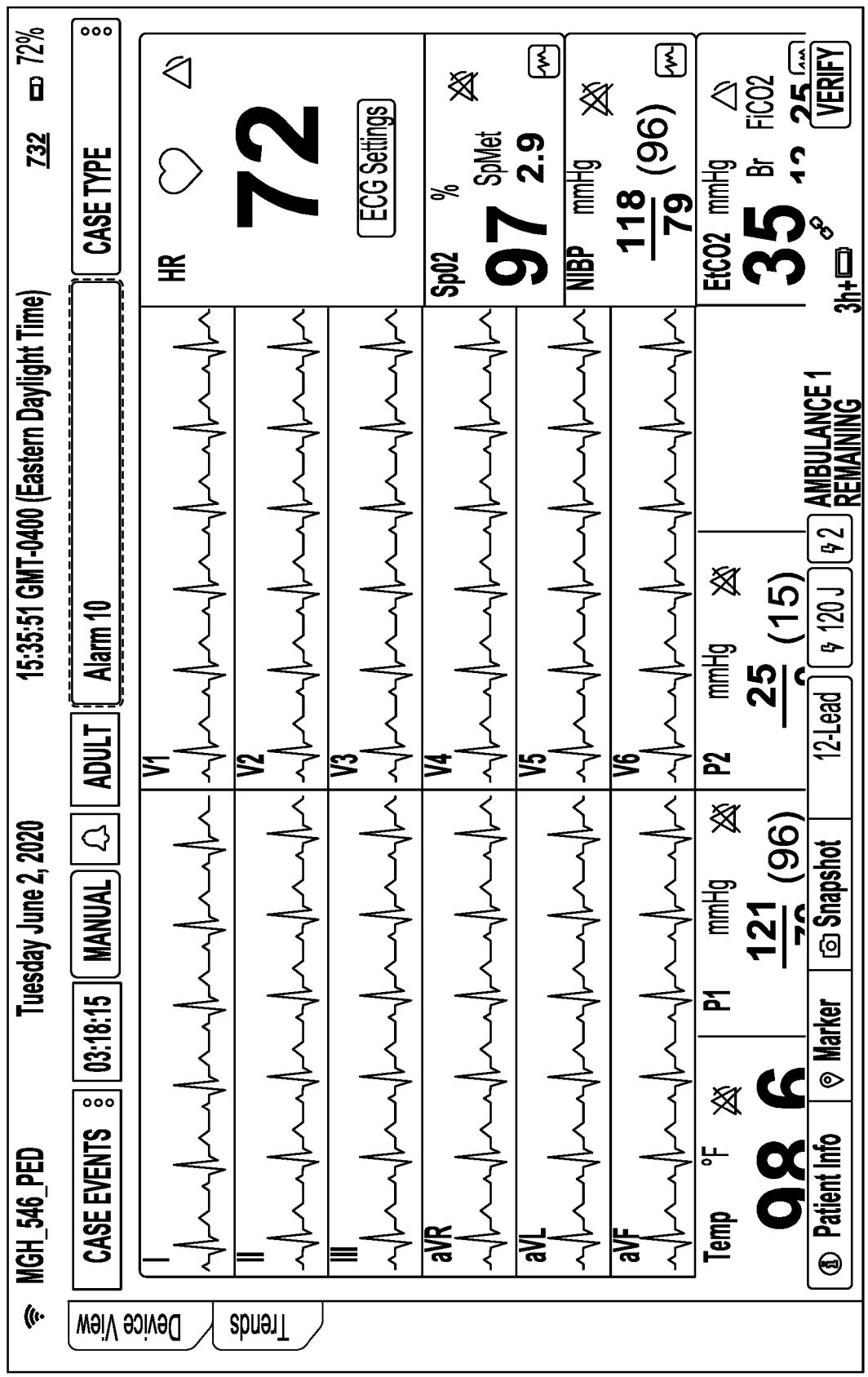
FIG. 7D illustrates an exemplary 12-lead ECG analysis user interface screen.

For example, 12-lead analysis UI screen 732 in FIG. 7D illustrates the 12-lead analysis data that is displayed at the companion device 110, 111, 119, 204. In some implementations, the 12-lead analysis UI screen 732 may only be displayed when the device view UI screen 600 is currently displayed. In other examples, the 12-lead analysis UI screen 732 may be displayed within any working view UI screen.

To close the 12-lead analysis UI screen 732, in some embodiments, the user can select any location on the UI screen 732. In some examples, companion device 110, 111, 119, 204 can request that a previously performed 12-lead analysis be displayed at the 12-lead analysis UI screen 732 because case information 242 is stored at the data repository 208 of the medical treatment device 202, the companion device 110, 111, 119, 204 can request the respective 12-lead data 250 for a selected previously performed 12-lead analysis from the medical treatment device 202. In response, the medical treatment device 202 may transmit the request 12-lead data 250 as a bulk transfer message to the companion device 110, 111, 119, 204 for display.

Figure 5E:
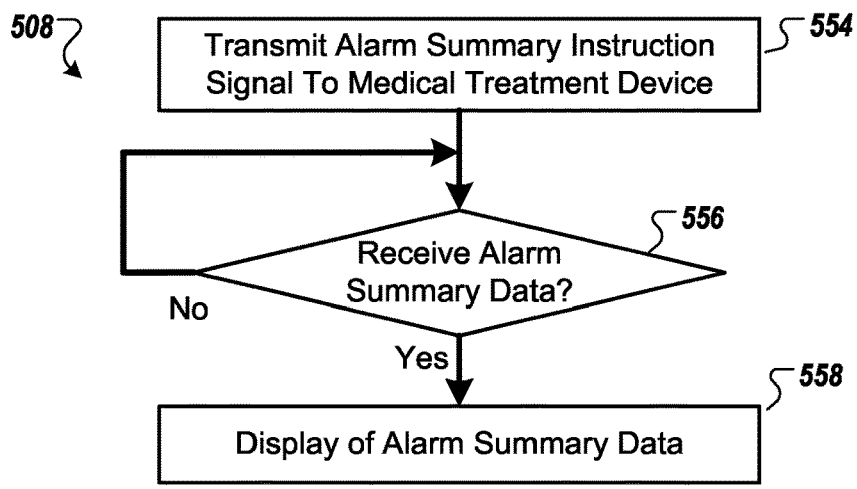

Turning to FIG. 5E, a method 508 for generating a medical treatment device alarm summary at a companion device is illustrated. In some implementations, upon receiving selection of alarm selector 608 at one of the display views of the companion device, the companion device 110, 111, 119, 204 can generate and transmit an alarm summary instruction signal to the medical treatment device (defibrillator) (554). In some examples, upon receiving the instruction signal, the medical treatment device 202 transmits the requested alarm data 256 for the medical event that is stored in data repository 208. In response to receiving the requested alarm data (556), in some implementations, the companion device displays the alarm data within an alarm summary UI screen (558).

Figure 7E:
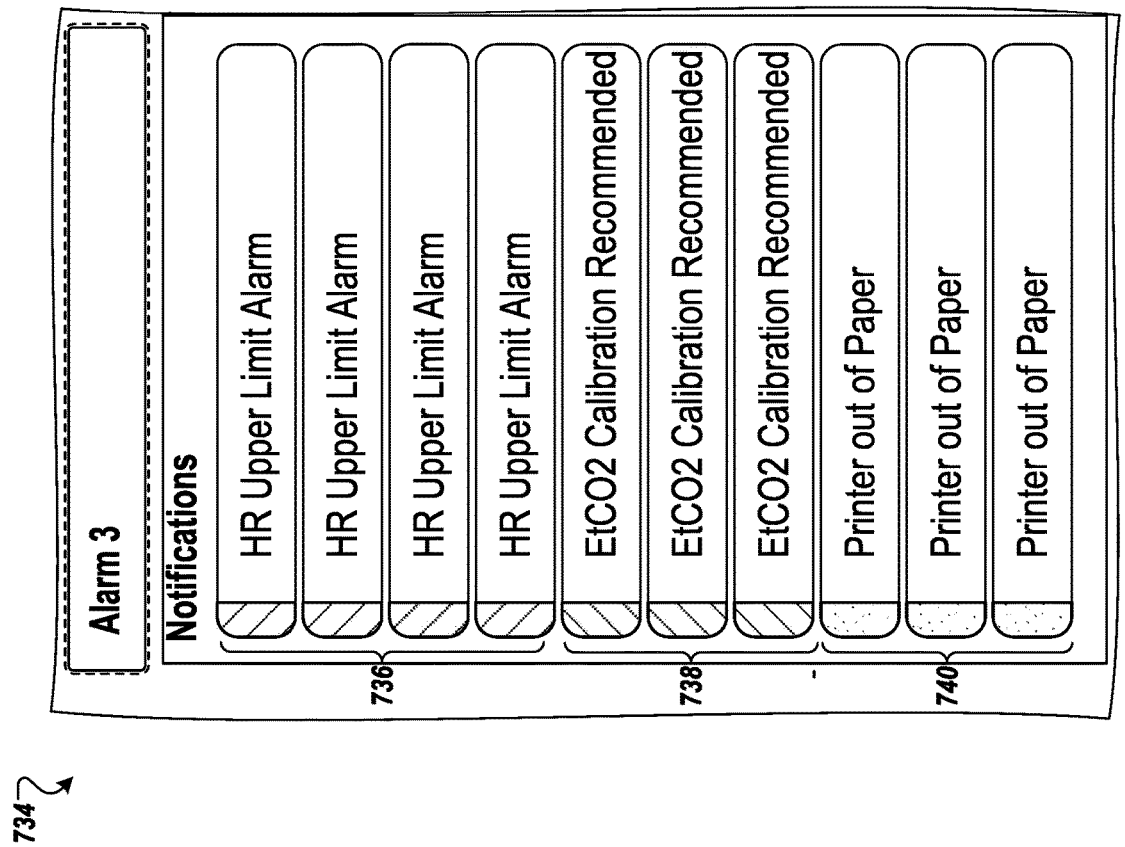
FIG. 7E illustrates an exemplary alarm summary user interface screen.

For example, FIG. 7E illustrates an example alarm summary UI screen 734 that displays a listing of alarms that have occurred at the medical treatment device 202 over the course of a medical event. In some examples, the alarming conditions presented in the UI screen 734 can include physiological alarm events and technological alarm events. For example, physiological alarm events, like HR upper limit alarm 736, may occur when a physiological sensor input detects a value that falls outside of threshold limits for the sensor. Alarm events can also be classified as life-threatening alarms or non-life-threatening alarms based on a magnitude of the detected sensor value relative to the predetermined threshold ranges. Technological alarms can indicate when a sensor may be malfunctioning or out of service or another technical issue has occurred at the medical treatment device. For example, $ETCO_2$ calibration recommended alarm 738 may be generated when a mainstream $CO_2$ sensor on an airway adapter is detecting erratic values or otherwise indicates that the sensor is due for calibration. Additionally, printer out of paper alarm 740 may be generated when no paper or less than a predetermined amount of paper is available at the medical treatment device 202. In some embodiments, each of the alarm events 736, 738, 740 at the UI screen 734 is selectable for presenting details about the respective alarming condition (e.g., time of alarm, patient condition at the time of alarm). In some examples, when a new alarming condition is detected at the medical treatment device 202, data associated with the alarming condition may be automatically transmitted to the companion device 110, 111, 119, 204, causing alarm selector 608 to flash or otherwise indicate to a companion device user that a new alarming condition has occurred.

FIG. 13A illustrates an example alarm summary UI screen 1320 displayed at companion device 110, 111, 119, 204 over the course of a medical event. In some implementations, the alarm summary UI screen 1320 displays alarming conditions associated with alarming conditions at ventilator 130, 1000 while the alarm summary UI screen 734 shown in FIG. 7E is associated with alarming conditions at defibrillator 108 (see FIG. 1A through FIG. 1C). In some examples, the alarm summary UI screen 1320 is displayed by the companion device 119, 204 in response to selection of alarm user input 1105 at companion device user interface screens 1101, 1102 shown in FIG. 11A and FIG. 11C.

The alarm summary UI screen 1320, in some examples, may categorize and/or sort alarming conditions according to time 1350, alarm name 1352, alarm type 1354, and/or alarm priority 1356. For example, alarm type 1354 can indicate whether a detected alarming condition is associated with patient safety, use environment, or a self-check alarm. In some implementations, alarm types 1534 can include patient safety alarms such as high/low airway pressure, high/low tidal volume, high/low breath rate/apnea, PEEP leak, insufficient flow, spontaneous breath-PIP high/low, spontaneous breath-VT high/low, patient inspiratory demand not met, auto-PEEP, patient disconnect, exhalation system failure/fault, calibration error, suspicious triggers, tubing compliance faults, $SpO_2$ sensor off/low/error, heart rate high/low, etc. Use environment alarms can include alarms for low battery, power faults, climatic environment faults, oxygen supply faults, gas intake faults, etc. Self-check alarms can include internal communication errors, pneumatic system failures, power system faults, pulse oximetry module faults, preventive maintenance alerts, etc. Alarm priorities 1356 can be categorized as "high," "medium," and "low" or another rating scheme (e.g., severity indicated as numbers or letters) based on the severity of the associated alarm. In some examples, all patient safety alarms are categorized as high priority alarms. In one example, each alarm is stored in data repository 256 of the respective medical treatment device along with corresponding alarm information (e.g., type, priority). When an alarming condition occurs at the respective medical treatment device 130, 202, 1000, the alarm and corresponding information are transmitted to the companion device 110, 111, 119, 204 for real-time display at alarm summary UI screen 1320. In some examples, responsive to detecting selection of one of the displayed alarming conditions, the companion device 119, 204 can be configured to display amplifying information associated with the alarm including instructions for resolving the respective alarming condition. In some embodiments, the companion device 110, 111, 119, 204 can also be configured to display alarming conditions as event markers (also referred to as alarm markers) at a display interface (e.g., event marker 1132 at trends view user interface 1150 in FIG. 11E).

In some implementations where multiple medical treatment devices are simultaneously connected to and in communication with companion device 110, 111, 119, 204 (e.g., defibrillator 108 and ventilator 130 in FIG. 1C), the features of alarm summary UI screens 734, 1320 can be combined into a single user interface screen that allows a supervisor 118 to simultaneously monitor alarming conditions at two or more medical treatment devices 108, 130, 202. For example, upon detecting selection of alarm user input 1107 at the multi-device working views 1100, 1194 shown in FIG. 11B and FIG. 11D and the multi-device trends view 1150 in FIG. 11E, the companion device 110, 111, 119, 204 can cause display of an alarm summary UI screen that includes alarming conditions from all connected medical treatment devices 108, 130, 202.

Figure 5F:
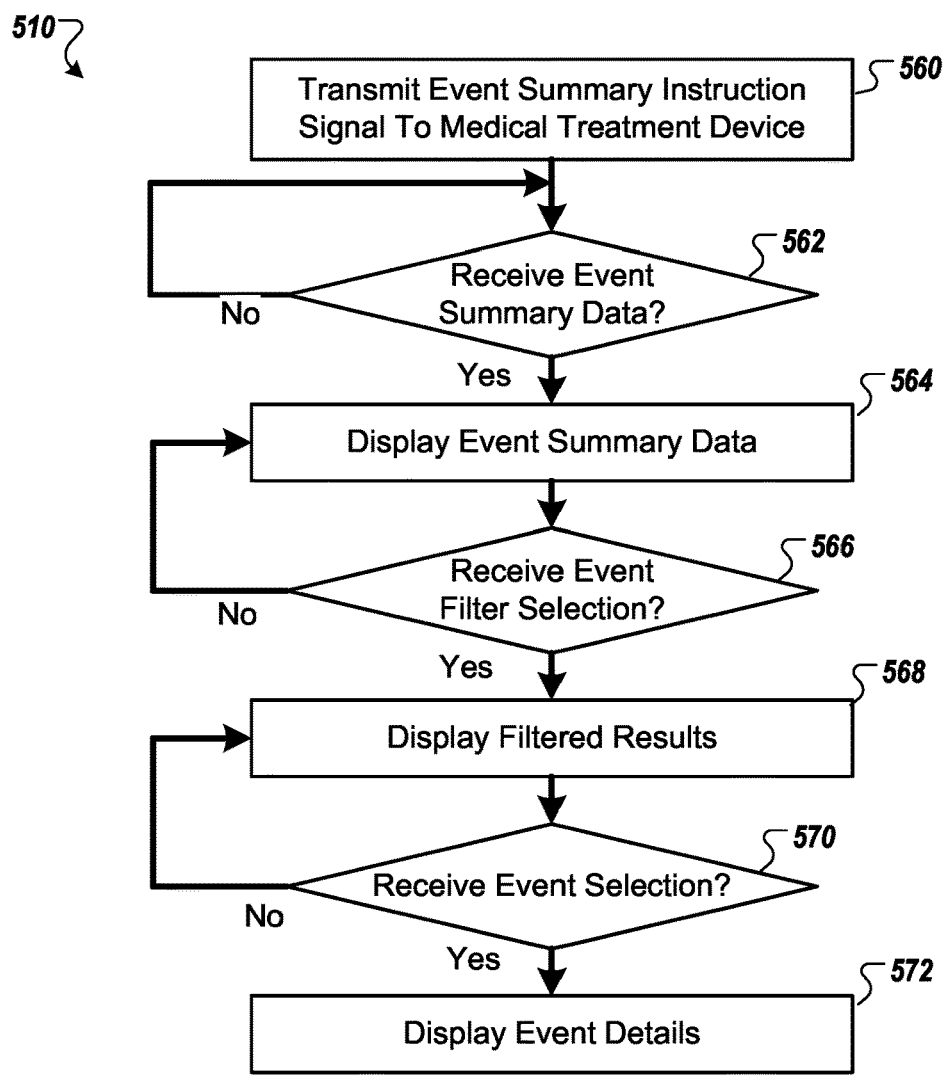
Figure 7F:
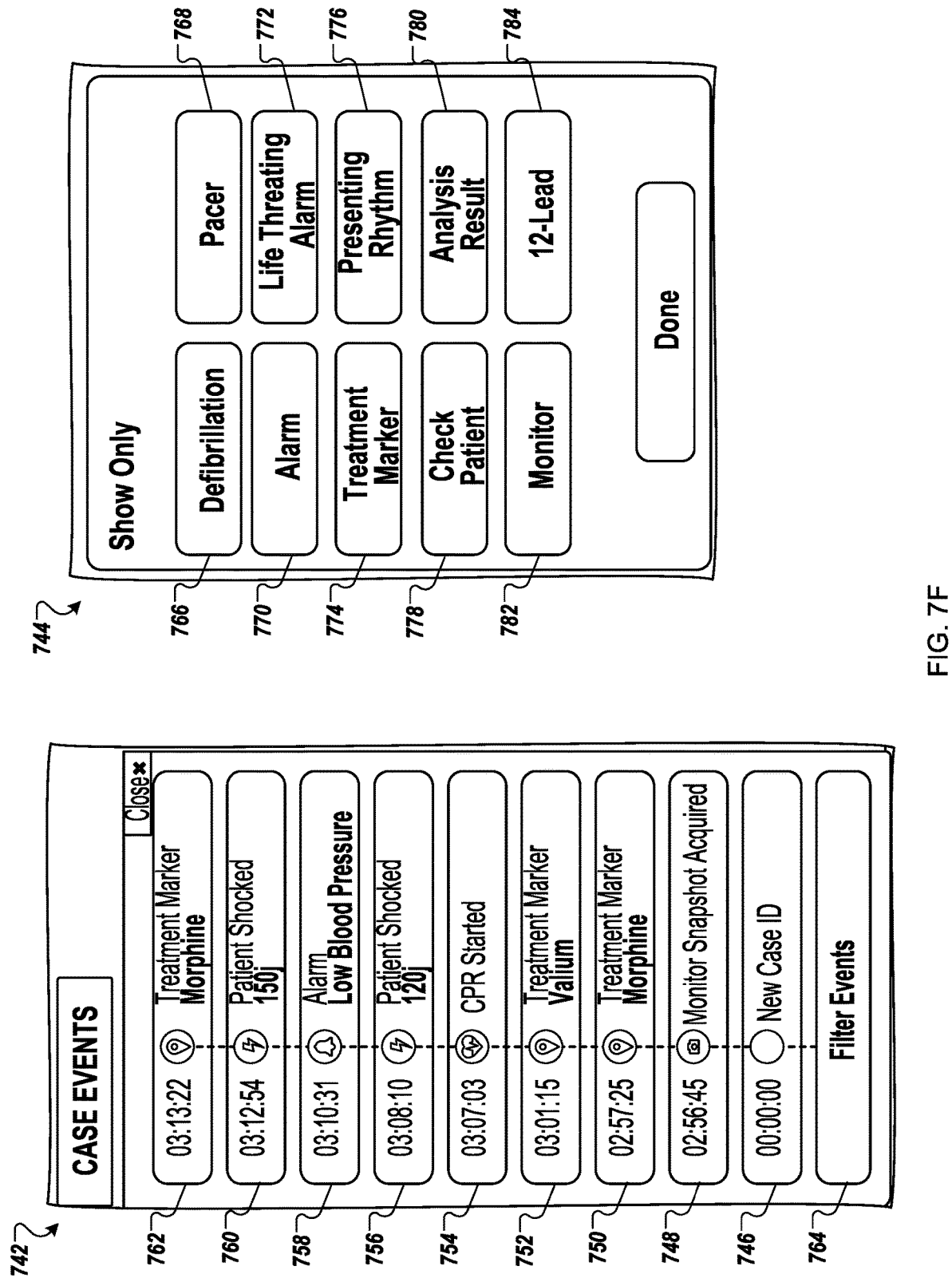
FIG. 7F illustrates exemplary case event summary user interface screens.

Turning to FIG. 5F, a method 510 for generating a medical event summary at a companion device is illustrated. In some implementations, upon receiving selection of case event selector 610 at one of the display views of the companion device, the companion device 110, 111, 119, 204 can generate and transmit an event summary instruction signal to the medical treatment device (defibrillator) (560). In some examples, upon receiving the instruction signal, the medical treatment device 202 transmits the requested case information 242 for the event summary that is stored in data repository 208. In response to receiving the requested medical event data for the event summary (562), in some implementations, the companion device displays the event summary data within an event summary UI screen (564). For example, FIG. 7F illustrates an example event summary UI screen 742 that presents one or more time-stamped events that have occurred over the course of treating a patient. In some examples, the displayed events can include automatically generated treatment markers (patient shocks 758, 760), initiation of CPR 754, manually-input treatment markers (morphine administration 750, 762, valium administration 752), alarm conditions 758, snapshot acquisitions 748, 12-lead ECG analyses, or patient/case input information 746. In some examples, the listed events may be color-coded based on event type. The event summary UI screen 742 can also include an event filter selector 764 that causes the companion device to filter the events presented in the UI screen 742 to only the types of events the companion device user wishes to see. For example, event filter UI screen 744 can be presented in response to selection of the event filter selector 764, which presents types of events that can be presented within the event summary UI screen 742.

In some implementations, upon detecting selection of one or more filtered event types at event filter UI screen 744 (566), the companion device can adjust the events presented within the event summary UI screen 742 to only include the filtered types of events (568). For example, filter types can include defibrillation 766, pacer events (when a patient has an installed pacemaker) 768, alarms 770, life-threatening alarms (e.g., life-threatening ECG rhythms) 772, treatment markers 774, presenting rhythms 776, check patient (e.g., when a continuous background ECG analysis detected a shockable rhythm and that the caregiver should immediately check on the patient) 778, analysis results (e.g., results from a caregiver selecting an "analyze" input for determining whether a rhythm is shockable/not shockable) 780, monitor (corresponding to "monitor" snapshots manually initiated at an operator request, such as in response to observing an event of interest) 782, and 12-lead ECG results (12-lead snapshot results that include all ECG leads at a high sample rate and with 12-lead analysis results include in the record) 784. Additionally, each of the events displayed at the event summary UI screen 742 is selectable such that when selected (570), in some implementations, additional details associated with the event are displayed (572). In some examples, the additional details that are displayed can include medication dosage, amount of time of or other information concerning chest compressions or ventilations, and/or an ECT snapshot when the event occurred.

Figure 5G:
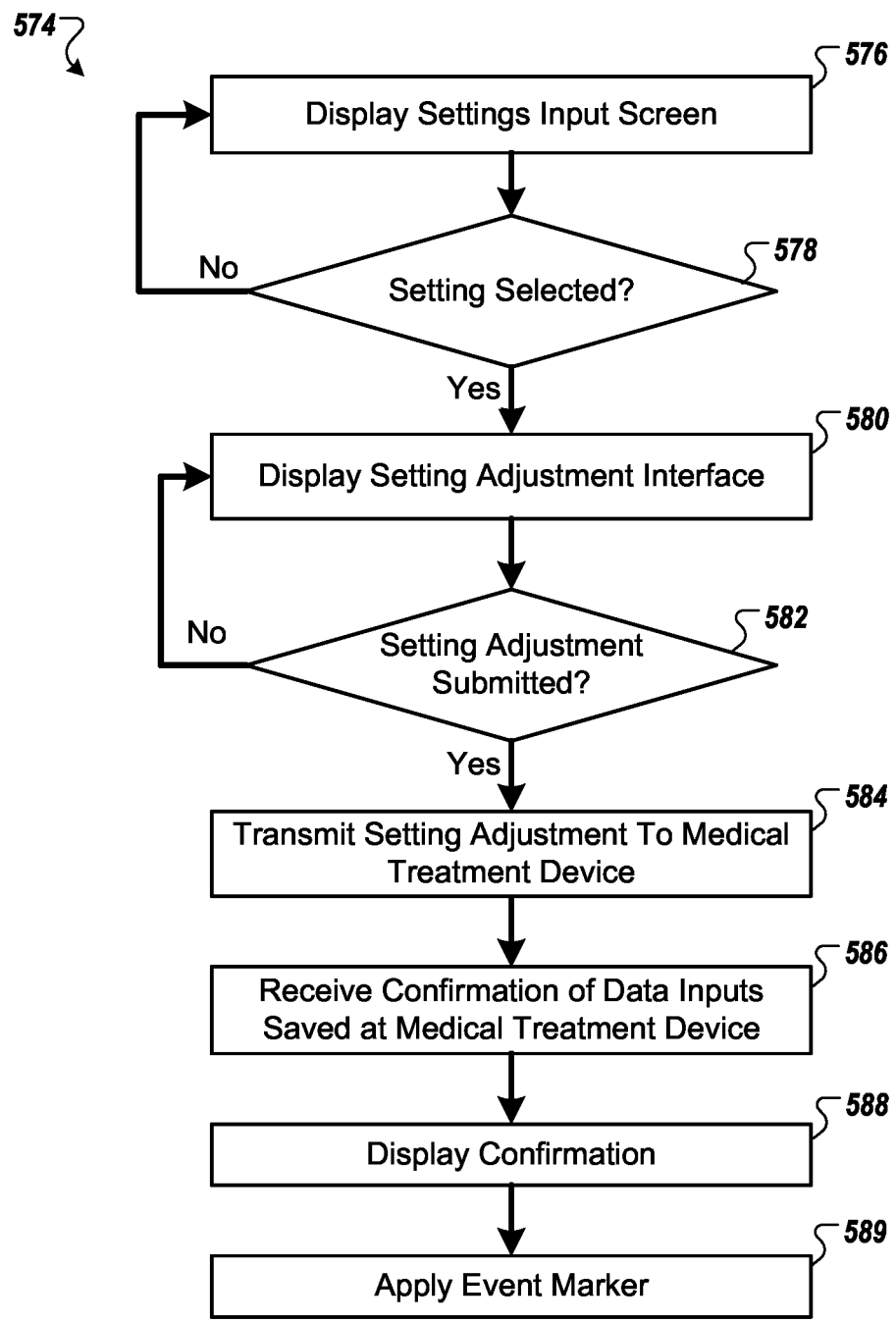

Turning to FIG. 5G, a method 574 for adjusting medical treatment device settings via a companion device is illustrated. In some implementations, the method 574 can be executed by companion device 110, 111, 119, 204 in communication with a ventilator 130, 1000 that includes one or more adjustable parameter and/or mode settings for providing positive pressure ventilation to a patient that can be modified at the companion device 110, 111, 119, 204. For example, a companion device user interface screen (e.g., user interface screen 1101 in FIG. 11A) can include a ventilator settings user input 1129 that causes ventilator settings adjustment user interface screen 1362 (FIG. 13C) to be displayed. In other examples, a companion device user interface (e.g., user interface screen 1100 in FIG. 11B) can activate a setting adjustment interface for any of the displayed ventilator settings (e.g., FIO$_2$, PEEP, V$_t$, I:E ratio, ventilator mode, PIP threshold, SPO$_2$, BPM) in response to detecting selection of a respective ventilator setting section of the user interface 1100. For example, selection of the breaths per minute (BPM) section 1112 of the user interface screen 1100 can cause the companion device 110, 111, 119, 204 to display a BPM adjustment interface 1360 (FIG. 13D-1) to provide for changing the BPM administered to the patient.

Figure 13C:
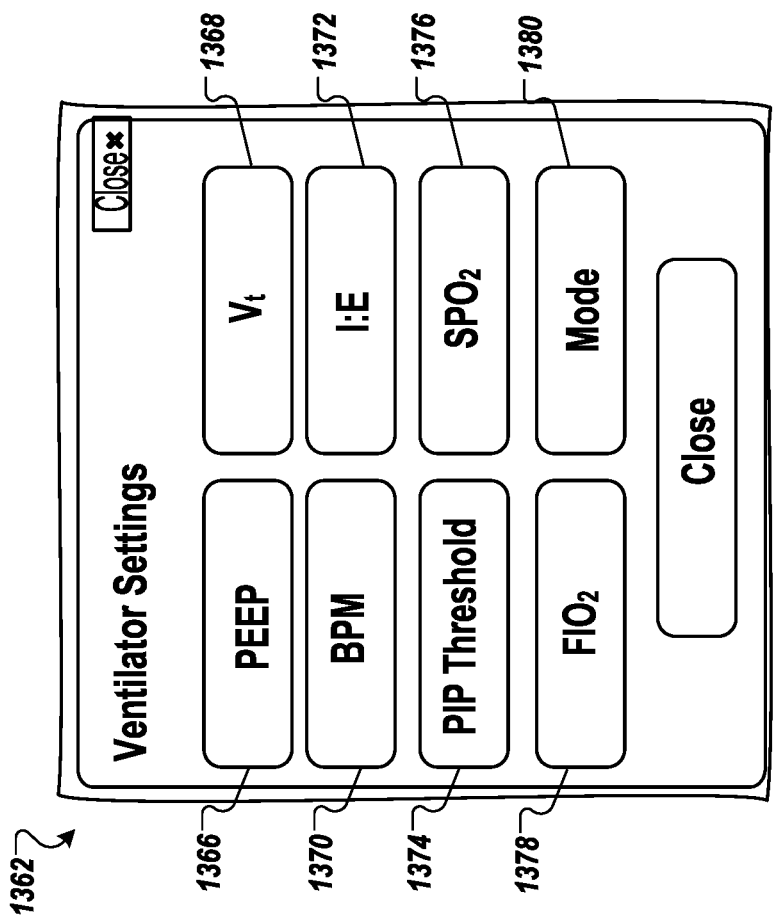
FIG. 13C illustrates an exemplary ventilation settings input user interface screen.

In some implementations, the method 574 commences with the companion device 110, 111, 119, 204, responsive to detecting selection of ventilator settings user input 1129, causes display of a settings input screen (576). In some examples, the settings input screen is settings adjustment user interface screen 1362 (FIG. 13C). The settings adjustment user interface screen 1362, in one example, can include user inputs that correspond to each adjustable ventilator setting. For example, the adjustable ventilator settings can include a fraction of inspired oxygen (FIO$_2$) setting 1378, a positive end-expiratory pressure (PEEP) setting 1366, a tidal volume (V$_t$) setting 1368, an inspiratory:expiratory ratio (I:E) setting 1372, a ventilator mode setting 1380, peak inspiratory pressure (PIP) threshold setting 1374, breaths per minute (BPM) setting 1370, or SpO$_2$ setting 1376. In some examples, if a setting input is selected (578), then the companion device 110, 111, 119, 204 can cause display of the respective setting adjustment interface (580). For example, if the BPM setting user input 1370 is selected, then the companion device 110, 111, 119, 204 may cause the BPM adjustment interface 1322 (FIG. 13D-1) to be displayed. In some implementations, the BPM setting adjustment user interface 1322 may include an input field 1326 that allows the user to increase or decrease the breaths per minute delivered to the patient by the ventilator 130, 1000. In one example, the input field 1326 includes increase/decrease inputs 1328a,b that allows the companion device user to raise or lower the BPM setting. In other examples, the input field 1326 may be a free text field that allows the user to input an adjusted BPM value at an interface keypad. In some implementations, the companion device 110, 111, 119, 204 may be configured to issue alerts to the user if an adjusted setting value is outside of one or more predetermined setting ranges. In some embodiments, the setting adjustment interfaces for PEEP 1366, V$_t$ 1368, I:E 1372, PIP threshold 1374, SPO$_2$ 1376, and FIO$_2$ 1378 can have substantially the same input fields and format as the BPM setting adjustment interface 1322. In some examples, if the ventilator mode setting 1380 is selected, then the companion device 110, 111, 119, 204 causes ventilator mode adjustment interface 1332 (FIG. 13D-2) to be displayed. In some embodiments, the ventilator mode adjustment interface 1332 can include individual mode inputs that correspond to each of the available operating modes for the ventilator 130, 1000 (e.g., assist/control (AC) mode 1336, a synchronized intermittent mandatory ventilation (SIMV) mode 1340, a continuous positive airway pressure (CPAP) mode 1338, or a bilevel (BL) mode 1342). To adjust the ventilator setting, the companion device user selects the user input 1336, 1338, 1340, 1342 that corresponds to the desired ventilator operating mode.

Figure 11A:
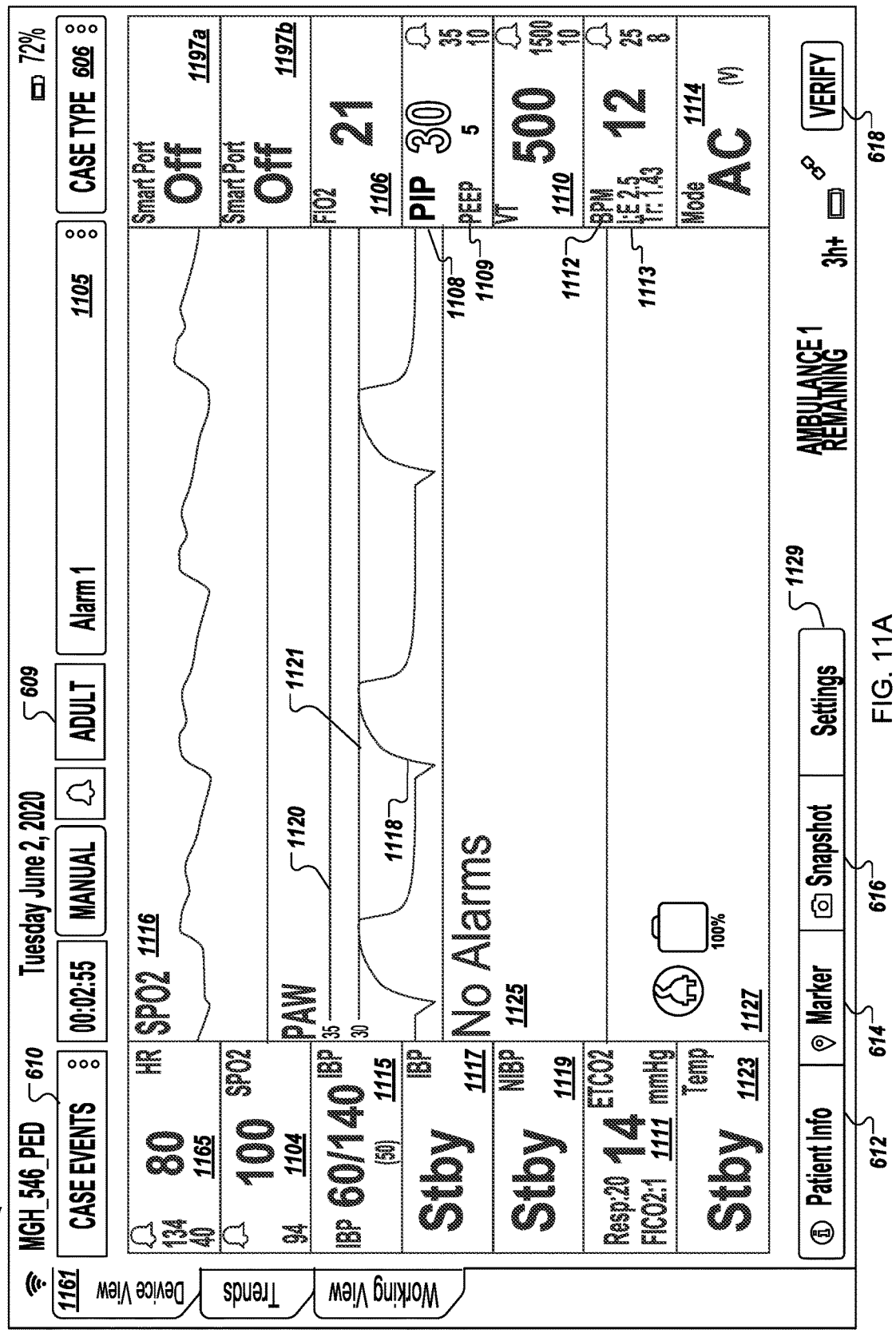
FIGS. 11A-11E illustrate exemplary graphical user interface screens for display at a companion device.
Figure 11B:
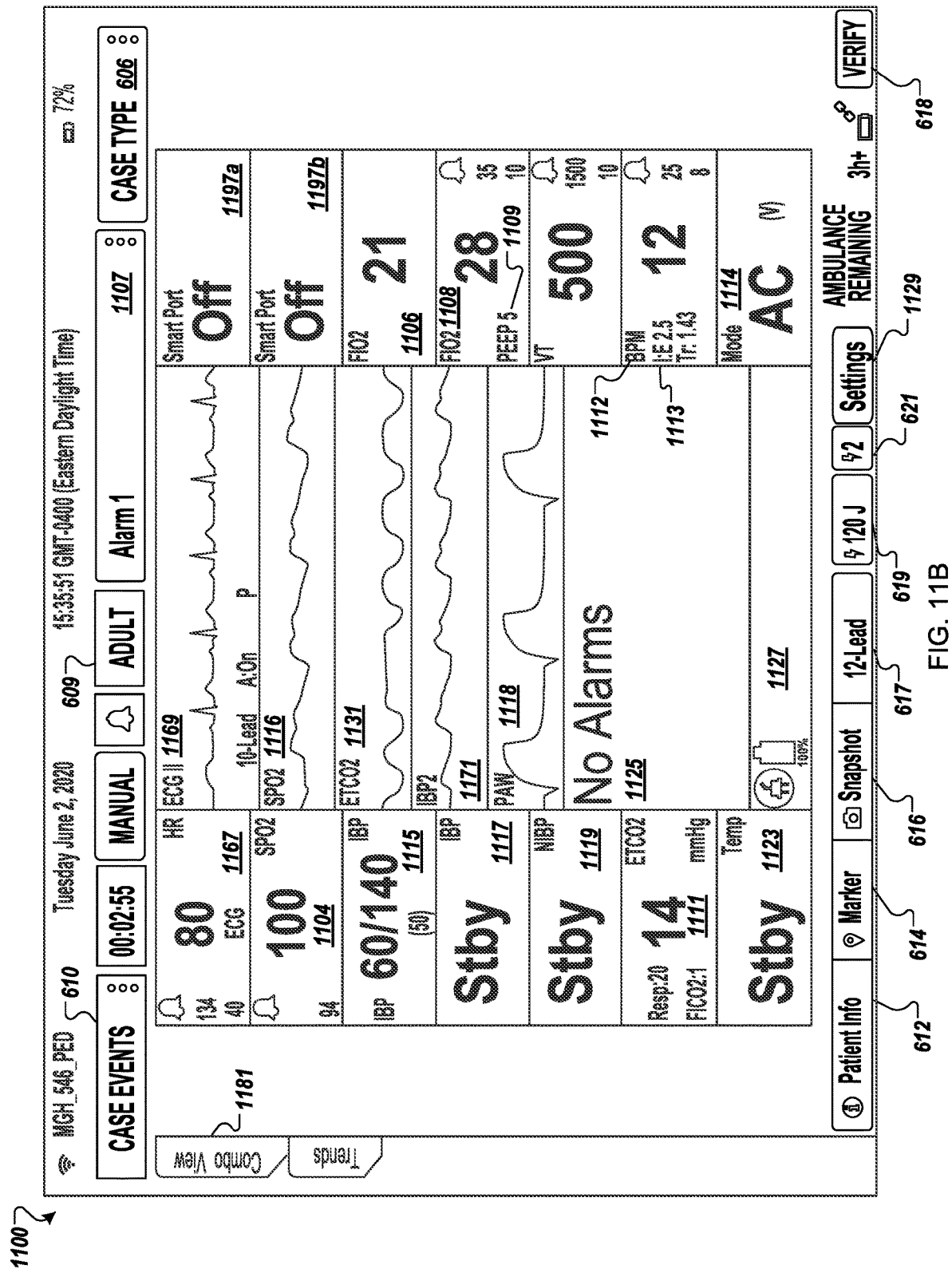
Figures 1, 13D:
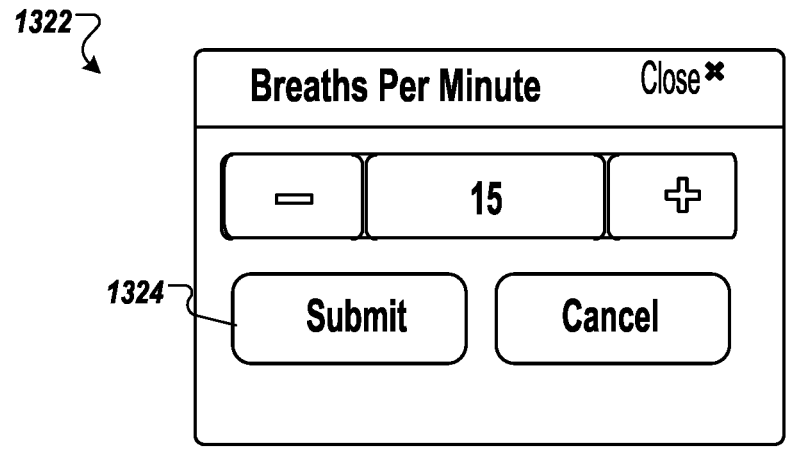
Figures 2, 13D:
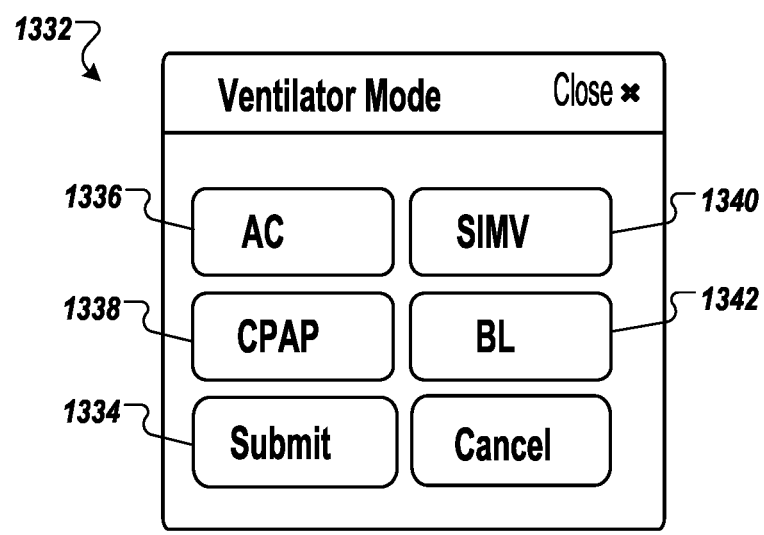

If a setting adjustment is submitted at a respective setting adjustment user interface (e.g., user input 1324 in FIG. 13D-1 or user input 1334 in FIG. 13D-2 is selected) (582), then in some embodiments, the companion device 110, 111, 119, 204 transmits the respective setting adjustment to the medical treatment device 202 (584). In some aspects, once the setting adjustment data has been received and applied at the ventilator 130, 1000, the ventilator 130, 1000 sends a confirmation signal to the companion device 110, 111, 119, 204 indicating that the respective ventilator setting has been adjusted. In response to receiving the confirmation signal (586), in some implementations the companion device 110, 111, 119, 204 causes display of a confirmation message at a display interface confirming that the submitted ventilator setting adjustment has been received and updated at the ventilator 130, 1000 (588). In some examples, the ventilator 130, 1000 may send confirmation signals to the companion device 110, 111, 119, 204 both when receiving and apply the respective setting adjustment. In such an example, separate confirmation messages may be displayed to confirm that a submitted setting adjustment has been received and that application of the setting adjustment at the ventilator 130, 1000 has been performed. In some implementations, instead of or addition to displaying the confirmation message, the companion device 110, 111, 119, 204 can also be configured to apply an event marker to one or more of the displayed user interface screens to indicate that a respective setting has been changed at the ventilator 130, 1000 (589). For example, as shown in FIG. 11E, trends view user interface screen 1150 includes an event marker 1130 corresponding to a change in BPM setting. In some examples, the event marker 1130 can be automatically applied to the user interface screen 1150 without any user intervention other than submitting the setting change. In addition, the event marker 1130 can automatically be applied at the display interface of the companion device 110, 111, 119, 204 regardless of whether a setting change is input at the ventilator 130, 1000 or at the companion device 110, 111, 119, 204. In some implementations, treatment markers described herein are a type of event marker and can be interchangeably referred to as such throughout the disclosure.

Although described as a particular series of steps, in other embodiments, more or fewer steps of the methods 500, 502, 504, 506, 508, 510, 574 may be included. For example, for the method 512 for generating an event summary at a companion device, the steps associated with filtering content displayed within the event summary UI screen 742 (566, 568) may not be performed. For the method 502 for inputting treatment marker information at a companion device (FIG. 5B), the companion device may display a notification both when the treatment marker has been received at the medical treatment device and when linking and storage of the treatment marker data has completed. In further embodiments, certain steps may be performed in a different order, or two or more steps may be performed in parallel. Other modifications of the methods 500-510 are possible while remaining in the scope and purpose of the methods 500-510.

In some implementations, the companion device 110, 111, 119, 204 can provide additional features to enhance patient care during medical events. In some examples, when a patient has an internal pacemaker, the medical treatment device 202 may detect pacing data, which can be transmitted to and displayed at the companion device 110, 111, 119, 204. In some examples, the companion device 110, 111, 119, 204 may automatically display tutorial bubbles at the device interface to instruct caregivers as to how to best use the companion device 110, 111, 119, 204 to monitor and care for the patient. In some examples, the companion device 110, 111, 119, 204 may generate and display the tutorial bubbles during a caregiver's one or more initial uses of the device 204. In some embodiments, the companion device 110, 111, 119, 204 can also provide medical care checklists and monitor completion, monitor for QA/protocol compliance, and/or export case information to an electronic health record (HER) or other registries.

Figure 10:
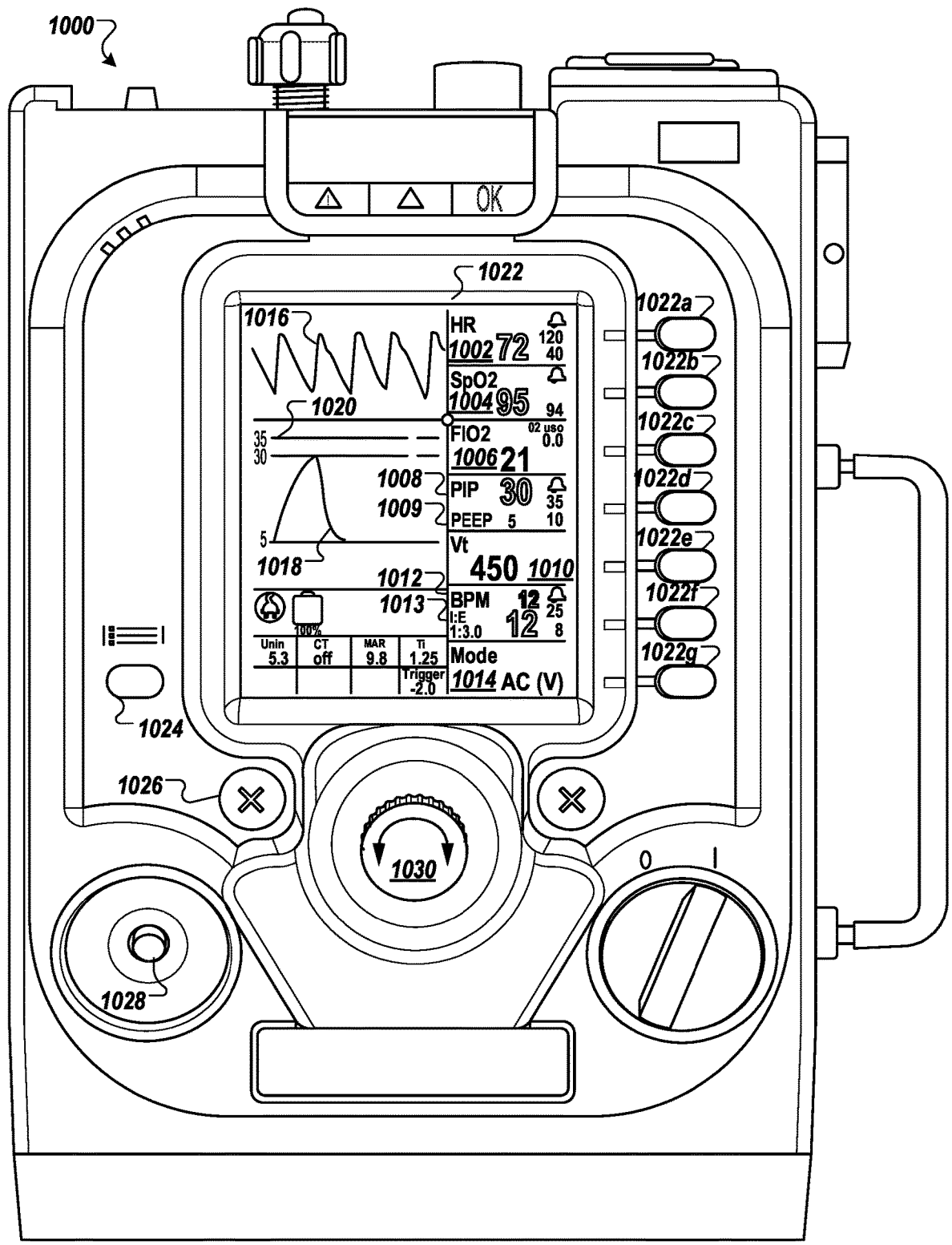
FIG. 10 illustrates an exemplary ventilator for a medical treatment system.

Turning to FIG. 10, an exemplary ventilator 1000 is illustrated. In some embodiments, the medical treatment device 202 (FIG. 2) may be a ventilator that is configured to provide positive pressure ventilation via an oxygen inlet (oxygen) to the patient through an appropriate mechanism, such as an intubation tube, mask, nasal cannula, etc. As discussed above, in some implementations, the companion device 110, 111, 119, 204 may be preconfigured to pair with or otherwise establish a connection with the ventilator 1000, so as exchange medical data in accordance with methods described herein. Embodiments of ventilators of the present disclosure may have functionality similar to that of the Z Vent© Ventilator, provided by ZOLL Medical Corporation, but other ventilators may be employed. In some examples, the ventilator 1000 is a portable ventilator that can be used in the hospital and/or pre-hospital environments such as aeromedical and ground transport, mass casualty situations, and extreme environments. In one example, the portable ventilator 1000 weighs less than 12 pounds, less than 10 pounds, or less than 5 pounds to provide for easy transport at emergency scenes. Ventilator data generated by the ventilator 1000 that may be transmitted to the companion device 110, 111, 119, 204, for visual reproduction thereon, may include, for example, ventilator settings, ventilation parameters, and/or physiological parameters collected by the ventilator. For instance, ventilator settings that may be provided to the companion device 110, 111, 119, 204, for visual reproduction thereof, may include the respiratory rate (breaths per minute (BPM)) 1012, inspiratory:expiratory ratio (I:E, ratio of inspiratory time to expiratory time) 1013, tidal volume (volume of air delivered per breath) (Vt) 1010, positive end-expiratory pressure (PEEP, pressure in the lungs above atmospheric pressure that exists at the end of expiration) 1009, peak inspiratory pressure (PIP) limit 1008, fraction of inspired oxygen (FiO2) 1006, mode setting (e.g., assist/control (AC), synchronized intermittent mandatory ventilation (SIMV), continuous positive airway pressure (CPAP), bilevel (BL)) 1014, etc. In some examples, each of the ventilator settings 1002, 1004, 1006, 1008/1009, 1010, and 1012/1013 may have a corresponding user input 1022a-g on the ventilator 1000 for adjusting the respective setting 1002, 1004, 1006, 1008/1009, 1010, and 1012/1013. Ventilator parameters may include, for example, inspiratory pressure data, expiratory pressure data, inspiratory flow data, expiratory flow data, leak detection, or other information measured from the ventilator. Examples of physiological parameters that may be provided to the companion device, for visual reproduction thereof, may include non-continuous pulse oximeter ($SpO_2$) measurements 1004, end-tidal $CO_2$ ($EtCO_2$) measurements, continuous $SpO_2$ waveform data 1016, airway pressure waveform data 1018, continuous $CO_2$ waveform data, heart rate 1002, blood pressure, amongst others.

In some examples, the ventilator 1000 can be configured to generate alarm signals (e.g., visual and/or audible indications) when one or more parameter setpoints have been exceeded. In one example, when airway pressure exceeds a high airway pressure limit 1020, an alarm can be generated. In some implementations, alarms generated by the ventilator 1000 can include patient safety alarms such as high/low airway pressure, high/low tidal volume, high/low breath rate/apnea, PEEP leak, insufficient flow, spontaneous breath-PIP high/low, spontaneous breath-VT high/low, patient inspiratory demand not met, auto-PEEP, patient disconnect, exhalation system failure/fault, calibration error, suspicious triggers, tubing compliance faults, $SPO_2$ sensor off/low/error, heart rate high/low, etc. The ventilator 1000 can also generate environmental alarms such as low battery, power faults, climatic environment faults, oxygen supply faults, gas intake faults, etc. Self-check alarms can include internal communication errors, pneumatic system failures, power system faults, pulse oximetry module faults, preventive maintenance alerts, etc. In some examples, when an alarm is generated, a pop-up message can be displayed at ventilator interface. In addition, one or more alarm setpoints can be adjustable by a user at the ventilator interface. For example, alarm setpoints for airway pressure high/low, tidal volume high/low, breath rate, spontaneous breath, $SPO_2$% low, and hear rate high/low can be manually adjusted by a device user. When an alarm signal is generated and/or when an alarm pop-up message is displayed at the ventilator interface 1022, the user may take one or more actions to mute the alarm signal and/or acknowledge the alarm.

In some implementations, the display on the ventilator may be inadequate to display all the clinically relevant information available in memory on the ventilator 1000, either due to size, resolution, color palette, brightness or other display performance specification. For example, the ventilator may be compact in design and ultra-portable, resulting in a minimal display interface. In one example, the one or more displays on the ventilator 1000 may be under-sized to enhance portability of the device, e.g., <2 sq. in., <1, 2.5, 4, 5, 6 sq. in. In other examples, there may be no graphical display at all and only indicator lights. In such cases, additional relevant information available in the ventilator 1000 memory but not viewable on the ventilator 1000 display may be transmitted to the companion device for display on the larger display of the companion device. In addition, the indicator lights may be configured to convey whether physiological sensor data and/or device parameters or settings are within acceptable ranges or have exceeded one or more thresholds. For example, the indicator lights may be configured to display different colors (e.g., green, yellow, red) based on whether the parameters and/or sensor data are in band, trending toward out of band, or out of band. In other examples, the indicator lights may flash at different speeds based on the relative parameters/sensor data values (e.g., constant when in band and flashing when out of band). In some implementations, the information on the smaller ventilator display may be one or more user input fields in response to a query from the companion device and may be limited to one or more user input fields, for instance "Patient Height," "Patient Weight" and up/down cursor or other numeric selector via a touch screen, jog wheel, input dial, buttons, soft keys, etc. For example, the small ventilator interface may provide the ability to input in patient characteristics and/or ventilation settings such as those described herein.

In some examples, the information may be abbreviated or limited to numeric values on the smaller ventilator display, but when the numeric display area of the ventilator display is double-tapped or otherwise selected, the graphical and numeric information clinically related to the value on the numeric display area is displayed in full graphical and information detail on the companion device. For instance, just the $SpO_2$ reading may be displayed numerically on the ventilator 1000 display, but when activated via a touch double tap, the full $SpO_2$ waveform, oxygen concentration graph, $CO_2$ waveforms along with ECG may be displayed on the companion device display, as provided in illustrative embodiments of the present disclosure.

In some implementations, when companion device 110, 111, 119, 204 is communicatively coupled to the ventilator 1000, the ventilator can transmit case information associated with physiological sensor inputs for display at the companion device 110, 111, 119, 204 in a similar way as when the medical treatment device 202 is a defibrillator. For example, in response to receiving user inputs at the companion device 110, 111, 119, 204 associated one of the control operations at the ventilator 1000, the companion device 110, 111, 119, 204, in some implementations, transmits an instruction signal to cause the respective operation to occur at the medical treatment device. In some examples, instruction signals sent from the companion device 110, 111, 119, 204 to the medical treatment device can instruct the ventilator 1000 to update patient information, treatment information, or diagnostic information for the medical event that is stored in a data repository of the ventilator 1000. In response to receiving the respective signal, the ventilator 1000 performs the respective operation associated with the instruction signal, which may include storing provided information (e.g., transmitting patient information for updating at the ventilator 1000) or recording a treatment marker (e.g., transmitting a treatment/event marker for the ventilator 1000 to record in the patient care record) or initiating a snapshot (e.g., transmitting an instruction signal for the medical treatment device to initiate a snapshot of one or more types of case information displayed on a display screen of the ventilator 1000) or activating an analysis feature at the ventilator. In one example, in response to receiving height, gender, and/or weight information for the patient that was input at the companion device 110, 111, 119, 204, the ventilator 1000 may automatically adjust volume and rate of ventilation being administered to the patient by the ventilator 1000.

In addition, the instruction signals generated by the companion device 110, 111, 119, 204 can also generate control signals for adjusting parameter settings and/or alarm setpoints at the ventilator 1000 based on user inputs provided at the companion device 110, 111, 119, 204. For example, a ventilator display interface at the companion device 110, 111, 119, 204 can include user inputs that correspond to ventilator setting inputs 1022a-g so that a companion device user can adjust values for ventilator settings 1002, 1004, 1006, 1008/1009, 1010, and 1012/1013. In addition, the ventilator display interface at the companion device 110, 111, 119, 204 can include a menu user input that corresponds to menu input 1024 on the ventilator. In some examples, the ventilator display interface can also include user inputs that correspond to other ventilator inputs such as a mute/cancel input 1026 that allows a companion device user to mute or suppress a ventilator alarm. In some implementations, the ventilator display interface can also include a user input that corresponds to a manual breath button/plateau pressure input 1028 on the ventilator 1000 that allows a companion device user to cause the ventilator 1000 to deliver a manual breath to the patient and/or measure plateau pressure. In some examples, ventilator display interfaces at companion device 110, 111, 119, 204 provide a much more user-friendly interface for efficient use of the ventilator to provide enhanced patient care without having to manipulate cumbersome interface controls such as selection dial 1030 on the ventilator 1000 where the user scrolls the dial 1030 back and forth to set ventilator parameters.

The ventilation display interface at the companion device 110, 111, 119, 204, in some implementations, is a selectable user interface that can be toggled for viewing via a respective selection tab. In some embodiments, similar to the embodiments discussed above for a defibrillator/monitor medical treatment device, a companion device 110, 111, 119, 204 can include one or more device view, working view, trend view, and/or case type view ventilator display interface screens that allow a companion device user to customize ventilator case information displayed at the companion device 110, 111, 119, 204. In some embodiments, the companion device 110, 111, 119, 204 can include selectable display interface screens for multiple types of medical treatment devices (e.g., monitors, defibrillator/monitors, ventilators) so that a companion device user can view case information associated with more than one medical treatment device being used to care for a patient during a medical event. In one example, case information for each type of medical treatment device is viewable at a respective separate display interface of the companion device. In another example, case information for different medical treatment devices can be combined within the same display interface screen at the companion device 110, 111, 119, 204.

In some embodiments, in addition to the embodiments described above, when the medical treatment device 202 is a ventilator 130, 1000, the companion device 110, 111, 119, 204 can be configured to display one or more user interface screens that include case information received from a connected ventilator 130, 1000. In some examples, the ventilator user interface screens configured for display at the companion device 110, 111, 119, 204 can include a device view, a working view, and/or a trends view as described above. For example, FIG. 11A shows a ventilator device view 1101 that is a visual reproduction of the display interface 1022 at the ventilator 1000 (FIG. 10). A visual reproduction of case information at the companion device 110, 111, 119, 204 can include data and formatting variations that can enhance viewing and comprehension of the case information by a companion device user. In some examples, display layout, magnification of each data section, physiologic waveform selection, physiologic numeric readout selection, resolution, waveform duration, waveform size, text size, font, and/or display colors can vary from what is displayed at the medical treatment device. In some examples where a display interface for a companion device 110, 111, 119, 204 is larger than a display interface for a ventilator 130, 1000, additional case information can be provided in the device view 1101 than what is displayed at the ventilator interface 1022. For example, device view 1101 includes blood pressure measurements 1115, 1117, 1119, which are not included at the ventilator interface 1022. In some embodiments, the visual reproduction of the case information displayed within the device view 1101 of the companion device 110, 111, 119, 204 can include rotating the orientation of the displayed case information. For example, the display interface 1022 of the ventilator 1000 has a portrait orientation while the display interface of the device view 1101 is rotated 90 degrees and has a landscape orientation. In some examples, the device view 1101 is one of multiple selectable display views of the companion device 110, 111, 119, 204 that can be selected via selection tab 1161.

In some implementations, the ventilator device view user interface 1101 displayed at the companion device 110, 111, 119, 204 can include a continuous $SpO_2$ waveform data 1116 and an airway pressure waveform 1118. In some examples, the airway pressure waveform 1118 can also include a PAW setpoint 1121 and a high airway pressure limit 1120. The device view 1101 can also include values for respiratory rate (BPM) 1112, I:E ratio 1113, tidal volume ($V_t$) 1110, PEEP 1109, PIP limit 1108, FiO2 1106, and mode setting (e.g., AC, SIMV, CPAP, BL) 1114. Examples of physiological parameters that may be displayed at the device view 1101 may also include non-continuous SpO2 measurements 1104, EtCO2 measurements 1111, heart rate 1165, temperature 1123, blood pressures 1115, 1117, 1119, and/or smart port data values 1197a,b. In some examples, smart port are ports that allow the medical treatment device 202 (e.g., ventilator 130, 1000) to connect to peripheral devices such as pulse oximeter, capnograph, spirometer, or ultrasound in lieu of, or in addition to physiologic sensing on the medical treatment device 202. These peripheral smart port sensors, in some examples, allow for close loop control ventilation algorithms and patient assessment to occur. In some example, the smart ports 1197a,b may also allow for a configuration of only a ventilator 130, 1000 and companion device 110, 111, 119, 204 without a defibrillator 108. In some examples, the device view user interface screen 1101 can also include an alarm section 1125 that displays any currently alarming conditions. A device status section 1127 can display one or more device status icons that indicate battery life and/or connection to an external power source.

Like other UI screens described above, the device view 1101 (and other display views shown in FIG. 11B through FIG. 11D as well as in FIG. 12A and FIG. 12B) can include status bars and navigation ribbons with one or more selection buttons and treatment information including a case event selector 610, patient type selector 609, alarm selector 1105 for displaying alarm summary interface 1320 (FIG. 13A), case type selector 606, patient information input selector 612 for causing display of patient information input interface 1300 (FIG. 13B), treatment/event marker input selector 614, snapshot recording selector 616, and/or a paired device verification input 618 that allows a companion device user to verify which medical treatment device 108, 130, 1000, 202 the companion device 110, 111, 119, 204 is connected to. In some examples, the device view user interface 1101 and any other user interfaces that display ventilator case information can include a ventilator settings user input 1129 that causes display of ventilator settings adjustment user interface screen 1362 (FIG. 13C) as described above.

Figure 11C:
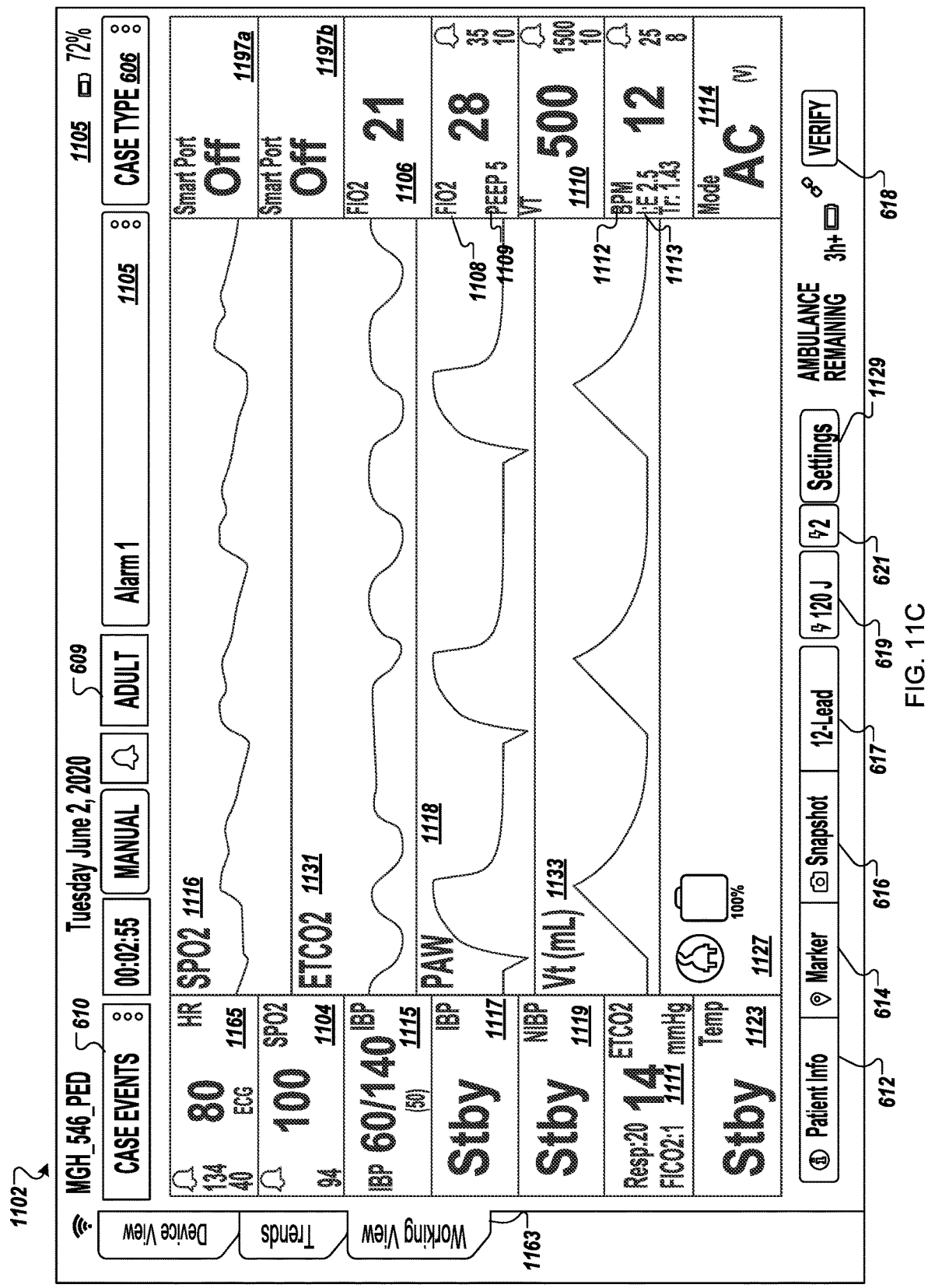

Turning to FIG. 11C, a ventilator working view user interface screen 1102 is illustrated. In some implementations, the working view user interface screen 1102 can be configured to display one or more ventilator waveforms, settings, and case information data as treatment is administered to a patient. In some implementations, the working view user interface screen 1102 can be customized based on preferences and/or role of the companion device user as well as which types of medical treatment devices 108, 130, 202 are connected to the companion device 110, 111, 119, 204 via wireless communication link. In some implementations, the working view screen 1102 can be a scrollable interface such that users can add as many data sections as desired to the working view 1102 for ready viewing by scrolling up or down on the working view screen 1102. In some examples, the working view 1102 is one of multiple selectable display views of the companion device 110, 111, 119, 204 that can be selected via selection tab 1163.

In one example, the working view screen 1102 includes a continuous $SpO_2$ waveform data 1116, an airway pressure waveform 1118, an ETCO2 waveform 1131, and a $V_t$ waveform 1131. The working view 1102 can also include values for respiratory rate (BPM) 1112, I:E ratio 1113, $V_t$ 1110, PEEP 1109, PIP limit 1108, and mode setting (e.g., AC, SIMV, CPAP, BL) 1114. Examples of physiological parameters that may be displayed at the device view 1102 may also include non-continuous SpO2 measurements 1104, EtCO2 measurements 1111, heart rate 1165, temperature 1123, and/or blood pressures 1115, 1117, 1119. Other ventilator parameters that may be displayed include, for example, inspiratory pressure data, expiratory pressure data, inspiratory flow data, expiratory flow data, leak detection, or other information measured from the ventilator. A device status section 1127 can display one or more device status icons that indicate battery life and/or connection to an external power source.

In some implementations, the companion device user can manually add/remove data sections or drag/reposition data sections in the working view 668 as desired. For example, each of the displayed data sections can function as a grab bar that can be moved to another position within the working view 1102, which automatically causes other data sections to shift to support the selected adjustment. In some examples, the user can store a manually configured working view layout as customization data 260a so that the companion device 110, 111, 119, 204 can preconfigure the customized working view for the user for future medical events. In some examples, such as in a situation when a caregiver is supervising administration of chest compressions by another team member, the working view can include a chest compression dashboard 670 (see compression dashboard in multi-device working view 1194 FIG. 11D) that provide feedback to the user regarding how care is being administered to the patient. In some implementations, the chest compression dashboard 670 displays chest compression case information from at least one chest compression sensor input. In one example, the chest compression sensor, connected to the ventilator 130, 1000 via wired or wireless connection, can be a motion sensor puck that is positioned beneath a caregiver's hands as the caregiver is administering chest compressions and detects chest compression depth and rate.

Figure 12A:
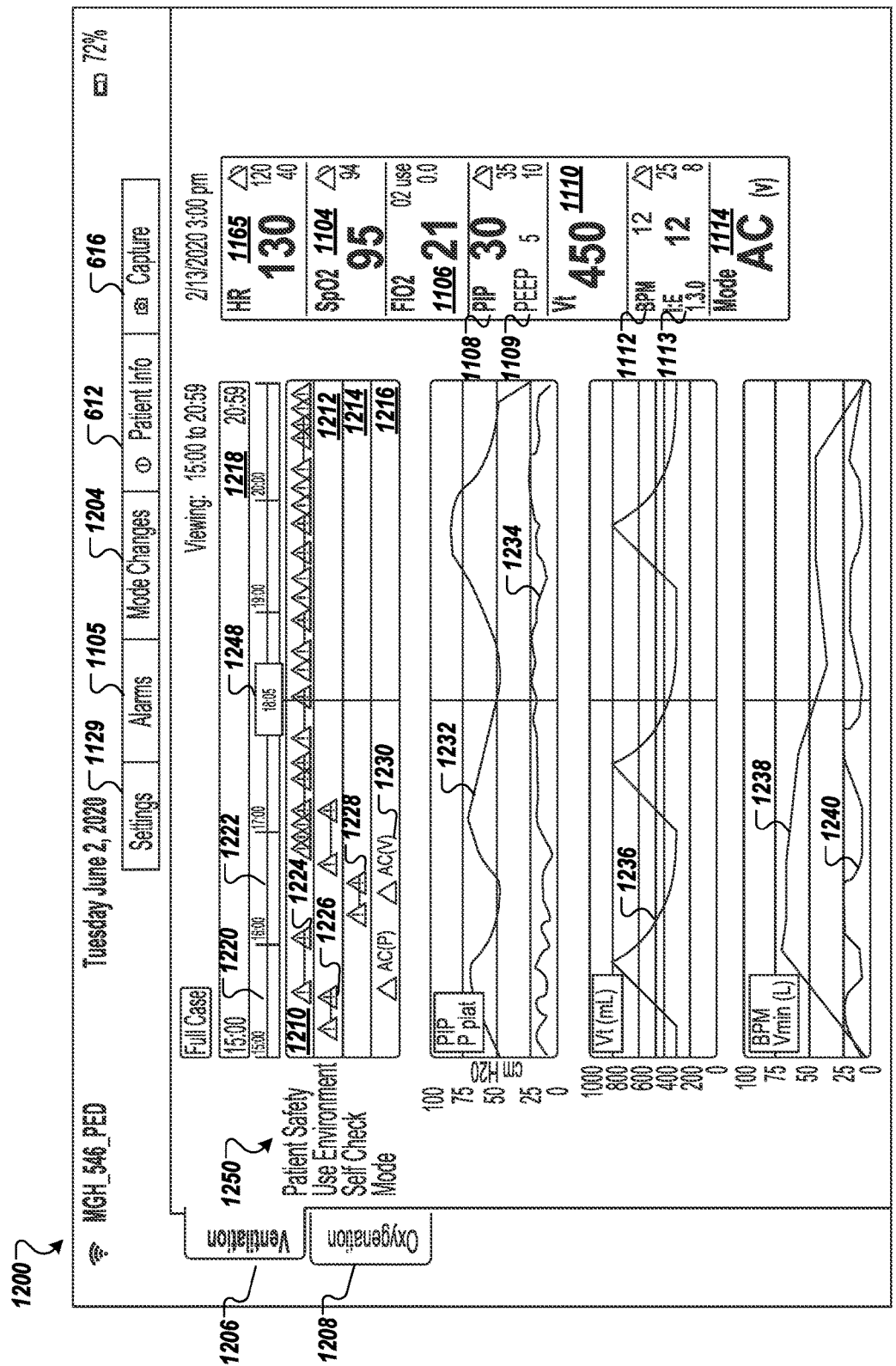
FIGS. 12A-12B illustrate exemplary graphical user interface screens for display at a companion device
Figure 12B:
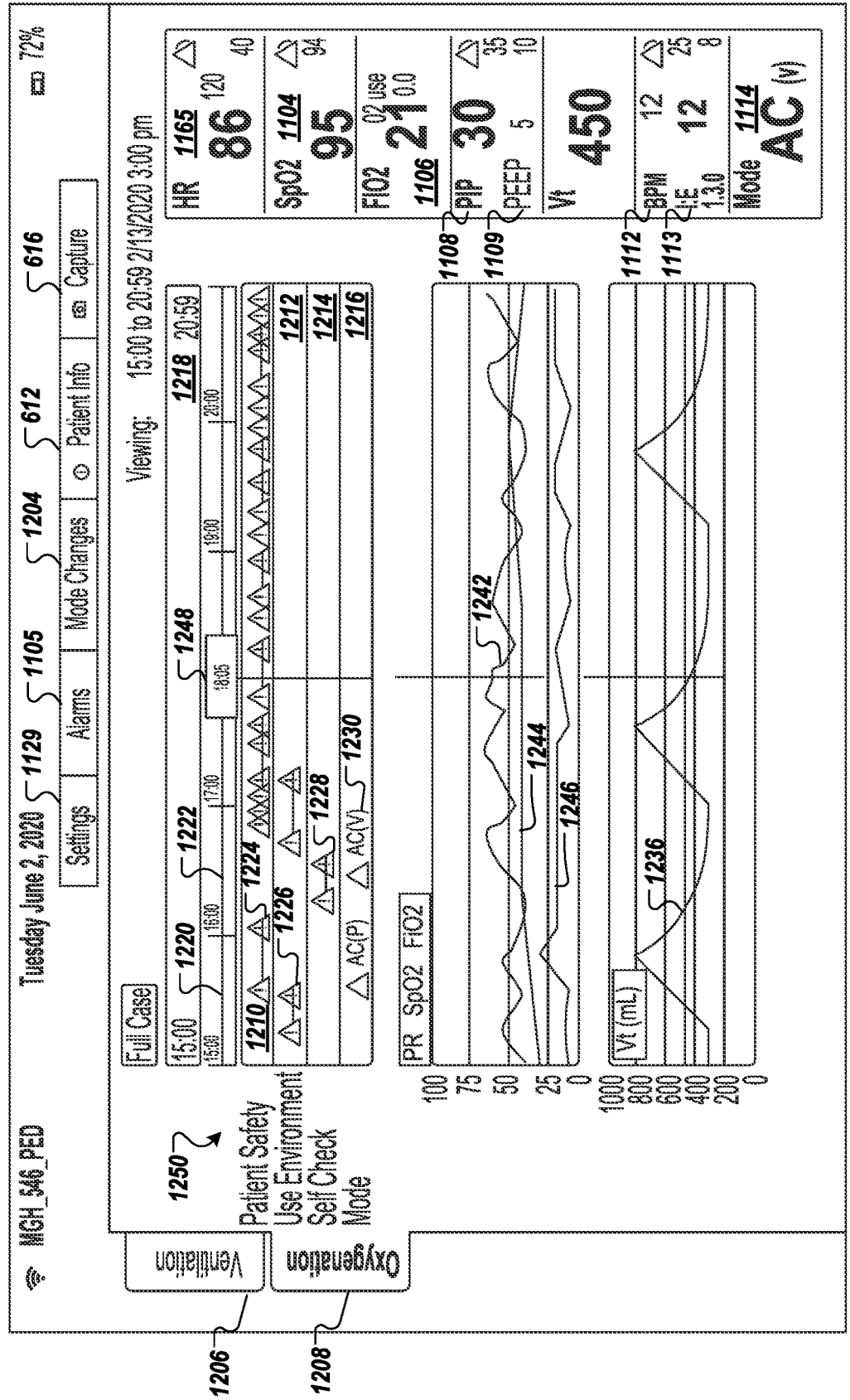

FIG. 12A and FIG. 12B show additional examples of working view user interface screens 1200, 1202 for a ventilator that can be displayed at a companion device 110, 111, 119, 204. In some examples, working view 1200 can include ventilation-based information associated with providing positive pressure ventilation to a patient, and working view 1202 can include oxygenation-based information. In some examples, a companion device user can toggle between the two views 1200, 1202 via tabs 1206, 1208. In some examples, both of the working views 1200, 1202 can include values for heart rate 1165, BPM 1112, I:E ratio 1113, $V_t$ 1110, PEEP 1109, PIP limit 1108, $FiO_2$ 1106, $SpO_2$ 1104, and mode setting (e.g., AC, SIMV, CPAP, BL) 1114. In one example, the ventilation working view 1200 can display waveforms for PIP 1232, $P_{plat}$ 1234, $V_t$ 1236, BPM 1238, and minimum volume ($V_{min}$) 1240. In addition, the oxygenation working view 1202 can display waveforms for PR 1242, $SpO_2$ 1244, $FiO_2$ 1246, and $V_t$ 1236.

In some implementations, the working views 1200, 1202 include an example of a navigation bar or ribbon that with one or more user input selections such as settings user input 1129, alarm summary user input 1105, mode selection user input 1204, patient information user input 612, and snapshot capture user input 616. In some examples, mode selection user input 1204 corresponds to mode selection user input 1380 at ventilator settings adjustment user interface 1362 (FIG. 13C). In addition, the working views 1200, 1202 can include an event marker section 1250 that displays one or more types of event markers that occur during the course of patient treatment. In some implementations, the event marker section 1250 can display one or more types of event markers associated with alarming conditions and/or mode changes at the ventilator. In some implementations, each of the event markers (e.g., markers 1224, 1226, 1228, 1230) are displayed at positions within one or more event sub-sections 1210, 1212, 1214, 1216 that correspond to a time that the respective event occurred. For example, the event marker section 1250 can include a patient safety sub-section 1210 that displays event markers (e.g., marker 1224) that correspond to patient safety alarms. Patient safety alarms displayed within sub-section 1210 can include alarms such as high/low airway pressure, high/low tidal volume, high/low breath rate/apnea, PEEP leak, insufficient flow, spontaneous breath-PIP high/low, spontaneous breath-VT high/low, patient inspiratory demand not met, auto-PEEP, patient disconnect, exhalation system failure/fault, calibration error, suspicious triggers, tubing compliance faults, $SPO_2$ sensor off/low/error, heart rate high/low, etc. In some implementations, a use environment alarm sub-section 1212 can display event markers (e.g., event marker 1226) for detected use environment alarms such as low battery, power faults, climatic environment faults, oxygen supply faults, gas intake faults, etc. A self-check alarm sub-section 1214 can display event markers (e.g., event marker 1228) for self-check alarms such as internal communication errors, pneumatic system failures, power system faults, pulse oximetry module faults, preventive maintenance alerts, etc. Event marker section 1250, in some embodiments, can also include a ventilator mode sub-section 1216 that can display event markers indicating when a ventilator mode has been adjusted. For example, event marker 1230 indicates when the ventilator mode was adjusted from AC(P) to AC(V).

The working views 1200, 1202, in some implementations, display real-time ventilator data over one or more adjustable periods of time. The working views 1200, 1202 can provide the ability for a companion device user to adjust the granularity of real-time time data displayed within the display interface of companion device 110, 111, 119, 204. For example, the working views 1200, 1202 may display case information for an entire patient case that occurs over time frame 1218. For the time frame 1218, the working view interface 1200, 1202 can include one or more selectable sub-sections of time (e.g., sub-sections 1220, 1222) that, when selected, allow the companion device user to view a zoomed-in version of the case information (e.g., waveforms 1232, 1234, 1236, 1238, 1240 in FIG. 12A). In some examples, the companion device user can easily toggle back and forth between the full case view 1218 and one or more of the zoomed-in time frames 1220, 1222 by selecting the respective time frame 1218, 1220, 1222 for viewing.

In some implementations, a slide control 1248 is provided in the full case view 1218 for perusing portions of the timeline including timeframes within the sub-sections 1220, 1222. For example, the slide control 1248 may be positioned to the far left to review a beginning of treatment (e.g., time 15:00) and to the far right (e.g., time 20:59) to view case information in real-time. As illustrated, the slide control 1248 is positioned at 18:05.

Returning to FIG. 2, in some implementations, the companion device 110, 111, 119, 204 can be configured to simultaneously connect to, monitor, and/or control more than one medical treatment device 202. In some examples, the companion device 110, 111, 119, 204 can connect to two or more defibrillator/monitors or two or more ventilators associated with different patients being treated at an emergency care scene. In other examples, the companion device 110, 111, 119, 204 can simultaneously connect to different types of medical treatment devices 108, 130, 202 being used to treat a single patient. For example, as shown in FIG. 1C, companion device 119 is connected to and in communication with defibrillator/monitor 108 and ventilator 130 being used to administer treatment to patient 102. In some implementations, the user interface screens presented at the display screen of the companion device 110, 111, 119, 204 can display case information received from one, some, or all of the connected medical treatment devices 108, 130, 202. In one example, the companion device can include selectable device views for each connected medical treatment device 108, 130, 202 (e.g., defibrillator device view 600 in FIG. 6A and ventilator device view 1101 in FIG. 11A). Instead of or in addition to the device views 600, 1101, the companion device 110, 111, 119, 204 can include a selectable combination device working view that displays case information from multiple connected medical treatment devices 108, 130, 202.

As discussed further below, in some embodiments, the companion device 110, 111, 119, 204 can be configured to present one or more working views and/or trend views that simultaneously display information received from multiple medical treatment devices 108, 130, 202 (e.g., working view user interface screens 1100, 1194 in FIG. 11B and FIG. 11D and trends view user interface screen 1150 in FIG. 11E). In some examples, providing a rescue team supervisor 118 with the ability to monitor and/or control the status of multiple medical treatment devices 108, 130, 202 provides a technical solution to a clinical problem. For example, the companion device 110, 111, 119, 204 can display real-time case information from multiple medical treatment devices 108, 130, 202 in real-time, which enhances quality of care provided to the patient. In addition, the companion device 110, 111, 119, 204 can coordinate transmission of instruction signals to one or more both medical treatment devices 108, 130, 202 in real-time based on received user inputs to control operation of the medical treatment devices 108, 130, 202, which further enhances patient care. In some implementations, based on the type of user input received, the companion device 110, 111, 119, 204 can be configured to transmit instruction signals to one or both of the connected medical treatment devices 108, 130, 202.

Figure 5H:
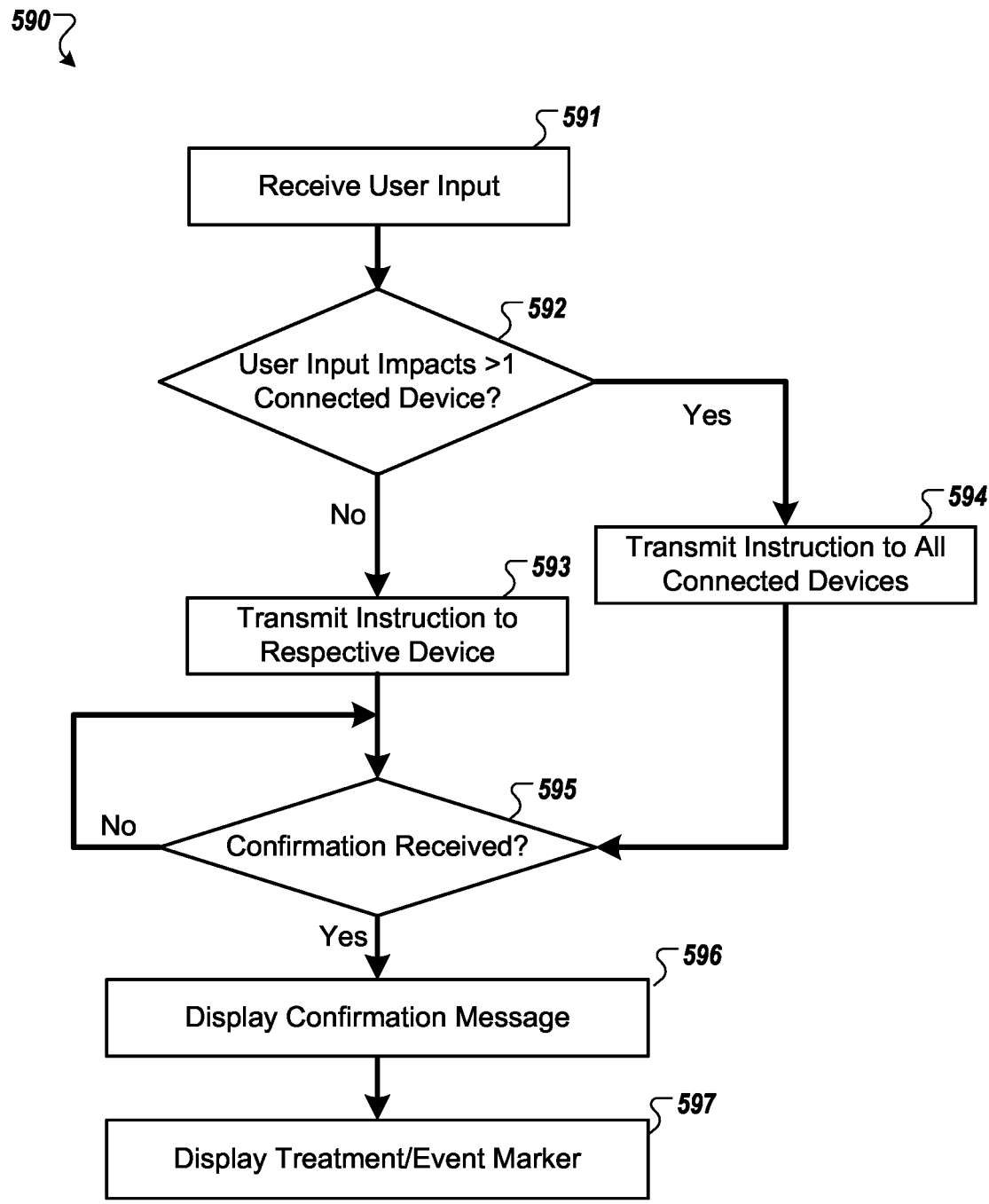

For example, turning to FIG. 5H, a method 590 for coordinating control of multiple medical treatment devices by a single companion device 110, 111, 119, 204 is illustrated. While described in relation to the example provided by the emergency scene 100c shown in FIG. 1C that includes a defibrillator 108 and ventilator 130 simultaneously connected to and in communication with a companion device 119, it can be understood that the method 590 can be applied to any combination of multiple medical treatment devices 108, 130, 202.

In some embodiments, the method 590 commences with receiving a user input at the companion device 110, 111, 119, 204 (591). In some examples, the received user input may be associated with one of the medical treatment devices 108, 130, 202 (e.g., a 12-lead analysis user input 617 corresponds to defibrillator 108 and settings user input 1129 corresponds to ventilator 130). In other examples, the received user input may be associated with both of the connected medical treatment devices (e.g., patient information user input 612 and user inputs associated with patient information user interface screens in FIG. 7A and FIG. 13B). Another example of a user input that impacts both medical treatment devices 108, 130, 202 is treatment marker user input 614 and any user inputs associated with treatment marker user interface screen 712. For example, submitting treatment marker information at treatment marker user interface screen can cause the companion device 110, 111, 119, 204 to transmit instruction signals to record treatment marker information at both the defibrillator 108 and the ventilator 130. In other examples, the user can select to transmit the treatment/event marker information to just one of the connected medical treatment devices 108, 130, 202. In some implementations, other user inputs may also correspond to instruction signals that can be transmitted to either or both medical treatment device 108, 130, 202. For example, the snapshot user input 616 may cause a snapshot of displayed case information to be recorded at the defibrillator 108 and/or the ventilator 130.

In some examples, if the received user input corresponds to all of the connected medical treatment devices 108, 130, 202 (e.g., both the defibrillator 108 and the ventilator 130 in the emergency scene 100c of FIG. 1C) (592), then the companion device 110, 111, 119, 204 can be configured to transmit the instruction signal to all of the connected medical treatment devices 108, 130, 202 (594). If the received user input corresponds to one but not all of the connected medical treatment devices 108, 130, 202, then in some implementations, the companion device 110, 111, 119, 204 transmits the corresponding instruction signal to the respective medical treatment device 108, 130, 202 associated with the received user input (593). In some embodiments, upon receiving a confirmation signal from one or more of the medical treatment devices 108, 130, 202 indicating that the respective action associated with the instruction signal has been taken (595), the companion device 110, 111, 119, 204 displays a confirmation message at the display interface (596). In some examples, when the instruction signal has been sent to both connected medical treatment devices 108, 130, 202, the companion device 110, 111, 119, 204 can be configured to display a confirmation message associated with each of the medical treatment devices 108, 130, 202 indicating that the respective action has been taken at the respective medical treatment device 108, 130, 202. In other examples, companion device 110, 111, 119, 204 can be configured to display a single confirmation message indicating that both of the medical treatment devices 108, 130, 202 have performed the requested action associated with the instruction signal.

In addition, in some implementations, responsive to receiving a confirmation signal from one or more of the medical treatment devices 108, 130, 202 indicating that the respective action has been taken, the companion device 110, 111, 119, 204 can be configured to display a corresponding treatment/event marker on one or more of the trend view user interface screens (e.g., markers 658, 662, 1130, 1132 (FIG. 11E)) (597).

Although described as a particular series of steps, in other embodiments, more or fewer steps may be included. For example, some user inputs may not be associated with a displayed event marker (597) (e.g., snapshot and/or 12-lead user input). In further embodiments, certain steps may be performed in a different order, or two or more steps may be performed in parallel. For example, a confirmation message may be displayed at the companion device 110, 111, 119, 204 (596) before, simultaneously with, or after the corresponding treatment/event marker is displayed (597). Other modifications of the method 590 are possible while remaining in the scope and purpose of the method 590.

FIG. 11B shows an example of a working view user interface screen 1100 that displays data received from multiple medical treatment devices (e.g., a defibrillator and a ventilator) connected to a single companion device (e.g., defibrillator 108 and ventilator 130 connected to companion device 119 in FIG. 1C). In some implementations, the multi-device working view 1100 can display case information that is exclusive to each of the medical treatment devices 108, 130, 202 (e.g., $P_{AW}$ waveform 1118 from ventilator 130 and ECG II waveform 1169 from defibrillator 108) and/or case information that can be obtained from either medical treatment device (e.g., e.g., SPO2 waveform 1116, ETCO2 waveform 1131, or IBP waveform 1171). In some examples, for each value of case information that can be obtained from more than one of the medical treatment devices 108, 130, 202, the companion device user can select whether the displayed value is received from the defibrillator 108 or the ventilator 130. For example, the displayed HR value 1167 is determined from ECG data received from defibrillator 108. In some examples, the multi-device working view 1100 can also include values for BPM 1112, I:E ratio 1113, $V_t$ 1110, PEEP 1109, PIP limit 1108, FiO2 1106, and mode setting (AC, SIMV, CPAP, BL) 1114. Examples of physiological parameters that may be displayed at the working view 1100 may also include SpO2 measurements 1104, EtCO2 measurements 1111, temperature 1123, and/or blood pressures 1115, 1117, 1119. In some examples, the multi-device working view 1100 can also include an alarm section 1125 that displays any currently alarming conditions. A device status section 1127 can display one or more device status icons that indicate battery life and/or connection to an external power source. In some implementations, the working view user interface screen 1100 is one of multiple views that can be presented at the display interface of companion device 110, 111, 119, 204 and is selectable via tab 1181. Upon detecting selection of alarm user input 1107 at working view 1100, the companion device 110, 111, 119, 204 can cause display of an alarm summary UI screen 1320 (FIG. 13A) that presents a summary of alarming conditions received from all connected medical treatment devices 108, 130, 202.

Figure 11D:
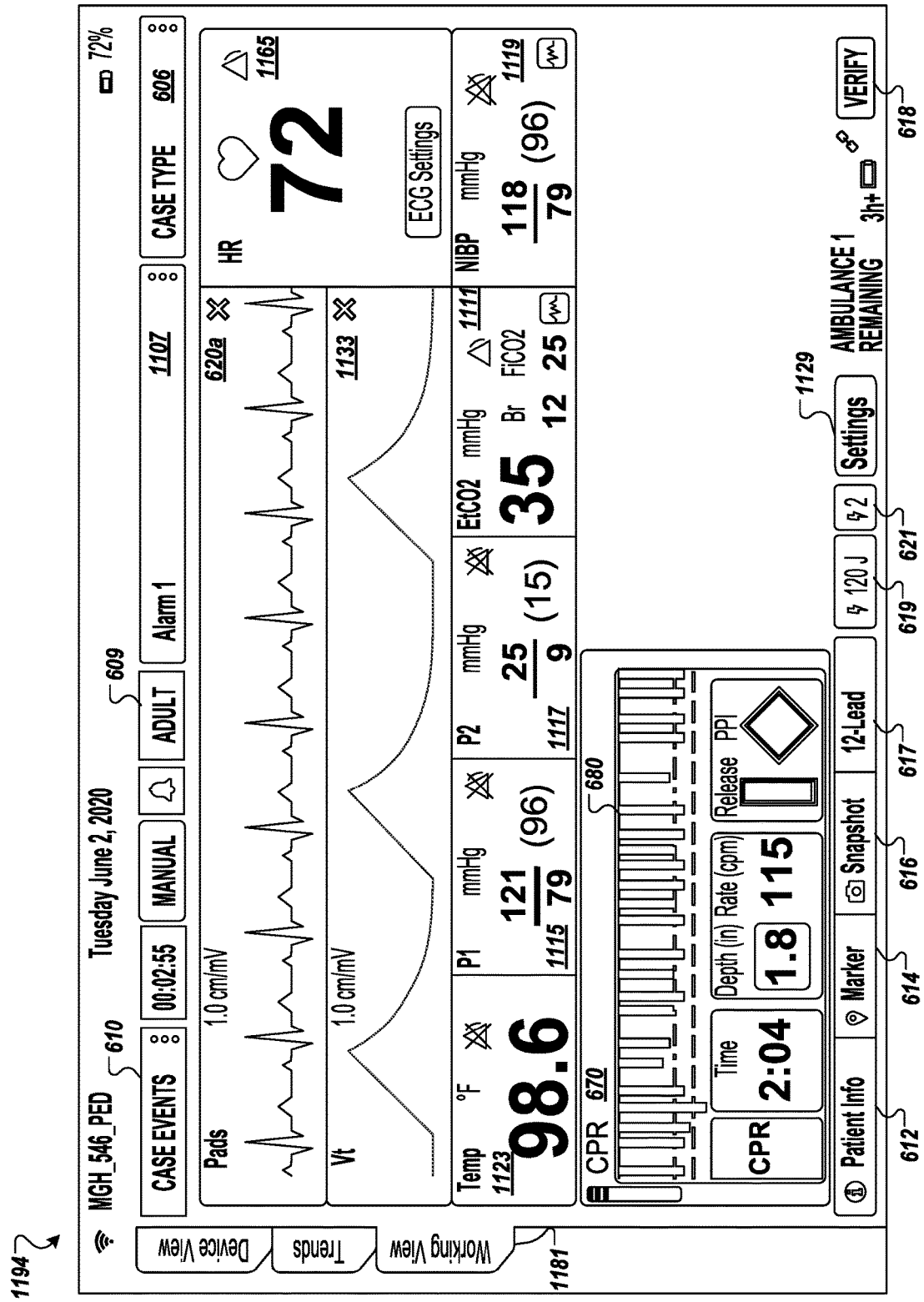
Figure 11E:
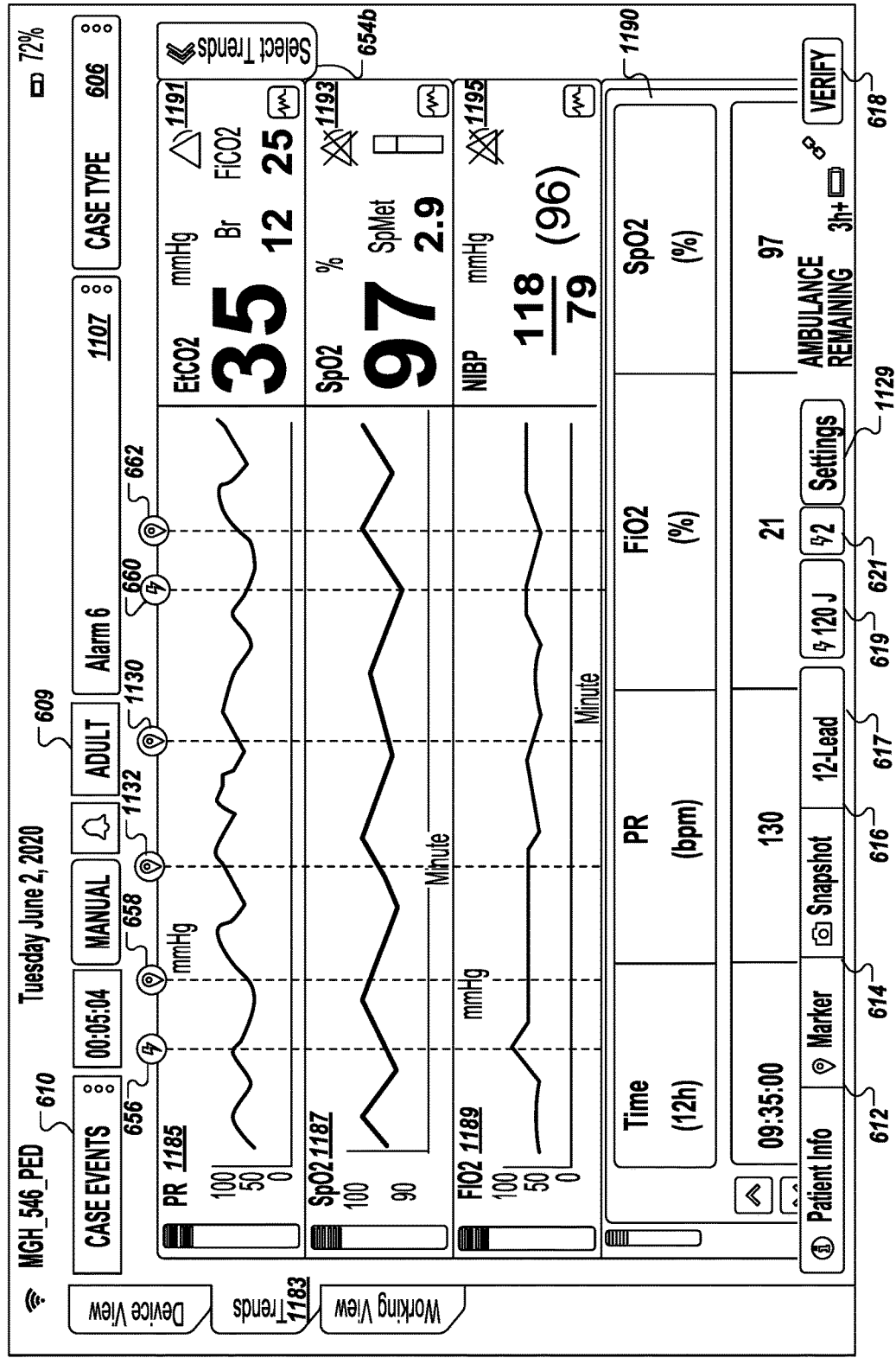

FIG. 11D shows another example of a working view user interface screen 1194 that includes data from a defibrillator 108 and a ventilator 130 simultaneously connected to a single companion device (e.g., companion device 119 in FIG. 1C). In one example, working view 1194 includes an ECG waveform 620a received from defibrillator 108 and a $V_t$ waveform received from ventilator 130. In addition, the working view 1194 can display values received from either medical treatment device 108, 130, 202 for temperature 1123, blood pressures 1115, 1117, 1119, $EtCO_2$ 1111, and HR 1165. In some implementations, the working view user interface screen 1194 also includes compression (CPR) dashboard 670 that displays caregiver performance data for a rescuer administering compressions to a patient. In some examples, a compression sensor that detects a depth and/or rate of compressions can be connected to either of the connected medical treatment devices 108, 130, 202, which in turn transmit caregiver performance data obtained from the compression sensor to the companion device 110, 111, 119, 204. In some implementations, upon detecting commencement of compressions based on data signals received from the connected compression sensor, the ventilator 130 may automatically adjust ventilations to a CPR-optimized mode. For example, the ventilator 130 may automatically shift to a 30:2 ratio of compressions to ventilations or another more advanced mode that provides for synchronization of ventilations to timing of specific features of the compressions displayed at CPR dashboard 670 and/or $V_t$ waveform 1133. In some examples, the companion device 110, 111, 119, 204 can provide visual indications of the synchronization between ventilations and compressions at CPR dashboard 670. For example, the companion device 110, 111, 119, 204 may overlay additional bars on compression graph 680 that correspond to synchronized ventilations.

In some examples, the bars on compression graph 680 that correspond to ventilations may be displayed in a different color from the bars associated with compressions. In some implementations, in response to receiving compression sensor data from one of the connected medical treatment devices 108, 130, 202, the companion device 110, 111, 119, 204 may automatically display CPR dashboard 670 within at least one working view user interface 1194.

Turning to FIG. 11E, an example of a trends view user interface screen 1108 is illustrated. In some implementations, the trends view user 1108 can be configured to display graphical, tabular, and/or numerical trends of case information generated by multiple medical treatment devices (e.g., defibrillator 108 and ventilator 130) simultaneously connected to a companion device 110, 111, 119, 204. Upon selection of the trends view selector 1183, in some examples, the companion device 110, 111, 119, 204 may initially present a default set of case information trends (e.g., measured physiological sensor data from the multiple connected medical treatment devices 108, 130 202) within trends view 1108 in a graphical and/or tabular format. For example, the default set of case information trends presented in the trends view can include graphs of PR 1185, $SPO_2$ 1187, and $FIO_2$ 1189 values over time. The displayed trends at the trend view UI screen 1108 can also include mean values of $ETCO_2$ 1191, $SPO_2$ 1193, and NIBP 1195 over the course of the medical treatment event. Additionally, the trend data can also be displayed in a tabular format such as in data table 1190. In some examples, the data table 652 can display one or more physiological information data trends (e.g., PR, $FIO_2$, $SPO_2$) at predetermined time intervals (e.g., every 10 seconds, 20 seconds, 30 seconds, 1 minute, 3 minutes, 5 minutes). For example, each row of the data table 1190 can correspond to values of one or more types of physiological information recorded at the predetermined time interval.

In some implementations, the companion device 110, 111, 119, 204 may annotate the trend graphs 1185, 1187, 1189 with treatment/event marker annotations 656, 658, 660, 662, 1130, 1132 so that a companion device user can readily discern an impact of a respective treatment on a patient's condition over the course of time. In some examples, upon selection of the trends view selector 1183, the companion device 110, 111, 119, 204 may transmit a data request, alone or as part of a bulk data transfer request, for treatment/event marker data to display overlaid on trend graphs 1185, 1187, 1189. Upon selection of one of the treatment/event marker annotations 656, 658, 660, 662, 1130, 1132, the companion device 110, 111, 119, 204 may cause display of details about the selected treatment/event marker, such as amount of energy in an applied shock, amount of medication administered, change in ventilator mode or other setting, display screen of defibrillator and/or ventilator waveforms at the time of treatment/event marker input, and/or a snapshot view of the ECG and/or ventilator data at the time associated with the selected treatment/event marker.

In some implementations, the trends view UI screen 1108 can also include a trend selection tab 654*b* that allows a companion device user to customize the trends that are displayed within the display interface. For example, upon selecting the trend selection tab 654*b*, the companion device 110, 111, 119, 204 can display one or more trends for the user to select and/or de-select based upon trend viewing preferences. In one example, the user can select display waveforms and/or mean values for one or more of HR, pulse rate (PR), $SPO_2$, NIBP, invasive blood pressure (systolic BP, diastolic BP, mean arterial pressure), $ETCO_2$, respiratory rate/breathing rate (RR/BR), pleth variability index (PVI), respiratory rate (BPM), I:E ratio, $V_t$, PEEP, PIP, and/or $FIO_2$. Additionally, the user can select whether to display data table 1190. In some embodiments, the user can also select a time interval for recording trend data that is displayed within the trend view 1108, such as within data table 1190. In some implementations, inputs provided at the trend selection tab 654*b* can also allow users to select the predetermined time interval e.g., every 10 seconds, 20 seconds, 30 seconds, 1 minute, 3 minutes, 5 minutes) for recording and/or displaying trend data in the trends view UI screen 1108.

Figure 9:
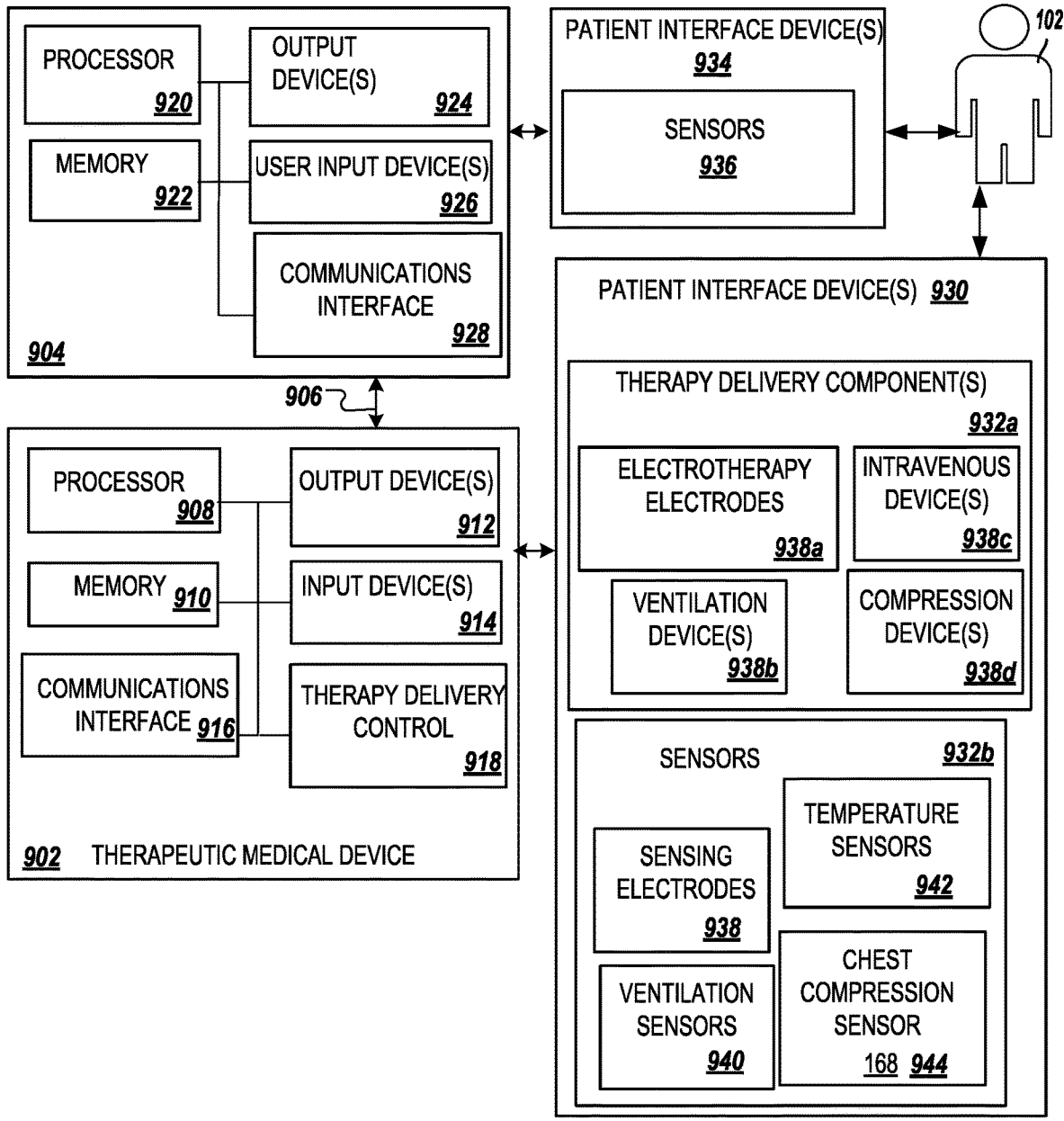
FIG. 9 illustrates an exemplary schematic block diagram of components of various devices in a medical treatment system.

Referring to FIG. 9, examples of components of various devices discussed with regard to FIGS. 1A-8G and 10-13D-2 are shown schematically. These devices may include medical treatment device 902 (e.g., medical treatment device 202 in FIG. 2) and one or more companion devices 904 (e.g., companion device 110, 111, 119, 204 in FIG. 2). In an implementation, the medical treatment device 110 may be a therapeutic medical device configured to deliver medical therapy to the patient and may not be limited to patient monitoring and/or diagnostic care. In some examples, the companion device 904 may be a portable computing device such as a tablet, laptop, or smart phone. The companion device 904 may be adapted to function as a medical device or be a display screen of an additional medical device such as when monitoring continuous NIBP measurements. In an implementation, the companion device 904 may not be a therapeutic medical device configured to deliver medical therapy to the patient. In such an implementation, the companion device 904 may be limited to patient monitoring and/or diagnostic care, such as monitoring a patient status via one or more display screens and/or controlling one or more functional operations at the medical treatment device 902 as described in the embodiments herein.

The medical treatment device 902 and one or more companion devices 904 may be communicatively coupled via communicative coupling 906, which may be a wired and/or a wireless communications link. The wired communications links may include a wired electrically coupling, an optical coupling via an optical cable, etc. The wireless communications link may include coupling via a radio frequency or other transmission media and/or via a network such as a local area network, an ad hoc network, a mesh network, a cellular and/or other communications network, a computer network, etc. The communications link as described herein may utilize protocols such as, for example, 802.11, ZigBee®, Bluetooth®, etc. The communications link may include near field communications which may be implemented via a communications RFID tag. The communications link may include one or more networks such as a local area network, a cellular network, a satellite network, and/or a computer network (e.g., an Internet Protocol (IP) network). In various implementations, the communicative couplings described herein may provide secure and/or authenticated communications channels. In an implementation, the devices described herein may encrypt and/or decrypt the data transmitted and/or received via the communicative couplings. In some implementations, communicative coupling 906 corresponds to the wireless communication link 206 (FIG. 2) described above.

In some embodiments, the memory 910 of the medical treatment device 902, and similarly memory 922 of companion device 904, may include a data store and corresponding data storage circuitry including one or more of non-transitory or non-volatile computer readable media, such as flash memory, solid state memory, magnetic memory, optical memory, cache memory, combinations thereof, and others. The data store can be configured to store executable instructions and data used for operation of the medical treatment device 902 and/or companion device 904. In certain implementations, the data storage processing circuitry, in combination with the data store, can include executable instructions that, when executed on the processor 908 and/or 920, are configured to cause the at least one processor 908 and/or 920 to perform one or more functions, such as portions of the methods described in relation to FIG. 3, FIG. 4A, FIG. 4B, and FIG. 5A through FIG. 5F.

In FIG. 9, the components 908, 910, 912, 914, 916, and 198 are communicatively coupled (directly and/or indirectly) to each other for bi-directional communication. Similarly, the components 920, 922, 924, 926, and 928 are communicatively coupled (directly and/or indirectly) to each other for bi-directional communication.

In some implementations, the components 902, 910, 916, and/or 918 of medical treatment device 902 may be combined into one or more discrete components and components 916 and/or 918 may be part of the processor 908. The processor 908 and the memory 910 may include and/or be coupled to associated circuitry in order to perform the functions described herein. Additionally, the components 920, 922, and 928 of companion device 904 may be combined into one or more discrete components and component 928 may be part of the processor 920. The processor 920 and the memory 921 may include and/or be coupled to associated circuitry in order to perform the functions described herein.

In some implementations, the medical treatment device 902 may include the therapy delivery control module 918. For example, the therapy delivery control module 918 may be an electrotherapy delivery circuit that includes one or more high-voltage capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 918 may be a compression device electro-mechanical controller configured to control a mechanical compression device. As a further example, the therapy delivery control module 918 may be an electro-mechanical controller configured to control drug delivery, temperature management, ventilation, and/or other type of therapy delivery.

The medical treatment device 902 may incorporate and/or be configured to couple to one or more patient interface devices 930. The patient interface devices 930 may include one or more therapy delivery component(s) 932a and one or more sensor(s) 932b. Similarly, the companion device 904 may be adapted for medical use and may incorporate and/or be configured to couple to one or more patient interface device(s) 934. The patient interface device(s) 934 may include one or more sensors 936. The sensor(s) 936 may be substantially as described herein with regard to the sensor(s) 932b.

The sensor(s) 932b and 936 may include sensing electrodes (e.g., the sensing electrodes 938), ventilation and/or respiration sensors (e.g., the ventilation and/or respiration sensors 940), temperature sensors (e.g., the temperature sensor 942), chest compression sensors (e.g., the chest compression sensor 944), etc. In some implementations, the information obtained from the sensors 932b and 936 can be used to generate information displayed at the medical treatment device 902 and simultaneously at the display views at companion device 904 and described above (e.g., in display views 600, 636, 668 in FIGS. 6A-6C and case type views 814, 820, 824, 834, 840, and 844 in FIGS. 8B-8G. In one example, the sensing electrodes 938 may include cardiac sensing electrodes. The cardiac sensing electrodes may be conductive and/or capacitive electrodes configured to measure changes in a patient's electrophysiology to measure the patient's ECG information. The sensing electrodes 938 may further measure the transthoracic impedance and/or a heart rate of the patient. The ventilation and/or respiration sensors 940 may include spirometry sensors, flow sensors, pressure sensors, oxygen and/or carbon dioxide sensors such as, for example, one or more of pulse oximetry sensors, oxygenation sensors (e.g., muscle oxygenation/pH), $O_2$ gas sensors and capnography sensors, impedance sensors, and combinations thereof. The temperature sensors 942 may include an infrared thermometer, a contact thermometer, a remote thermometer, a liquid crystal thermometer, a thermocouple, a thermistor, etc. and may measure patient temperature internally and/or externally. The chest compression sensor 944 may include one or more motion sensors including, for example, one or more accelerometers, one or more force sensors, one or more magnetic sensors, one or more velocity sensors, one or more displacement sensors, etc. The chest compression sensor 944 may provide one or more signals indicative of the chest motion to the medical treatment device 902 via a wired and/or wireless connection. The chest compression sensor 944 may be, for example, but not limited to, a compression puck, a smart phone, a hand-held device, a wearable device, etc. The chest compression sensor 944 may be configured to detect chest motion imparted by a rescuer and/or an automated chest compression device (e.g., a belt system, a piston system, etc.). The chest compression sensor 944 may provide signals indicative of chest compression data including displacement data, velocity data, release velocity data, acceleration data, force data, compression rate data, dwell time data, hold time data, blood flow data, blood pressure data, etc. In an implementation, the defibrillation and/or pacing electrodes may include or be configured to couple to the chest compression sensor 944.

In various implementations, the sensors 932b and 936 may include one or more sensor devices configured to provide sensor data that includes, for example, but not limited to electrocardiogram (ECG), blood pressure, heart rate, respiration rate, heart sounds, lung sounds, respiration sounds, end tidal $CO_2$, saturation of muscle oxygen ($SMO_2$), oxygen saturation (e.g., $SpO_2$ and/or $PaO_2$), cerebral blood flow, point of care laboratory measurements (e.g., lactate, glucose, etc.), temperature, electroencephalogram (EEG) signals, brain oxygen level, tissue pH, tissue fluid levels, images and/or videos via ultrasound, laryngoscopy, and/or other medical imaging techniques, near-infrared spectroscopy, pneumography, cardiography, and/or patient movement. Images and/or videos may be two-dimensional or three-dimensional, such a various forms of ultrasound imaging.

The one or more therapy delivery components 932a may include electrotherapy electrodes (e.g., the electrotherapy electrodes 938a), ventilation device(s) (e.g., the ventilation devices 938b), intravenous device(s) (e.g., the intravenous devices 938c), compression device(s) (e.g., the compression devices 938d), etc. For example, the electrotherapy electrodes 938a may include defibrillation electrodes, pacing electrodes, and combinations thereof. The ventilation devices 938b may include a tube, a mask, an abdominal and/or chest compressor (e.g., a belt, a cuirass, etc.), etc. and combinations thereof. The intravenous devices 938c may include drug delivery devices, fluid delivery devices, and combinations thereof. The compression devices 938d may include mechanical compression devices such as abdominal compressors, chest compressors, belts, pistons, and combinations thereof. In various implementation, the therapy delivery component(s) 932a may be configured to provide sensor data and/or be coupled to and/or incorporate sensors. For example, the electrotherapy electrodes 938a may provide sensor data such as transthoracic impedance, ECG, heart rate, etc. Further the electrotherapy electrodes 938a may include and or be coupled to a chest compression sensor. As another example, the ventilation devices 938b may be coupled to and/or incorporate flow sensors, gas species sensors (e.g., oxygen sensor, carbon dioxide sensor, etc.), etc. As a further example, the intravenous devices 938c may be coupled to and/or incorporate temperature sensors, flow sensors, blood pressure sensors, etc. As yet another example, the compression devices 938d may be coupled to and/or incorporate chest compression sensors, patient position sensors, etc. The therapy delivery control modules 918 may be configured to couple to and control the therapy delivery component(s) 932a, respectively.

The one or more sensor(s) 932b and 936 and/or the therapy delivery component(s) 932a may provide sensor data. The patient data provided at the operational interface(s) and/or playback interface(s) of the medical treatment device 902 and companion device 904 may display the sensor data. For example, the medical treatment device 902 may process signals received from the sensor(s) 932b and/or the therapy delivery component(s) 932a to determine the sensor data. Similarly, the companion device 904 may process signals received from the sensor(s) 936 and/or sensor data from the sensors 932b received via the medical treatment device 902 to determine the sensor data.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus and/or distributed processing systems having processing circuitry, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors. The virtual processors, for example, may be part of one or more physical computing systems such as a computer farm or a cloud drive.

Aspects of the present disclosure may be implemented by software logic, including machine readable instructions or commands for execution via processing circuitry. The software logic may also be referred to, in some examples, as machine readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the computing device to perform, in some examples, the method 300 of FIG. 3, the method 400 of FIG. 4A and FIG. 4B, the method 500 of FIG. 5A, the method 502 of FIG. 5B, the method 504 of FIG. 5C, the method 506 of FIG. 5D, the method 508 of FIG. 5E, the method 510 of FIG. 5F, the method 574 of FIG. 5G, and/or the method 590 of FIG. 5H.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi®, Bluetooth®, Zigbee®, or another wireless form of communication. The network, for example, may support communications between one or both of the companion devices 110, 111 and/or 119 and the medical treatment device 108 as illustrated in FIG. 1A through FIG. 1C, the medical treatment device 202 and the companion device 204 of FIG. 2, the companion device 204 and the sensors/monitors 213 of FIG. 2, the medical treatment device 202 and the data repository 208 of FIG. 2, the companion device 204 and the data storage region 210 of FIG. 2, the physiological sensors 212 and/or therapy delivery sensors 214 and the medical treatment device 202, the patient interface device(s) 934 and the companion device(s) 904, the patient interface device(s) 930 and the therapeutic medical device 902, and/or the therapeutic medical device 902 and the companion device(s) 904.

The computing device, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display. The display controller and display may enable presentation of the screen shots illustrated, in some examples, in FIG. 6A through FIG. 6F, FIG. 7A through FIG. 7F, FIG. 8A through FIG. 8G, FIG. 10, FIG. 11A through FIG. 11E, FIG. 12A and FIG. 12B, and/or FIG. 13A through FIG. 13D-2.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™ or Amazon™ Web Services (AWS™), may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google™ Cloud Storage or Amazon™ Elastic File System (EFS™), may store processed and unprocessed data supplied by systems described herein. For example, the contents of the data repository 208 and/or the data storage region 210 of FIG. 2 may be maintained in a database structure.

The systems described herein may communicate with the cloud computing environment through a secure gateway. In some implementations, the secure gateway includes a database querying interface, such as the Google BigQuery™ platform or Amazon RDS™. The data querying interface, for example, may support access by the data logging and storage engine 218 of FIG. 2.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A medical treatment system for providing resuscitative care to a patient during a medical event, the medical treatment system comprising:
    a medical treatment device configured to monitor and provide treatment to the patient, the medical treatment device comprising
        at least one physiological sensor input configured to generate physiological signals corresponding to the patient during the medical event,
        a medical treatment device screen for presenting medical information based on the generated physiological signals, and
        at least one first processor operably coupled with the at least one physiological sensor input, and the medical treatment device screen, the at least one first processor configured to
            receive and process the physiological signals corresponding to the patient, generate medical data based on the processed physiological signals,
            display, on the medical treatment device screen in a first display format, case information comprising physiological information visually rendered from the generated medical data, and
            transmit the case information and generated medical data to a companion device; and
        the companion device communicatively coupled to the medical treatment device via a communication link, the companion device comprising
            a device interface having a display screen configured to allow a user to input one or more instructions for the medical treatment device during the medical event,
                the one or more instructions comprising patient information input and case information identification input, and
            at least one second processor operably coupled with the device interface, the at least one second processor configured to:
                process the case information and generated medical data received from the medical treatment device,
                link the patient information and case information identification to the processed case information and generated medical device data, cause display, at the device interface in a second display format, of a real time device view of the case information comprising the physiological information displayed on the medical treatment device screen, wherein the second display format provides a visual reproduction of the first display format, and transmit, responsive to detecting at least one user input at the device interface, one or more instruction signals to the medical treatment device.

2. The system of claim 1, wherein:

the at least one user input comprises an input for providing an instruction signal of the one or more instruction signals to the medical treatment device; and transmitting the one or more instruction signals to the medical treatment device comprises, responsive to detecting selection of one of the at least one user input, transmitting an instruction signal of the one or more instruction signals to update at least one of: patient information, treatment information, or diagnostic information for the medical event.

3. The system of claim 2, wherein:

the at least one user input includes a patient information input; and the at least one second processor is further configured to, responsive to detecting a user input signal associated with the patient information input, cause display of a patient information input interface at the device interface, wherein the patient information input interface includes a plurality of patient information input fields for entering patient background information.

4. The system of claim 3, wherein:

the plurality of patient information input fields includes a patient gender input field and a patient height input field;

transmitting the one or more instruction signals from the at least one second processor to the medical treatment device includes transmitting, upon submission of a respective patient gender at the patient gender input field and a respective patient height at the patient height input field, the respective patient gender and the respective patient height to the medical treatment device; and the at least one first processor is further configured to, responsive to receiving the respective patient gender and the respective patient height, automatically adjust a tidal volume ($V_t$) setting at the medical treatment device based on the respective patient gender and the respective patient height.

5. The system of claim 3, wherein:

the plurality of patient information input fields includes at least one of a patient age input field, a patient gender input field, a patient name input field, patient weight input field, patient height input field, or a patient identification input field, and a case information identification input field; and transmitting the one or more instruction signals from the at least one second processor to the medical treatment device includes transmitting, upon submission of patient information at a portion of the plurality of patient information input fields, the patient information to the medical treatment device.

6. The system of claim 5, wherein the at least one first processor is further configured to:

responsive to receiving the portion of the patient information, link the patient information with the case information for the patient; and responsive to linking the patient information with the case information for the patient, transmit a linking confirmation signal to the companion device.

7. The system of claim 6, wherein:

the at least one second processor is further configured to, responsive to receiving the linking confirmation signal from the medical treatment device, cause display at the device interface of a patient information transfer confirmation message; and the at least one first processor is further configured to responsive to receiving the portion of the patient information, store the patient information with the case information in a data storage region of the medical treatment device, and responsive to storing the patient information with the case information for the patient, transmit a storage confirmation signal to the companion device;

wherein, responsive to receiving the storage confirmation signal from the medical treatment device, the at least one second processor is configured to cause display, at the device interface, of a patient information transfer confirmation message.

8. The system of claim 3, wherein the device interface comprises at least one sensor configured to scan patient information from a document, and wherein the at least one second processor is further configured to automatically populate respective input fields of the plurality of patient information input fields with the scanned patient information.

9. The system of claim 2, wherein:

the at least one user input includes a medical treatment settings input; and the at least one second processor is further configured to, responsive to detecting a user input signal associated with the medical treatment settings input, cause display of a medical treatment settings interface at the device interface, wherein the medical treatment settings interface includes a plurality of medical treatment setting inputs for adjusting a plurality of medical treatment settings on the medical treatment device.

10. The system of claim 9, wherein:

responsive to detecting selection of one of the plurality of medical treatment setting inputs at the medical treatment settings interface, the at least one second processor is configured to cause display of a setting adjusting interface for the respective medical treatment setting, wherein the setting adjustment interface includes an interface for inputting a numeric value for the respective medical treatment setting;

transmitting the one or more instruction signals from the at least one second processor to the medical treatment device comprises transmitting, upon submission of a medical treatment setting adjustment at a respective medical treatment setting adjustment interface, the medical treatment setting adjustment for the respective medical treatment setting to the medical treatment device; and the at least one first processor is further configured to, responsive to receiving the medical treatment setting adjustment for the respective setting, automatically adjust the respective medical treatment setting on the medical treatment device based on the medical treatment setting adjustment.

11. The system of claim 10, wherein, responsive to receiving a confirmation signal from the medical treatment device confirming adjustment of the respective setting, the at least one second processor is configured to cause display, at one or more selectable display views of a plurality of selectable display views at the companion device, of an event marker associated with the adjustment of the respective setting at the medical treatment device, wherein
the confirmation signal includes a time that the adjustment of the respective setting occurred at the medical treatment device, and
the event marker is displayed in the one or more selectable display views at a position relative to the time that the adjustment of the respective setting occurred.

12. The system of claim 9, wherein:
responsive to detecting selection of a medical treatment mode adjustment setting at the medical treatment settings interface, the at least one second processor is configured to cause display of a mode selection interface at the device interface, wherein
the mode selection interface includes a plurality of medical treatment mode inputs, each medical treatment mode input associated with a respective operating mode of the medical treatment device;
transmitting the one or more instruction signals from the at least one second processor to the medical treatment device comprises transmitting, upon detecting selection of a respective medical treatment mode input at the mode selection interface, the respective medical treatment mode input to the medical treatment device; and
the at least one first processor is further configured to, responsive to receiving the respective medical treatment mode input, automatically adjust the respective operating mode at the medical treatment device.

13. The system of claim 12, wherein, responsive to receiving a confirmation signal from the medical treatment device confirming adjustment the respective operating mode, the at least one second processor is configured to cause display, at the one or more of a plurality of selectable display views at the display screen of the companion device, of an event marker associated with the adjustment of the respective operating mode at the medical treatment device, wherein
the confirmation signal includes a time that the adjustment of the respective operating mode occurred at the medical treatment device, and
the event marker is displayed in the one or more of selectable display views at a position relative to the time that the adjustment of the respective operating mode occurred.

14. The system of claim 2, wherein:
the at least one user input includes an alarm summary input; and
the at least one second processor is further configured to, responsive to detecting selection of the alarm summary input, cause display of an alarm interface at the device interface,
wherein
the alarm interface comprises a listing of one or more alarm-causing events at the medical treatment device, and
the listing of the one or more alarm-causing events includes, for each listed alarm-causing event, at least one of a respective alarm triggering time, a respective alarm description, a respective alarm type, or a respective alarm priority.

15. The system of claim 2, wherein:
the at least one user input includes an event marker input; and
the at least one second processor is further configured to, responsive to detecting a user input signal associated with the event marker input, cause display of an event marker input interface at the device interface, wherein
the event marker input interface includes a plurality of event marker selections for marking patient events at the medical treatment device, wherein the plurality of event marker selections comprises a plurality of treatment marker selections.

16. The system of claim 15, wherein the plurality of treatment marker selections comprises:
at least one of: drugs, oxygen, anticoagulants, or return of spontaneous circulation (ROSC); and
a customizable treatment marker selection for manually entering a treatment name.

17. The system of claim 16, wherein:
transmitting the one or more instruction signals from the at least one second processor to the medical treatment device includes transmitting, upon submission of one or more event marker selections of the plurality of event marker selections, an event marker instruction signal for recording the one or more event marker selections to the medical treatment device;
the at least one first processor is configured to
responsive to receiving the event marker instruction signal, record the one or more event marker selections at a data storage region of the medical treatment device, and
responsive to commencing recording the one or more event marker selections, transmit an in-progress event marker recording confirmation signal to the companion device;
and
the at least one second processor is configured to, responsive to receiving the in-progress event marker recording confirmation signal from the medical treatment device, cause display at the device interface of an in-progress event marker recording confirmation message;
wherein, responsive to completion of recording of the one or more event marker selections, the at least one first processor is configured to transmit an event marker recording completion confirmation signal to the companion device;
and wherein, responsive to receiving the event marker recording completion confirmation signal from the medical treatment device, the at least one second processor is further configured to cause display at the device interface of an event marker recording completion confirmation message.

18. The system of claim 15, wherein the device interface comprises at least one audio sensor configured to receive an audio input of one or more event market selections of the plurality of event marker selections, and
wherein transmitting the one or more instruction signals from the at least one second processor to the medical treatment device includes transmitting, upon receiving the audio input, an event marker instruction signal for recording the one or more event marker selections to the medical treatment device.

19. The system of claim 13, wherein the at least one second processor is configured to cause display, within the one or more of a plurality of selectable display views at the display screen of the companion device, of an alarm marker associated with each detected alarming condition at the medical treatment device, wherein
   at least one of a color or a shape of the displayed alarm marker is based on a priority level associated with the respective detected alarming condition, and
   wherein the alarm marker is displayed in the one or more selectable display views at a position relative to the time that the adjustment of the respective operating mode occurred.

20. The system of claim 2, wherein:
the at least one user input includes a 12-lead ECG analysis input;
transmitting the one or more instruction signals from the at least one second processor to the medical treatment device includes transmitting, responsive to detecting selection of the 12-lead ECG analysis input, a 12-lead analysis instruction signal for initiating a 12-lead ECG analysis at the medical treatment device;
the at least one first processor is configured to
   responsive to receiving the 12-lead analysis instruction signal, perform a 12-lead ECG analysis at the medical treatment device, and
   responsive to commencing the 12-lead ECG analysis, transmit an in-progress 12-lead analysis confirmation signal to the companion device; and
the at least one second processor is configured to, responsive to receiving the in-progress 12-lead analysis confirmation signal from the medical treatment device, cause display at the device interface of an in-progress 12-lead analysis confirmation message;
wherein, responsive to completion of the 12-lead ECG analysis, the at least one first processor is further configured to transmit a 12-lead analysis completion confirmation signal to the companion device;
and wherein, responsive to receiving the 12-lead analysis completion confirmation signal from the medical treatment device, the at least one second processor is further configured to cause display at the device interface of a 12-lead analysis completion confirmation message.

21. The system of claim 20, wherein:
the 12-lead ECG analysis input provides for user selection of a previously-performed 12-lead ECG analysis for viewing at the device interface of the companion device; and
   the at least one second processor is further configured to
      responsive to detecting selection of the previously-performed 12-lead ECG analysis for viewing, issue an instruction signal to the medical treatment device to obtain 12-lead ECG analysis data associated with the previously-performed 12-lead ECG analysis, and
      responsive to receiving the 12-lead ECG analysis data from the medical treatment device, cause display of the 12-lead ECG analysis data for the previously-performed 12-lead ECG analysis at the device interface of the companion device.

22. The system of claim 2, wherein:
the at least one user input includes a medical treatment device snapshot input;
transmitting the one or more instruction signals from the at least one second processor to medical treatment device includes transmitting, responsive to detecting selection of the medical treatment device snapshot input, a snapshot instruction signal for initiating capture of a snapshot of the medical treatment device screen;
the at least one first processor is further configured to
   responsive to receiving the snapshot instruction signal, cause capture of a snapshot of the medical treatment device screen, and
   responsive to causing capture of the snapshot of the medical treatment device screen, transmit an in-progress snapshot confirmation signal to the companion device; and
the at least one second processor is further configured to, responsive to receiving the in-progress snapshot confirmation signal from the medical treatment device, cause display at the device interface of an in-progress snapshot confirmation message.

23. The system of claim 4, wherein:
the at least one first processor is further configured to, responsive to a completed capture of the snapshot of the medical treatment device screen, transmit a snapshot completion confirmation signal to the companion device; and
the at least one second processor is further configured to, responsive to receiving the snapshot completion confirmation signal from the medical treatment device, cause display at the device interface of a snapshot completion confirmation message.

24. The system of claim 2, wherein:
the at least one user input includes a case event summary input;
an event summary interface comprises a chronological listing of events associated with care of the patient recorded at the medical treatment device; and
the at least one second processor is configured to
   responsive to detecting selection of the case event summary input, cause display of an event summary interface at the device interface, and obtain the chronological listing of the events from the medical treatment device, and
   responsive to selection of an event in the chronological listing of events at the event summary interface, cause display of details associated with the selected event, wherein
      the displayed details for the selected event comprise a snapshot of the medical treatment device screen at a time associated with the selected event.

25. The system of claim 2, wherein:
the at least one user input includes an alarm summary input;
the at least one second processor is further configured to, responsive to detecting selection of the alarm summary input, cause display of an alarm interface at the device interface,
   wherein
      the alarm interface comprises a listing of one or more alarm-causing events at the medical treatment device, and
      the alarm-causing events include physiological alarm events and technological alarm events, wherein the physiological alarm events include threshold limits associated with the at least one physiological sensor input.

26. The system of claim 2, wherein:
the at least one user input comprises a non-invasive blood pressure (NIBP) initiation input; and
transmitting the one or more instruction signals from the at least one second processor to the medical treatment device includes transmitting, responsive to detecting selection of the NIBP initiation input, a NIBP instruction signal for initiating a NIBP measurement at the medical treatment device.

27. The system of claim 1, wherein:
the medical treatment device screen comprises a screen configured to display the case information in a first display format;
the at least one second processor is configured to cause display, at the device interface in a second display format, of the real time device view of the case information comprising the physiological information displayed on the medical treatment device screen, wherein the second display format provides a visual reproduction of the first display format; and
providing the visual reproduction of the first display format in the second display format comprises adjusting one or more visual aspects of the case information presented in the second display format from the case information displayed in the first display format.

28. The system of claim 1, wherein the at least one second processor is configured to cause display, at the device interface, of a plurality of display views, wherein:
each of the plurality of display views is selectable via a respective display view selection portion of the device interface; and
the plurality of display views includes
the real time device view of the case information comprising the physiological information stored in the memory of the medical treatment device, and
a working view including one or more customized display sections.

29. The system of claim 28, wherein the working view is displayed at an interface screen of the device interface separate from the real time device view.

30. The system of claim 28, wherein the working view is a scrollable interface to provide more information than is displayed at the real time device view.

31. The system of claim 28, wherein one of the plurality of display views is a case type view including one or more case type display sections customized to a type of case associated with the medical event, wherein
the case type view is one of a plurality of case type views, wherein each of the plurality of case type views is selectable for viewing via a respective user input at the device interface.

32. The system of claim 31, wherein the plurality of case type views includes two or more of basic monitoring case type view, advanced monitoring case type view, cardiac arrest case type view, traumatic brain injury (TBI) case type view, respiratory distress case type view, or critical care monitoring case type view.

33. The system of claim 1, wherein the medical treatment device further comprises:
at least one caregiver performance sensor input configured to generate caregiver performance signals associated with a respective caregiver role of a plurality of caregiver roles during the medical event, wherein the at least one first processor is further configured to
receive and process the caregiver performance signals, and
generate caregiver performance data from the processed caregiver performance signals, and
wherein the case information further comprises caregiver performance information visually rendered from the generated caregiver performance data.

34. The system of claim 33, wherein the at least one caregiver performance sensor input comprises at least one CPR sensor input, and wherein the case information comprises CPR case information derived from the at least one CPR sensor input, wherein:
the at least one CPR sensor input comprises a chest compression sensor input;
the CPR case information comprises chest compression information; and
the chest compression information comprises chest compression feedback during the medical event, wherein the chest compression feedback includes at least one of: compression depth feedback, compression rate feedback, or release velocity feedback.

35. The system of claim 34, wherein:
the at least one first processor is configured to
detect, from the chest compression sensor input, a compression rate of compressions delivered to the patient, and
synchronize delivery of positive pressure ventilation delivered to the patient with delivered compressions based on the detected compression rate; and
the at least one second processor is configured to cause display of a visual depiction of the synchronization of the delivered positive pressure ventilation and the delivered compressions.

36. The system of claim 1, wherein the medical treatment device comprises a defibrillator comprising:
a high-voltage capacitor configured to store and release electrical charge for providing electrotherapy to the patient, and
an electrode output configured to be electrically coupled with the high-voltage capacitor and to transmit at least a portion of the electrical charge from the high-voltage capacitor to the patient.

37. The system of claim 1, wherein providing the visual reproduction of the first display format at the second display format comprises adjusting one or more visual aspects of the case information presented in the second display format from the case information displayed in the first display format.

38. The system of claim 1, wherein providing the visual reproduction of the first display format at the second display format comprises adding or subtracting one or more items of the case information displayed in the second display format from the case information displayed in the first display format.

39. The system of claim 1, wherein:
the communication link is a wireless communication link having a preconfigured pairing between the medical treatment device and the companion device; and
the at least one first processor is further configured to
detect, via the wireless communication link, a wireless communication signal associated with the preconfigured pairing for the companion device, and
connect, responsive to the detection of the wireless communication signal, to the companion device via the wireless communication link.

40. The system of claim 39, wherein transmitting the generated medical data to the companion device includes automatically initiating transmission of the generated medical data upon connecting to the companion device.

41. The system of claim 39, wherein the at least one first processor is further configured to
detect, based on a loss of the wireless communication signal, a disconnection of the companion device from the medical treatment device, and halt, responsive to detecting the disconnection, transmitting the generated medical data to the companion device.

42. The system of claim 39, wherein the at least one second processor is configured to
detect, via the wireless communication link, a proximal presence of the medical treatment device, and
connect, via the preconfigured pairing, to the medical treatment device with a proximity-based connection.

43. The system of claim 1, wherein the at least one second processor is further configured to cause display, at the device interface, of a verification input that, when actuated, causes the medical treatment device to generate an indication of pairing between the companion device and the medical treatment device.

44. The system of claim 43, wherein the at least one second processor is further configured to, responsive to detecting actuation of the verification input at the device interface, transmit an instruction signal to the medical treatment device for generating the indication of pairing between the companion device and the medical treatment device, wherein
the indication of pairing at the medical treatment device is at least one of: a visual indication or an audio indication.

45. The system of claim 1, wherein:
the companion device is one of a plurality of companion devices connectable to the medical treatment device; and
the at least one first processor is further configured to simultaneously transmit at least a portion of the generated medical data to each of the plurality of companion devices for display at a respective device interface for each of the plurality of companion devices.

46. The system of claim 1, wherein the physiological information includes an ECG waveform, a pulse oximetry waveform, invasive blood pressure (IBP) and/or a $CO_2$ waveform, wherein
the physiological information includes current values for at least one of: peripheral capillary oxygen saturation ($SpO_2$), carbon monoxide saturation (SpCO), methemoglobin (SpMet), total hemoglobin (SpHB), blood oxygen content (SpOC), pleth variability index (PVI), perfusion index (PI), end-tidal carbon dioxide ($ETCO_2$), non-invasive blood pressure, invasive blood pressure value, heart rate (HR), respiration rate, fraction of inspired oxygen ($FiO_2$), or temperature.

47. The system of claim 1, further comprising one or more additional physiological sensor inputs communicatively coupled to the companion device, wherein:
the one or more additional physiological sensor inputs are configured to generate one or more additional physiological signals corresponding to the patient during the medical event; and
the at least one second processor is further configured to
receive and process the one or more additional physiological signals corresponding to the patient,
generate additional medical data based on the processed one or more additional physiological signals,
display, at the device interface, additional case information comprising additional physiological information visually rendered from the generated additional medical data, and
transmit the additional case information to the medical treatment device for display at the medical treatment device screen.

48. The system of claim 47, wherein the one or more additional physiological sensor inputs comprise at least one of a continuous NIBP sensor, an ultrasound imaging sensor, or a laryngoscopic sensor.

49. The system of claim 1, wherein the at least one second processor is further configured to:
receive, from the medical treatment device, an amount of shock energy to be provided by the medical treatment device and a number of shocks applied by the medical treatment device to the patient; and
cause display, at the device interface, of the amount of shock energy to be provided by the medical treatment device and the number of shocks applied by the medical treatment device to the patient.

50. The system of claim 1, wherein:
the device view displayed at the device interface is one of a plurality of views for displaying at the device interface of the companion device, wherein
the plurality of views for displaying at the device interface comprises a trend view for presenting trend data from the generated medical data associated with the patient care during the medical event, wherein the trend data comprises physiological values from the at least one physiological sensor input over time; and
the at least one second processor is further configured to cause display of a portion of the plurality of views at the device interface.

51. The system of claim 50, wherein the trend data comprises at least one of $SpO_2$, ETCO2, systolic blood pressure, diastolic blood pressure, mean arterial pressure, or heart rate values over time.

52. The system of claim 1, wherein:
the at least one second processor is configured to
cause display, at the device interface, of a plurality of data display views, wherein:
each of the plurality of data display views is selectable via a respective display view selection portion of the device interface; and
the plurality of data display views includes
the real time device view of the case information comprising the physiological information displayed on the medical treatment device screen, and
a working view including one or more customized display sections.

53. The system of claim 52, wherein:
the medical treatment device further comprises at least one caregiver performance sensor input configured to generate caregiver performance signals associated with a respective caregiver role of a plurality of caregiver roles during the medical event, wherein
the respective caregiver role is administering chest compressions to the patient during the medical event, and
the at least one caregiver performance sensor input comprises a chest compression sensor input;
the at least one first processor is further configured to
receive and process the caregiver performance signals, and
generate caregiver performance data from the processed caregiver performance signals; and
the case information further comprises caregiver performance information visually rendered from the generated caregiver performance data, wherein
the caregiver performance information comprises chest compression information.

54. The system of claim 53, wherein the chest compression information comprises chest compression feedback during the medical event, wherein the chest compression feedback includes at least one of compression depth feedback, compression rate feedback, or release velocity feedback, wherein
- the compression depth feedback includes a visual indication of a respective depth of each chest compression applied to the patient, and
- the visual indication of the respective depth of each chest compression applied to the patient is displayed relative to a target range of chest compression depth.

55. The system of claim 53, wherein the chest compression information comprises a summary of chest compression performance during the medical event, wherein
- the summary of chest compression performance comprises at least one of average compression depth, average compression rate, average release velocity, pre-shock pause, post-shock pause, or percentage of compressions within a target compression depth range.

56. The system of claim 55, wherein the at least one second processor is configured to cause display the summary of the chest compression performance i) in the working view in real-time during the medical event or ii) upon completion of the medical event.

57. The system of claim 53, wherein:
- the at least one caregiver performance sensor input comprises at least one ventilation sensor input;
- the respective caregiver role is administering ventilation to the patient during the medical event;
- the case information comprises ventilation feedback during the medical event,
  - wherein
    - the ventilation feedback includes at least one of tidal volume, ventilation rate, or minute volume; and
- the caregiver performance information comprises ventilation case information derived from
  - the at least one ventilation sensor input, wherein
    - the at least one ventilation sensor input comprises an airflow sensor input, and
    - the one or more customized display sections of the working view comprises a ventilation performance data section displaying the ventilation case information.

58. The system of claim 57, wherein the ventilation case information comprises a summary of ventilation performance during the medical event comprising display of at least one of average tidal volume, average ventilation rate, average minute volume, or percentage of ventilations within a target volume range or a target rate range.

59. The system of claim 58, wherein the at least one second processor is configured to cause display of the summary of the ventilation performance i) in the working view in real-time during the medical event or ii) upon completion of the medical event.

60. The system of claim 1, wherein the medical treatment device is a ventilator comprising:
- an oxygen inlet configured to supply oxygen for providing positive pressure ventilation to the patient; and
- a ventilation outlet configured to be pneumatically coupled with the oxygen inlet and to deliver the positive pressure ventilation having the supplied oxygen to the patient.

61. The system of claim 60, wherein the one or more instruction signals comprise one or more control signals for adjusting one or more ventilator control settings comprising at least one of: a fraction of inspired oxygen (FIO2) setting, a positive end-expiratory pressure (PEEP) setting, a tidal volume (Vt) setting, or an inspiratory:expiratory ratio (I:E).

62. The system of claim 1, wherein the physiological information comprises graphs of at least one of: end-tidal carbon dioxide (ETCO2), non-invasive blood pressure (NIBP), or pulse rate (PR) over time.

63. The system of claim 1, wherein the physiological information comprises current values of at least one of: end-tidal carbon dioxide (ETCO2), non-invasive blood pressure (NIBP), invasive blood pressure (IBP), or heart rate (HR).

* * * * *